United States Patent
Arrington et al.

(10) Patent No.: US 9,718,819 B2
(45) Date of Patent: *Aug. 1, 2017

(54) NON-NUCLEOSIDE REVERSE TRANSCRIPTASE INHIBITORS

(71) Applicant: Merck Sharp & Dohme Corp., Rahway, NJ (US)

(72) Inventors: Kenneth L. Arrington, Philadelphia, PA (US); Christopher Burgey, Ambler, PA (US); Robert Gilfillan, Lexington, MA (US); Yongxin Han, Needham, MA (US); Mehul Patel, Blue Bell, PA (US); Chun Sing Li, Dollard-des-Ormeaux (CA); Yunfu Luo, Shanghai (CN); Zhiyu Lei, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/012,445

(22) Filed: Feb. 1, 2016

(65) Prior Publication Data

US 2016/0145255 A1 May 26, 2016

Related U.S. Application Data

(63) Continuation of application No. 14/047,515, filed on Oct. 7, 2013, now Pat. No. 9,469,634.

(30) Foreign Application Priority Data

Oct. 8, 2012 (WO) ................ PCT/CN2012/001358

(51) Int. Cl.
| | | |
|---|---|---|
| *A01N 43/58* | (2006.01) | |
| *A01N 43/60* | (2006.01) | |
| *A61K 31/50* | (2006.01) | |
| *A61K 31/495* | (2006.01) | |
| *C07D 471/04* | (2006.01) | |
| *A61K 31/513* | (2006.01) | |
| *A61K 45/06* | (2006.01) | |
| *C07D 403/06* | (2006.01) | |
| *C07D 405/14* | (2006.01) | |
| *C07D 401/14* | (2006.01) | |
| *C07D 239/56* | (2006.01) | |
| *C07D 403/14* | (2006.01) | |
| *C07D 239/52* | (2006.01) | |
| *C07D 239/54* | (2006.01) | |

(52) U.S. Cl.
CPC .......... *C07D 471/04* (2013.01); *A61K 31/513* (2013.01); *A61K 45/06* (2013.01); *C07D 239/52* (2013.01); *C07D 239/54* (2013.01); *C07D 239/56* (2013.01); *C07D 401/14* (2013.01); *C07D 403/06* (2013.01); *C07D 403/14* (2013.01); *C07D 405/14* (2013.01)

(58) Field of Classification Search
CPC .... A61K 31/513; A61K 45/06; C07D 471/04; C07D 239/52; C07D 239/54; C07D 239/56; C07D 401/14; C07D 403/06; C07D 403/14; C07D 405/14

See application file for complete search history.

(56) References Cited

U.S. PATENT DOCUMENTS

| | | |
|---|---|---|
| 5,519,021 A | 5/1996 | Young et al. |
| 7,189,718 B2 | 3/2007 | Dunn et al. |

(Continued)

FOREIGN PATENT DOCUMENTS

| | | |
|---|---|---|
| WO | 0003998 A1 | 1/2000 |
| WO | 0134578 A1 | 5/2001 |

(Continued)

OTHER PUBLICATIONS

Beaumont, K., et al,, "Design of Ester Prodrugs to Enhance Oral Absorption of Poorly Permeable Compounds: Challenges to the Discovery Scientist", Current Drug Metabolism, 2003, pp. 461-485, vol. 4.

(Continued)

*Primary Examiner* — Jean Cornet
(74) *Attorney, Agent, or Firm* — Carol S. Quagliato; Catherine D. Fitch

(57) ABSTRACT

Compounds of Formula I:

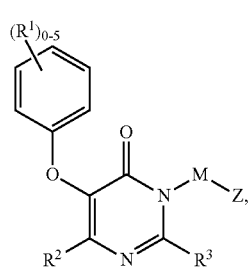

(I)

are HIV reverse transcriptase inhibitors, wherein $R^1$, $R^2$, $R^E$, L, M and Z are defined herein. The compounds of Formula I and their pharmaceutically acceptable salts are useful in the inhibition of HIV reverse transcriptase, the prophylaxis and treatment of infection by HIV and in the prophylaxis, delay in the onset or progression, and treatment of AIDS. The compounds and their salts can be employed as ingredients in pharmaceutical compositions, optionally in combination with other antivirals, immunomodulators, antibiotics or vaccines.

19 Claims, No Drawings

(56) References Cited

U.S. PATENT DOCUMENTS

| | | | |
|---|---|---|---|
| 8,486,975 | B2 | 7/2013 | Burch et al. |
| 2004/0192704 | A1 | 9/2004 | Dunn et al. |
| 2005/0215554 | A1 | 9/2005 | Dunn et al. |
| 2008/0207654 | A1 | 8/2008 | Kuroita et al. |
| 2009/0176812 | A1 | 7/2009 | Kuroita et al. |
| 2013/0296382 | A1 | 11/2013 | Burch et al. |
| 2014/0100231 | A1 | 4/2014 | Arrington et al. |

FOREIGN PATENT DOCUMENTS

| | | |
|---|---|---|
| WO | 2004069812 A1 | 1/2004 |
| WO | 2004074257 A1 | 9/2004 |
| WO | 2004085406 A1 | 10/2004 |
| WO | 2005070901 A2 | 8/2005 |
| WO | 2005102989 A1 | 11/2005 |
| WO | 2006067587 A1 | 6/2006 |
| WO | 2007015812 A2 | 2/2007 |
| WO | 2007045572 A1 | 4/2007 |
| WO | 2007045573 A1 | 4/2007 |
| WO | 2008076225 A1 | 6/2008 |
| WO | 2009067166 A2 | 5/2009 |
| WO | 2011120133 A1 | 10/2011 |
| WO | 2011126969 A1 | 10/2011 |
| WO | 2015153304 A1 | 4/2014 |
| WO | 2004074257 A1 | 10/2015 |

OTHER PUBLICATIONS

Butters, M., et al,, "Process Development of Voriconazole: A Novel Broad-Spectrum Triazole Antifungal Agent", Org. Proc. Res. & Dev., 2001, pp. 28-36, vol. 5.

Clemo, G.R., et al, "The Lupin Alkaloids. Part XV. Some Derivatives of the 4-Oxo-3-2'-Pyridylpyridocoline System", J. Chem. Soc., 1954, pp. 2693-2702.

Hale, et al, Phosphorylated Morpholine Acetal Human Neurokinin-1 Receptor Antagonists as Water-Soluble Prodrugs, J. Med. Chem, 2000, 1234-1241, vol. 43.

Ji, L., et al,, "Synthesis and Anti-HIV-1 Activity evaluation of 5-alkyl-2-alkylthio-6-(Arylcarbonyl or a-Cyanoarylmethyl)-3,4-Dihydropyrimidin-4(3H)-Ones as Novel Non-Nucleoside HIV-1 Reverse Transcriptase Inhibitors", Journal of Medicinal Chemistry, 2007, pp. 1778-1786, vol. 50.

Kesisoglou, F, et al, "Nanosizing—Oral Formulation Development and Biopharmaceutical Evaluation", Advanced Drug Delivery Reviews, 2007, pp. 631-644, vol. 59, US.

Larsen, C.S., et al,, "Design and Application of Prodrugs", Textbook of Drug Design and Discovery, 3rd Ed, 2002, pp. 410-458, Chapter 14, US.

Li, A., et al,, "Novel Pyridinone Derivatives as Non-Nucleoside Reverse Transcriptase Inhibitors (NNRTIs) with High Potency Against NNRTI-Resistant HIV-1 Strains", Journal of Medicinal Chemistry, 2013, pp. 3593-3608, vol. 56, ACS Publications.

PCT Written Opinion of International Search Authority—PCT/US2015/22868, mailing date Jun. 29, 2015.

Radi, M., et al,, "Discovery of Chiral Cyclopropyl Dihydro-Alkylthio-Benzyl-Oxopyrimidine (S-DABO) Derivatives as Potent HIV-1 Reverse Transcriptase Inhibitors With High Activity Against Clinically Relevant Mutants", J. Med. Chem., 2009, pp. 840-851, vol. 52, American Chemical Society, US.

Serajuddin, A., et al,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.

Sweeney, Z.K., et al, "Discovery of Triazolinone Non-Nucleoside Inhibitors of HIV Reverse Transcriptase", Bioorganic & Medicinal Chemistry Letters, Aug. 1, 2008, pp. 4348-4351, vol. 18, No. 15.

Thenappan, A., et al,, "An Expedient Synthesis of a-Fluoro-b-Ketoesters", Tetrahedron Letters, 1989, pp. 3113-6116, vol. 30, No. 45.

NON-NUCLEOSIDE REVERSE TRANSCRIPTASE INHIBITORS

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz, abacavir, emtricitabine, and tenofovir.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a particular need for new RT inhibitors that are effective against mutant HIV strains.

The following references are of interest as background:

Clemo et al., *J. Chem. Soc.* 1954, pp. 2693-2702 discloses certain derivatives of the 4-oxo-3-(2-pyridyl)pyridocoline system and in particular discloses 6-methyl-6'-phenoxy-2, 2'-methylenedipyridine.

Sweeney et al., *Bioorganic & Medicinal Chem. Letters* 2008, vol. 18, pp. 4348-4351 discloses a series of triazolinones that were found to be non-nucleoside inhibitors of HIV reverse transcriptase.

WO 2001/034578 discloses certain substituted azoles (including, for example, certain imidazoles and benzimidazoles) having anti-*Helicobacter pylori* activity. In particular, WO '578 discloses 1-[(3-methyl-4-phenoxy-2-pyridinyl) methyl]-1H-benzimidazole (see Compound 91 on page 40).

WO 2004/085406 and corresponding U.S. Pat. No. 7,189, 718 disclose certain benzyl pyridazinones as reverse transcriptase inhibitors.

WO 2005/102989 and corresponding U.S. Pat. No. 7,166, 738 disclose certain N-phenyl 2-phenylacetamides to be non-nucleoside reverse transcriptase inhibitors.

WO 2006/067587 discloses certain biaryl ether derivatives to be modulators of the reverse transcriptase enzyme.

WO 2007/045572 and WO 2007/045573 disclose certain 2-(2-phenoxyphenyl) N-phenyl acetamides as non-nucleoside reverse transcriptase inhibitors.

WO 2008/076225 discloses certain indazoles, benzotriazoles and related bicyclic compounds as HIV reverse transcriptase inhibitors.

WO 2009/067166 discloses certain aryloxy-, cycloalkyloxy-, and heterocyclyloxy-pyridines and related compounds. The compounds are HIV reverse transcriptase inhibitors suitable, for example, for the treatment of infection by HIV. Among the compounds disclosed are certain 3-(3,5-disubstituted phenoxy)-1-(1H-pyrazolo[3,4-b]pyridin-3-ylmethyl)-4-(substituted)pyridin-2(1H)-ones.

US 2004/0192704 discloses certain 3-(phenoxy)benzyl substituted 5-membered triazolones, oxadiazolones, and thiadiazolones. The compounds are disclosed to be non-nucleoside reverse transcriptase inhibitors useful for the treatment or prophylaxis of HIV mediated diseases.

US 2007/0021442 and WO 2007/015812 disclose certain substituted aromatic compounds. The compounds are HIV reverse transcriptase inhibitors suitable, for example, for the treatment of infection by HIV.

WO 2009/067166 and WO2011/120133 discloses HIV non-nucleoside reverse transcriptase inhibitors.

SUMMARY OF THE INVENTION

The present invention is directed to 4-pyrimidinone derivatives and their use in the inhibition of HIV reverse transcriptase, the prophylaxis of infection by HIV, the treatment of infection by HIV, and the prophylaxis, treatment, and delay in the onset or progression of AIDS and/or ARC.

DETAILED DESCRIPTION OF THE INVENTION

An embodiment of the invention ("Embodiment 1") encompasses compounds of Formula I:

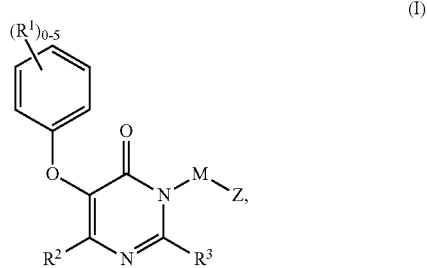

or a pharmaceutically acceptable salt thereof, wherein:
M is $CH_2$, $CH_2CH_2$, $CH_2CH_2CH_2$, $CH(CH_3)$, $C(CH_3)_2$ or $C(O)N(R^4)$; Z is selected from the group consisting of: pyridazine, pyridazinone, pyrimidine, pyrimidinone, pyrazine, pyrazinone, triazine and triazinone, each optionally substituted with one or more substituents up to the maximum number allowed by valence selected from $R^4$ and $R^5$;

each $R^1$ is independently selected from the group consisting of: halogen, CN, $NO_2$, $C_{1-4}$ alkyl, $C_{1-4}$ haloalkyl, $C_{2-4}$ alkenyl, OH, O—$C_{1-4}$ alkyl, O—$C_{1-4}$ haloalkyl, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, $SO_2N(R^A)C(O)R^B$ or $C_{2-4}$ alkenyl substituted with CN;

$R^2$ is selected from the group consisting of:
(1) H,
(2) $C_{1-6}$ alkyl,
(3) $C_{1-6}$ haloalkyl,
(4) $C_{1-6}$ alkyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(5) O—$C_{1-6}$ alkyl in which the alkyl is optionally substituted with 1 to 3 substituents independently selected from OH, O—$C_{1-6}$ alkyl, O—$C_{1-6}$ haloalkyl, CN, $N(R^A)R^B$, $C(O)N(R^A)R^B$, $C(O)R^A$, $CO_2R^A$, $SR^A$, $S(O)R^A$, $S(O)_2R^A$, or $S(O)_2N(R^A)R^B$,
(6) O—$C_{1-6}$ haloalkyl,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-6}$ haloalkyl,
(14) $C(O)OR^A$,
(15) $OC(O)R^A$,
(16) $OC(O)N(R^A)R^B$,
(17) $SR^A$,
(18) $S(O)R^A$,
(19) $S(O)_2R^A$,
(20) $S(O)_2N(R^A)R^B$,
(21) $N(R^A)S(O)_2R^B$,
(22) $N(R^A)S(O)_2N(R^A)R^B$,
(23) $N(R^A)C(O)R^B$,
(24) $N(R^A)C(O)N(R^A)R^B$,
(25) $N(R^A)C(O)$—$C(O)N(R^A)R^B$,
(26) $N(R^A)CO_2R^B$,
(27) $N(R^C)R^D$,
(28) $C(O)N(R^C)R^D$,
(29) $OC(O)N(R^C)R^D$,
(30) $S(O)_2N(R^C)R^D$,
(31) $N(R^A)S(O)_2N(R^C)R^D$,
(32) $N(R^A)C(O)N(R^C)R^D$,
(33) $N(R^A)C(O)$—$C(O)N(R^C)R^D$,
(34) CycA,
(35) —O-CycA,
(36) ArylA, or
(37) HetA;

$R^3$ is H, $C_{1-6}$ alkyl, halogen, CN, $C_{1-6}$ fluoroalkyl, OH, O—$C_{1-6}$ alkyl and O—$C_{1-6}$ haloalkyl;

$R^4$ and $R^5$ are each independently selected from:
(1) H,
(2) $C_{1-6}$ alkyl, $C_{2-6}$ alkenyl or $C_{2-6}$ alkynyl, each optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, CycB, ArylB and HetB,
(3) $C_{1-6}$ haloalkyl optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, CycB, ArylB and HetB,
(4) O—$C_{1-6}$ alkyl in which the alkyl portion is optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, CycB, ArylB and HetB,
(5) O—$C_{1-6}$ haloalkyl, optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, CycB, ArylB and HetB,
(6) halogen,
(7) CN,
(8) $NO_2$,
(9) $N(R^A)R^B$,
(10) $C(O)N(R^A)R^B$,
(11) $C(O)R^A$,
(12) $C(O)$—$C_{1-6}$ haloalkyl,
(13) $C(O)OR^A$,
(14) $OC(O)R^A$,
(15) $OC(O)N(R^A)R^B$,
(16) $SR^A$,
(17) $S(O)R^A$,
(18) $S(O)_2R^A$,
(19) $S(O)_2N(R^A)R^B$,
(20) $N(R^A)S(O)_2R^B$,
(21) $N(R^A)S(O)_2N(R^A)R^B$,
(22) $N(R^A)C(O)R^B$,
(23) $N(R^A)C(O)N(R^A)R^B$,
(24) $N(R^A)C(O)$—$C(O)N(R^A)R^B$,
(25) $N(R^A)CO_2R^B$,
(26) $N(R^C)R^D$,
(27) $C(O)N(R^C)R^D$,
(28) $OC(O)N(R^C)R^D$,
(29) $S(O)_2N(R^C)R^D$,
(30) $N(R^A)S(O)_2N(R^C)R^D$,
(31) $N(R^A)C(O)N(R^C)R^D$,
(32) $N(R^A)C(O)$—$C(O)N(R^C)R^D$,
(33) OH,
(34) CycB,
(35) ArylB,
(36) HetB,
(37) -J-CycB,
(38) -J-ArylB, and
(39) -J-HetB, or $R^4$ and $R^5$ on adjacent atoms may be joined together with the atoms to which they are attached to form a fused CycC, ArylC or HetC;

CycA, CycB and CycC are independently a carbocyclyl which is a $C_{3-8}$ cycloalkyl, a $C_{5-8}$ cycloalkenyl, or a $C_{7-12}$ bicyclic, saturated or unsaturated, non-aromatic ring system wherein one ring is fused to or bridged with the other ring; wherein the carbocyclyl is optionally substituted with a total of from 1 to 6 substituents, wherein:
(i) from zero to 6 substituents are each independently:
  (1) halogen,
  (2) CN,
  (3) $C_{1-6}$ alkyl,
  (4) OH,
  (5) O—$C_{1-6}$ alkyl,
  (6) $C_{1-6}$ haloalkyl,
  (7) O—$C_{1-6}$ haloalkyl,
  (8) $C_{1-6}$ alkenyl, or
  (9) $C_{1-6}$ alkenyl substituted with CN, and
(ii) from zero to 2 substituents are each independently:
  (1) CycQ,
  (2) AryQ,
  (3) HetQ,
  (4) HetR,
  (5) J-CycQ,
  (6) J-AryQ,
  (7) J-HetQ,
  (8) J-HetR,
  (9) $C_{1-6}$ alkyl substituted with CycQ, AryQ, HetQ, HetR, J-CycQ, J-AryQ, J-HetQ, or J-HetR,
  (10) $C_{2-6}$ alkenyl substituted with CycQ, AryQ, HetQ, HetR, J-CycQ, J-AryQ, J-HetQ, or J-HetR, or
  (11) $C_{2-6}$ alkynyl substituted with CycQ, AryQ, HetQ, HetR, J-CycQ, J-AryQ, J-HetQ, or J-HetR;

ArylA, ArylB and ArylC are independently aryl which is optionally substituted with a total of from 1 to 8 substituents, wherein:
(i) from zero to 8 substituents are each independently:
  (1) $C_{1-6}$ alkyl,
  (2) $C_{1-6}$ haloalkyl, which is optionally substituted with 1 to 3 additional substituents each of which is independently selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (3) $C_{1-6}$ alkyl substituted with from 1 to 3 substituents each of which is independently selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (4) C2-6 alkenyl,
  (5) C2-6 alkenyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (6) $C_{2-6}$ alkynyl,
  (7) $C_{2-6}$ alkynyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (8) O—$C_{1-6}$ alkyl,
  (9) O—$C_{1-6}$ haloalkyl,
  (10) OH,
  (11) halogen,
  (12) CN,
  (13) $NO_2$,
  (14) $N(R^A)R^B$,
  (15) $C(O)N(R^A)R^B$,
  (16) $C(O)R^A$,
  (17) $C(O)$—$C_{1-6}$ haloalkyl,
  (18) $C(O)OR^A$,
  (19) $OC(O)N(R^A)R^B$,
  (20) $SR^A$,
  (21) $S(O)R^A$,
  (22) $S(O)_2R^A$,
  (23) $S(O)_2N(R^A)R^B$,
  (24) $N(R^A)S(O)_2R^B$,
  (25) $N(R^A)S(O)_2N(R^A)R^B$,
  (26) $N(R^A)C(O)R^B$,
  (27) $N(R^A)C(O)N(R^A)R^B$,
  (28) $N(R^A)C(O)$—$C(O)N(R^A)R^B$, or
  (29) $N(R^A)CO_2R^B$, and
(ii) from zero to 2 substituents are each independently:
  (1) CycQ,
  (2) AryQ,
  (3) HetQ,
  (4) HetR,
  (5) CycQ,
  (6) AryQ,
  (7) J-HetQ,
  (8) J-HetR,
  (9) $C_{1-6}$ alkyl substituted with CycQ, AryQ, HetQ, HetR, J-CycQ, J-AryQ, J-HetQ, or J-HetR,
  (10) $C_{2-6}$ alkenyl substituted with CycQ, AryQ, HetQ, HetR, J-CycQ, J-AryQ, J-HetQ, or J-HetR, or
  (11) C2-6 alkynyl substituted with CycQ, AryQ, HetQ, HetR, J-CycQ, J-AryQ, J-HetQ, or J-HetR;

HetA, HetB and HetC are independently a heterocyclyl or heteroaryl which is optionally substituted with a total of from 1 to 8 substituents, wherein:
(i) from zero to 8 substituents are each independently:
  (1) $C_{1-6}$ alkyl,
  (2) $C_{1-6}$ haloalkyl, which is optionally substituted with 1 to 3 additional substituents each of which is independently selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (3) $C_{1-6}$ alkyl substituted with from 1 to 3 substituents each of which is independently selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (4) $C_{2-6}$ alkenyl,
  (5) $C_{2-6}$ alkenyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$, (6) C2-6 alkynyl,
(7) $C_{2-6}$ alkynyl substituted with from 1 to 3 substituents each of which is independently OH, O—$C_{1-6}$ alkyl, O—$C_{1-6}$ haloalkyl, CN, $NO_2$, $N(R^A)R^B$, C(O)N($R^A$)$R^B$, C(O)$R^A$, $CO_2R^A$, $SR^A$, S(O)$R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(8) O—$C_{1-6}$ alkyl,
(9) O—$C_{1-6}$ haloalkyl,
(10) OH,
(11) oxo,
(12) halogen,
(13) CN,
(14) $NO_2$,
(15) $N(R^A)R^B$,
(16) $C(O)N(R^A)R^B$,
(17) $C(O)R^A$,
(18) C(O)—$C_{1-6}$ haloalkyl,
(19) $C(O)OR^A$,
(20) $OC(O)N(R^A)R^B$,
(21) $SR^A$,
(22) $S(O)R^A$,
(23) $S(O)_2R^A$,
(24) $S(O)_2N(R^A)R^B$,
(25) $N(R^A)S(O)_2R^B$,
(26) $N(R^A)S(O)_2N(R^A)R^B$,
(27) $N(R^A)C(O)R^B$,
(28) $N(R^A)C(O)N(R^A)R^B$,
(29) $N(R^A)C(O)$—$C(O)N(R^A)R^B$, or
(30) $N(R^A)CO_2R^B$, and
(ii) from zero to 2 substituents are each independently:
(1) CycQ,
(2) AryQ,
(3) HetQ,
(4) HetR,
(5) J-CycQ,
(6) J-AryQ,
(7) J-HetQ,
(8) J-HetR,
(9) $C_{1-6}$ alkyl substituted with CycQ, AryQ, HetQ, HetR, J-CycQ, J-AryQ, J-HetQ, or J-HetR,
(10) $C_{2-6}$ alkenyl substituted with CycQ, AryQ, HetQ, HetR, J-CycQ, J-AryQ, J-HetQ, or J-HetR, or
(11) $C_{2-6}$ alkynyl substituted with CycQ, AryQ, HetQ, HetR, J-CycQ, J-AryQ, J-HetQ, or J-HetR;
each CycQ is independently $C_{3-8}$ cycloalkyl or $C_{5-8}$ cycloalkenyl, wherein the cycloalkyl or cycloalkenyl is optionally substituted with from 1 to 4 substituents, each of which is independently halogen, $C_{1-6}$ alkyl, OH, O—$C_{1-6}$ alkyl, $C_{1-6}$ haloalkyl, or O—$C_{1-6}$ haloalkyl;
each AryQ is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;
each HetQ is independently a heteroaryl which is optionally substituted with from 1 to 4 substituents each of which is independently halogen, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SO_2R^A$, $N(R^A)C(O)N(R^A)R^B$, or $N(R^A)CO_2R^B$;
each HetR is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)N(R^A)R^B$, $C(O)R^A$, $CO_2R^A$, or $SO_2R^A$;
each J is independently:
(i) O,
(ii) S,
(iii) S(O),
(iv) $S(O)_2$,
(v) O—$C_{1-6}$ alkylene,
(vi) S—$C_{1-6}$ alkylene,
(vii) S(O)—$C_{1-6}$ alkylene,
(viii) $S(O)_2$—$C_{1-6}$ alkylene,
(ix) $N(R^A)$, or
(x) $N(R^A)$—$C_{1-6}$ alkylene;
each $R^A$, $R^B$, $R^C$ and $R^D$ are independently selected from H, $C_{1-6}$ alkyl and $C_{3-6}$cycloalkyl, wherein said $C_{1-6}$ alkyl and $C_{3-6}$ cycloalkyl are optionally substituted with one or more substituents up to the maximum number allowed by valence selected from the group consisting of: halogen, OH, CN, $C_{1-4}$alkoxy, $C_{3-6}$cycloalkyl and phenyl;
or alternatively each pair of $R^C$ and $R^D$ together with the nitrogen to which they are both attached form a 4- to 7-membered saturated or mono-unsaturated ring which optionally contains a heteroatom in addition to the N to which $R^C$ and $R^D$ are attached, wherein the additional heteroatom is selected from N, O, and S; wherein the ring is optionally substituted with 1 or 2 substituents each of which is independently $C_{1-6}$ alkyl, $C(O)R^A$, $C(O)OR^A$, $C(O)N(R^A)R^B$, or $S(O)_2R^A$; and wherein the optional S in the ring is optionally in the form of S(O) or $S(O)_2$;
each aryl is independently (i) phenyl, (ii) a 9- or 10-membered bicyclic, fused carbocylic ring system in which at least one ring is aromatic, or (iii) an 11-to 14-membered tricyclic, fused carbocyclic ring system in which at least one ring is aromatic;
each heterocyclyl is independently (i) a 4- to 8-membered, saturated or unsaturated monocyclic ring, (ii) a 7-to 12-membered bicyclic ring system, or (iii) a 10-to 18-membered tricyclic ring system, wherein each ring in (ii) or (iii) is independent of, fused to, or bridged with the other ring or rings and each ring is saturated or unsaturated; wherein the monocyclic ring contains from 1 to 4 heteroatoms and a balance of carbon atoms; the bicyclic ring system or tricyclic ring system contains from 1 to 8 heteroatoms and a balance of carbon atoms, wherein one or more of the rings contain one or more of the heteroatoms; wherein the heteroatoms are selected from N, O and S; and wherein any one or more of the nitrogen and sulfur heteroatoms is optionally oxidized, and any one or more of the nitrogen heteroatoms is optionally quaternized;
each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered heterobicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$.

An embodiment of the invention ("Embodiment 1A") encompasses compounds of Formula I, or a pharmaceutically acceptable salt thereof, wherein two $R^1$ groups are present and selected from the group consisting of: F, Br, Cl, $OCHF_2$, $CF_3$ or CN.

Another embodiment of the invention ("Embodiment 2") encompasses compounds of Formula Ia, or a pharmaceutically acceptable salt thereof:

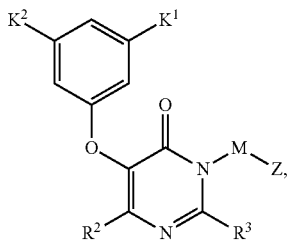

Ia wherein $K^1$ and $K^2$ are each independently F, Br, Cl, $OCHF_2$, $CF_3$ or CN, and all other variables are defined as in Embodiment 1.

Another embodiment of the invention ("Embodiment 3") encompass compounds of Formula Ia, or a pharmaceutically acceptable salt thereof, wherein:
$K^2$ is chloro and $K^1$ is cyano, or
$K^2$ is bromo and $K^1$ chloro, or
$K^2$ is cyano and $K^1$ is cyano, or
$K^2$ is cyano and $K^1$ is difluoromethoxy, or
$K^2$ is chloro and $K^1$ is chloro, or
$K^2$ is cyano and $K^1$ is fluoro,
and all other variables are defined as in Embodiment 1.

Another embodiment of the invention ("Embodiment 4") encompasses compounds of Formula I, or a pharmaceutically acceptable salt thereof, wherein:
$R^2$ is independently:
(1) H,
(2) $C_{1-3}$ alkyl,
(3) $CF_2H$,
(4) $CF_3$,
(5) $CH_2CF_3$,
(6) $CF_2CH_3$,
(7) $CH_2OH$,
(8) $CH_2OCH_3$,
(9) $CH_2CN$,
(10) $CH_2NH_2$,
(11) $CH_2N(H)CH_3$,
(12) $CH_2N(CH_3)_2$,
(13) $CH_2C(O)NH_2$,
(14) $CH_2C(O)N(H)CH_3$,
(15) $CH_2C(O)N(CH_3)_2$,
(16) $CH_2C(O)CH_3$,
(17) $CH_2CO_2CH_3$,
(18) $CH_2S(O)_2CH_3$,
(19) O—$C_{1-3}$ alkyl,
(20) $OCF_2H$,
(21) $OCF_3$,
(22) Cl,
(23) Br,
(24) F,
(25) CN,
(26) $NO_2$,
(27) $NH_2$,
(28) $N(H)CH_3$,
(29) $N(CH_3)_2$,
(30) $C(O)NH_2$,
(31) $C(O)N(H)CH_3$,
(32) $C(O)N(CH_3)_2$,
(33) $C(O)CH_3$,
(34) $C(O)CF_3$,
(35) $CO_2CH_3$,
(36) $S(O)_2CH_3$, or
(37) cyclopropyl
and all other variables are defined as in Embodiment 1.

Another embodiment of the invention ("Embodiment 5") encompasses compounds of Formula I, or a pharmaceutically acceptable salt thereof, wherein $R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN, and all other variables are defined as in Embodiment 1.

Another embodiment of the invention ("Embodiment 6") encompasses compounds of Formula I, or a pharmaceutically acceptable salt thereof, wherein $R^2$ is $CF_3$, and all other variables are defined as in Embodiment 1.

Another embodiment of the invention ("Embodiment 7") encompasses compounds of Formula Ia, or a pharmaceutically acceptable salt thereof, wherein:
$R^2$ is independently:
(1) H,
(2) $C_{1-3}$ alkyl,
(3) $CF_2H$,
(4) $CF_3$,
(5) $CH_2CF_3$,
(6) $CF_2CH_3$,
(7) $CH_2OH$,
(8) $CH_2OCH_3$,
(9) $CH_2CN$,
(10) $CH_2NH_2$,
(11) $CH_2N(H)CH_3$,
(12) $CH_2N(CH_3)_2$,
(13) $CH_2C(O)NH_2$,
(14) $CH_2C(O)N(H)CH_3$,
(15) $CH_2C(O)N(CH_3)_2$,
(16) $CH_2C(O)CH_3$,
(17) $CH_2CO_2CH_3$,
(18) $CH_2S(O)_2CH_3$,
(19) O—$C_{1-3}$ alkyl,
(20) $OCF_2H$,
(21) $OCF_3$,
(22) Cl,
(23) Br,
(24) F,
(25) CN,
(26) $NO_2$,
(27) $NH_2$,
(28) $N(H)CH_3$,
(29) $N(CH_3)_2$,
(30) $C(O)NH_2$,
(31) $C(O)N(H)CH_3$,
(32) $C(O)N(CH_3)_2$,
(33) $C(O)CH_3$,
(34) $C(O)CF_3$,
(35) $CO_2CH_3$,
(36) $S(O)_2CH_3$, or
(37) cyclopropyl;
and all other variables are defined as in Embodiment 2 or Embodiment 3.

Another embodiment of the invention ("Embodiment 8") encompasses compounds of Formula Ia, or a pharmaceutically acceptable salt thereof, wherein $R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN, and all other variables are defined as in Embodiment 2 or Embodiment 3.

Another embodiment of the invention ("Embodiment 9") encompasses compounds of Formula Ia, or a pharmaceutically acceptable salt thereof, wherein $R^2$ is $CF_3$, and all other variables are defined as in Embodiment 2 or Embodiment 3.

Another embodiment of the invention ("Embodiment 10") encompasses compounds of Formula I, or a pharmaceutically acceptable salt thereof, wherein M is $CH_2$ or $CH(CH_3)$, and all other variables are defined as in Embodiment 1, Embodiment 4, Embodiment 5 or Embodiment 6.

Another embodiment of the invention ("Embodiment 11") encompasses compounds of Formula Ia, or a pharmaceutically acceptable salt thereof, wherein M is $CH_2$ or $CH(CH_3)$, and all other variables are defined as in Embodiment 2, Embodiment 3, Embodiment 7, Embodiment 8 or Embodiment 9.

Another embodiment of the invention ("Embodiment 12") encompasses compounds of Formula I, or a pharmaceutically acceptable salt thereof, wherein M is $CH_2$, and all other variables are defined as in Embodiment 1, Embodiment 4, Embodiment 5 or Embodiment 6.

Another embodiment of the invention ("Embodiment 13") encompasses compounds of Formula Ia, or a pharmaceutically acceptable salt thereof, wherein M is $CH_2$, and all other variables are defined as in and all other variables are defined as in Embodiment 2, Embodiment 3, Embodiment 7, Embodiment 8 or Embodiment 9.

Another embodiment of the invention ("Embodiment 14") encompasses compounds of Formula I, or a pharmaceutically acceptable salt thereof, wherein Z is selected from the group consisting of:

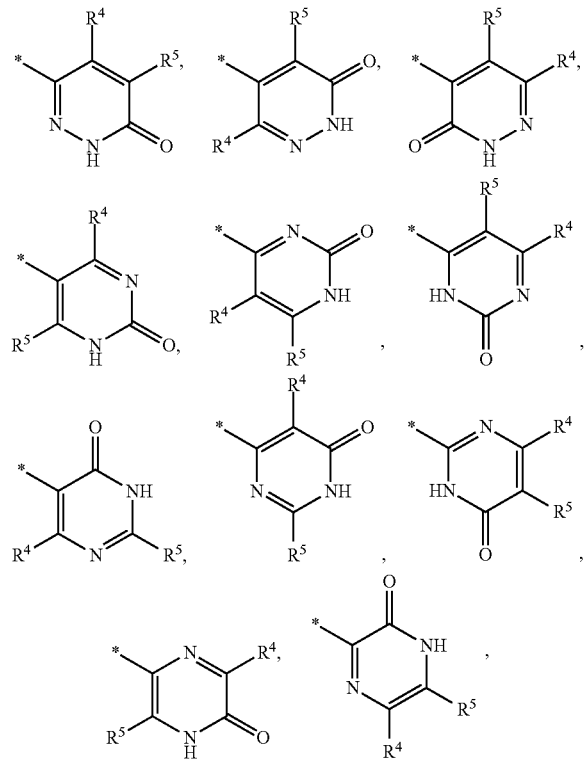

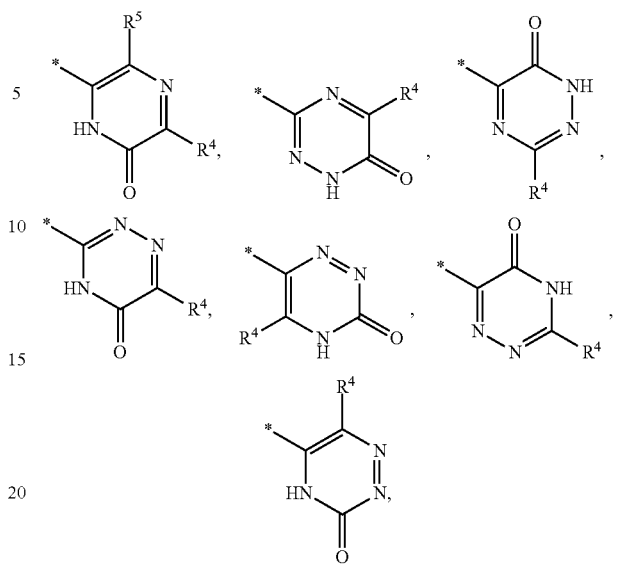

wherein * is the point of attachment to M, and all other variables are defined as in Embodiment 1, Embodiment 4, Embodiment 5, Embodiment 6, Embodiment 10 or Embodiment 12.

Another embodiment of the invention ("Embodiment 15") encompasses compounds of Formula Ia, or a pharmaceutically acceptable salt thereof, wherein Z is selected from the group consisting of:

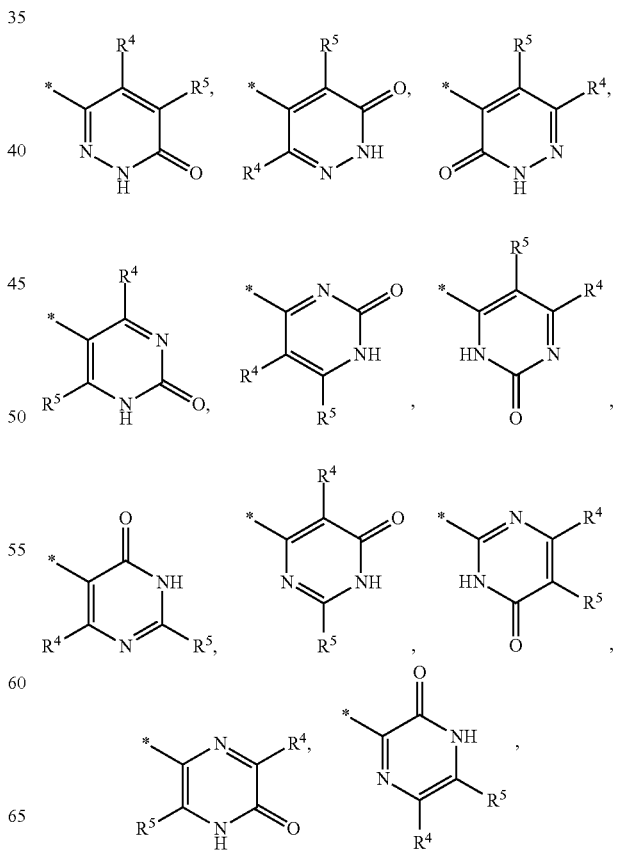

-continued

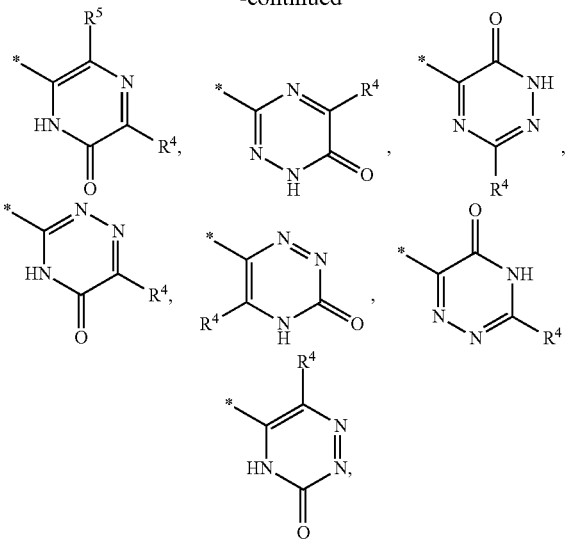

wherein * is the point of attachment to M, and all other variables are defined as in Embodiment 2, Embodiment 3, Embodiment 7, Embodiment 8, Embodiment 9, Embodiment 11 or Embodiment 13.

Another embodiment of the invention ("Embodiment 16") encompasses compounds of Formula I, or a pharmaceutically acceptable salt thereof, wherein
$R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN; $R^3$ is H; and M is $CH_2$ or $CH(CH_3)$, and all other variables are defined as in Embodiment 1, Embodiment 4, Embodiment 5, Embodiment 6, Embodiment 10, Embodiment 12 or Embodiment 14.

Another embodiment of the invention ("Embodiment 17") encompasses compounds of Formula Ia, or a pharmaceutically acceptable salt thereof, wherein
$R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN; $R^3$ is H; and M is $CH_2$ or $CH(CH_3)$, and all other variables are defined as in Embodiment 2, Embodiment 3, Embodiment 7, Embodiment 8, Embodiment 9, Embodiment 11, Embodiment 13 or Embodiment 15.

Another embodiment of the invention ("Embodiment 18") encompasses compounds of Formula I, or a pharmaceutically acceptable salt thereof, wherein
Z is selected from the group consisting of:

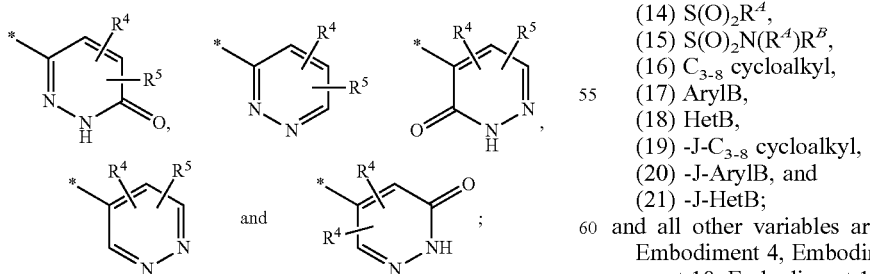

wherein * is the point of attachment to M, and all other variables are defined as in Embodiment 1, Embodiment 4, Embodiment 5, Embodiment 6, Embodiment 10, Embodiment 12 or Embodiment 16.

Another embodiment of the invention ("Embodiment 19") encompasses compounds of Formula I, or a pharmaceutically acceptable salt thereof, wherein
$R^4$ and $R^5$ are each independently selected from:
(1) H,
(2) $C_{1-6}$ alkyl, $C_{2-6}$ alkenyl or $C_{2-6}$ alkynyl, each optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(3) $C_{1-6}$ haloalkyl optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(4) O—$C_{1-6}$ alkyl in which the alkyl portion is optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(5) O—$C_{1-6}$ haloalkyl, optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(6) halogen,
(7) OH,
(8) CN
(9) $C(O)R^A$,
(10) $N(R^A)R^B$,
(11) $C(O)N(R^A)R^B$,
(12) $C(O)OR^A$,
(13) $SR^A$,
(14) $S(O)_2R^A$,
(15) $S(O)_2N(R^A)R^B$,
(16) $C_{3-8}$ cycloalkyl,
(17) ArylB,
(18) HetB,
(19) -J-$C_{3-8}$ cycloalkyl,
(20) -J-ArylB, and
(21) -J-HetB;
and all other variables are defined as in Embodiment 1, Embodiment 4, Embodiment 5, Embodiment 6, Embodiment 10, Embodiment 12, Embodiment 14, Embodiment 16 or Embodiment 18. In another embodiment, $R^4$ is H, one $R^5$ is present and is defined as above.

Another embodiment of the invention ("Embodiment 20") encompasses compounds of Formula Ia, or a pharmaceutically acceptable salt thereof, wherein Z is selected from the group consisting of:

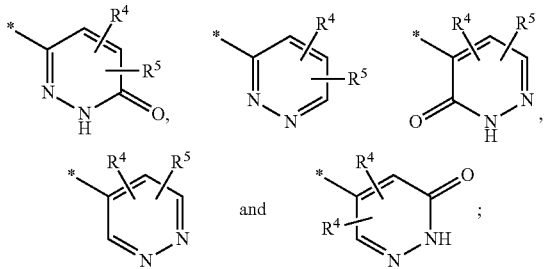

and wherein * is the point of attachment to M, and all other variables are defined as in Embodiment 2, Embodiment 3, Embodiment 7, Embodiment 8, Embodiment 9, Embodiment 11, Embodiment 13 or Embodiment 17.

Another embodiment of the invention ("Embodiment 21") encompasses compounds of Formula I, or a pharmaceutically acceptable salt thereof, wherein $R^4$ and $R^5$ are each independently selected from:
(1) H,
(2) $C_{1-6}$ alkyl, C2-6 alkenyl or C2-6 alkynyl, each optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(3) $C_{1-6}$ haloalkyl optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(4) O—$C_{1-6}$ alkyl in which the alkyl portion is optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(5) O—$C_{1-6}$ haloalkyl, optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(6) halogen,
(7) OH,
(8) CN
(9) $C(O)R^A$,
(10) $N(R^A)R^B$,
(11) $C(O)N(R^A)R^B$,
(12) $C(O)OR^A$,
(13) $SR^A$,
(14) $S(O)_2R^A$,
(15) $S(O)_2N(R^A)R^B$,
(16) $C_{3-8}$ cycloalkyl,
(17) ArylB,
(18) HetB,
(19) -J-C3-8 cycloalkyl,
(20) -J-ArylB, and
(21) -J-HetB;
and all other variables are defined as in Embodiment 2, Embodiment 3, Embodiment 7, Embodiment 8, Embodiment 9, Embodiment 11, Embodiment 13, Embodiment 15, Embodiment 17 or Embodiment 20.

Another embodiment of the invention ("Embodiment 22") encompasses compounds of Formula Ib, or a pharmaceutically acceptable salt thereof,

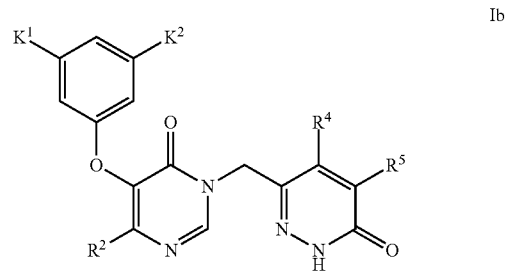

Ib or a pharmaceutically acceptable salt thereof, wherein $K^1$ and $K^2$ are each independently F, Br, Cl, $OCHF_2$, $CF_3$ or CN; $R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN; and all other variables are defined as in Embodiment 1 or Embodiment 21. Within this embodiment the invention encompasses compounds of Formula Ib as defined above wherein $R^2$ is $CF_3$ and $R^4$ is H.

Another embodiment of the invention ("Embodiment 23") encompasses compounds of Formula Ic, or a pharmaceutically acceptable salt thereof,

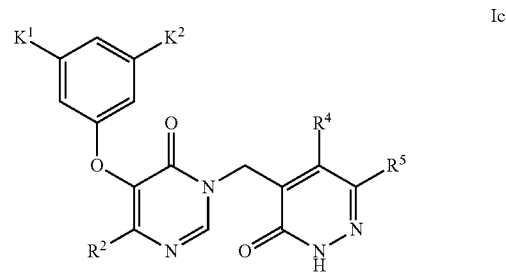

Ic or a pharmaceutically acceptable salt thereof, wherein $K^1$ and $K^2$ are each independently F, Br, Cl, $OCHF_2$, $CF_3$ or CN; $R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN; and all other variables are defined as in Embodiment 1 or Embodiment 21. Within this embodiment the invention encompasses compounds of Formula Ic as defined above wherein $R^2$ is $CF_3$ and $R^4$ is H.

Another embodiment of the invention ("Embodiment 24") encompasses compounds of Formula Id, or a pharmaceutically acceptable salt thereof,

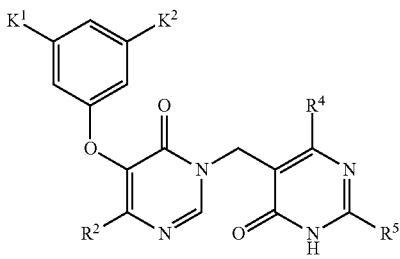

or a pharmaceutically acceptable salt thereof, wherein $K^1$ and $K^2$ are each independently F, Br, Cl, $OCHF_2$, $CF_3$ or CN; $R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN; and all other variables are defined as in Embodiment 1 or Embodiment 21. Within this embodiment the invention encompasses compounds of Formula Id as defined above wherein $R^2$ is $CF_3$ and $R^4$ is H.

The compounds of Formula I, Formula Ia, Formula Ib, Formula Ic or Formula Id above, and pharmaceutically acceptable salts thereof, are HIV reverse transcriptase inhibitors. The compounds are useful for inhibiting HIV reverse transcriptase and for inhibiting HIV replication in vitro and in vivo. More particularly, the compounds of Formula I inhibit the polymerase function of HIV-1 reverse transcriptase. The testing of representative compounds of the invention in the assay set forth in Example 184 below, illustrate the ability of compounds of the invention to inhibit the RNA-dependent DNA polymerase activity of HIV-1 reverse transcriptase. Representative compounds of the present invention (see, e.g., the compounds of Examples 1 to 182) also exhibit activity against drug resistant forms of HIV (e.g., mutant strains of HIV-1 in which reverse transcriptase has a mutation at lysine 103→asparagine ($K^{103}N$) and/or tyrosine 181→cysteine (Y181C)).

Another embodiment of the present invention ("Embodiment 25") is a compound of Formula I, Formula Ia, Formula Ib, Formula Ic or Formula Id, or a pharmaceutically acceptable salt thereof, as originally defined or as defined in any of the foregoing embodiments, aspects, classes, sub-classes or features, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 99 wt. %), and most preferably at least about 99 wt. % of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

The present invention also includes prodrugs of the compounds of Formula I, Formula Ia, Formula Ib, Formula Ic or Formula Id. The term "prodrug" refers to a derivative of a compound of the aforementioned formulae, or a pharmaceutically acceptable salt thereof, which is converted in vivo into the active moiety. Prodrugs of compounds of Formula I, Formula Ia, Formula Ib, Formula Ic or Formula Id can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). When the compound contains, for example, a hydroxy group, the prodrug can be a derivative of the hydroxy group such as an ester (—OC(O)R), a carbonate ester (—OC(O)OR), a phosphate ester (—O—P(=O)(OH)$_2$), or an ether (—OR). Other examples include the following: When the compound of Formula I, Formula Ia, Formula Ib, Formula Ic or Formula Id contains a carboxylic acid group, the prodrug can be an ester or an amide, and when the compound of Formula I, Formula Ia, Formula Ib, Formula Ic or Formula Id contains a primary amino group or another suitable nitrogen that can be derivatized, the prodrug can be an amide, carbamate, urea, imine, or a Mannich base. Conventional procedures for the selection and preparation of suitable prodrug derivatives are described, for example, in *Design of Prodrugs*, edited by H. Bundgaard, Elsevier, 1985; J. J. Hale et al., *J. Med. Chem.* 2000, vol. 43, pp. 1234-1241; C. S. Larsen and J. Ostergaard, "Design and application of prodrugs" in: *Textbook of Drug Design and Discovery*, 3$^{rd}$ edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties.

Other embodiments of the present invention include the following:

(a) A pharmaceutical composition comprising an effective amount of a compound of Formula I, Formula Ia, Formula Ib, Formula Ic or Formula Id as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I, Formula Ia, Formula Ib, Formula Ic or Formula Id as defined above, or a prodrug or pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, and HIV entry inhibitors.

(e) A combination which is (i) a compound of Formula I, Formula Ia, Formula Ib, Formula Ic or Formula Id as defined above, or a prodrug or pharmaceutically acceptable salt thereof, and (ii) an anti-HIV agent selected from the group consisting of HIV antiviral agents, immunomodulators, and anti-infective agents; wherein the compound and the anti- HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, and HIV entry inhibitors.

(g) A method for the inhibition of HIV reverse transcriptase in a subject in need thereof which comprises administering to the subject an effective amount of a compound of Formula I, Formula Ia, Formula Ib, Formula Ic or Formula Id or a prodrug or pharmaceutically acceptable salt thereof.

(h) A method for the prophylaxis or treatment of infection by HIV (e.g., HIV-1) in a subject in need thereof which comprises administering to the subject an effective amount of a compound of Formula I, Formula Ia, Formula Ib, Formula Ic or Formula Id or a prodrug or pharmaceutically acceptable salt thereof.

(i) The method of (h), wherein the compound of Formula I, Formula Ia, Formula Ib, Formula Ic or Formula Id is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(j) A method for the prophylaxis, treatment or delay in the onset or progression of AIDS in a subject in need thereof which comprises administering to the subject an effective amount of a compound of Formula I, Formula Ia, Formula Ib, Formula Ic or Formula Id or a prodrug or pharmaceutically acceptable salt thereof.

(k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I, Formula Ia, Formula Ib, Formula Ic or Formula Id or a prodrug or pharmaceutically acceptable salt thereof, (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes, sub-classes, or features described above. In all of these embodiments etc., the compound may optionally be used in the form of a prodrug or pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its prodrug or salt and a pharmaceutically acceptable carrier and optionally one or more excipients, it is understood that the term "substantially pure" is in reference to a compound of Formula I, Formula Ia, Formula Ib, Formula Ic or Formula Id or its prodrug or salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I, Formula Ia, Formula Ib, Formula Ic or Formula Id is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors and HIV-1 entry inhibitors.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_{2-6}$ alkenyl" (or "$C_2$-$C_6$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl). A class of alkenyls of interest with respect to the invention are alkenyls of formula —CH=CH—(CH$_2$)$_{1-3}$CH$_3$.

The term "alkynyl" refers to a monovalent straight or branched chain aliphatic hydrocarbon radical containing one carbon-carbon triple bond and having a number of carbon atoms in the specified range. Thus, for example, "$C_{2-6}$ alkynyl" (or "$C_2$-$C_6$ alkynyl") refers to all of the hexynyl and pentynyl isomers as well as 1-butynyl, 2-butynyl, 3-butynyl, 1-propynyl, 2-propynyl, and ethynyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—.

The term "cycloalkyl" refers to any monocyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "cycloalkenyl" refers to any monocyclic ring of an alkene having a number of carbon atoms in the specified range. Thus, for example, "$C_{5-8}$ cycloalkenyl" (or "$C_5$-$C_8$ cycloalkenyl") refers to cyclopentenyl, cyclohexenyl, cycloheptenyl, and cyclooctenyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}$ $CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

An asterisk ("*") at the end of an open bond in a chemical group denotes the point of attachment of the group to the rest of the compound.

The term "aryl" refers to (i) phenyl, (ii) 9- or 10-membered bicyclic, fused carbocyclic ring systems in which at least one ring is aromatic, and (iii) 11-to 14-membered tricyclic, fused carbocyclic ring systems in which at least one ring is aromatic. Suitable aryls include, for example, phenyl, naphthyl, tetrahydronaphthyl (tetralinyl), indenyl, anthracenyl, and fluorenyl. A class of aryls of interest with respect to the invention is phenyl and napthyl. An aryl of particular interest is phenyl.

The term "heteroaryl" refers to (i) a 5- or 6-membered heteroaromatic ring containing from 1 to 4 heteroatoms independently selected from N, O and S, wherein each N is optionally in the form of an oxide, (ii) a 9- or 10-membered bicyclic fused ring system, wherein the fused ring system of (ii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or $S(O)_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl (e.g., benzo-1,3-dioxolyl:

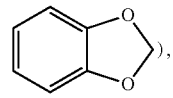

benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl (i.e.,

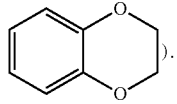

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated, non-aromatic heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings and ring systems suitable for use in the present invention are not limited to those listed in the preceding paragraphs. These rings and ring systems are merely representative.

Unless expressly stated to the contrary in a particular context, any of the various cyclic rings and ring systems described herein may be attached to the rest of the compound at any ring atom (i.e., any carbon atom or any heteroatom) provided that the attachment is chemically allowed and a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 6 substituents" is intended to include as aspects thereof, an aryl or heteroaryl substituted with 1 to 6 substituents, 2 to 6 substituents, 3 to 6 substituents, 4 to 6 substituents, 5 to 6 substituents, 6 substituents, 1 to 5 substituents, 2 to 5 substituents, 3 to 5 substituents, 4 to 5 substituents, 5 substituents, 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $R^A$ or $R^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

As would be recognized by one of ordinary skill in the art, certain of the compounds of the present invention can exist as tautomers. All tautomeric forms of these compounds, whether isolated individually or in mixtures, are within the scope of the present invention. For example, in instances where an oxo (=O) substituent is permitted on a heteroaromatic ring and keto-enol tautomerism is possible, it is understood that the substituent might in fact be present, in whole or in part, in the hydroxy form.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I, Formula Ia, Formula Ib, Formula Ic or Formula Id.

As a result of the selection of substituents and substituent patterns, certain compounds of the present invention can have asymmetric centers and can occur as mixtures of stereoisomers, or as individual diastereomers, or enantiomers. All isomeric forms of these compounds, whether individually or in mixtures, are within the scope of the present invention.

The atoms in a compound of Formula I, Formula Ia, Formula Ib, Formula Ic or Formula Id may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of Formula I, Formula Ia, Formula Ib, Formula Ic or Formula Id mean providing the compound or a prodrug of the compound to the individual in need of treatment or prophylaxis. When a compound or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

Ingredients suitable for inclusion in a pharmaceutical composition are pharmaceutically acceptable ingredients, which means the ingredients must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV reverse transcriptase (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the method of the present invention (i.e., inhibiting HIV reverse transcriptase, treating or prophylaxis of HIV infection or treating, prophylaxis of, or delaying the onset or progression of AIDS), the compounds of Formula I, Formula Ia, Formula Ib, Formula Ic or Formula Id optionally in the form of a salt or a prodrug, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington— The Science and Practice of Pharmacy,* 21st edition, Lippincott Williams & Wilkins, 2005.

Formulations of compounds described by Formula I, Formula Ia, Formula Ib, Formula Ic or Formula Id that result in drug supersaturation and/or rapid dissolution may be utilized to facilitate oral drug absorption. Formulation approaches to cause drug supersaturation and/or rapid dissolution include, but are not limited to, nanoparticulate systems, amorphous systems, solid solutions, solid dispersions, and lipid systems. Such formulation approaches and techniques for preparing them are well known in the art. For example, solid dispersions can be prepared using excipients and processes as described in reviews (e.g., A. T. M. Serajuddin, J Pharm Sci, 88:10, pp. 1058-1066 (1999)). Nanoparticulate systems based on both attrition and direct synthesis have also been described in reviews such as Wu et al (F. Kesisoglou, S. Panmai, Y. Wu, Advanced Drug Delivery Reviews, 59:7 pp 631-644 (2007)).

The compounds of Formula I, Formula Ia, Formula Ib, Formula Ic or Formula Id can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. Compounds of the invention can be administered as a single dose, once-daily or less frequently.

As noted above, the present invention is also directed to use of a compound of Formula I, Formula Ia, Formula Ib, Formula Ic or Formula Id with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, imunomodulators, antiinfectives, or vaccines useful for treating HIV infection or AIDS. Suitable HIV antivirals for use in combination with the compounds of the present invention include, for example, those listed in Table A as follows:

TABLE A

Antiviral Agents for Treating HIV infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T,didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.

Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in editions of the *Physicians' Desk Reference*, such as the 63rd edition (2009) and earlier editions. The dosage ranges for a compound of the invention in these combinations can be the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition.

Compounds of the invention can be prepared by methods well known in the art of organic chemistry. See, for example, J. March, '*Advanced Organic Chemistry*' $6^{th}$ Edition, John Wiley and Sons. During synthetic sequences it may be necessary and/or desirable to protect sensitive or reactive groups on any of the molecules concerned. This is achieved by means of conventional protecting groups, such as those described in T. W. Greene and P. G. M. Wutts '*Protective Groups in Organic Synthesis*' 4th Edition, John Wiley and Sons. The protective groups are optionally removed at a convenient subsequent stage using methods well known in the art.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme I depicts a method for preparing compounds of Formula I in which a substituted pyrimidinone I-1 is halogenated to give 1-2 wherein J is a halogen, typically bromine or chlorine. The pyrimidinone can be protected, with for example a 4-methoxybenzyl group, to give 1-3 wherein PG is the protecting group. 1-3 can be converted to 1-4 via a nucleophilic aromatic substitution ($S_NAr$) reaction using a suitable phenol and an appropriate base, such as potassium carbonate. Removal of the protecting group affords 1-5, which may be alkylated to give the desired 1-6 with a suitable base and an alkylating agent X-M-Z wherein X is a suitable leaving group, such as chloro, bromo, iodo, mesyl or tosyl, and M is typically $CH_2$. Alternatively, this transformation may be performed under Mitsunobu conditions with a suitable alcohol HO-M-Z where M is typically $CH_2$.

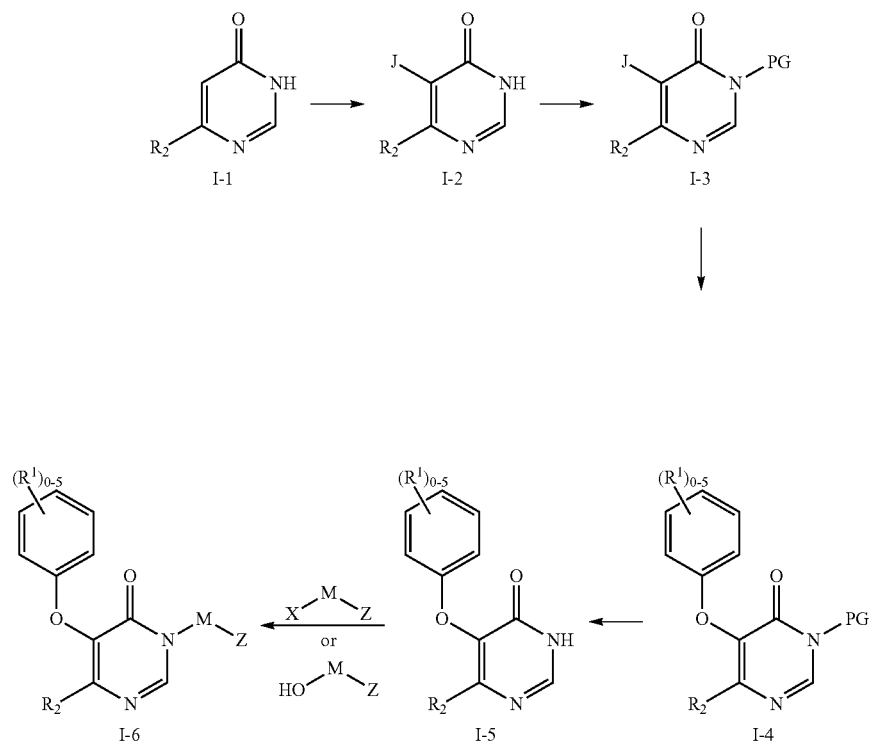

Scheme II illustrates another method for preparing compounds of Formula I. Fluorinated pyrimidinone II-1 can be prepared using known methodology (see Organic Process Research & Development, 2001, 5, 28-36 and Tetrahedron Letters, Vol. 30, No. 45, pp 6113-6116, 1989) and may be alkylated to give 11-2 via a nucleophilic substitution reaction with an alkylating agent X-M-Z wherein X is a leaving group, such as chloro, bromo, iodo, mesyl or tosyl, and M is typically CH$_2$. In analogy with Scheme I, this transformation may also be accomplished via a Mitsunobu reaction with a suitable alcohol HO-M-Z wherein M is typically CH$_2$. 11-2 can be converted to the desired 11-3 via a nucleophilic aromatic substitution (S$_N$Ar) reaction using a suitable phenol and an appropriate base, for example potassium carbonate.

III-2 with formamidine at elevated temperature affords pyrimidinone III-3, which may be converted to the compounds of the present invention using either standard alkylation or Mitsunobu methodology, as described in Scheme I.

Scheme III

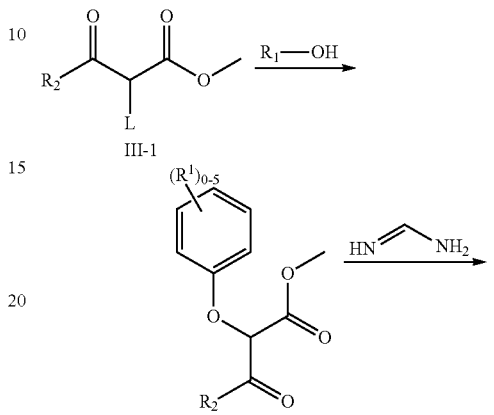

Scheme II

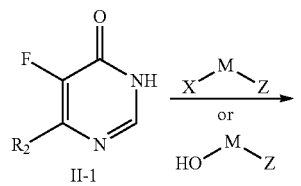

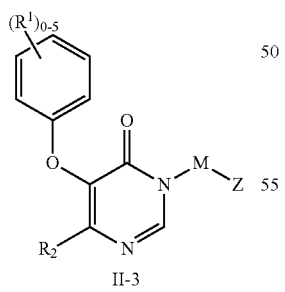

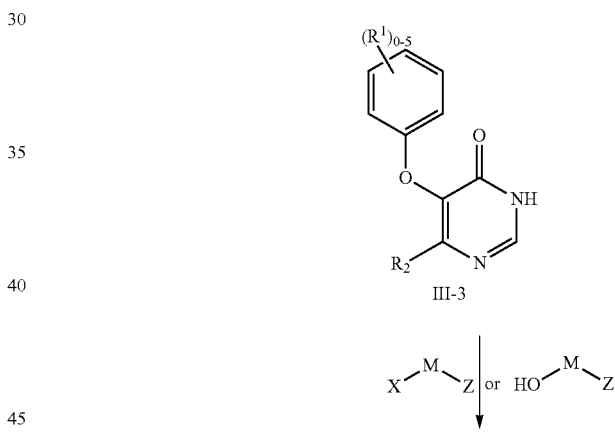

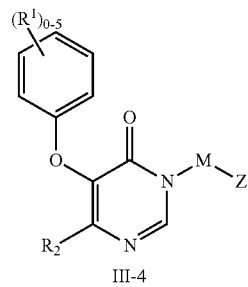

Scheme III depicts another method for preparing compounds of Formula I from commercially available β-ketoester III-1 wherein L is a halogen, typically bromine or chlorine. III-1 can be converted via nucleophilic substitution reaction with a suitable phenol in the presence of a base, such as potassium carbonate, to give III-2. Condensation of Scheme IV depicts another method for preparing compounds of Formula I in which IV-1 can be alkylated with a suitable alkylating agent IV-2, wherein L is a suitable leaving group, for example chloro, bromo, iodo, mesyl or tosyl, in the presence of a base such as potassium carbonate or N,N-diisopropylethylamine or, wherein L is hydroxyl, via a Mitsunobu reaction to afford a methyl-protected intermediate IV-3. Removal of the methyl protecting group, using for example TMSCl and KI, gives the desired IV-4. The methodology depicted in Scheme IV is not limited to the preparation of compounds of Formula I wherein Z is a pyridazinone, but straightforward variations can also be used to prepare examples wherein Z is an alternative heterocycle as defined above.

Scheme IV

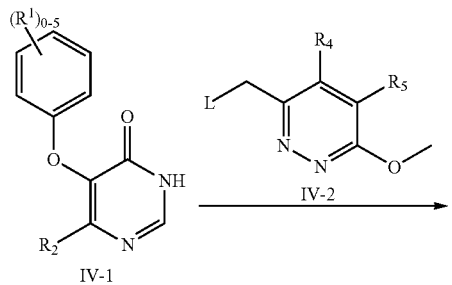

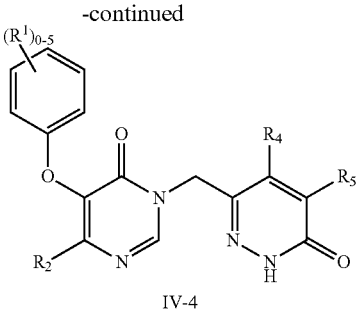

IV-4

In Scheme V, another method for preparing compounds of Formula I wherein Z is a substituted pyridazinone is shown. The ester V-1 may be brominated under standard conditions to give V-2, which can be protected, with for example a 4-methoxybenzyl group, to give V-3 wherein PG is the protecting group. Reduction of the ester using a reducing agent such as sodium borohydride or lithium aluminum hydride provides the alcohol V-4, which can be used directly to give V-6 via a Mitsunobu reaction. Alternatively, V-4 may be converted to V-5 wherein L is a suitable leaving group, such as chloro, bromo, mesyl or tosyl, and V-5 may be used to alkylate 1-5 under basic conditions to provide the key intermediate V-6, which may be used to provide a variety of compounds of interest. For example, the bromopyridazinone V-6 can be converted to V-7 wherein $R_5$ is aryl or heteroaryl via a palladium-catalyzed transformation, such as a Suzuki reaction with a suitable aryl or heteroaryl boronic acid or ester, or a Stille coupling with a suitable aryl or heteroaryl stannane derivative. The bromopyridazinone V-6 can also undergo a number of other palladium-catalyzed reactions and transformations including cyanation with $ZnCN_2$, carbonylation with CO and an alcohol such as methanol, Buchwald amination and Heck reaction to give V-7 wherein $R_5$ is a cyano, amine, ester or alkene substituent, respectively. The bromopyridazinone V-6 may also be converted to V-7 via nucleophilic aromatic substitution ($S_NAr$) reaction with a suitable nucleophile, including for example thiol, alcohol, amine or heteroaryl such as pyrazole or triazole, in the presence of a suitable base. Finally, V-7 can be deprotected to give the desired V-8.

Scheme V

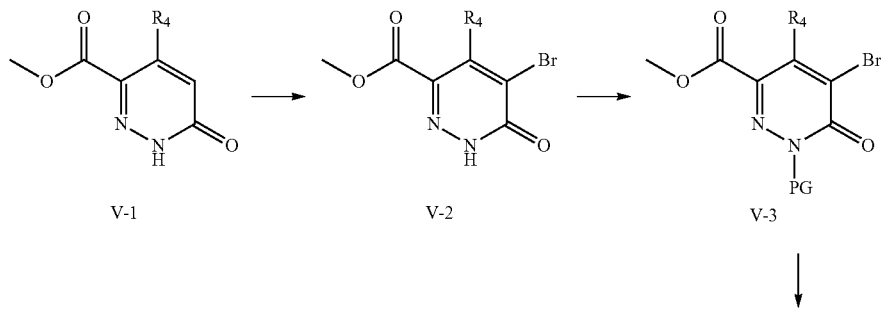

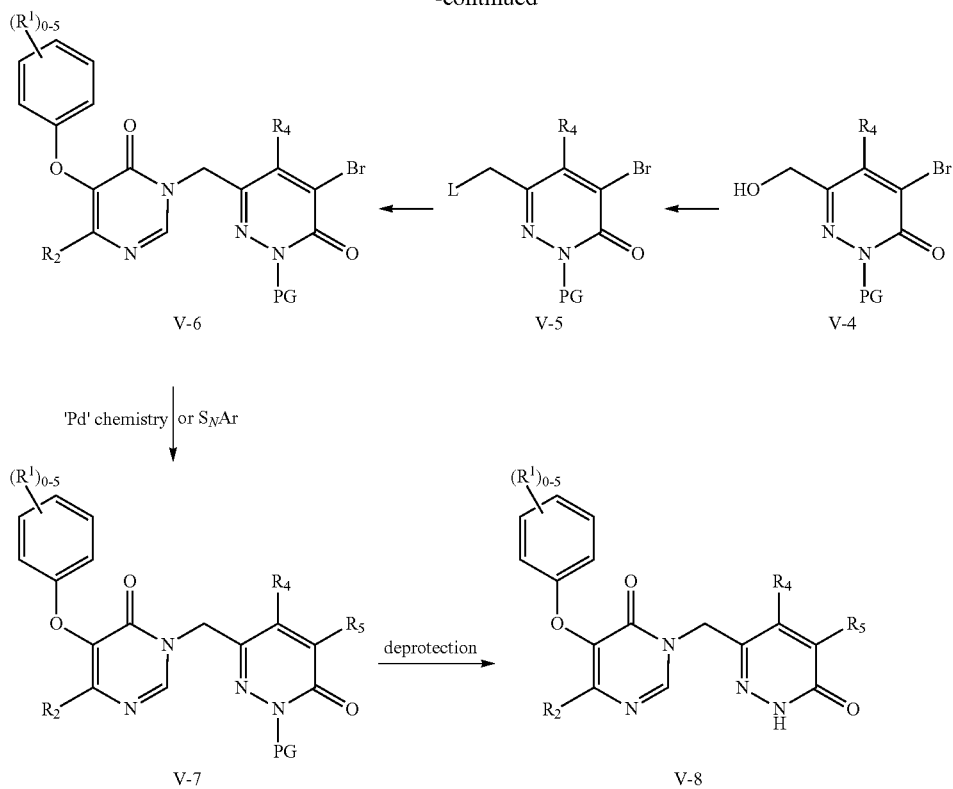

Scheme VI illustrates a method for preparing compounds of Formula I wherein Z is an isomer of the pyridazinones described in Scheme V. The halogenated pyridazinone intermediate VI-1 can be converted to VI-2 using similar methodology to that described in Scheme V. For example, compounds of the present invention wherein $R_5$ is aryl or heteroaryl may be obtained via a Suzuki reaction with a suitable aryl or hetereoaryl boronic acid or ester, or via a Stille coupling with a suitable aryl or heteroaryl stannane, in the presence of a suitable palladium catalyst. The halopyridazinone VI-1 can also undergo a number of other palladium-catalyzed reactions and transformations including cyanation with $ZnCN_2$, carbonylation with CO and an alcohol such as methanol, Buchwald amination and Heck reaction to give VI-3 wherein $R_5$ is a cyano, amine, ester or alkene substituent, respectively. Deprotection, with for example TMSCl and KI, can afford the desired product VI-3.

Scheme VI

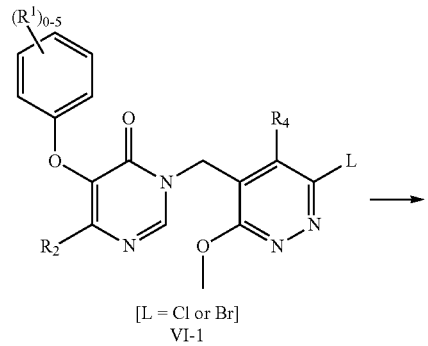

Scheme VII illustrates a method for preparing compounds of Formula I bearing a difluoroalkyl substituent. The suitably protected ketone VII-3 can be prepared from VII-1 via a Stille coupling followed by hydrolysis of VII-2. VII-3 can be fluorinated with a fluorinating agent such as DAST to give the difluoroethyl derivative VII-4. The protecting group PG may be removed to give the alcohol VII-5 which can be converted to the desired VII-7 via a Mitsunobu reaction with an appropriate pyrimidinone (I-5) followed by removal of the methyl protecting group. Alternatively VII-5 can be converted to VII-6 wherein L is a good leaving group, such as halo, mesyl or tosyl. VII-6 may be used to alkylate I-5 in the presence of a suitable base to provide, after deprotection, VII-7.

as fluorination with DAST to give VIII-6 and oxidation with, for example, Dess-Martin periodinane to give VIII-5. The aldehyde VIII-5 may also be fluorinated with, for example, DAST to give VIII-7 or be converted to alcohol VIII-8, in which A is an alkyl substituent, via a Grignard reaction with an alkylmagnesium bromide reagent. The secondary alcohol VIII-8 may be deprotected to give desired secondary alcohol or treated with DAST and deprotected to provide the corresponding fluoride VIII-9. Alternatively, VIII-8 can be

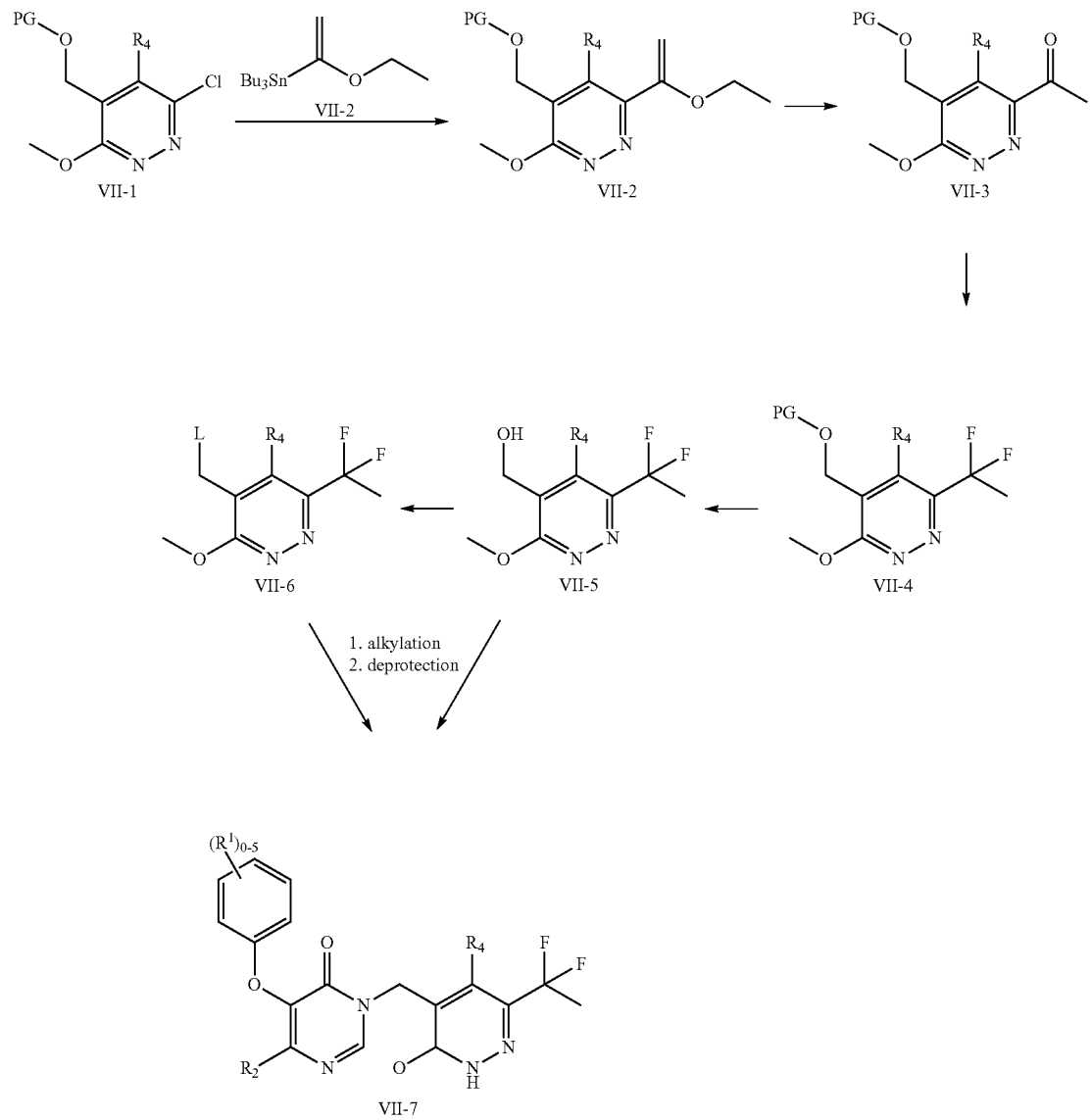

Scheme VIII illustrates methods that may be used to prepare compounds of Formula I wherein Z bears a substituent such as hydroxyalkyl, formyl, keto, fluoroalkyl or difluoroalkyl. Coupling of pyrimidinone VIII-1 with a suitably functionalized and protected pyridazinone VIII-2, in which L is a leaving group such as chloro, bromo, or mesyl, provides VIII-3, which can be deprotected to give the hydroxymethyl derivative VIII-4. Alcohol VIII-4 can be deprotected to give the desired hyroxyalkyl derivative or undergo a number of functional group transformations, such oxidized to give ketone VIII-10, which may be fluorinated then deprotected to give VIII-11 as previously described. Variations of the methods and functional group transformations illustrated in Scheme VIII may be used to prepare other compounds of Formula I in which Z is a heteroaryl ring other than the pyridazinone shown. Additionally, it may be advantageous to perform some of the functional group transformations earlier in the synthesis to prepare suitably functionalized intermediates such as HO-M-Z or X-M-Z as described in the Schemes I-III above.

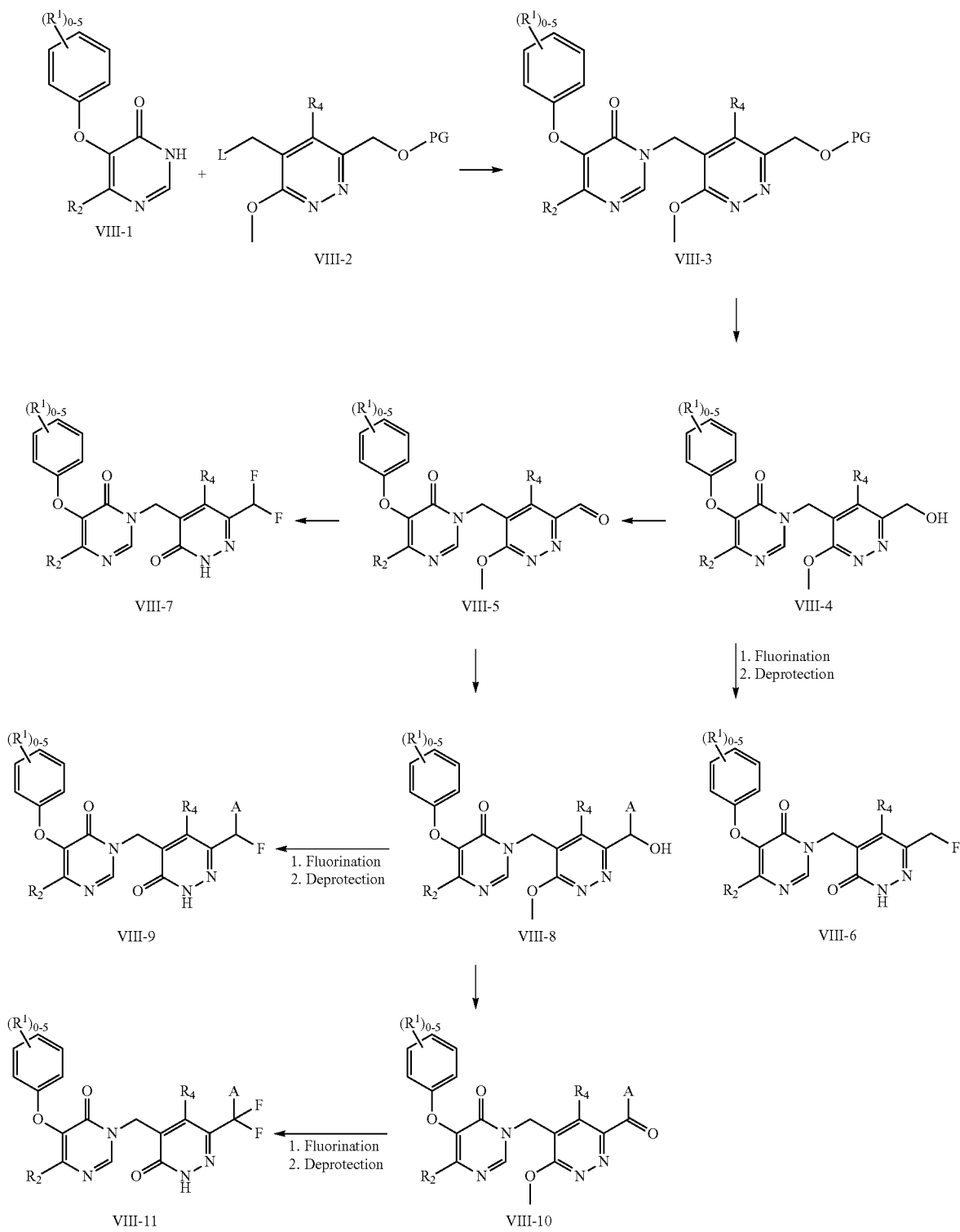

Scheme IX depicts another method for preparing compounds of Formula I bearing a variety of substituents $R_5$. The methylsulfone-substituted pyrimidine IX-1 can be converted to IX-2 via a nucleophilic aromatic substitution reaction with a suitable nucleophile, such as an amine, a phenol, an alcohol, or a heteroaryl ring, such as pyrazole or triazole, in the presence of a suitable base, such as potassium carbonate or triethylamine. Sulfone IX-1 can also be converted to IX-2 wherein $R_5$ is alkyl via a Grignard reaction with an alkylmagnesium bromide. Finally, IX-2 may be deprotected to give the desired IX-3.

Scheme IX

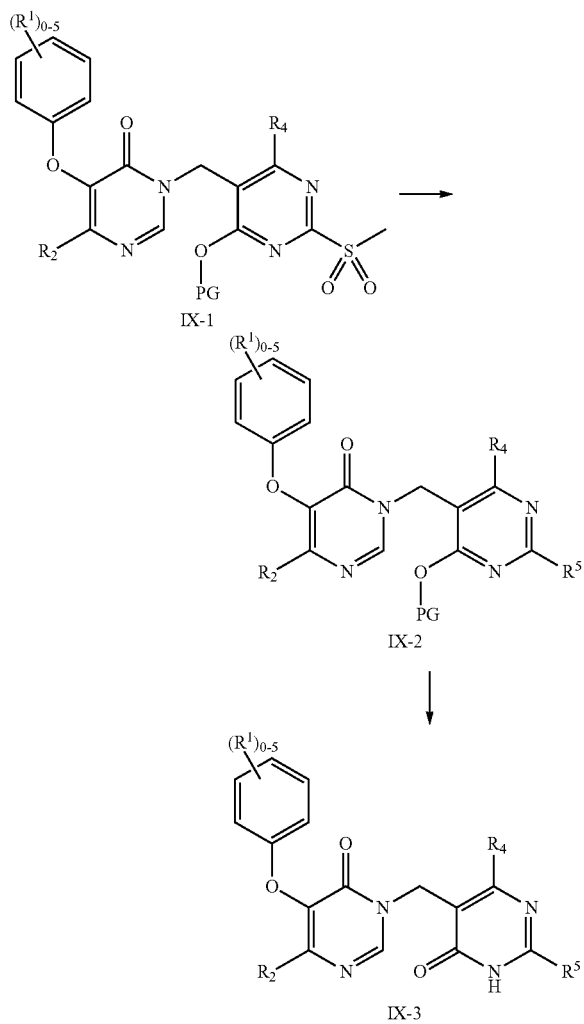

Methods

General Chemical Procedures: All reagents were either purchased from common commercial sources or synthesized according to literature procedures beginning from commercial reagents. Commercial reagents were used without further purification. Unless otherwise indicated, percent is percent by weight given the component and the total weight of the composition, temperature is in ° C. or is at ambient temperature and pressure is at or near atmospheric. $^1$H NMR spectra were obtained on a Varian VNMR System 400 (400 MHz) and are reported as ppm downfield from Me$_4$Si with number of protons, multiplicities, and coupling constants in Hertz indicated parenthetically. Where LC/MS data are presented, analyses was performed using an Agilent 6110A MSD or an Applied Biosystems API-100 mass spectrometer. The parent ion is given. Preparative HPLC was performed on a Waters preparative HPLC system fitted with a Waters Xselect.C18 column, typically using gradient elution with water/acetonitrile containing 0.075% trifluoro acetic acid. Flash column chromatography was performed using pre-packed normal phase silica from Biotage, Inc. or bulk silica from Fisher Scientific. Unless otherwise indicated, column chromatography was performed using a gradient elution of petroleum ether/ethyl acetate, from petroleum ether 100% to 100% ethyl acetate. The term "room temperature" in the examples refers to the ambient temperature which was typically in the range of about 20° C. to about 26° C.

The following abbreviations have the indicated meanings:

ABBREVIATIONS

AcOH=acetic acid
CAN=ceric amonium nitrate
DAST=(diethylamino)sulfur trifluoride
DCE=1,2-dichloroethane
DEAD=diethyl azodicarboxylate
DHP=3,4-dihydro-2H-pyran
DIBAL-H=diisobutylaluminum hydride
DIPEA—diisopropylethylamine
DMF=N,N-dimethylformamide
Dess-Martin periodinane=1,1,1-Triacetoxy-1,1-dihydro-1,2-benziodoxol-3(1H)-one
DMSO=dimethyl sulfoxide
EDTA=ethylenediaminetetraacetic acid
EtOAc=ethyl acetate
EtOH=ethanol
FBS=fetal bovine serum
HIV=human immunodeficiency virus
HPLC=high performance liquid chromatography
hr=hour
LCAP=liquid chromatography area percent
LC-MS=liquid chromatography-mass spectroscopy
m-CPBA=3-chloroperbenzoic acid
Me=methyl
MeOH=methanol
Me-THF=2-methyltetrahydrofuran
min=minute
NBS=N-bromosuccinimide
NHS=normal human serum
NMP=N-methyl-2-pyrrolidinone
NMR=nuclear magnetic resonance
PBS=phosphate buffered saline
PMB=4-methyoxybenzyl
PMBCl=4-methoxybenzyl chloride
PPTS=4-toluenesulfonic acid
r.t.=room temperature
SNAr=nucleophilic aromatic substitution
TBAF=tetrabutylammonium fluoride
Tc=thiophene carboxylate
t-BuOH=tert-butanol
THF=tetrahydrofuran
TFA=trifluoroacetic acid
TFAA=trifluoroacetic anhydride
TLC=thin layer chromatography
TMSCl=trimethylsilyl chloride

EXAMPLE 1

3-chloro-5-((6-oxo-1-((5-oxo-5,6-dihydropyrido[2,3-d]pyridazin-8-yl)methyl)-4-(trifluoromethyl)-1,6-dihydropyrimidin-5-yl)oxy)benzonitrile

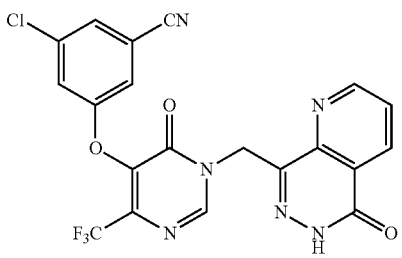 [SMILES: N#Cc1cc(Cl)cc(Oc2c(C(F)(F)F)ncn(Cc3n[nH]c(=O)c4cccnc34)c2=O)c1]

Step 1:
8-(bromomethyl)pyrido[2,3-d]pyridazin-5(6H)-one

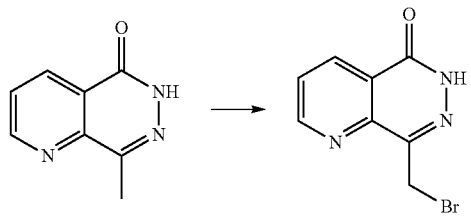

To a solution of 8-methylpyrido[2,3-d]pyridazin-5(6H)-one (300 mg, 1.86 mmol) in CHCl₃ (5 mL) was added NBS (363 mg, 2.05 mmol) and benzoyl peroxide (225 mg, 0.93 mmol) in turn. The mixture was stirred at 80° C. for 6 hr. After cooling to room temperature, the mixture was concentrated under reduced pressure and the residue was purified by preparative TLC (petroleum ether/ethyl acetate (1:1) as eluent) to afford 8-(bromomethyl)pyrido [2,3-d] pyridazin-5(6H)-one (210 mg).
MS (ESI) m/z 240, 242 (M+H)⁺

Step 2:
5-bromo-6-(trifluoromethyl)-4(3H)-pyrimidione

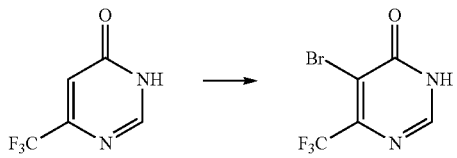 [SMILES: O=c1cc(C(F)(F)F)nc[nH]1 ; O=c1[nH]cnc(C(F)(F)F)c1Br]

To a solution of 8-(bromomethyl)pyrido[2,3-d]pyridazin-5(6H)-one (0.3 g, 1.8 mmol) in acetic acid (2 mL) was added CH₃COOK (0.54 g, 5.5 mmol). Then to the mixture was added a solution of Br₂ in acetic acid (1 mL) dropwise. The mixture was heated to 80° C. and stirred overnight. After cooling to room temperature, the mixture was diluted with EtOAc, washed with water and brine, dried over Na₂SO₄, and evaporated to afford 5-bromo-6-(trifluoromethyl)-4 (3H)-pyrimidione (0.3 g).

Step 3: 5-bromo-3-(4-methoxybenzyl)-6-(trifluoromethyl)pyrimidin-4(3H)-one

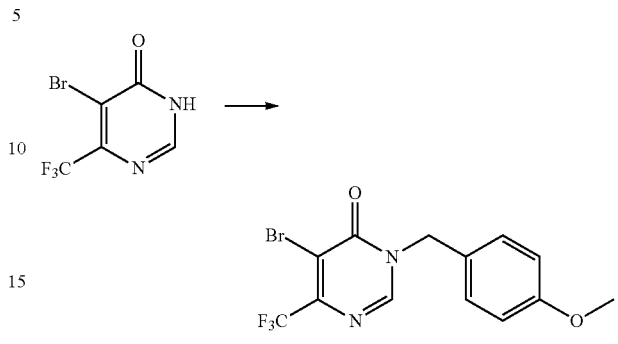

To a solution of 5-bromo-6-(trifluoromethyl)pyrimidin-4 (3H)-one (190 mg, 0.91 mmol) in DMF (2 mL) was added K₂CO₃ (250 mg, 1.82 mmol) and PMBCl (210 mg, 1.3 mmol). The mixture was stirred at room temperature for 5 hr. The mixture was poured into water, and extracted with EtOAc (40 mL×3). The organic layer was washed with water and brine, dried over anhydrous Na₂SO₄ and concentrated. The residue was purified by column chromatography on silica gel (petroleum ether/ethyl acetate (5:1 to 1:1) as eluent) to afford 1 5-bromo-3-(4-methoxybenzyl)-6-(trifluoromethyl)pyrimidin-4(3H)-one (80 mg).
¹H-NMR J000159069 H11896-((16-3 CDCl₃, 400 MHz δ 7.97 (s, 1H, ArH), 7.27 (d, J=8.8, 2H, ArH), 6.87 (d, J=8.8, 2H, ArH), 5.04 (s, 2H, CH), 3.78 (s, 3H, CH).

Step 4: 3-chloro-5-(1-(4-methoxybenzyl)-6-oxo-4-(trifluoromethyl)-1,6-dihydropyrimidin-5-yloxy)benzonitrile

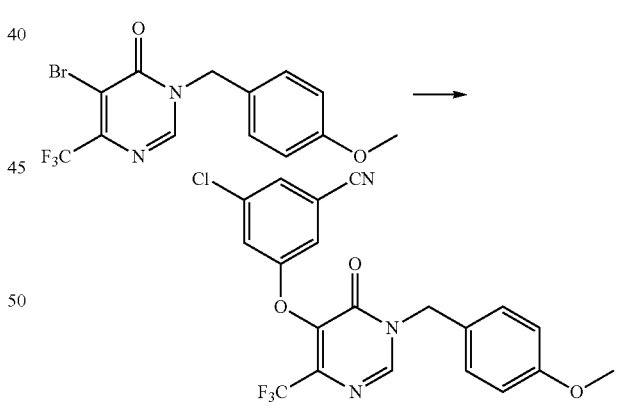

To a solution of 5-bromo-3-(4-methoxybenzyl)-6-(trifluoromethyl)pyrimidin-4(3H)-one (5 g, 13.8 mmol) in NMP (50 mL) was added K₂CO₃ (5.7 g, 41.3 mmol) and 3-chloro-5-hydroxy-benzonitrile (3.2 g, 20.7 mmol). The mixture was stirred at 120° C. for 20 hr. The mixture was poured into water, and extracted with EtOAc (60 mL×3). The organic layer was washed with water and brine, dried over anhydrous Na₂SO₄, and concentrated. The residue was purified by column (petroleum ether/ethyl acetate (5:1 to 1:1) as eluent) to afford 3-chloro-5-(1-(4-methoxybenzyl)-6-oxo-4-(trifluoromethyl)-1,6-dihydropyrimidin-5-yloxy)benzonitrile (3.5 g).

$^1$H-NMR J000169946 H11896-128-3 DMSO, 400 MHz δ 8.86 (s, 1H, ArH), 7.76 (s, 1H, ArH), 7.70 (s, 1H, ArH), 7.68 (s, 1H, ArH), 7.34 (d, J=8.6, 2H, ArH), 6.90 (d, J=8.6, 2H, ArH), 5.10 (s, 2H, CH), 3.72 (s, 3H, CH).

Step 5: 3-chloro-5-(6-oxo-4-(trifluoromethyl)-1,6-dihydropyrimidin-5-yloxy)benzonitrile

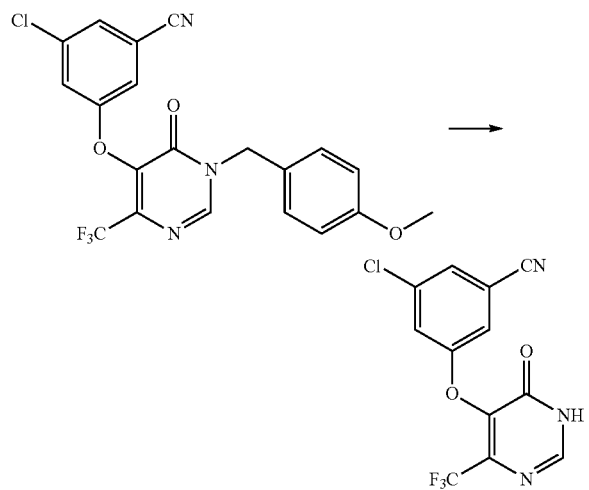

To a solution of 3-chloro-5-(1-(4-methoxybenzyl)-6-oxo-4-(trifluoromethyl)-1,6-dihydropyrimidin-5-yloxy)benzonitrile (2 g, 4.6 mmol) in CH$_3$CN (20 mL) and H$_2$O (8 mL) was added Ce(NH$_4$)$_2$(NO$_3$)$_6$ (10 g, 18.4 mmol) in portions. The mixture was stirred at room temperature overnight and then poured into water, and extracted with EtOAc (60 mL×3). The organic layer was washed with water and brine, dried over anhydrous Na$_2$SO$_4$, and concentrated. The residue was purified by column chromatography on silica gel (petroleum ether/ethyl acetate (5:1 to 1:1) as eluent) to afford 3-chloro-5-(6-oxo-4-(trifluoro methyl)-1,6-dihydropyrimidin-5-yloxy)benzonitrile (0.8 g)

$^1$H-NMR J000170654 H11896-138-3 DMSO, 400 MHz δ 13.59 (s, 1H, NH), 8.36 (s, 1H, ArH), 7.76 (s, 1H, ArH), 7.73 (s, 1H, ArH), 7.70 (s, 1H, ArH).

Step 6: 3-chloro-5-((6-oxo-1-((5-oxo-5,6-dihydropyrido[2,3-c]pyridazin-8-yl)methyl)-4-(trifluoromethyl)-1,6-dihydropyrimidin-5-yl)oxy)benzonitrile

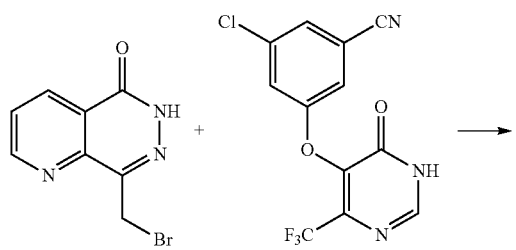

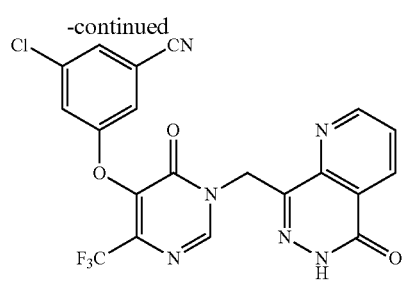

A mixture of 8-(bromomethyl)pyrido[2,3-d]pyridazin-5(6H)-one (210 mg, 0.895 mmol), 3-chloro-5-((6-oxo-4-(trifluoromethyl)-1,6-dihydropyrimidin-5-yl)oxy)benzonitrile (300 mg, 0.95 mmol) and potassium carbonate (360 mg, 2.625 mmol) in DMF (3 mL) was stirred at r.t. for 1 hr. The mixture was filtered and the residue was purified by preparative HPLC to give 3-chloro-5-((6-oxo-1-((5-oxo-5,6-dihydropyrido[2,3-d]pyridazin-8-yl)methyl)-4-(trifluoromethyl)-1,6-dihydropyrimidin-5-yl)oxy)benzonitrile (220 mg).

$^1$H NMR (DMSO-d6, 400 MHz): δ 9.16 (dd, J$_1$=1.6 Hz, J$_2$=4.4 Hz, 1H), 8.83 (s, 1H), 8.59 (dd, J$_1$=1.6 Hz, J$_2$=8.0 Hz, 1H), 7.89 (dd, J$_1$=4.8 Hz, J$_2$=8.0 Hz, 1H), 7.75 (t, J=0.8 Hz, 1H), 7.60-7.66 (m, 2H), 5.61 (s, 2H).
MS (ESI) m/z 476, 478 (M+H)$^+$

EXAMPLE 2

3-chloro-5-((1-((5-hydroxypyrazin-2-yl)methyl)-6-oxo-4-(trifluoromethyl)-1,6-dihydropyrimidin-5-yl)oxy)benzonitrile

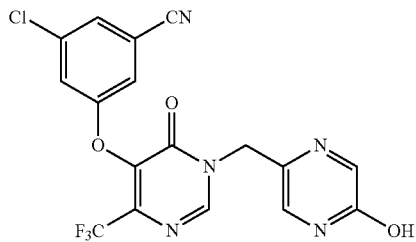 [SMILES: N#Cc1cc(Cl)cc(Oc2c(C(F)(F)F)ncn(Cc3cnc(O)cn3)c2=O)c1]

Step 1: (5-chloropyrazin-2-yl)methyl methanesulfonate

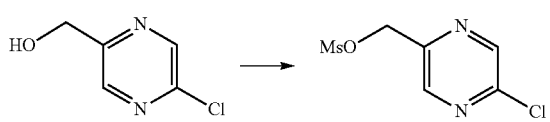 [SMILES: OCc1cnc(Cl)cn1 ; CS(=O)(=O)OCc1cnc(Cl)cn1]

To a solution of (5-chloropyrazin-2-yl)methanol (750 mg, 5.2 mmol) and DIPEA (1.34 g, 10.4 mmol) in dichloromethane (10 mL) was added methanesulfonyl chloride (1.18 g, 10.4 mmol) dropwise at 0° C. The resulting mixture was stirred at r.t. for 0.5 hr. The mixture was diluted with ethyl acetate (30 mL) and washed with water, dried over sodium sulfate, filtered and concentrated under reduced pressure to give (5-chloropyrazin-2-yl)methyl methanesulfonate (800 mg).
MS (ESI): m/z 223, 225 (M+H)$^+$ Step 2: 3-chloro-5-((1-((5-chloropyrazin-2-yl)methyl)-6-oxo-4-(trifluoromethyl)-1,6-dihydropyrimidin-5-yl)oxy)benzonitrile

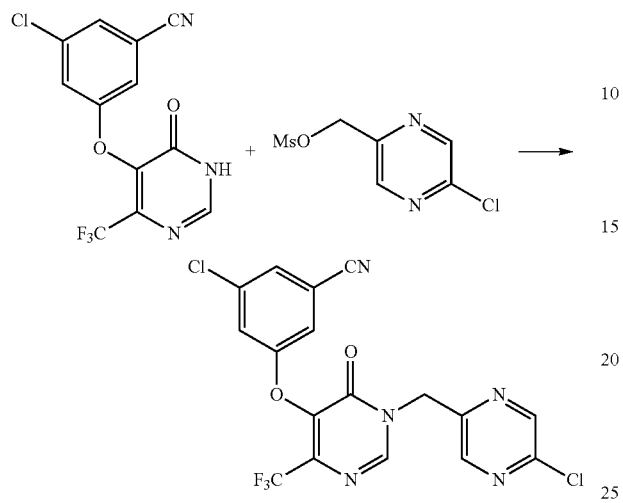

A mixture of (5-chloropyrazin-2-yl)methyl methanesulfonate (800 mg, 3.6 mmol), 3-chloro-5-((6-oxo-4-(trifluoromethyl)-1,6-dihydropyrimidin-5-yl)oxy)benzonitrile (907 mg, 2.88 mmol) and potassium carbonate (993 mg, 7.2 mmol) in DMF (10 mL) was stirred at r.t. for 3 hr. Water (20 mL) was added and the mixture was extracted with ethyl acetate (20 mL×3). The combined organic extracts were dried over sodium sulfate, filtered and concentrated under reduced pressure to give 3-chloro-5-((1-((5-chloropyrazin-2-yl)methyl)-6-oxo-4-(trifluoromethyl)-1,6-dihydropyrimidin-5-yl)oxy)benzonitrile (370 mg).

MS (ESI): m/z 442, 444 (M+H)$^+$

Step 3: 3-chloro-5-((1-((5-hydroxypyrazin-2-yl)methyl)-6-oxo-4-(trifluoromethyl)-1,6-dihydropyrimidin-5-yl)oxy)benzonitrile

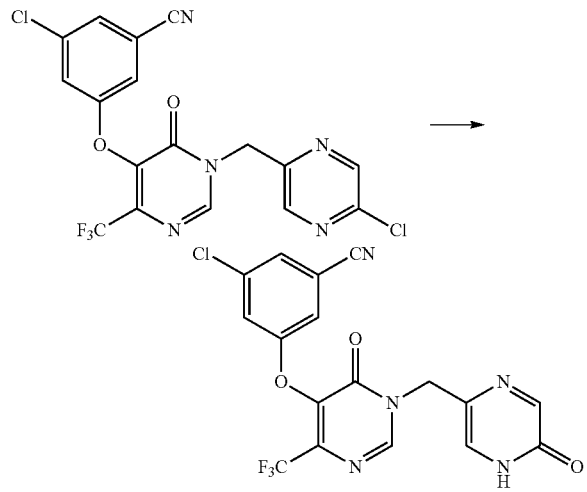

A solution of 3-chloro-5-((1-((5-chloropyrazin-2-yl)methyl)-6-oxo-4-(trifluoromethyl)-1,6-dihydropyrimidin-5-yl)oxy)benzonitrile (200 mg, 0.45 mmol) in TFA (2 mL) was heated to 120° C. for 40 min under microwave. After cooling to r.t., the mixture was concentrated under reduced pressure. The residue was purified by preparative HPLC to give 3-chloro-5-((1-((5-hydroxypyrazin-2-yl)methyl)-6-oxo-4-(trifluoromethyl)-1,6-dihydropyrimidin-5-yl)oxy)benzonitrile (60 mg).

$^1$H NMR (CD3OD, 400 MHz): δ 8.62 (s, 1H), 8.05 (s, 1H), 7.53 (s, 1H), 7.52 (s, 1H), 7.34 (s, 2H), 5.06 (s, 2H).

MS (ESI) m/z 424, 426 (M+H)$^+$

EXAMPLE 3

3-chloro-5-((1-((4-methyl-5-oxo-4,5-dihydropyrazin-2-yl)methyl)-6-oxo-4-(trifluoromethyl)-1,6-dihydropyrimidin-5-yl)oxy)benzonitrile

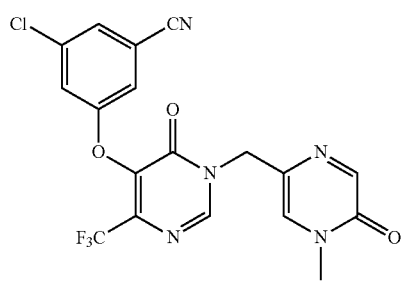 [SMILES: Cn1cc(Cn2cnc(C(F)(F)F)c(Oc3cc(Cl)cc(C#N)c3)c2=O)ncc1=O]

Step 1: 3-chloro-5-((1-((4-methyl-5-oxo-4,5-dihydropyrazin-2-yl)methyl)-6-oxo-4-(trifluoromethyl)-1,6-dihydropyrimidin-5-yl)oxy)benzonitrile

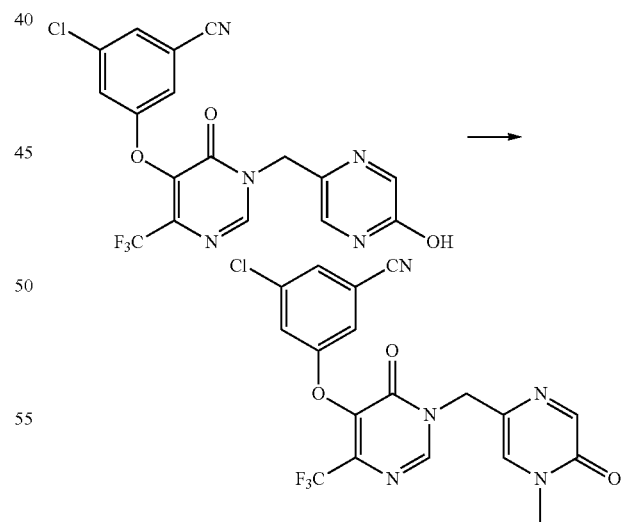

To a suspension of 3-chloro-5-((1-((5-hydroxypyrazin-2-yl)methyl)-6-oxo-4-(trifluoromethyl)-1,6-dihydropyrimidin-5-yl)oxy)benzonitrile (30 mg, 0.07 mmol) and Cs$_2$CO$_3$ (68 mg, 0.21 mmol) in 1,4-dioxane was added CH$_3$I (30 mg, 0.21 mmol). The mixture was stirred at r.t for 20 hr, filtered and concentrated under reduced pressure. The residue was purified by preparative HPLC to give the desired product 3-chloro-5-((1-((4-methyl-5-oxo-4,5-dihydro pyrazin-2-yl)methyl)-6-oxo-4-(trifluoromethyl)-1,6-dihydropyrimidin-5-yl)oxy)benzonitrile (10 mg).

$^1$H NMR (CD3OD, 400 MHz): δ 8.63 (s, 1H), 8.01 (s, 1H), 7.71 (s, 1H), 7.54 (s, 1H), 7.35 (dd, J$_1$=2.4 Hz, J$_2$=4.4 Hz, 1H), 7.33 (d, J=2.4 Hz, 1H), 5.06 (s, 2H), 3.50 (s, 3H).

MS (ESI) m/z 438, 440 (M+H)$^+$

EXAMPLE 4

3-chloro-5-((6-oxo-1-((3-oxo-3,4-dihydropyrazin-2-yl)methyl)-4-(trifluoromethyl)-1,6-dihydropyrimidin-5-yl)oxy)benzonitrile

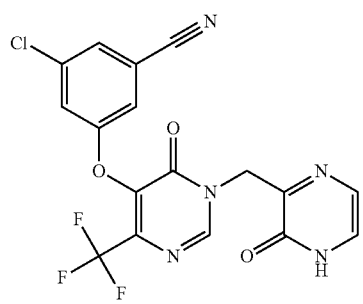 [SMILES: N#Cc1cc(Cl)cc(Oc2c(C(F)(F)F)ncn(Cc3ncc[nH]c3=O)c2=O)c1]

Step 1: (3-methoxypyrazin-2-yl)methanol

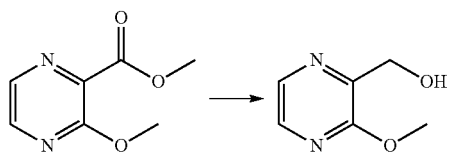

To a suspension of methyl 3-methoxypyrazine-2-carboxylate (1.0 g, 6.9 mmol) and CaCl$_2$ (0.4 g, 3.5 mmol) in ethanol (15 mL) was added NaBH$_4$ (0.4 g, 10.4 mmol) in portions at 0° C. The resulting mixture was stirred at r.t. for 2 hr. Water (20 mL) was added and the mixture was extracted with ethyl acetate (50 mL×3). The combined organic extracts were washed with aq. HCl (2 N), dried over sodium sulfate, filtered and concentrated under reduced pressure. The residue was purified by preparative TLC (petroleum ether/ethyl acetate (1:1) as eluent) to give (3-methoxypyrazin-2-yl)methanol (220 mg).

MS (ESI) m/z 141 (M+H)$^+$

Step 2: 3-chloro-5-((1-((3-methoxypyrazin-2-yl)methyl)-6-oxo-4-(trifluoromethyl)-1,6-dihydropyrimidin-5-yl)oxy)benzonitrile

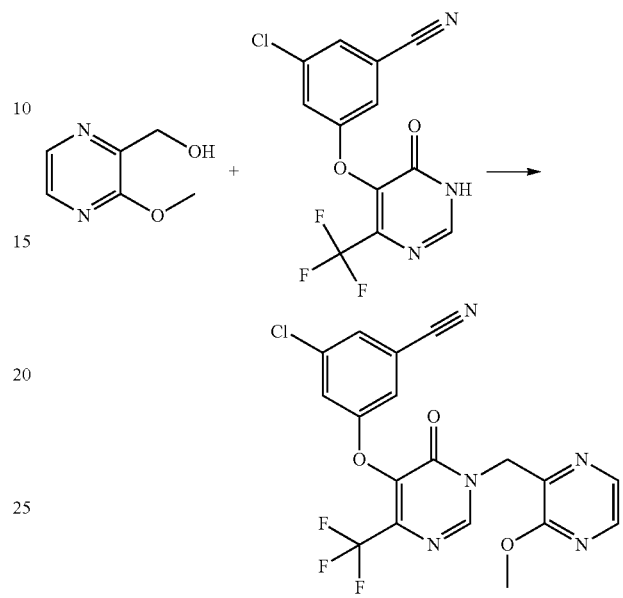

To a solution of (3-methoxypyrazin-2-yl)methanol (220.0 mg, 1.6 mmol), 3-chloro-5-((6-oxo-4-(trifluoromethyl)-1,6-dihydropyrimidin-5-yl)oxy)benzonitrile (0.6 g, 1.9 mmol) and PPh$_3$ (0.6 g, 2.4 mmol) in dichloromethane (10 mL) was added dropwise DEAD (0.56 g, 3.2 mmol) at 0° C. under a nitrogen atmosphere. The mixture was stirred at r.t. for 1 hr. Water (10 mL) was added and the mixture was extracted with dichloromethane (20 mL×3). The combined organic extracts were dried over sodium sulfate, filtered and concentrated under reduced pressure. The crude product was purified by chromatography on silica gel (petroleum ether/ethyl acetate (10:1 to 6:1) as eluent) to give 3-chloro-5-((1-((3-methoxypyrazin-2-yl)methyl)-6-oxo-4-(trifluoromethyl)-1,6-dihydropyrimidin-5-yl)oxy)benzonitrile (160 mg).

$^1$H NMR (CD3OD, 400 MHz) δ 8.53 (s, 1H), 8.08 (s, 1H), 8.06 (s, 1H), 7.51 (s, 1H), 7.35 (s, 1H), 730 (s, 1H), 5.35 (s, 2H), 4.04 (S, 3H).

MS (ESI) m/z 440, 442 (M+H)$^+$

Step 3: 3-chloro-5-((6-oxo-1-((3-oxo-3,4-dihydropyrazin-2-yl)methyl)-4-(trifluoromethyl)-1,6-dihydropyrimidin-5-yl)oxy)benzonitrile

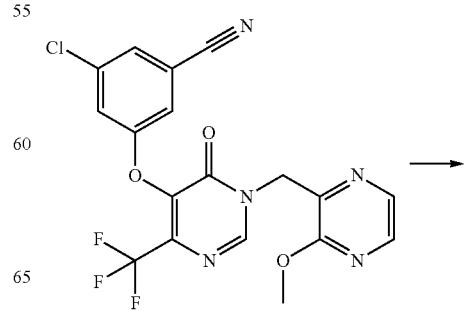

-continued

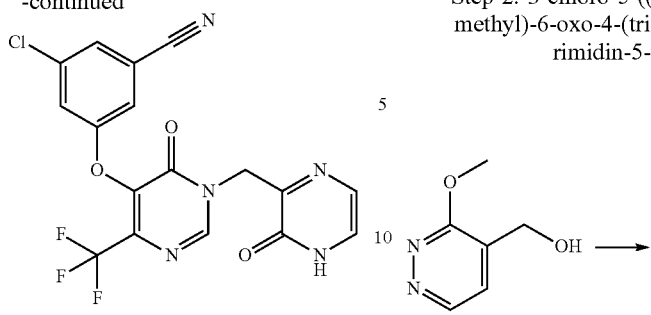

To a mixture of 3-chloro-5-((1-((3-methoxypyrazin-2-yl)methyl)-6-oxo-4-(trifluoromethyl)-1,6-dihydropyrimidin-5-yl)oxy)benzonitrile (120.0 mg, 0.3 mmol) and KI (68.0 mg, 0.4 mmol) in dichloromethane (3 mL) was added TMSCl (43.6 mg, 0.4 mmol) at r.t. The mixture was stirred at r.t. for 3 hr. Water (10 mL) was added and the mixture was extracted with dichloromethane (10 mL×3). The combined organic extracts were dried over sodium sulfate, filtered and concentrated under reduced pressure. The residue was purified by preparative HPLC to give the desired product 3-chloro-5-((6-oxo-1-((3-oxo-3,4-dihydropyrazin-2-yl)methyl)-4-(trifluoromethyl)-1,6-dihydropyrimidin-5-yl)oxy)benzonitrile (80 mg).

$^1$H NMR (CD3OD, 400 MHz) δ 8.50 (s, 1H), 8.20 (s, 1H), 7.52 (d, J=6.4 Hz, 1H), 7.38 (s, 1H), 7.35 (d, J=5.3 Hz, 1H), 7.30 (s, 1H), 5.29 (s, 2H).

MS (ESI) m/z 424, 426 (M+H)$^+$

EXAMPLE 5

3-chloro-5-((6-oxo-1-((3-oxo-2,3-dihydropyridazin-4-yl)methyl)-4-(trifluoromethyl)-1,6-dihydropyrimidin-5-yl)oxy)benzonitrile

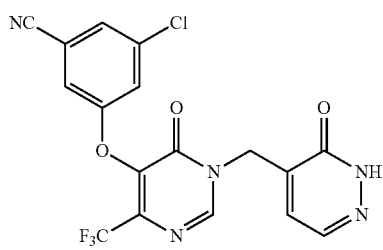 [SMILES: N#Cc1cc(Cl)cc(Oc2c(C(F)(F)F)ncn(Cc3ccn[nH]c3=O)c2=O)c1]

Step 1: (3-methoxypyridazin-4-yl)methanol

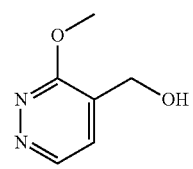

(3-methoxypyridazin-4-yl)methanol was prepared by reduction of methyl 3-methoxypyridazine-4-carboxylate using a method similar to that described for Example 4.

Step 2: 3-chloro-5-((1-((3-methoxypyridazin-4-yl)methyl)-6-oxo-4-(trifluoromethyl)-1,6-dihydropyrimidin-5-yl)oxy)benzonitrile

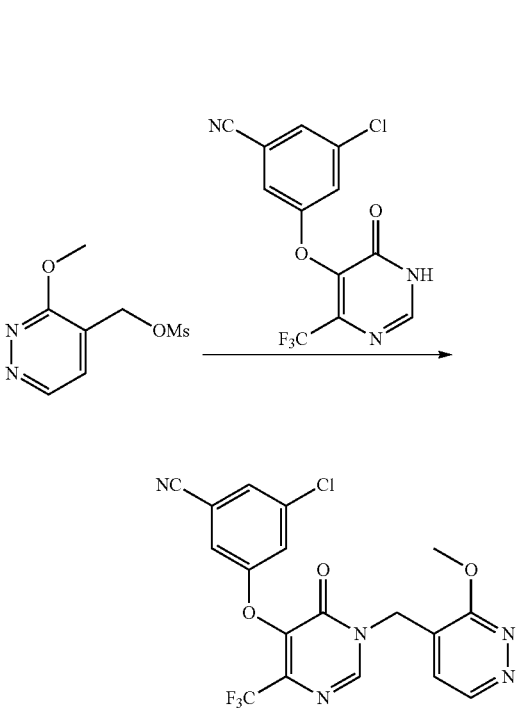

To a solution of (3-methoxypyridazin-4-yl)methanol (80 mg, 0.57 mmol) and DIPEA (110 mg, 0.86 mmol) in dichloromethane (3 mL) was added methanesulfonyl chloride (130 mg, 1.14 mmol) dropwise at 0° C. The mixture was stirred at r.t. for 1 hr, diluted with dichloromethane and washed with water. The organic layer was dried over sodium sulfate, filtered and concentrated under reduced pressure to give (3-methoxypyridazin-4-yl)methyl methanesulfonate (120 mg crude). This was added to mixture of 3-chloro-5-((6-oxo-4-(trifluoromethyl)-1,6-dihydropyrimidin-5-yl)oxy)benzonitrile (150 mg, 0.48 mmol), LiBr (82 mg, 0.96 mmol) and potassium carbonate (138 mg, 0.96 mmol) in DMF (5 mL) and stirred at 70° C. for 1 hr. After cooling, the mixture was diluted with water (15 mL) and extracted with ethyl acetate (15 mL×2). The combined organic extracts were dried over sodium sulfate, filtered and concentrated under reduced pressure to give 3-chloro-5-((1-((3-methoxypyridazin-4-yl)methyl)-6-oxo-4-(trifluoromethyl)-1,6-dihydropyrimidin-5-yl)oxy)benzonitrile (60 mg) which was used in the next step without further purification.

MS (ESI) m/z 438, 440 (M+H)$^+$

Step 3: 3-chloro-5-((6-oxo-1-((3-oxo-2,3-dihydro-pyridazin-4-yl)methyl)-4-(trifluoromethyl)-1,6-dihydropyrimidin-5-yl)oxy)benzonitrile

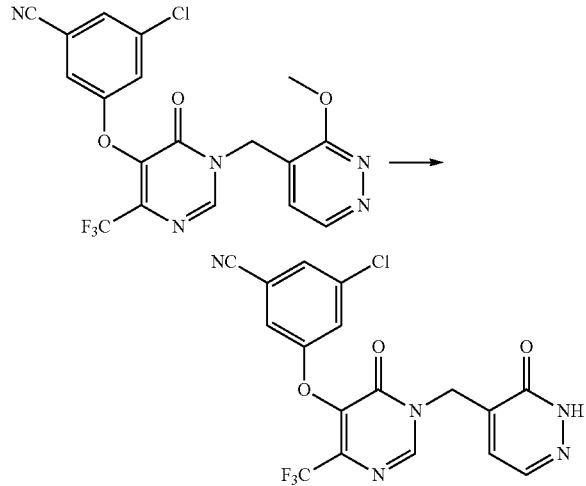

To a mixture of 3-chloro-5-((1-((3-methoxypyridazin-4-yl)methyl)-6-oxo-4-(trifluoromethyl)-1,6-dihydropyrimidin-5-yl)oxy)benzonitrile (60 mg, 0.137 mmol) and KI (45 mg, 0.274 mmol) in acetonitrile (3 mL) was added TMSCl (30 mg, 0.274 mmol) dropwise at r.t. After addition, the mixture was heated to 60° C. for 1 hr. After cooling to r.t., the reaction mixture was concentrated under reduced pressure. The residue was purified by preparative HPLC to afford 3-chloro-5-((6-oxo-1-((3-oxo-2,3-dihydropyridazin-4-yl)methyl)-4-(trifluoromethyl)-1,6-dihydropyrimidin-5-yl)oxy)benzonitrile (30 mg).

$^1$H NMR (CD$_3$OD, 400 MHz): δ 8.66 (s, 1H), 7.84 (d, J=4.0 Hz, 1H), 7.54 (s, 1H), 7.36-7.41 (m, 3H), 5.06 (s, 2H).

MS (ESI): m/z 424, 426 (M+H)$^+$

EXAMPLE 6

3-chloro-5-((6-oxo-1-((6-oxo-5-(trifluoromethyl)-1,6-dihydropyridazin-3-yl)methyl)-4-(trifluoromethyl)-1,6-dihydropyrimidin-5-yl)oxy)benzonitrile

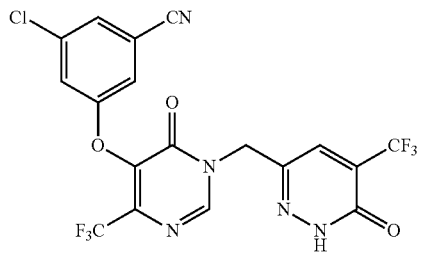 [SMILES: N#Cc1cc(Cl)cc(Oc2c(C(F)(F)F)ncn(Cc3cc(C(F)(F)F)c(=O)[nH]n3)c2=O)c1]

Step 1: 6-(bromomethyl)-4-(trifluoromethyl) pyridazin-3(2H)-one

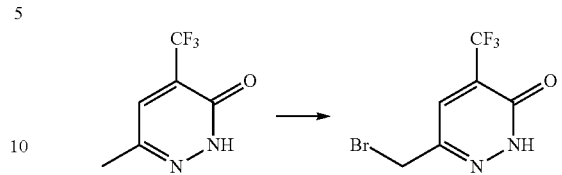

To a mixture of 6-methyl-4-(trifluoromethyl)pyridazin-3(2H)-one (2 g, 11.2 mmol) in 20 mL of CCl$_4$ was added NBS (3 g, 17.2 mmol) and benzoyl peroxide (100 mg) at r.t. The resulting mixture was heated at reflux for 18 hr. LCMS showed the reaction completed, the mixture was poured into ice-water and extracted with dichloromethane. The combined extracts were dried and concentrated under reduced pressure. The residue was purified by column chromatography on silica gel (petroleum ether/ethyl acetate (5:1) as eluent) to afford 6-(bromomethyl)-4-(trifluoromethyl) pyridazin-3(2H)-one (1.4 g).

Step 2: 3-chloro-5-((6-oxo-1-((6-oxo-5-(trifluoromethyl)-1,6-dihydropyridazin-3-yl)methyl)-4-(trifluoromethyl)-1,6-dihydropyrimidin-5-yl)oxy)benzonitrile

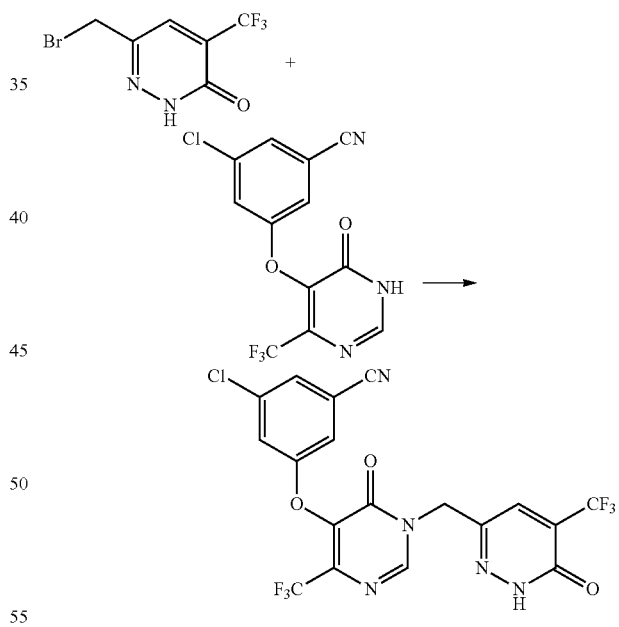

A mixture of 3-chloro-5-(6-oxo-4-(trifluoromethyl)-1,6-dihydropyrimidin-5-yloxy)benzonitrile (as described in Step 5 of Example 1) (400 mg, 1.27 mmol), 6-(bromomethyl)-4-(trifluoromethyl)pyridazin-3(2H)-one (260 mg, 1.0 mmol) and potassium carbonate (170 mg, 1.23 mmol) in DMF (6 mL) was stirred at room temperature for 18 hr. The mixture was diluted with water, extracted with ethyl acetate. The combined organic layers were washed with water and brine, dried over sodium sulfate, filtered and under reduced pressure. The residue was purified by preparative HPLC to afford 3-chloro-5-((6-oxo-1-((6-oxo-5-(trifluoromethyl)-1, 6-dihydropyridazin-3-yl)methyl)-4-(trifluoromethyl)-1,6-dihydropyrimidin-5-yl)oxy)benzonitrile (300 mg).

$^1$H NMR (DMSO-d6, 400 MHz): δ 13.72 (s, 1H), 8.77 (s, 1H), 8.02 (s, 1H), 7.78 (s, 1H), 7.71 (s, 1H), 7.68 (s, 1H), 5.19 (s, 2H).

MS (ESI) m/z 492, 494 (M+H)$^+$

EXAMPLE 7

3-chloro-5-((6-oxo-1-((6-oxo-1,6-dihydropyridazin-3-yl)methyl)-4-(trifluoromethyl)-1,6-dihydropyrimidin-5-yl)oxy)benzonitrile

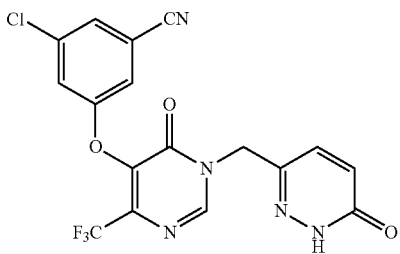 [SMILES: N#Cc1cc(Cl)cc(Oc2c(C(F)(F)F)ncn(Cc3ccc(=O)[nH]n3)c2=O)c1]

Step 1: (6-methoxypyridazin-3-yl)methanol

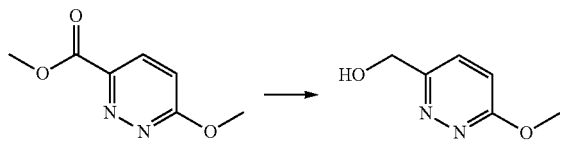

To a solution of methyl 6-methoxypyridazine-3-carboxylate (10 g, 62.8 mmol) in THF (200 mL) and MeOH (40 mL) was added a mixture of NaBH$_4$ (10.2 g, 283 mmol) and CaCl$_2$ (10.2 g, 92 mmol) in portions. The mixture was stirred at room temperature for 30 min, quenched with saturated NH$_4$Cl, then extracted with ethyl acetate (80 mL×3). The organic layer was washed with water and brine, dried over anhydrous sodium sulfate, filtered and concentrated under reduced pressure to afford (6-methoxypyridazin-3-yl)methanol (3.6 g).

MS (ESI) m/z 141 (M+H)$^+$

Step 2: 3-chloro-5-((1-((6-methoxypyridazin-3-yl)methyl)-6-oxo-4-(trifluoromethyl)-1,6-dihydropyrimidin-5-yl)oxy)benzonitrile

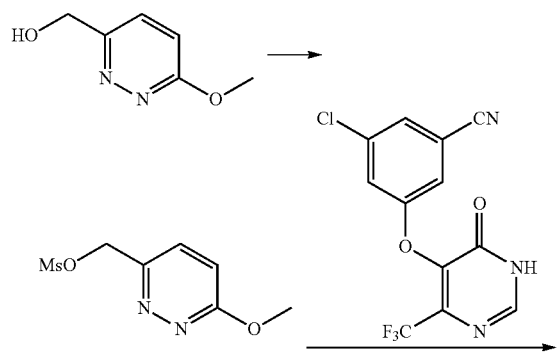

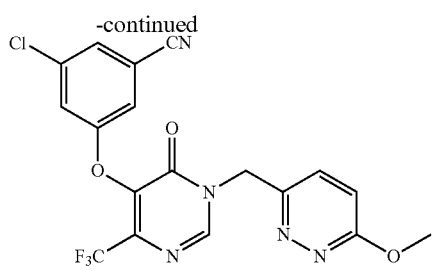

To a solution of (6-methoxypyridazin-3-yl)methanol (3.6 g crude, 25.7 mmol) and ethyl acetate (16 mL, 115 mmol) in dichloromethane (100 mL) was added methanesulfonyl chloride (77 mg, 0.67 mmol) slowly at −60° C. The mixture stirred at room temperature for 2 hr, quenched with saturated NaHCO$_3$, and extracted with ethyl acetate (60 mL×3). The organic layer was washed with water and brine, dried over anhydrous sodium sulfate, filtered and concentrated under reduced pressure to afford the crude product (crude 3.7 g, 66%) used next step without purification. To a solution of 3-chloro-5-((6-oxo-4-(trifluoromethyl)-1,6-dihydropyrimidin-5-yl)oxy)benzonitrile (4.5 g, 14.2 mmol) in DMF (50 mL) was added Et$_3$N (4.2 mL, 30 mmol) and (6-methoxypyridazin-3-yl)methyl methanesulfonate (crude 3.7 g, 17 mmol). The mixture was stirred at room temperature for 5 hr. The reaction mixture was poured into water, extracted with ethyl acetate (60 mL×3). The organic layer was washed with water and brine, dried over anhydrous sodium sulfate, filtered and concentrated under reduced pressure. The residue was purified by column (petroleum ether/ethyl acetate (3:1) as eluent) to afford 3-chloro-5-((1-((6-methoxypyridazin-3-yl)methyl)-6-oxo-4-(trifluoromethyl)-1,6-dihydropyrimidin-5-yl)oxy)benzonitrile (1.2 g).

MS (ESI) m/z 438, 440 (M+H)$^+$

Step 3: 3-chloro-5-((6-oxo-1-((6-oxo-1,6-dihydropyridazin-3-yl)methyl)-4-(trifluoromethyl)-1,6-dihydropyrimidin-5-yl)oxy)benzonitrile

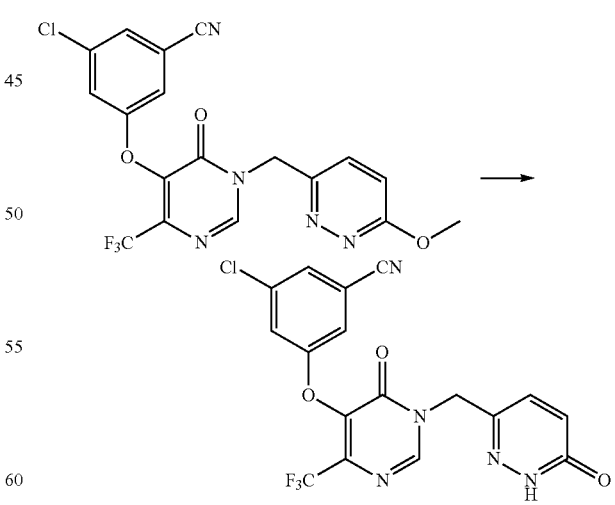

To a mixture of 3-chloro-5-((1-((6-methoxypyridazin-3-yl)methyl)-6-oxo-4-(trifluoromethyl)-1,6-dihydropyrimidin-5-yl)oxy)benzonitrile (1.2 g, 2.7 mmol) and KI (1.5 g, 9 mmol) in CH$_3$CN (30 mL) was added TMSCl (1.5 mL, 15 mmol) at r.t. The mixture was stirred for 30 min then heated to 60° C. for 6 hr. After cooling to r.t., the mixture was quenched with MeOH and concentrated under reduced pressure. The residue was purified by preparative HPLC to afford 3-chloro-5-((6-oxo-1-((6-oxo-1,6-dihydropyridazin-3-yl)methyl)-4-(trifluoromethyl)-1,6-dihydropyrimidin-5-yl)oxy)benzonitrile (0.78 g).

$^1$H NMR (DMSO-d6, 400 MHz): δ 12.99 (s, 1H), 8.77 (s, 1H), 7.77 (s, 1H), 7.70 (s, 1H), 7.66 (s, 1H), 7.50 (d, 1H), 6.88 (d, 1H), 5.14 (s, 2H).

MS (ESI) m/z 424, 426 (M+H)$^+$

Using the same procedure of Example 7 and LiAlD$_4$ in THF in Step 1 in place of the NaBH$_4$, CaCl$_2$ in methanol, the following compound was also synthesized and characterized as indicated in the table below:

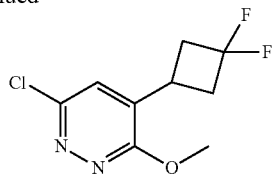

To a solution of 3-chloro-6-methoxypyridazine (50 mg, 0.35 mmol), 3,3-difluorocyclobutanecarboxylic acid (80 mg, 0.57 mmol), AgNO$_3$ (30 mg, 0.17 mmol) and TFA (20 mg, 0.17 mmol) in H$_2$O (0.8 mL) was added a solution of (NH$_4$)$_2$S$_2$O$_8$ (142 mg, 0.62 mmol) in H$_2$O (0.4 mL) drop-

| Example | Structure | IUPAC name | MS (M + H)$^+$/NMR |
|---|---|---|---|
| 8 | 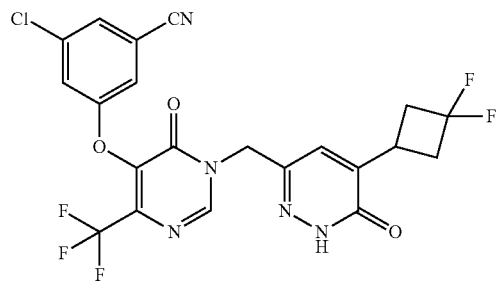 [SMILES: N#Cc1cc(Cl)cc(Oc2c(C(F)(F)F)ncn(Cc3cc(C4CC(F)(F)C4)c(=O)[nH]n3)c2=O)c1] | 3-chloro-5-({6-oxo-1-[(6-oxo-1,6-dihydropyridazin-3-yl)($^2$H$_2$)methyl]-4-(trifluoromethyl)-1,6-dihydropyrimidin-5-yl}oxy)benzonitrile | MS (ESI) m/z 426, 428 $^1$H NMR (DMSO-d6, 400 MHz) δ 12.96 (s, 1H), 8.75 (s, 1H), 7.75 (s, 1H), 7.68 (s, 1H), 7.64 (s, 1H), 7.48 (d, J = 10.0 Hz, 1H), 6.86 (d, J = 9.6 Hz, 1H). |

EXAMPLE 9

3-chloro-5-((1-((5-(3,3-difluorocyclobutyl)-6-oxo-1,6-dihydropyridazin-3-yl)methyl)-6-oxo-4-(trifluoromethyl)-1,6-dihydropyrimidin-5-yl)oxy)benzonitrile

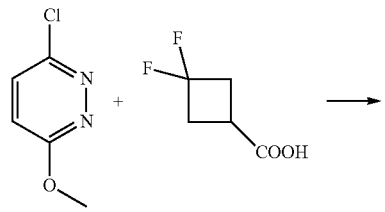

Step 1: 6-chloro-4-(3,3-difluorocyclobutyl)-3-methoxypyridazine wise at 70° C. The mixture was stirred at 70° C. for 1.5 h, cooled to r.t., then quenched with aqueous NH$_4$OH and extracted with ethyl acetate (60 mL×3). The organic layer was washed with water and brine, dried over anhydrous sodium sulfate, filtered and concentrated under reduced pressure. The residue was purified by preparative TLC to afford 6-chloro-4-(3,3-difluorocyclobutyl)-3-methoxypyridazine (25 mg).

MS (ESI): m/z 235, 237 (M+H)$^+$ $^1$HNMR (CDCl$_3$, 400 MHz) δ 7.20 (s, 1H), 4.13 (s, 3H), 3.40-3.43 (m, 1H), 2.97-3.00 (m, 2H), 2.65-2.68 (m, 2H).

Step 2: methyl 5-(3,3-difluorocyclobutyl)-6-methoxypyridazine-3-carboxylate

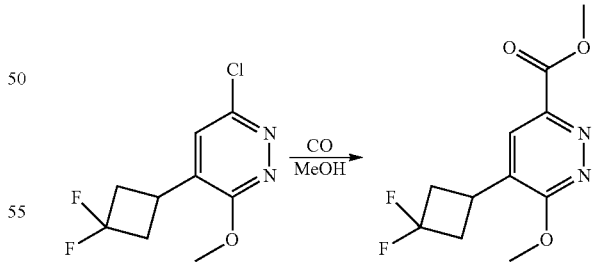

A suspension of 6-chloro-4-(3,3-difluorocyclobutyl)-3-methoxypyridazine (25 mg, 0.11 mmol), triethyl amine (32 mg, 0.32 mmol) and Pd(dppf)$_2$Cl$_2$ (5 mg, 0.0053 mmol) in 5 mL of methanol was stirred under carbon monoxide (50 psi) at 60° C. for overnight. The reaction mixture was poured into water and extracted with ethyl acetate (60 mL×3). The combined organic layers were washed with water and brine, dried over anhydrous sodium sulfate, filtered and concentrated under reduced pressure. The residue was purified by preparative TLC to afford methyl 5-(3,3-difluorocyclobutyl)-6-methoxypyridazine-3-carboxylate (21 mg).

MS (ESI): m/z 259 (M+H)+

The title compound, 3-chloro-5-((1-((5-(3,3-difluorocyclobutyl)-6-oxo-1,6-dihydropyridazin-3-yl)methyl)-6-oxo-4-(trifluoromethyl)-1,6-dihydropyrimidin-5-yl)oxy)benzonitrile, was prepared from the above ester according to the procedure given for Example 7.

$^1$H NMR (DMSO-d6, 400 MHz): δ 12.99 (s, 1H), 8.77 (s, 1H), 7.78 (s, 1H), 7.71-7.67 (m, 2H), 7.48 (s, 1H), 5.14 (s, 2H), 2.89-2.91 (m, 1H), 2.87-2.89 (m, 2H), 2.73-2.74 (m, 2H).

MS (ESI): m/z 514, 516 (M+H)+

Example 10 in the table below were prepared according to the procedure given for Example 9.

To a solution of methyl 6-chloro-3-methoxypyridazine-4-carboxylate (2.0 g, 0.01 mol) in 20 mL of THF was added MeMgBr (7.4 ml, 0.022 mol) at −30° C. under a nitrogen atmosphere. The resulting mixture was stirred at 0° C. for 1 hr. After finished, the mixture was poured into water and acidified with sat. aq. NH$_4$Cl, extracted with ethyl acetate. The combined organic layers were washed with brine, dried over sodium sulfate, filtered and concentrated under reduced pressure. The residue was purified by column chromatography (petroleum ether:ethyl acetate=5:1) to afford 2-(6-chloro-3-methoxypyridazin-4-yl)propan-2-ol (550 mg).

MS (ESI): m/z 203, 205 (M+H)+.

| Example | Structure | IUPAC Name | MS (M + H)+/NMR |
|---|---|---|---|
| 10 | 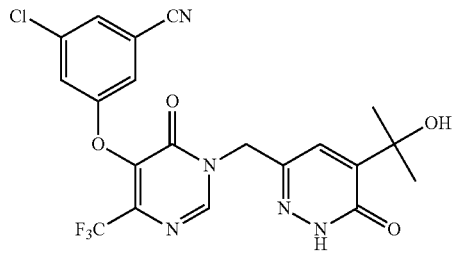 | 3-chloro-5-((1-((5-isopropyl-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 466, 468 $^1$H NMR (DMSO-d6, 400 MHz): δ 12.83 (s, 1H), 8.75 (s, 1H), 7.77 (s, 1H ), 7.70 (s, 1H), 7.66 (s, 1H), 7.31 (s, 1H), 5.12 (s, 2H), 2.90-3.00 (m, 1H), 1.10 (d, J = 7.6 Hz, 6H). |

EXAMPLE 11

3-chloro-5-((1-((5-(2-hydroxypropan-2-yl)-6-oxo-1,6-dihydropyridazin-3-yl)methyl)-6-oxo-4-(trifluoromethyl)-1,6-dihydropyrimidin-5-yl)oxy)benzonitrile

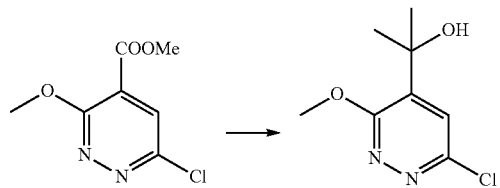

Step 1:
2-(6-chloro-3-methoxypyridazin-4-yl)propan-2-ol

Step 2: methyl 5-(2-hydroxypropan-2-yl)-6-methoxypyridazine-3-carboxylate

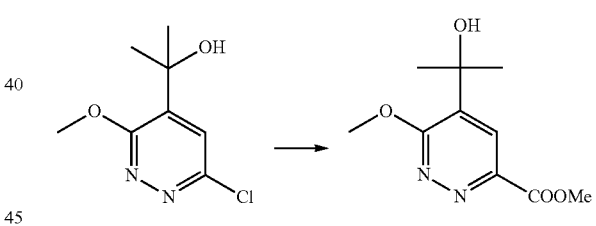

A suspension of 2-(6-chloro-3-methoxypyridazin-4-yl)propan-2-ol (200 mg, 0.99 mmol), triethyl amine (200 mg, 2 mmol) and Pd(dppf)Cl$_2$ (20 mg) in 5 mL of methanol was stirred under carbon monoxide (50 psi) at 60° C. overnight. Then the reaction mixture was poured into water, extracted with ethyl acetate (60 mL×3). The organic extracts were washed with water and brine, dried over anhydrous sodium sulfate, filtered and concentrated under reduced pressure. The residue was purified by column chromatography (petroleum ether:ethyl acetate (2:1 to 1:1) as eluent to give methyl 5-(2-hydroxypropan-2-yl)-6-methoxypyridazine-3-carboxylate (100 mg).

MS (ESI): m/z 227 (M+H)+

The title compound was subsequently prepared from methyl 5-(2-hydroxypropan-2-yl)-6-methoxypyridazine-3-carboxylate according to the procedure given for Example 7.

$^1$H NMR (CD$_3$OD, 400 MHz): δ 8.55 (s, 1H), 7.61 (s, 1H), 7.53 (s, 1H), 7.35 (s, 2H), 5.20 (s, 2H), 1.54 (s, 6H).

MS (ESI): m/z 482, 484 (M+H)+

EXAMPLE 12

3-chloro-5-((1-((5-(hydroxymethyl)-6-oxo-1,6-dihydropyridazin-3-yl)methyl)-6-oxo-4-(trifluoromethyl)-1,6-dihydropyrimidin-5-yl)oxy)benzonitrile

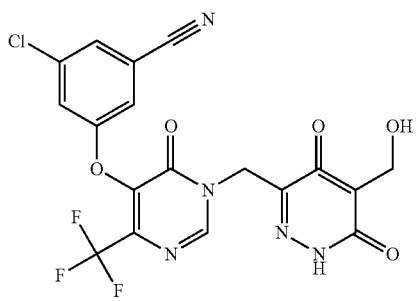

Step 1:
4-(tert-butoxymethyl)-6-chloro-3-methoxypyridazine

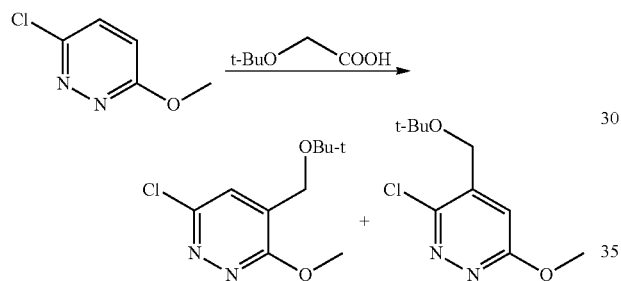

To a mixture of tert-butoxy-acetic acid (5.7 g, 43 mmol) in TFA/water (20 mol %, 48 mL) were added 3-chloro-6-methoxypyridazine (3.8 g, 26 mmol) and AgNO$_3$ (0.42 g, 2.4 mmol). The mixture was heated to 70° C., then a solution of (NH$_4$)$_2$S$_2$O$_8$ (10.6 g, 46 mmol) in water (8 mL) was added dropwise. After addition, the mixture was stirred at 70-80° C. for 30 min. After cooling to r.t, the mixture was extracted with ethyl acetate. The organic layer was washed with brine, dried over sodium sulfate, filtered and concentrated under reduced pressure. The residue was purified by column chromatography (petroleum ether:ethyl acetate (6:1) as eluent) to afford a mixture containing 4-(tert-butoxymethyl)-6-chloro-3-methoxypyridazine and 20-30% 4-(tert-butoxymethyl)-3-chloro-6-methoxypyridazine (1.5 g).

MS (ESI) m/z 231, 233 (M+H)$^+$

Step 2: methyl 5-(tert-butoxymethyl)-6-methoxypyridazine-3-carboxylate and methyl 4-(tert-butoxymethyl)-6-methoxypyridazine-3-carboxylate

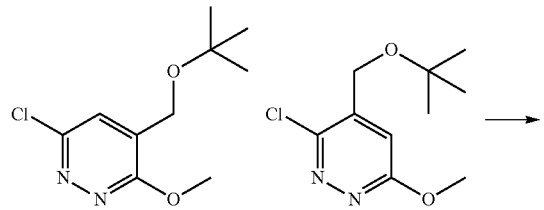

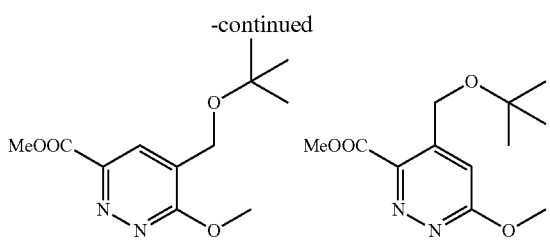

A mixture of 4-(tert-butoxymethyl)-6-chloro-3-methoxypyridazine containing 20-30% 4-(tert-butoxymethyl)-3-chloro-6-methoxypyridazine (1.3 g, 5.6 mmol), ethyl acetate (1 mL, 7.2 mmol) and Pd(dppf)Cl$_2$ (130 mg) in MeOH (100 mL) was heated to 70° C. with stirring under CO (50 psi) for 10 hr. After cooling, the mixture was poured into water and extracted with ethyl acetate. The combined organic layers were washed with brine, dried over sodium sulfate, filtered and concentrated under vacuum. The residue was purified by column chromatography (petroleum ether/ethyl acetate (3:1) as eluent to afford methyl-5-(tert-butoxymethyl)-6-methoxypyridazine-3-carboxylate (0.36 g) and methyl 4-(tert-butoxymethyl)-6-methoxy pyridazine-3-carboxylate (0.1 g).

MS (ESI) m/z 255 (M+H)$^+$

Methyl 4-(tert-butoxymethyl)-6-methoxypyridazine-3-carboxylate $^1$H NMR (CDCl$_3$, 400 MHz): δ 8.22 (s, 1H), 4.40 (s, 2H), 4.22 (s, 3H), 4.02 (s, 3H), 1.29 (s, 9H).

Methyl 5-(tert-butoxymethyl)-6-methoxypyridazine-3-carboxylate $^1$H NMR (CDCl3, 400 MHz): δ 7.40 (s, 1H), 4.77 (s, 2H), 4.20 (s, 3H), 4.00 (s, 3H), 1.29 (s, 9H).

Step 3: (5-(tert-butoxymethyl)-6-methoxypyridazin-3-yl)methanol

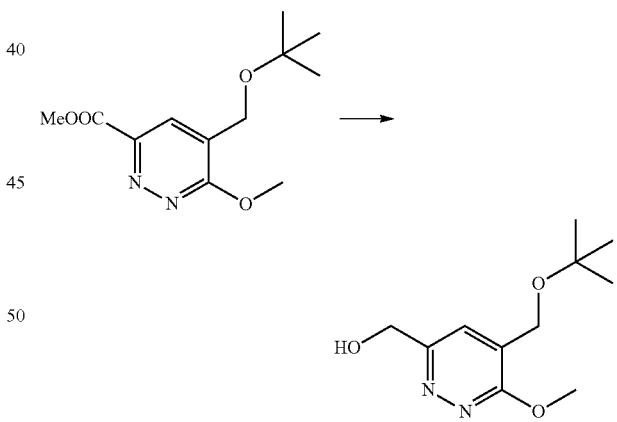

To a solution of methyl 5-(tert-butoxymethyl)-6-methoxypyridazine-3-carboxylate (290 mg, 1.2 mmol) in THF (5 mL) and MeOH (0.8 mL) was added in portions a mixture of NaBH$_4$ (210 mg, 5.8 mmol) and CaCl$_2$ (210 mg, 1.9 mmol) at 5° C. Then the mixture was stirred for 30 min at rt. The mixture was poured into sat.aq NH$_4$Cl and extracted with ethyl acetate. The combined organic layers were washed with brine, dried over sodium sulfate, filtered and concentrated under reduced pressure to afford (5-(tert-butoxymethyl)-6-methoxy pyridazin-3-yl)methanol (190 mg) which was used without further purification.

MS (ESI) m/z 227 (M+H)$^+$

Step 4: (5-(tert-butoxymethyl)-6-methoxypyridazin-3-yl)methyl methanesulfonate

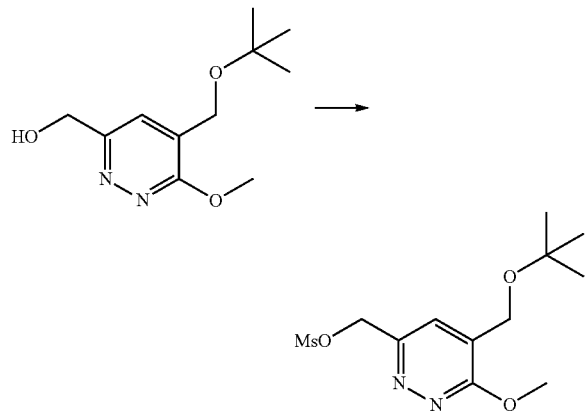

To a solution of (5-(tert-butoxymethyl)-6-methoxypyridazin-3-yl)methanol (190 mg, 0.84 mmol) in dichloromethane (12 mL) was added DIPethyl acetate (0.25 mL, 1.5 mmol) and degassed with N₂. methanesulfonyl chloride (0.1 mL, 1.3 mmol) was added at −30° C. After addition, it was allowed to warm up to 0° C. and stirred for 2 hr. The mixture was diluted with dichloromethane, washed with brine, dried over sodium sulfate, filtered and concentrated under reduced pressure to afford (5-(tert-butoxymethyl)-6-methoxypyridazin-3-yl)methyl methanesulfonate (260 mg crude) which was used without further purification.

MS (ESI) m/z 305 (M+H)⁺.

Step 5: 3-((1-((5-(tert-butoxymethyl)-6-methoxypyridazin-3-yl)methyl)-6-oxo-4-(trifluoromethyl)-1,6-dihydropyrimidin-5-yl)oxy)-5-chlorobenzonitrile

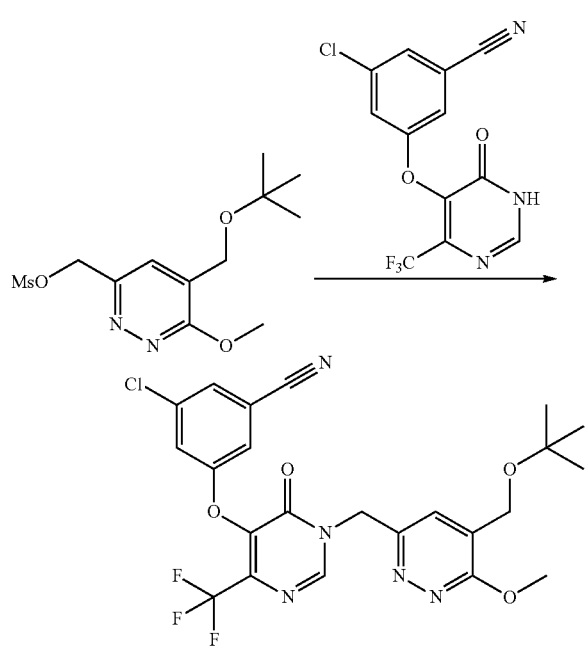

To a solution of 3-chloro-5-((6-oxo-4-(trifluoromethyl)-1,6-dihydropyrimidin-5-yl)oxy)benzonitrile (260 mg, 0.82 mmol) in DMF (6 mL) was added ethyl acetate (0.27 mL, 1.9 mmol) and (5-(tert-butoxymethyl)-6-methoxypyridazin-3-yl)methyl methanesulfonate (280 mg crude, 0.91 mmol). The resulting mixture was stirred for 20 hr at r.t. then poured into water and extracted with ethyl acetate. The combined organic layers were washed with brine, dried over sodium sulfate, filtered and concentrated under reduced pressure. The residue was purified by preparative TLC (petroleum ether/ethyl acetate (1:2) as eluent) to afford 3-((1-((5-(tert-butoxymethyl)-6-methoxypyridazin-3-yl)methyl)-6-oxo-4-(trifluoromethyl)-1,6-dihydropyrimidin-5-yl)oxy)-5-chlorobenzonitrile (110 mg).

MS (ESI) m/z 525, 527 (M+H)⁺.

Step 6: 3-chloro-5-((1-((5-(hydroxymethyl)-6-methoxypyridazin-3-yl)methyl)-6-oxo-4-(trifluoromethyl)-1,6-dihydropyrimidin-5-yl)oxy)benzonitrile

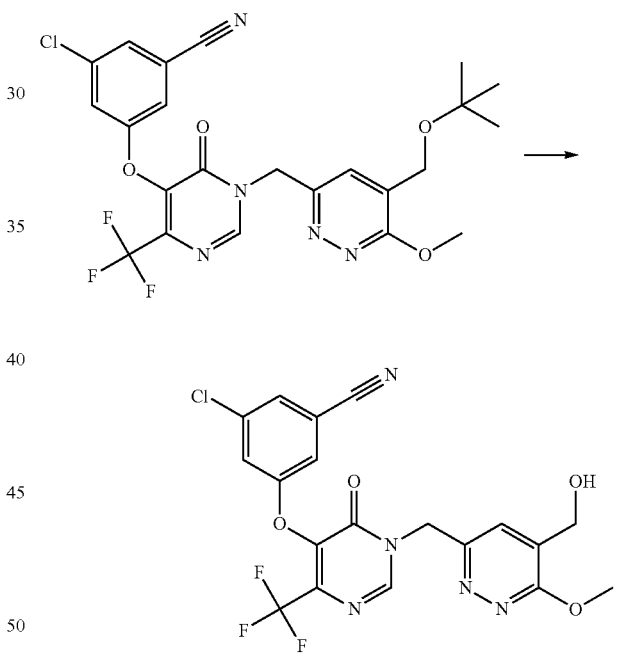

To a solution of 3-((1-((5-(tert-butoxymethyl)-6-methoxypyridazin-3-yl)methyl)-6-oxo-4-(trifluoromethyl)-1,6-dihydropyrimidin-5-yl)oxy)-5-chlorobenzonitrile (110 mg, 0.2 mmol) in DCE (2 mL) was added TFA (1 mL, 12 mmol). The resulting mixture was refluxed for 13 hr. After cooling to r.t., the mixture was concentrated under reduced pressure and purified by preparative TLC (petroleum ether/ethyl acetate (1:3) as eluent) to afford 3-chloro-5-((1-((5-(hydroxymethyl)-6-methoxypyridazin-3-yl)methyl)-6-oxo-4-(trifluoromethyl)-1,6-dihydropyrimidin-5-yl)oxy)benzonitrile (80 mg).

MS (ESI) m/z 468, 470 (M+H)⁺.

Step 7: 3-chloro-5-((1-((5-(hydroxymethyl)-6-oxo-1,6-dihydropyridazin-3-yl)methyl)-6-oxo-4-(trifluoromethyl)-1,6-dihydropyrimidin-5-yl)oxy)benzonitrile

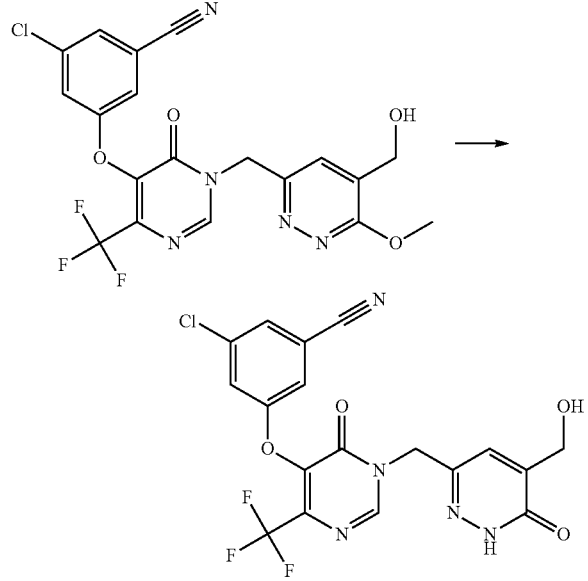

To a mixture of 3-chloro-5-((1-((5-(hydroxymethyl)-6-methoxypyridazin-3-yl)methyl)-6-oxo-4-(trifluoromethyl)-1,6-dihydropyrimidin-5-yl)oxy)benzonitrile (80 mg, 0.16 mmol) and KI (65 mg, 0.39 mmol) in MeCN (10 mL) was added TMSCl (20 μL, 0.2 mmol). The resulting mixture was stirred for 30 min at 10° C., then heated to 50° C. and stirred for 6 hr. After cooling to r.t., the mixture was diluted with ethyl acetate and washed with sat. aq Na₂S₂O₃. The organic layer was dried over sodium sulfate and concentrated under reduced pressure. The residue was purified by preparative HPLC to afford 3-chloro-5-((1-((5-(hydroxymethyl)-6-oxo-1,6-dihydropyridazin-3-yl)methyl)-6-oxo-4-(trifluoromethyl)-1,6-dihydropyrimidin-5-yl)oxy)benzonitrile (40 mg).

¹H NMR (DMSO-d6, 400 MHz): δ 12.92 (s, 1H), 8.78 (s, 1H), 7.78 (s, 1H), 7.71 (s, 1H), 7.67 (s, 1H), 7.46 (s, 1H), 5.45 (br, 1H), 5.17 (s, 2H), 4.34 (s, 2H).
MS (ESI) m/z 454, 456 (M+H)⁺.

EXAMPLE 13

3-chloro-5-((4-methyl-6-oxo-1-((6-oxo-1,6-dihydropyridazin-3-yl)methyl)-1,6-dihydropyrimidin-5-yl)oxy)benzonitrile

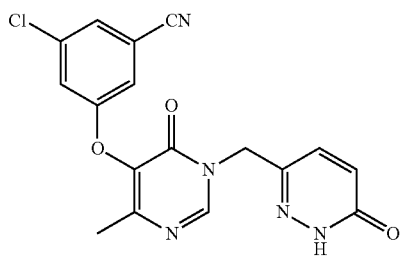 [SMILES: Cc1ncn(Cc2ccc(=O)[nH]n2)c(=O)c1Oc1cc(Cl)cc(C#N)c1]

Step 1: methyl 6-oxo-1-(tetrahydro-2H-pyran-2-yl)-1,6-dihydropyridazine-3-carboxylate

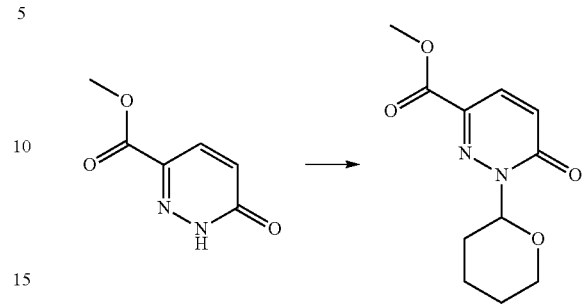

To a solution of methyl-6-oxo-1,6-dihydropyridazine-3-carboxylate (5 g, 32.4 mmol) in anhydrous THF (130 mL) was added DHP (8.90 mL, 97 mmol) and catalytic PPTS (1.631 g, 6.49 mmol). The resulting mixture was heated at reflux (75° C.) for 17 hr. Additional DHP (3.0 mL, 32.4 mmol, 1.0 eq) was added and the mixture was stirred at reflux for an additional 19 hr. The dark solution was cooled and partitioned between ethyl acetate (2×150 mL) and water (200 mL). The combined organic layers were dried over sodium sulfate, filtered and the solvent was evaporated under reduced pressure. The residue was purified by column chromatography (silica; hexanes/EtOAc 1:0 to 0:1 as eluent) to give methyl 6-oxo-1-(tetrahydro-2H-pyran-2-yl)-1,6-dihydropyridazine-3-carboxylate (7.06 g).

¹H NMR (CDCl₃-d3, 500 MHz) δ 7.82 (d, J=9.7 Hz, 1H), 6.96 (s, J=9.7 Hz, 1H), 6.09 (m, 1H), 4.12 (m, 1H), 3.95 (s, 3H), 3.74 (m, 1H), 2.32 (m, 1H), 2.07 (m, 1H), 1.75 (m, 2H), 1.57 (m, 2H).

Step 2: 6-(hydroxymethyl)-2-(tetrahydro-2H-pyran-2-yl)pyridazin-3(2H)-one

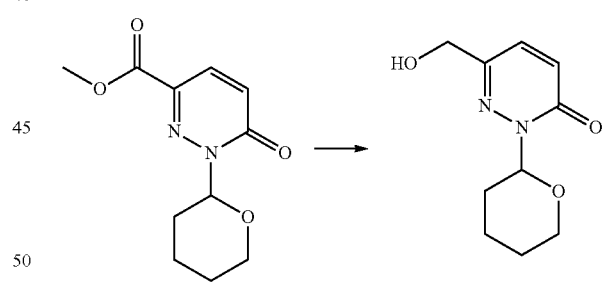

A solution of methyl 6-oxo-1-(tetrahydro-2H-pyran-2-yl)-1,6-dihydropyridazine-3-carboxylate (7.06 g, 29.6 mmol) in anhydrous 2-methyl tetrahydrofuran (150 mL) was cooled down to 0° C. (water/wet ice) and slowly charged with lithium borohydride (44.5 mL, 89 mmol) (2M in THF). The reaction was stirred at 0° C. for 3 hr. The solution was quenched with water (10 mL), allowed to stir and then partitioned between ethyl acetate (2×300 mL) and water (350 mL). The combined organic layers were dried over sodium sulfate, filtered and the solvent was evaporated under reduced pressure. The residue was purified via flash column chromatography (dichloromethane\methanol (1:0 to 9:1) as eluent) to afford 6-(hydroxymethyl)-2-(tetrahydro-2H-pyran-2-yl)pyridazin-3(2H)-one (3.34 g).

MS (ESI) m/z 211, 211 found (M+H)⁺

Step 3: 3-chloro-5-((4-methyl-6-oxo-1-((6-oxo-1-(tetrahydro-2H-pyran-2-yl)-1,6-dihydropyridazin-3-yl)methyl)-1,6-dihydropyrimidin-5-yl)oxy)benzonitrile

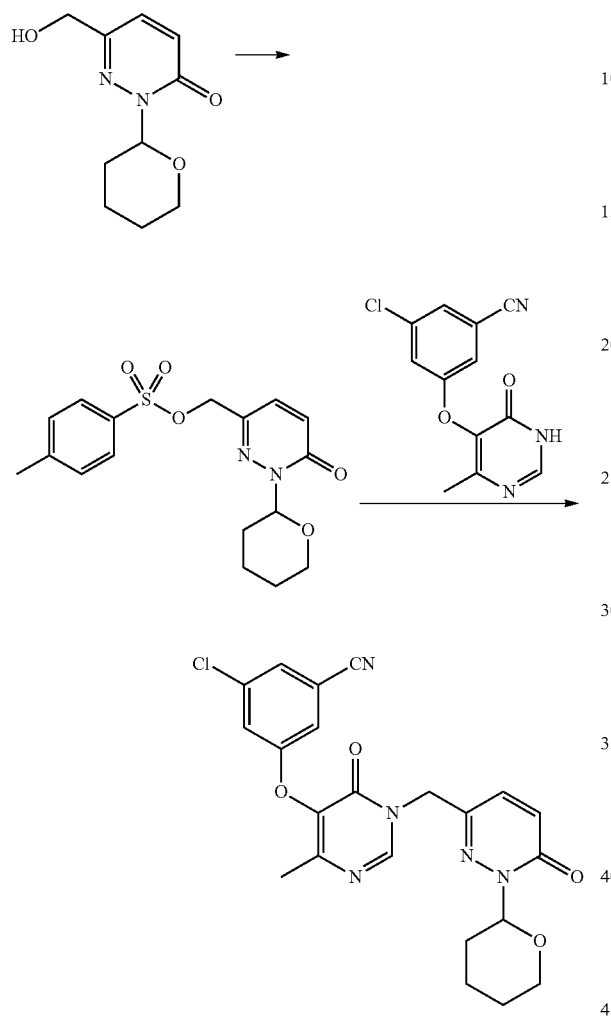

A suspension of 6-(hydroxymethyl)-2-(tetrahydro-2H-pyran-2-yl)pyridazin-3(2H)-one (360 mg, 1.712 mmol) and triethylamine (0.716 mL, 5.14 mmol) combined in anhydrous dichloromethane (10 mL) was cooled to 0° C. A solution of para-toluenesulfonylchloride (359 mg, 1.884 mmol) in dichloromethane (3 mL) was added dropwise over 5 min. The reaction was allowed to warm to r.t. and allowed to stir for 3 days. The yellow solution was diluted with water (30 mL) and extracted with dichloromethane (2×50 mL). The combined organic extracts were dried over sodium sulfate, filtered and concentrated under reduced pressure to yield (6-oxo-1-(tetrahydro-2H-pyran-2-yl)-1,6-dihydropyridazin-3-yl)methyl 4-methylbenzene sulfonate (624 mg), which was used with no further purification.

To a solution of 3-chloro-5-((4-methyl-6-oxo-1,6-dihydropyrimidin-5-yl)oxy)benzonitrile (40 mg, 0.153 mmol) in anhydrous DMF (1 mL) was added (6-oxo-1-(tetrahydro-2H-pyran-2-yl)-5-(trifluoromethyl)-1,6-dihydropyridazin-3-yl)methyl 4-methylbenzenesulfonate (112 mg, 0.260 mmol), followed by potassium carbonate (42.3 mg, 0.306 mmol). The resulting mixture was stirred at 23° C. for 20 hr. The mixture was purified by preparative HPLC to yield 3-chloro-5-((4-methyl-6-oxo-1-((6-oxo-1-(tetrahydro-2H-pyran-2-yl)-1,6-dihydropyridazin-3-yl)methyl)-1,6-dihydropyrimidin-5-yl)oxy)benzonitrile (23 mg).

MS (ESI) m/z 453, 454 found (M+H)$^+$

Step 4: 3-chloro-5-((6-oxo-1-((6-oxo-1,6-dihydropyridazin-3-yl)methyl)-4-(trifluoromethyl)-1,6-dihydropyrimidin-5-yl)oxy)benzonitrile

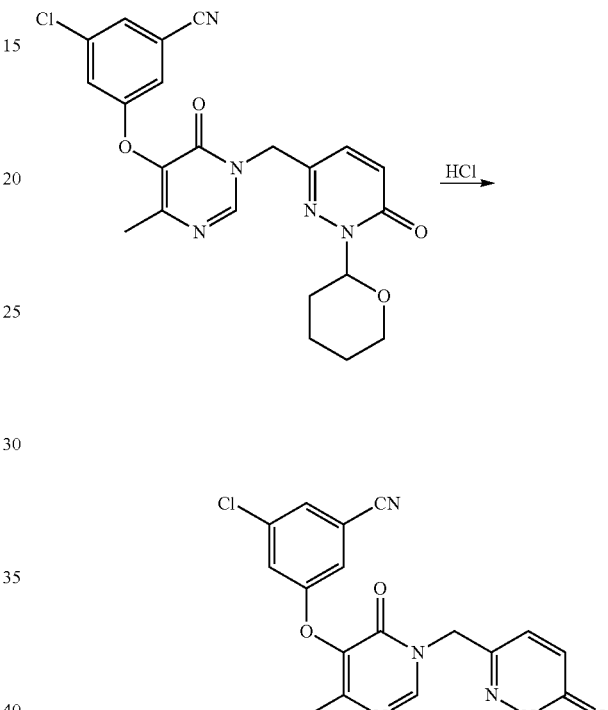

A solution of 3-chloro-5-((4-methyl-6-oxo-1-((6-oxo-1-(tetrahydro-2H-pyran-2-yl)-1,6-dihydropyridazin-3-yl)methyl)-1,6-dihydropyrimidin-5-yl)oxy)benzonitrile (23 mg, 0.051 mmol) in HCl (1267 μL, 5.07 mmol) (4 N HCl in 1,4-dioxanedioxane (600 μL)/water (600 μL) —used 1.3 mL of this commercially available solution) was allowed to stir at 23° C. for 48 hr. The 1,4-dioxane was removed via concentration and the mixture was partitioned between ethyl acetate (35 mL) and saturated aqueous sodium bicarbonate (35 mL). The organic layer was dried over sodium sulfate and concentrated under reduced pressure. The crude off-white solid was purified by preparative HPLC and the desired fractions were freebased by partitioning between ethyl acetate (35 mL) and saturated aqueous sodium bicarbonate (35 mL). The organic layer was dried over sodium sulfate and concentrated to afford 3-chloro-5-((4-methyl-6-oxo-1-((6-oxo-1,6-dihydropyridazin-3-yl)methyl)-1,6-dihydropyrimidin-5-yl)oxy)benzonitrile (8 mg) as an off-white solid.

$^1$H NMR (DMSO-d6, 500 MHz): δ 12.99 (s, 1H), 8.49 (s, 1H), 7.74 (s, 1H), 7.70 (m, 2H), 7.45 (s, 1H), 6.85 (d, 1H), 5.06 (s, 2H), 2.20 (s, 3H).

MS (ESI) m/z 369, 370 (M+H)$^+$

EXAMPLE 14

3-chloro-5-((1-((5-(1-hydroxyethyl)-6-oxo-1,6-dihydropyridazin-3-yl)methyl)-6-oxo-4-(trifluoromethyl)-1,6-dihydropyrimidin-5-yl)oxy)benzonitrile

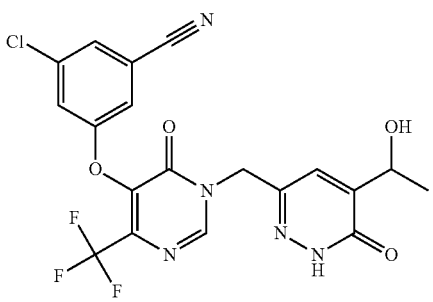 [SMILES: CC(O)c1cc(Cn2cnc(C(F)(F)F)c(Oc3cc(Cl)cc(C#N)c3)c2=O)n[nH]c1=O]

Step 1: 3-chloro-5-((1-((5-formyl-6-methoxypyridazin-3-yl)methyl)-6-oxo-4-(trifluoromethyl)-1,6-dihydropyrimidin-5-yl)oxy)benzonitrile

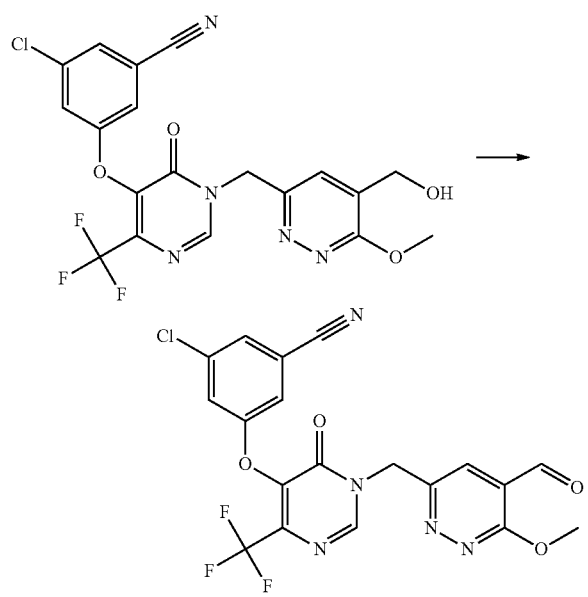

To a solution of 3-chloro-5-((1-((5-(hydroxymethyl)-6-methoxypyridazin-3-yl)methyl)-6-oxo-4-(trifluoromethyl)-1,6-dihydropyrimidin-5-yl)oxy)benzonitrile (620 mg, 1.3 mmol) in 10 mL of dichloromethane was added DMP (740 mg, 1.7 mmol) at 0° C. under a nitrogen atmosphere. After stirring for 3 hr at r.t. the mixture was poured into water and extracted with dichloromethane. The extracts were dried over sodium sulfate, filtered and concentrated under reduced pressure. The residue was purified by column chromatography on silica gel (petroleum ether/ethyl acetate (2:1) as eluent) to afford 3-chloro-5-((1-((5-formyl-6-methoxypyridazin-3-yl)methyl)-6-oxo-4-(trifluoromethyl)-1,6-dihydropyrimidin-5-yl)oxy)benzonitrile (410 mg).

MS (ESI) m/z 466, 468 (M+H)⁺.

Step 2: 3-chloro-5-((1-((5-(1-hydroxyethyl)-6-methoxypyridazin-3-yl)methyl)-6-oxo-4-(trifluoromethyl)-1,6-dihydropyrimidin-5-yl)oxy)benzonitrile

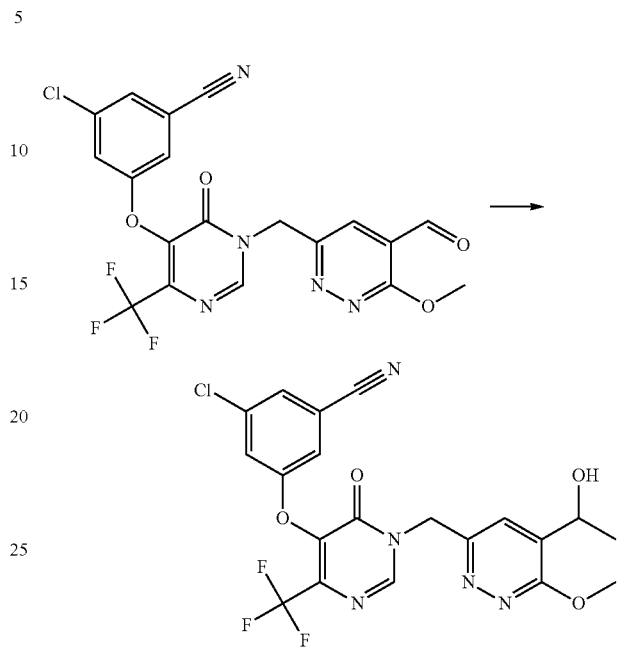

To a solution of 3-chloro-5-((1-((5-formyl-6-methoxypyridazin-3-yl)methyl)-6-oxo-4-(trifluoromethyl)-1,6-dihydropyrimidin-5-yl)oxy)benzonitrile (200 mg, 0.43 mmol) in 8 mL of THF was added MeMgBr (0.21 mL, 0.63 mmol) at −30° C. under a nitrogen atmosphere. The resulting mixture was stirred at −30° C. to 0° C. for 1 hr. The mixture was quenched with sat. aq. NH₄Cl, extracted with ethyl acetate. The combined organic extracts were dried, filtered and concentrated under reduced pressure. The residue was purified by preparative TLC (dichloromethane/ethyl acetate (7:10) as eluent) to afford 3-chloro-5-((1-((5-(1-hydroxyethyl)-6-methoxypyridazin-3-yl)methyl)-6-oxo-4-(trifluoromethyl)-1,6-dihydropyrimidin-5-yl)oxy)benzonitrile (124 mg).

MS (ESI) m/z 482, 484 (M+H)⁺.

Step 3: 3-chloro-5-((1-((5-(1-hydroxyethyl)-6-oxo-1,6-dihydropyridazin-3-yl)methyl)-6-oxo-4-(trifluoromethyl)-1,6-dihydropyrimidin-5-yl)oxy)benzonitrile

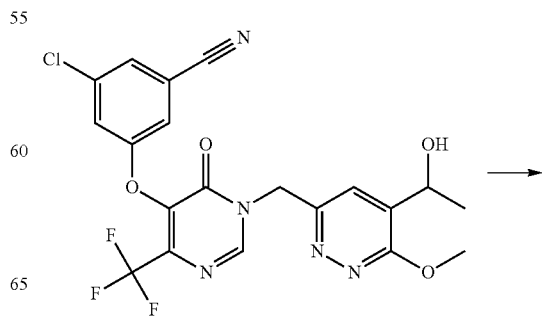

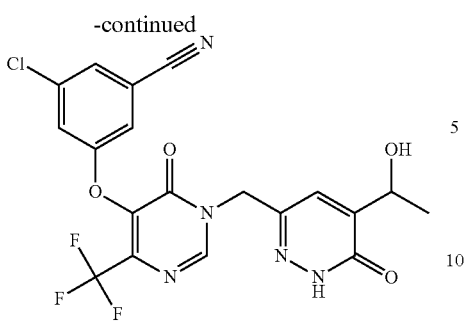

To a mixture of 3-chloro-5-((1-((5-(1-hydroxyethyl)-6-methoxypyridazin-3-yl)methyl)-6-oxo-4-(trifluoromethyl)-1,6-dihydropyrimidin-5-yl)oxy)benzonitrile (120 mg, 0.23 mmol) and KI (500 mg, 3 mmol) in 10 mL of acetonitrile was added TMSCl (0.22 mL, 4 mmol) at 10° C., and the resulting mixture was stirred for 5 hr at 50° C. After cooling to r.t., the mixture was concentrated under reduced pressure and purified by preparative HPLC to afford 3-chloro-5-((1-((5-(1-hydroxyethyl)-6-oxo-1,6-dihydropyridazin-3-yl)methyl)-6-oxo-4-(trifluoromethyl)-1,6-dihydropyrimidin-5-yl)oxy)benzonitrile (62 mg).

$^1$H NMR (DMSO-d6, 400 MHz): δ 12.90 (s, 1H), 8.78 (s, 1H), 7.79 (s, 1H), 7.71 (s, 1H), 7.65-7.68 (m, 2H), 7.49 (s, 1H), 5.17 (s, 2H), 4.68 (q, J=6.3 Hz, 1H), 1.26 (d, J=6.3 Hz, 3H).

MS (ESI) m/z 468, 470 (M+H)$^+$.

EXAMPLE 15

3-chloro-5-((1-((5-(1-fluoroethyl)-6-oxo-1,6-dihydropyridazin-3-yl)methyl)-6-oxo-4-(trifluoromethyl)-1,6-dihydropyrimidin-5-yl)oxy)benzonitrile

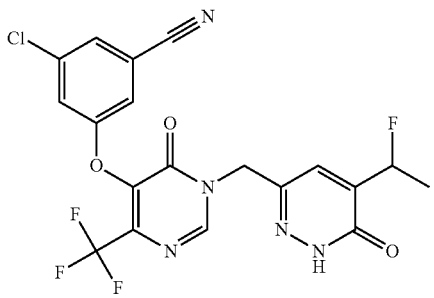 [SMILES: CC(F)c1cc(Cn2cnc(C(F)(F)F)c(Oc3cc(Cl)cc(C#N)c3)c2=O)n[nH]c1=O]

To a mixture of 3-chloro-5-((1-((5-(1-hydroxyethyl)-6-oxo-1,6-dihydropyridazin-3-yl)methyl)-6-oxo-4-(trifluoromethyl)-1,6-dihydropyrimidin-5-yl)oxy)benzonitrile (80 mg, 0.17 mmol) in 10 mL of dichloromethane was added DAST (3 mL, 20.7 mmol) at −50° C. under a nitrogen atmosphere. The resulting mixture was stirred at −50° C. to −20° C. over 30 min. The mixture was poured into ice-water and extracted with dichloromethane. The combined organic extracts were dried, filtered and concentrated under reduced pressure and purified by preparative HPLC to afford 3-chloro-5-((1-((5-(1-fluoroethyl)-6-oxo-1,6-dihydropyridazin-3-yl)methyl)-6-oxo-4-(trifluoromethyl)-1,6-dihydropyrimidin-5-yl)oxy)benzonitrile (26 mg) $^1$H NMR (DMSO-d6, 400 MHz): δ 13.15 (s, 1H), 8.77 (s, 1H), 7.77 (s, 1H), 7.70 (s, 1H), 7.67 (s, 1H), 7.53 (s, 1H), 5.65 (dt, J=47.2 Hz, J=6.4 Hz, 1H), 5.18 (s, 2H), 1.52 (dd, J=24.8 Hz, J=6.4 Hz, 3H).

MS (ESI) m/z 470, 472 (M+H)$^+$.

EXAMPLE 16

3-chloro-5-((1-((5-(fluoromethyl)-6-oxo-1,6-dihydropyridazin-3-yl)methyl)-6-oxo-4-(trifluoromethyl)-1,6-dihydropyrimidin-5-yl)oxy)benzonitrile

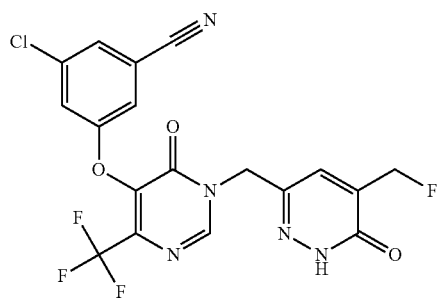 [SMILES: N#Cc1cc(Cl)cc(Oc2c(C(F)(F)F)ncn(Cc3cc(CF)c(=O)[nH]n3)c2=O)c1]

Step 1: 3-chloro-5-((1-((5-(fluoromethyl)-6-methoxypyridazin-3-yl)methyl)-6-oxo-4-(trifluoromethyl)-1,6-dihydropyrimidin-5-yl)oxy)benzonitrile

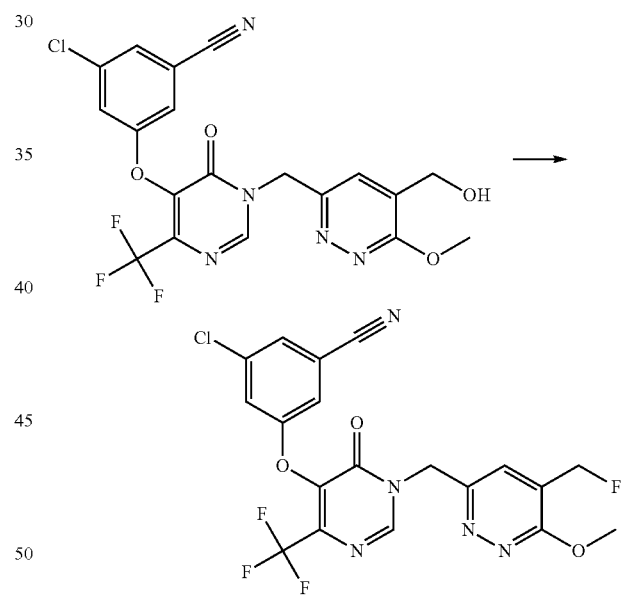

To a mixture of 3-chloro-5-((1-((5-(hydroxymethyl)-6-methoxypyridazin-3-yl)methyl)-6-oxo-4-(trifluoromethyl)-1,6-dihydropyrimidin-5-yl)oxy)benzonitrile (400 mg, 0.85 mmol) in 7 mL of dichloromethane was added DAST (1.2 mL, 8.3 mmol) at −30° C. under a nitrogen atmosphere, the resulting mixture was stirred for 2 hr at r.t. The mixture was quenched with ice-water and extracted with dichloromethane. The combined organic extracts were dried, filtered and doncentrated in vacuum. The residue was purified by preparative TLC to afford 3-chloro-5-((1-((5-(fluoromethyl)-6-methoxypyridazin-3-yl)methyl)-6-oxo-4-(trifluoromethyl)-1,6-dihydropyrimidin-5-yl)oxy)benzonitrile (110 mg).

MS (ESI) m/z 470, 472 (M+H)$^+$.

Step 2: 3-chloro-5-((1-((5-(fluoromethyl)-6-oxo-1,6-dihydropyridazin-3-yl)methyl)-6-oxo-4-(trifluoromethyl)-1,6-dihydropyrimidin-5-yl)oxy)benzonitrile

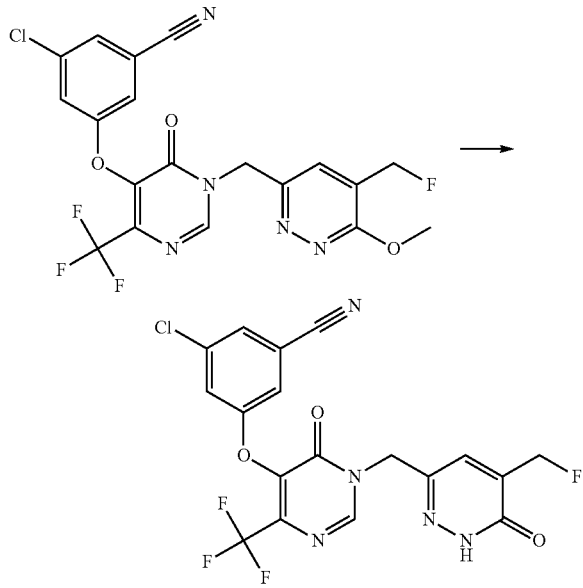

To a mixture of 3-chloro-5-((1-((5-(fluoromethyl)-6-methoxypyridazin-3-yl)methyl)-6-oxo-4-(trifluoromethyl)-1,6-dihydropyrimidin-5-yl)oxy)benzonitrile (110 mg, 0.23 mmol) and KI (740 mg, 4.4 mmol) in acetonitrile (10 mL) was added TMSCl (0.3 mL, 4 mmol) at room temperature, and the resulting mixture was stirred for 5 hr at r.t. After finished, the mixture was diluted with ethyl acetate and washed with aq. Na$_2$S$_2$O$_3$ and brine, dried over anhydrous sodium sulfate and concentrated under reduced pressure. The residue was purified by preparative HPLC to afford the desired product (14 mg).

$^1$H NMR (DMSO-d6, 400 MHz): δ 13.16 (s, 1H), 8.77 (s, 1H), 7.69 (s, 1H), 7.66-7.67 (m, 2H), 7.54 (s, 1H), 5.30 (d, J=46.4, 2H), 5.17 (s, 2H).
MS (ESI) m/z 456, 458 (M+H)$^+$.

EXAMPLE 17

3-chloro-5-((1-((5-(cyclopropyl(hydroxy)methyl)-6-oxo-1,6-dihydropyridazin-3-yl)methyl)-6-oxo-4-(trifluoromethyl)-1,6-dihydropyrimidin-5-yl)oxy)benzonitrile

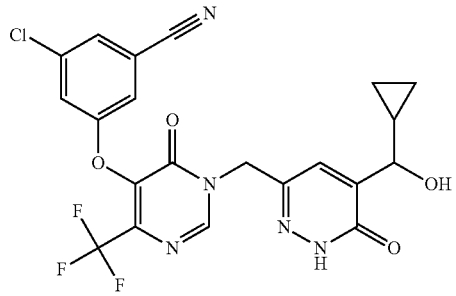 [SMILES: N#Cc1cc(Cl)cc(Oc2c(C(F)(F)F)ncn(Cc3cc(C(O)C4CC4)c(=O)[nH]n3)c2=O)c1]

Step 1: 3-chloro-5-((1-((5-(cyclopropyl(hydroxy)methyl)-6-methoxypyridazin-3-yl)methyl)-6-oxo-4-(trifluoromethyl)-1,6-dihydropyrimidin-5-yl)oxy)benzonitrile

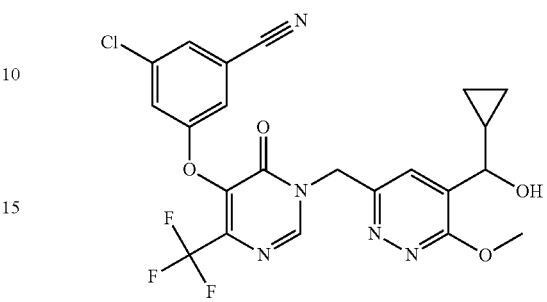

3-chloro-5-((1-((5-(cyclopropyl(hydroxy)methyl)-6-methoxypyridazin-3-yl)methyl)-6-oxo-4-(trifluoromethyl)-1,6-dihydropyrimidin-5-yl)oxy)benzonitrile was prepared from 3-chloro-5-((1-((5-formyl-6-methoxypyridazin-3-yl)methyl)-6-oxo-4-(trifluoromethyl)-1,6-dihydropyrimidin-5-yl)oxy)benzonitrile according to the procedure described for Step 2 of Example 14.
MS (ESI) m/z 508, 510 (M+H)$^+$.

Step 2: 3-chloro-5-((1-((5-(cyclopropyl(hydroxy)methyl)-6-oxo-1,6-dihydropyridazin-3-yl)methyl)-6-oxo-4-(trifluoromethyl)-1,6-dihydropyrimidin-5-yl)oxy)benzonitrile

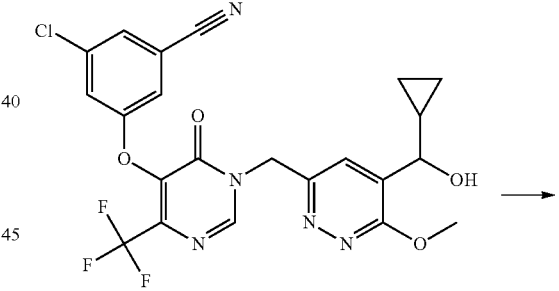

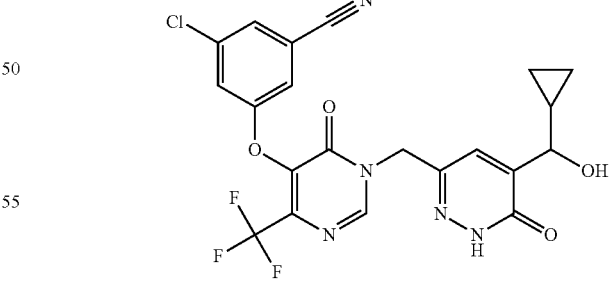

A mixture of 3-chloro-5-((1-((5-(cyclopropyl(hydroxy)methyl)-6-methoxypyridazin-3-yl)methyl)-6-oxo-4-(trifluoromethyl)-1,6-dihydropyrimidin-5-yl)oxy)benzonitrile (150 mg, 0.29 mmol) and anhydrous LiCl (1.2 g, 29 mmol) in DMF was heated to 170° C. for 6 hr under a nitrogen atmosphere. After cooling to r.t., the mixture was filtered and concentrated under reduced pressure. The residue was purified by preparative HPLC to afford 3-chloro-5-((1-((5-(cyclopropyl(hydroxy)methyl)-6-oxo-1,6-dihydropyridazin-3-yl)methyl)-6-oxo-4-(trifluoromethyl)-1,6-dihydropyrimidin-5-yl)oxy)benzonitrile (32 mg).

$^1$H NMR (DMSO-d6, 400 MHz): δ 12.91 (s, 1H), 8.78 (s, 1H), 7.77 (s, 1H), 7.71 (s, 1H), 7.66 (s, 1H), 7.47 (s, 1H), 5.17 (s, 2H), 4.36 (d, J=6.4 Hz, 1H), 1.07-1.09 (m, 1H), 0.46-0.49 (m, 1H), 0.30-0.35 (m, 3H).

MS (ESI) m/z 494, 496 (M+H)$^+$.

EXAMPLE 18

2,5-dichloro-3-((6-oxo-1-((6-oxo-1,6-dihydropyridazin-3-yl)methyl)-4-(trifluoromethyl)-1,6-dihydropyrimidin-5-yl)oxy)benzonitrile

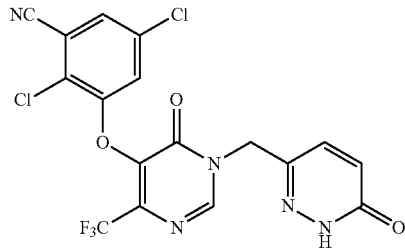 [SMILES: N#Cc1cc(Cl)cc(Oc2c(C(F)(F)F)ncn(Cc3ccc(=O)[nH]n3)c2=O)c1Cl]

Step 1: 2,5-dichloro-3-((6-oxo-4-(trifluoromethyl)-1,6-dihydropyrimidin-5-yl)oxy)benzonitrile

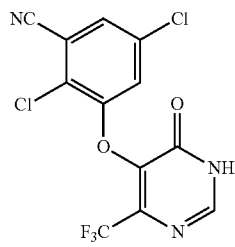 [SMILES: N#Cc1cc(Cl)cc(Oc2c(C(F)(F)F)nc[nH]c2=O)c1Cl]

The above intermediate was prepared from 2,5-dichloro-3-cyanophenol and 5-bromo-6-(trifluoromethyl)-4(3H)-pyrimidione in an analogous manner to 3-chloro-5-(6-oxo-4-(trifluoromethyl)-1,6-dihydropyrimidin-5-yloxy) benzonitrile as described in Steps 5-8 of Example 1.

MS (ESI) m/z 350, 352 (M+H)$^+$

Step 2: 2,5-dichloro-3-((6-oxo-1-((6-oxo-1,6-dihydropyridazin-3-yl)methyl)-4-(trifluoromethyl)-1,6-dihydropyrimidin-5-yl)oxy)benzonitrile

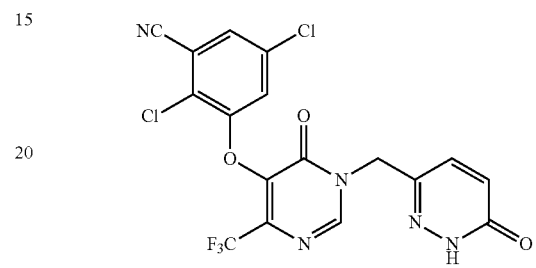

The title compound was prepared from 2,5-dichloro-3-((6-oxo-4-(trifluoromethyl)-1,6-dihydropyrimidin-5-yl)oxy)benzonitrile according to the procedures given for Steps 3 and 4 of Example 7.

$^1$H NMR (DMSO-d6, 400 MHz): δ 12.95 (s, 1H), 8.76 (s, 1H), 7.93 (d, J=2.0 Hz, 1H), 7.72 (d, J=2.0 Hz, 1H), 7.45 (d, J=8.4 Hz, 1H), 6.74-6.87 (m, 1H), 5.10 (s, 2H).

MS (ESI): m/z 458, 460 (M+H)$^+$

Using the same procedure for Example 18 and the corresponding phenols in Step 1 in place of the 2,5-dichloro-3-hydroxy-benzonitrile, the following compounds were also synthesized and characterized as indicated in the table below.

| Example | Structure | IUPAC name | MS (M + H)$^+$/NMR |
|---|---|---|---|
| 19 | 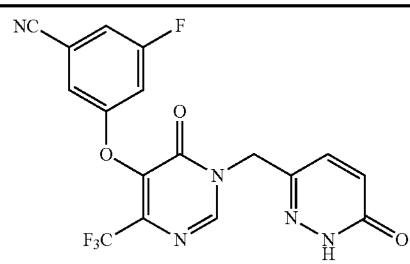 | 3-fluoro-5-((6-oxo-1-((6-oxo-1,6-dihydropyridazin-3-yl)methyl)-4-(trifluoromethyl)-1,6-dihydropyrimidin-5-yl)oxy)benzonitrile | MS (ESI) m/z 408<br>$^1$H NMR (DMSO-d6, 400 MHz): δ 12.94 (s, 1H), 9.74 (s, 1H), 7.46-7.59 (m, 4H), 6.85 (d, J = 9.2 Hz, 1H), 5.10(s, 2H). |
| 20 | 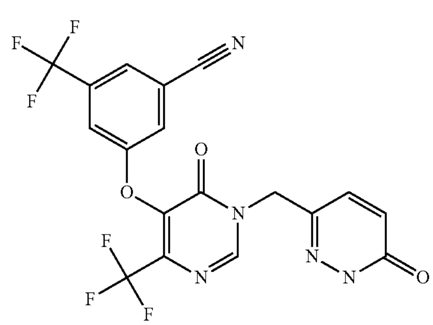 [SMILES: N#Cc1cc(Oc2c(C(F)(F)F)ncn(Cc3ccc(=O)[nH]n3)c2=O)cc(C(F)(F)F)c1] | 3-((6-oxo-1-((6-oxo-1,6-dihydropyridazin-3-yl)methyl)-4-(trifluoromethyl)-1,6-dihydropyrimidin-5-yl)oxy)-5-(trifluoromethyl)benzonitrile | MS (ESI) m/z 458<br>$^1$H NMR (CD3OD, 400 MHz) δ 8.56 (s, 1H), 7.83 (s, 1H), 7.65 (s, 1H), 7.60 (s, 1H), 7.52 (d, J = 9.6 Hz, 1H), 6.94 (d, J = 9.6 Hz, 1H), 5.18 (s, 2H). |

| Example | Structure | IUPAC name | MS (M + H)⁺/NMR |
|---|---|---|---|
| 21 | 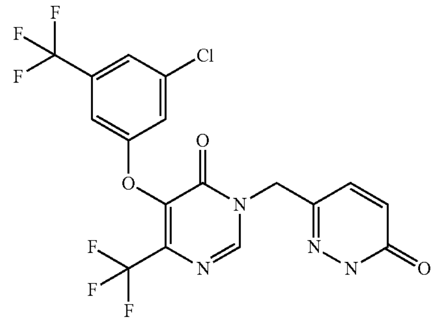 [SMILES: O=c1ccc(Cn2cnc(C(F)(F)F)c(Oc3cc(Cl)cc(C(F)(F)F)c3)c2=O)n[nH]1] | 6-((5-(3-chloro-5-(trifluoromethyl)phenoxy)-6-oxo-4-(trifluoromethyl) pyrimidin-1(6H)-yl)methyl)pyridazin-3(2H)-one | MS (ESI) m/z 467, 469 ¹H NMR (CD3OD, 400 MHz) δ 8.54 (s, 1H), 7.52 (d, J = 9.6 Hz, 1H), 7.41 (s, 1H), 7.24 (s, 1H), 7.19 (s, 1H), 6.94 (d, J = 9.6 Hz, 1H), 5.17 (s, 2H). |

EXAMPLE 22

3-chloro-5-(((6-oxo-1-((6-oxo-5-phenyl-1,6-dihydro-pyridazin-3-yl)methyl)-4-(trifluoromethyl-1,6-dihydropyrimidin-5-yl)oxy)benzonitrile

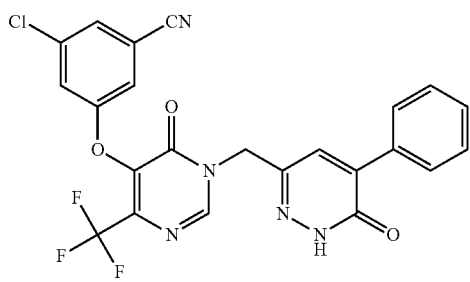 [SMILES: N#Cc1cc(Cl)cc(Oc2c(C(F)(F)F)ncn(Cc3cc(-c4ccccc4)c(=O)[nH]n3)c2=O)c1]

Step 1: 3-chloro-6-methoxypyridazine

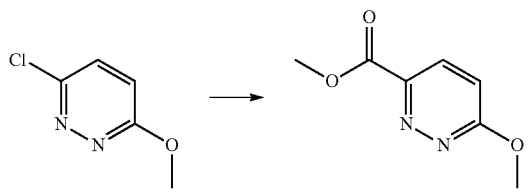

A suspension of 3-chloro-6-methoxypyridazine (3 g, 20.7 mmol), triethylamine (0.9 mL) and Pd(dppf)Cl₂ (0.9 g, 1 mmol) in 30 mL of methanol was stirred under carbon monoxide (50 psi) at 60° C. overnight. After cooling to r.t., the mixture was poured into water and extracted with ethyl acetate (80 mL×3). The organic extracts were washed with water and brine, dried over anhydrous sodium sulfate, filtered and concentrated under reduced pressure. The residue was purified by flash chromatography (petroleum ether: ethyl acetate 2:1-1:1) to afford the desired product methyl 6-methoxypyridazine-3-carboxylate (2.8 g).

MS (ESI): m/z 169 (M+H)⁺

Step 2: methyl 6-oxo-1,6-dihydropyridazine-3-carboxylate

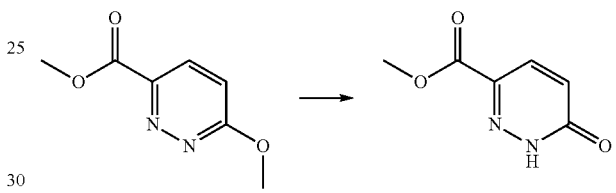

To a solution of methyl 6-methoxypyridazine-3-carboxylate (1 g, 5.9 mmol) in acetonitrile (20 mL) was added KI (1.6 g, 9.5 mmol) and TMSCl (1 g, 9.5 mmol) slowly at 0° C. After addition, the mixture was stirred at 60° C. for 30 min. After cooling to r.t, the mixture was quenched with sat. Na₂S₂O₃ and then extracted with ethyl acetate (60 mL×3). The combined organic layers were washed with water and brine, dried over anhydrous sodium sulfate, filtered and evaporated to afford methyl 6-oxo-1,6-dihydropyridazine-3-carboxylate (0.74 g) which was used without further purification.

MS (ESI): m/z 155 (M+H)⁺

Step 3: methyl 5-bromo-6-oxo-1,6-dihydropyridazine-3-carboxylate

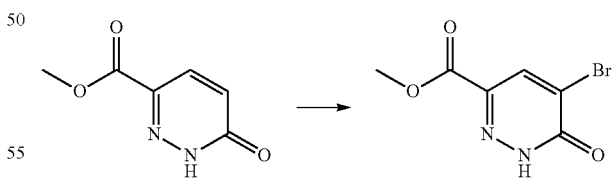

To a solution of methyl 6-oxo-1,6-dihydropyridazine-3-carboxylate (0.2 g, 1.3 mmol) in CH₃COOH (3 mL) was added CH₃COOK (0.4 g, 3.9 mmol) and Br₂ (0.4 g, 2.6 mmol) slowly at 0° C. The mixture was stirred at 80° C. for 3 hr. After cooling to r.t., the mixture was quenched with sat. aq. Na₂S₂O₃ and then extracted with ethyl acetate (80 mL×3). The combined organic extracts were washed with sat. NaHCO₃, water and brine, dried over anhydrous sodium sulfate, filtered and evaporated to afford methyl 5-bromo-6-oxo-1,6-dihydropyridazine-3-carboxylate (0.23 g).

¹HNMR (DMSO-d6, 400 MHz) δ 13.95 (s, 1H), 7.34 (s, 1H), 3.84 (s, 3H).

MS (ESI): m/z 233, 235 (M+H)⁺

Step 4: methyl 5-bromo-1-(4-methoxybenzyl)-6-oxo-1,6-dihydropyridazine-3-carboxylate

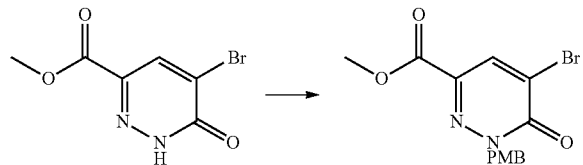

To a solution of methyl 5-bromo-6-oxo-1,6-dihydropyridazine-3-carboxylate (1.0 g, 4.3 mmol) in DMF (10 mL) was added potassium carbonate (1.8 g, 12.9 mmol) and PMBCl (1 g, 6.4 mmol). The mixture was stirred at room temperature for 3 hr, poured into water and extracted with ethyl acetate (60 mL×3). The combined extracts were washed with water and brine, dried over anhydrous sodium sulfate, filtered and concentrated under reduced pressure. The residue was purified by flash chromatography on silica (petroleum ether/ethyl acetate (5:1 to 2:1) as eluent) to afford methyl 5-bromo-1-(4-methoxybenzyl)-6-oxo-1,6-dihydropyridazine-3-carboxylate (1.2 g).

MS (ESI): m/z 353, 355 (M+H)⁺

Step 5: 4-bromo-6-(hydroxymethyl)-2-(4-methoxybenzyl)pyridazin-3(2H)-one

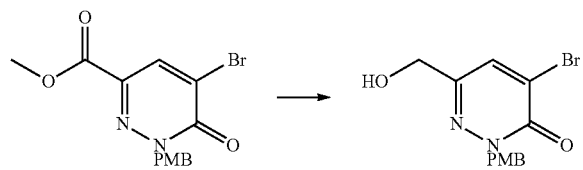

To a solution of methyl 5-bromo-1-(4-methoxybenzyl)-6-oxo-1,6-dihydropyridazine-3-carboxylate (40 g, 0.11 mol) in THF (300 mL) at −30° C. was added NaBH₄ (12.85 g, 0.33 mol) and CaCl₂ (12.85 g, 0.11 mol), then methanol (7 mL) was added dropwise at −30° C. The mixture was stirred at −30° C. for 30 min, warmed to 10° C. slowly and then poured into saturated NH₄Cl solution and extracted with ethyl acetate. The organic layer was dried over anhydrous sodium sulfate, filtered and concentrated under reduced pressure. The crude product was purified by column chromatography on a silica gel (dichloromethane/methanol (50:1) as eluent) to give 4-bromo-6-(hydroxymethyl)-2-(4-methoxybenzyl)pyridazin-3(2H)-one (12.1 g).

¹H NMR: (CD₃OD, 400 MHz) δ 7.94 (s, 1H), 7.22 (d, J=8.8 Hz, 2H), 6.85 (d, J=8.8 Hz, 2H), 5.26 (s, 2H), 4.47 (s, 2H), 3.75 (s, 3H).

MS (ESI): m/z 325, 327 (M+H)⁺

Step 6: (5-bromo-1-(4-methoxybenzyl)-6-oxo-1,6-dihydropyridazin-3-yl)methyl methanesulfonate

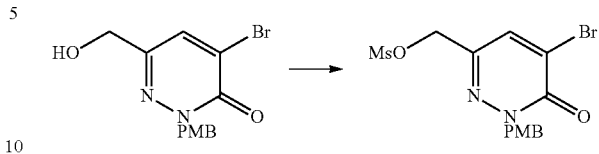

To a solution of 4-bromo-6-(hydroxymethyl)-2-(4-methoxybenzyl)pyridazin-3(2H)-one (1.1 g, 3.4 mmol) and DIPEA (1.3 g, 10.4 mmol) in THF (20 mL) was added methanesulfonyl chloride (0.5 g, 4 mmol) slowly at 0° C. The mixture was stirred at room temperature for 30 min, quenched with sat. NaHCO₃ and then extracted with ethyl acetate (60 mL×3). The organic extracts were washed with water and brine, dried over anhydrous sodium sulfate, filtered and concentrated under reduced pressure to afford (5-bromo-1-(4-methoxybenzyl)-6-oxo-1,6-dihydropyridazin-3-yl)methyl methanesulfonate (1.4 g) which was used without further purification.

MS (ESI): m/z 403, 405 (M+H)⁺

Step 7: 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile

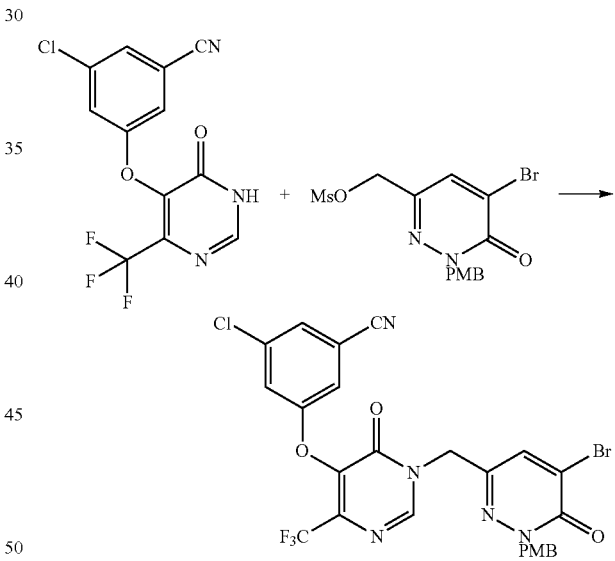

To a solution of 3-chloro-5-(((6-oxo-4-(trifluoromethyl)-1,6-dihydropyrimidin-5-yl)oxy)benzonitrile (1.6 g, 5.2 mmol) in DMF (10 mL) was added triethyl amine (1.5 mL, 10.4 mmol) and (5-bromo-1-(4-methoxybenzyl)-6-oxo-1,6-dihydropyridazin-3-yl)methylmethane-sulfonate (1.4 g). The mixture was stirred at room temperature for 5 h, poured into water and then extracted with ethyl acetate (80 mL×3). The combined organic extracts were washed with water and brine, dried over anhydrous sodium sulfate, filtered and concentrated under reduced pressure. The residue was purified by chromatography on silica gel (petroleum ether:ethyl acetate 5:1-2:1) to afford 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (0.56 g).

MS (ESI): m/z 622, 624, 626 (M+H)⁺

Step 8: 3-chloro-5-((1-((1-(4-methoxybenzyl)-6-oxo-5-phenyl-1,6-dihydropyridazin-3-yl)methyl)-6-oxo-4-(trifluoromethyl)-1,6-dihydropyrimidin-5-yl)oxy)benzonitrile Step 9: 3-chloro-5-((6-oxo-1-((6-oxo-5-phenyl-1,6-dihydropyridazin-3-yl)methyl)-4-(trifluoromethyl)-1,6-dihydropyrimidin-5-yl)oxy)benzonitrile

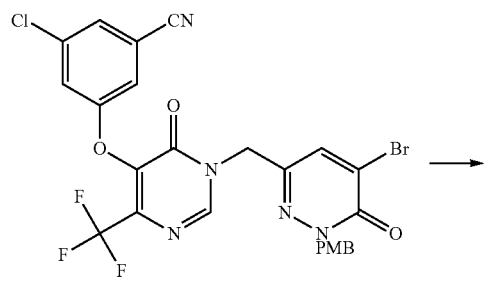

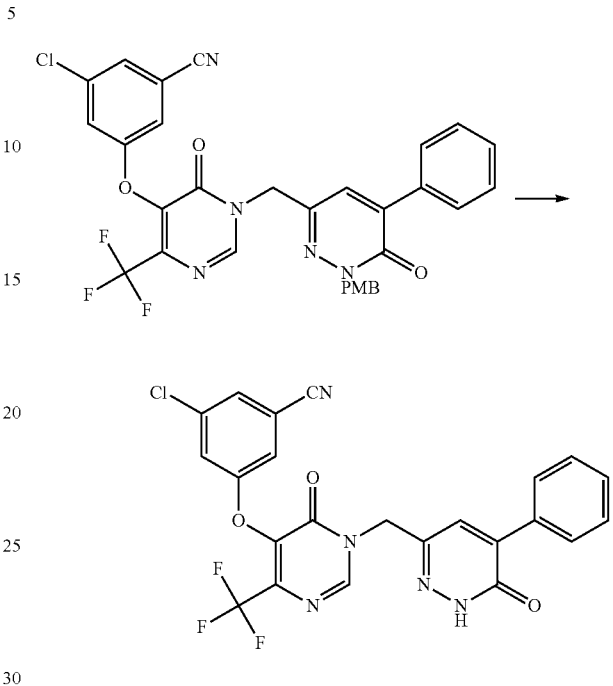

A mixture of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (150 mg, 0.24 mmol), phenylboronic acid (41 mg, 0.29 mmol), $K_3PO_4$ (102 mg, 0.49 mmol), Pd(dppf)Cl$_2$ (22 mg, 0.024 mmol) in 1,4-dioxanedioxane/H$_2$O (3:1) was heated to reflux overnight under a nitrogen atmosphere atmosphere. After cooling to r.t., the reaction mixture was diluted with H$_2$O, and extracted with ethyl acetate. The combined organic layers were dried on sodium sulfate, filtered and concentrated under reduced pressure. The residue was purified by preparative TLC (petroleum ether/ethyl acetate (3:1) as eluent) to afford 3-chloro-5-((1-((1-(4-methoxybenzyl)-6-oxo-5-phenyl-1,6-dihydropyridazin-3-yl)methyl)-6-oxo-4-(trifluoromethyl)-1,6-dihydropyrimidin-5-yl)oxy)benzonitrile (95 mg).

MS (ESI): m/z 620, 622 (M+H)$^+$

A solution of 3-chloro-5-((1-((1-(4-methoxybenzyl)-6-oxo-5-phenyl-1,6-dihydropyridazin-3-yl)methyl)-6-oxo-4-(trifluoromethyl)-1,6-dihydropyrimidin-5-yl)oxy)benzonitrile (95 mg, 0.15 mmol) in TFA:TFAA (2:1, total 5 mL) was stirred under microwave irradiation at 100° C. for 5 min. After cooling to r.t., the mixture was concentrated under reduced pressure. The residue was purified with preparative HPLC to give the title compound 3-chloro-5-((6-oxo-1-((6-oxo-5-phenyl-1,6-dihydropyridazin-3-yl)methyl)-4-(trifluoromethyl)-1,6-dihydropyrimidin-5-yl)oxy)benzonitrile (27 mg).

$^1$H-NMR (DMSO-d6, 400 MHz): δ 13.10 (s, 1H), 8.74 (s, 1H), 7.63-7.77 (m, 6H), 7.40 (s, 3H), 5.14 (s, 2H).

MS (ESI): m/z 500, 502 (M+H)$^+$

Using the same procedures as given for Steps 1-7 in Example 22 and methyl iodide in Step 4 in place of the PMBCl, the following compound was also synthesized and characterized as indicated in the table below:

| Example | Structure | IUPAC name | MS (M + H)$^+$/NMR |
|---|---|---|---|
| 23 | 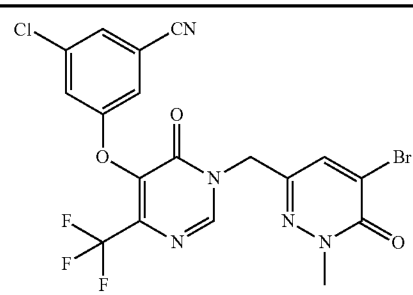 | 3-((1-((5-bromo-1-methyl-6-oxo-1,6-dihydropyridazin-3-yl)methyl)-6-oxo-4-(trifluoromethy)-1,6-dihydropyrimidin-5-yl)oxy)-5-chlorobenzonitrile | MS (ESI) m/z 516, 518 $^1$H NMR: (DMSO-d6, 400 MHz) δ 8.74 (s, 1H), 8.09 (s, 1H), 7.78-7.67 (m, 3H), 5.11 (s, 2H), 3.66 (s, 3H). |

Using the same procedures as given for Steps 1-7 in Example 22 and the corresponding boronate ester or boronic acid in Step 8 in place of phenylboronic acid, the following compounds were also synthesized and characterized as indicated in the table below:

| Example | Structure | IUPAC Name | MS (M + H)⁺/NMR |
|---|---|---|---|
| 24 | 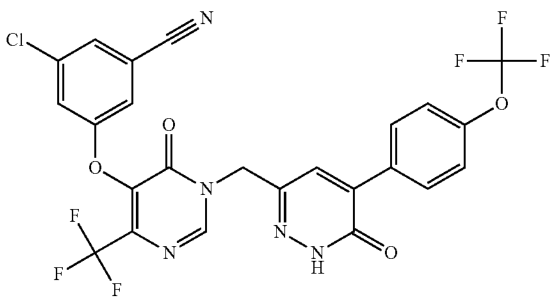 [SMILES: N#Cc1cc(Cl)cc(Oc2c(C(F)(F)F)ncn(Cc3cc(-c4ccc(OC(F)(F)F)cc4)c(=O)[nH]n3)c2=O)c1] | 3-chloro-5-((6-oxo-1-((6-oxo-5-(4-(trifluoromethoxy)phenyl)-1,6-dihydropyridazin-3-yl)methyl)-4-(trifluoromethyl)-1,6-dihydropyrimidin-5-yl)oxy)benzonitrile | MS (ESI) m/z 584, 586<br>$^1$H NMR (DMSO-d6, 400 MHz)<br>δ 13.20 (s, 1H), 8.74 (s, 1H), 7.90 (d, J = 8.8 Hz, 2H), 7.62-7.71 (m, 4H), 7.41 (d, J = 8.4 Hz, 2H), 5.14 (s, 2H). |
| 25 | 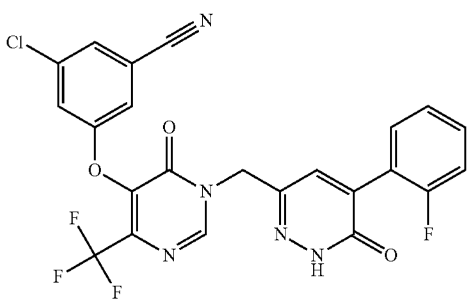 [SMILES: N#Cc1cc(Cl)cc(Oc2c(C(F)(F)F)ncn(Cc3cc(-c4ccccc4F)c(=O)[nH]n3)c2=O)c1] | 3-chloro-5-((1-((5-(2-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 518, 520<br>$^1$H NMR (DMSO-d6, 400 MHz)<br>δ 13.17 (s, 1H), 8.75 (s, 1H), 7.60-7.74 (m, 4H), 7.43-7.49 (m, 2H), 7.23-7.28 (m, 2H), 5.15 (s, 2H). |
| 26 | 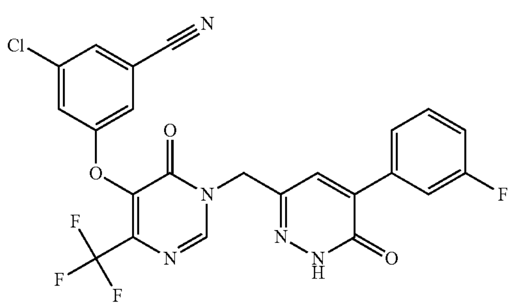 [SMILES: N#Cc1cc(Cl)cc(Oc2c(C(F)(F)F)ncn(Cc3cc(-c4cccc(F)c4)c(=O)[nH]n3)c2=O)c1] | 3-chloro-5-((1-((5(3-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 518, 520<br>$^1$H NMR (DMSO-d6, 400 MHz)<br>δ 13.20 (s, 1H), 8.76 (s, 1H), 7.64-7.77 (m, 6H), 7.49 (t, J = 7.2 Hz, 1H), 7.28 (t, J = 7.2 Hz, 1H), 5.15 (s, 2H). |
| 27 | 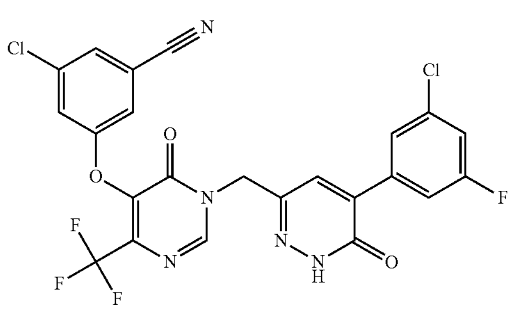 [SMILES: N#Cc1cc(Cl)cc(Oc2c(C(F)(F)F)ncn(Cc3cc(-c4cc(F)cc(Cl)c4)c(=O)[nH]n3)c2=O)c1] | 3-chloro-5-((1-((5-(3-chloro-5-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 552, 554, 556<br>$^1$H NMR (DMSO-d6, 400 MHz)<br>δ 13.29 (s, 1H), 8.76 (s, 1H), 7.62-7.86 (m, 6H), 7.52 (t, J = 8.8 Hz, 1H), 5.14 (s, 2H). |

| Example | Structure | IUPAC Name | MS (M + H)+/NMR |
|---|---|---|---|
| 28 | 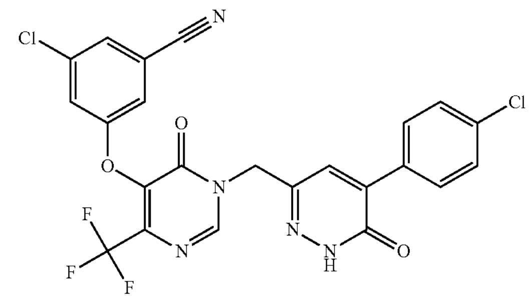 [SMILES: N#Cc1cc(Cl)cc(Oc2c(C(F)(F)F)ncn(Cc3cc(-c4ccc(Cl)cc4)c(=O)[nH]n3)c2=O)c1] | 3-chloro-5-((1-((5-(4-chlorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 534, 536, 538<br>¹HNMR (DMSO-d6, 400 MHz)<br>δ 13.18 (s, 1H), 8.75 (s, 1H), 7.84 (d, J = 8.4 Hz, 2H), 7.63-7.74 (m, 4H), 7.49 (d, J = 8.8 Hz, 2H), 5.14 (s, 2H). |
| 29 | 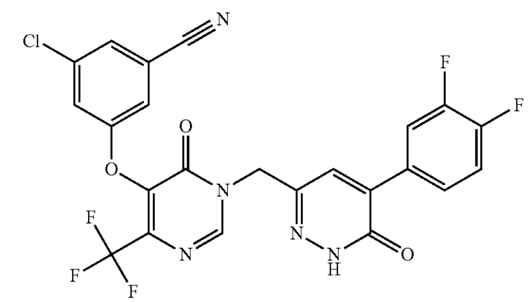 [SMILES: N#Cc1cc(Cl)cc(Oc2c(C(F)(F)F)ncn(Cc3cc(-c4ccc(F)c(F)c4)c(=O)[nH]n3)c2=O)c1] | 3-chloro-5-((1-((5-(3,4-difluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 536, 538<br>¹H NMR (DMSO-d6, 400 MHz)<br>δ 13.23 (s, 1H), 8.76 (s, 1H), 7.93-7.99 (m, 1H), 7.63-7.77 (m, 5H), 7.51 (q, J = 8.8 Hz, 1H), 5.14 (s, 2H). |
| 30 | 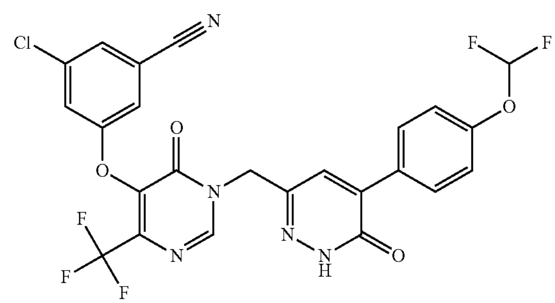 [SMILES: N#Cc1cc(Cl)cc(Oc2c(C(F)(F)F)ncn(Cc3cc(-c4ccc(OC(F)F)cc4)c(=O)[nH]n3)c2=O)c1] | 3-chloro-5-((1-((5-(4-(difluoromethoxy)phenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 566, 568<br>¹H NMR (DMSO-d6, 400 MHz)<br>δ 13.14 (s, 1H), 8.75 (s, 1H), 7.87 (d, J = 8.8 Hz, 2H), 7.63-7.74 (m, 4H), 7.26 (t, J = 147.6 Hz, 1H), 7.22 (d, J = 8.8 Hz, 2H), 5.15 (s, 2H). |
| 31 | 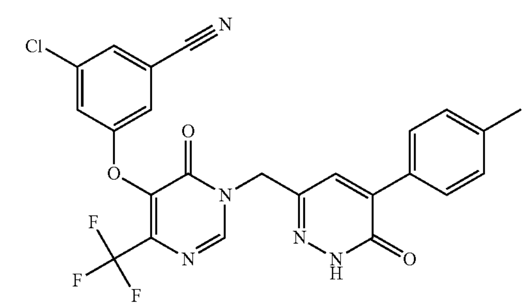 [SMILES: Cc1ccc(-c2cc(Cn3cnc(C(F)(F)F)c(Oc4cc(Cl)cc(C#N)c4)c3=O)n[nH]c2=O)cc1] | 3-chloro-5-((6-oxo-1-((6-oxo-5-(p-tolyl)-1,6-dihydropyridazin-3-yl)methyl)-4-(trifluoromethyl)-1,6-dihydropyrimidin-5-yl)oxy)benzonitrile | MS (ESI) m/z 514, 516<br>¹H NMR (DMSO-d6, 400 MHz)<br>δ 13.06 (s, 1H) 8.76 (s, 1H), 7.64-7.74 (m, 6H), 7.22 (d, J = 7.6 Hz, 2H), 5.14 (s, 2H), 2.30 (s, 3H). |
| 32 | 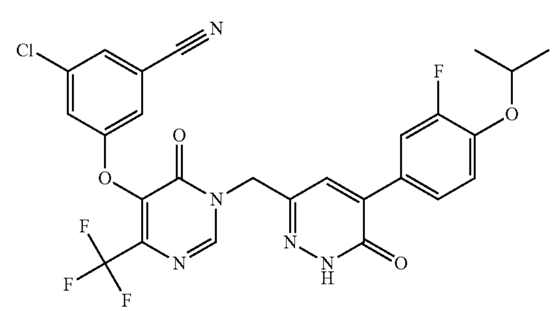 [SMILES: CC(C)Oc1ccc(-c2cc(Cn3cnc(C(F)(F)F)c(Oc4cc(Cl)cc(C#N)c4)c3=O)n[nH]c2=O)cc1F] | 3-chloro-5-((1-((5-(3-fluoro-4-isopropoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 576, 578<br>¹H NMR (DMSO-d6, 400 MHz)<br>δ 13.11 (s, 1H), 8.75 (s, 1H), 7.63-7.83 (m, 6H), 7.26 (t, J = 17.6 Hz, 1H), 5.13 (s, 2H), 4.66-4.72 (m, 1H), 1.26 (d, J = 5.9 Hz, 6H). |

| Example | Structure | IUPAC Name | MS (M + H)⁺/NMR |
|---|---|---|---|
| 33 | 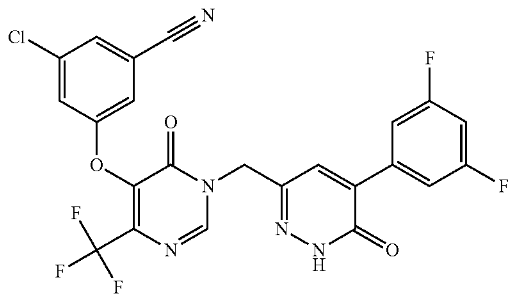 | 3-chloro-5-((1-((5-(3,5-difluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 536, 538 ¹H NMR (DMSO-d6, 400 MHz) δ 13.30 (s, 1H), 8.77 (s, 1H), 7.86 (s, 1H), 7.62-7.75 (m, 5H), 7.32-7.37 (m, 1H), 5.16 (s, 2H). |
| 34 | 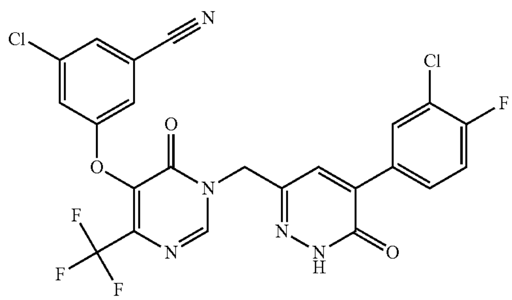 | 3-chloro-5-((1-((5-(3-chloro-4-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 552, 554, 556 ¹H NMR (DMSO-d6, 400 MHz) δ 13.23 (s, 1H), 8.76 (s, 1H), 8.10-8.13 (m, 1H), 7.48-7.87 (m, 6H), 5.14 (s, 2H). |
| 35 | 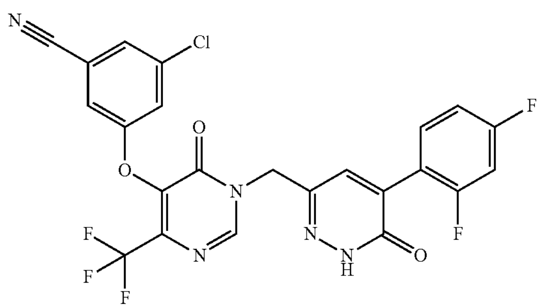 [SMILES: N#Cc1cc(Cl)cc(Oc2c(C(F)(F)F)ncn(Cc3cc(-c4ccc(F)cc4F)c(=O)[nH]n3)c2=O)c1] | 3-chloro-5-((1-((5-(2,4-difluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 536, 538 ¹H NMR (DMSO-d6, 400 MHz) δ 13.27 (s, 1H), 8.81 (s, 1H), 7.81 (s, 1H), 7.74 (s, 1H), 7.70 (s, 1H), 7.80 (s, 1H), 7.40-7.43 (m, 2H), 7.20 (d, J = 2.4 Hz, 1H), 5.20 (s, 2H). |
| 36 | 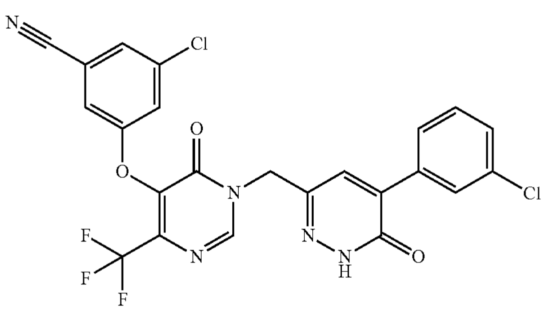 [SMILES: N#Cc1cc(Cl)cc(Oc2c(C(F)(F)F)ncn(Cc3cc(-c4cccc(Cl)c4)c(=O)[nH]n3)c2=O)c1] | 3-chloro-5-((1-((5-(3-chlorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 534, 536 ¹H NMR (DMSO-d6, 400 MHz) δ 13.28 (s, 1H), 8.82 (s, 1H), 7.97 (s, 1H), 7.83-7.97 (m, 3H), 7.74 (s, 1H), 7.68 (s, 1H), 7.54 (s, 1H), 7.52 (s, 1H), 5.21 (s, 2H). |
| 37 | 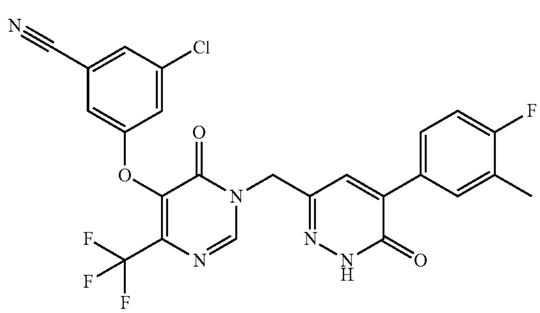 [SMILES: Cc1cc(-c2cc(Cn3cnc(C(F)(F)F)c(Oc4cc(Cl)cc(C#N)c4)c3=O)n[nH]c2=O)ccc1F] | 3-chloro-5-((1-((5-(4-fluoro-3-methylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 532, 534 ¹H NMR (DMSO-d6, 400 MHz) δ 13.13 (s, 1H), 8.77 (s, 1H), 7.77 (s, 1H), 7.69 (s, 1H), 7.64-7.69 (m, 3H), 7.64 (s, 1H), 7.21 (t, J = 7.6 Hz, 1H), 5.15 (s, 2H), 2.24 (s, 3H). |

| Example | Structure | IUPAC Name | MS (M + H)+/NMR |
|---|---|---|---|
| 38 | 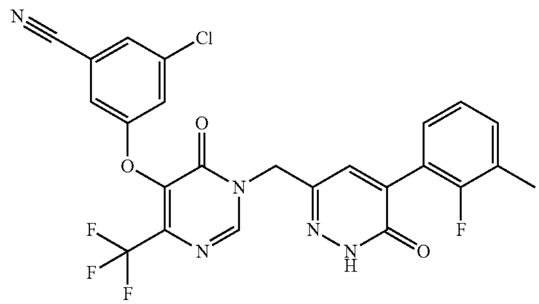 [SMILES: Cc1cccc(-c2cc(Cn3cnc(C(F)(F)F)c(Oc4cc(Cl)cc(C#N)c4)c3=O)n[nH]c2=O)c1F] | 3-chloro-5-((1-((5-(2-fluoro-3-methylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 532, 534 ¹H NMR (DMSO-d6, 400 MHz) δ 13.19 (s, 1H), 8.76 (s, 1H), 7.75 (s, 1H), 7.69 (s, 1H), 7.66 (s, 1H), 7.48 (s, 1H), 7.18-7.27 (m, 2H), 6.99 (d, J = 7.2 Hz, 1H), 5.14 (s, 2H), 2.00 (s, 3H). |
| 39 | 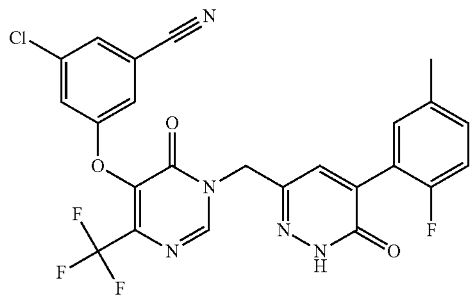 [SMILES: Cc1ccc(F)c(-c2cc(Cn3cnc(C(F)(F)F)c(Oc4cc(Cl)cc(C#N)c4)c3=O)n[nH]c2=O)c1] | 3-chloro-5-((1-((5-(2-fluoro-5-methylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 532, 534 ¹H NMR (DMSO-d6, 400 MHz) δ 13.16 (s, 1H), 8.77 (s, 1H), 7.75 (s, 1H), 7.68 (s, 1H), 7.64 (s, 1H), 7.59 (s, 1H), 7.12-7.27 (m, 3H), 5.15 (s, 2H), 2.27 (s, 3H). |
| 40 | 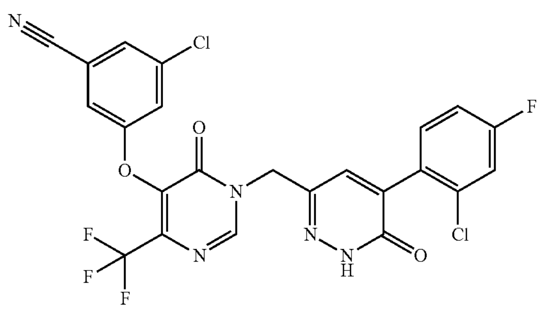 | 3-chloro-5-((1-((5-(2-chloro-4-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 552, 554 ¹H NMR (DMSO-d6, 400 MHz) δ 13.21 (s, 1H), 8.77 (s, 1H), 7.75 (s, 1H), 7.69 (s, 1H), 7.65 (s, 1H), 7.40-7.42 (m, 2H), 7.27-7.31 (m, 2H), 5.15 (s, 2H). |
| 41 | 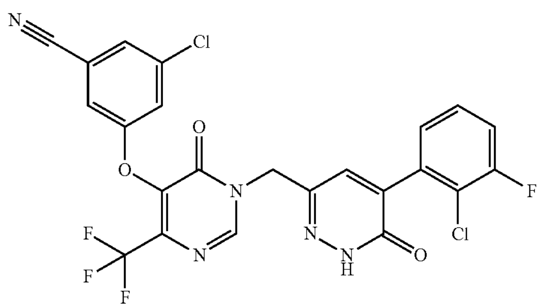 [SMILES: N#Cc1cc(Cl)cc(Oc2c(C(F)(F)F)ncn(Cc3cc(-c4cccc(F)c4Cl)c(=O)[nH]n3)c2=O)c1] | 3-chloro-5-((1-((5-(2-chloro-3-fluorophenyl)-6-oxo-1,6-dihydropyridazin-3-yl)methyl)-6-oxo-4-(trifluoromethyl)-1,6-dihydropyrimidin-5-yl)oxy)benzonitrile | S (ESI) m/z 552, 554 ¹H NMR (DMSO-d6, 400 MHz) δ 13.26 (s, 1H), 8.77 (s, 1H), 7.76 (s, 1H), 7.69 (s, 1H), 7.66 (s, 1H), 7.59 (s, 1H), 7.44-7.49 (m, 2H), 7.18 (d, J = 6.4 Hz, 1H), 5.16 (s, 2H). |
| 42 | 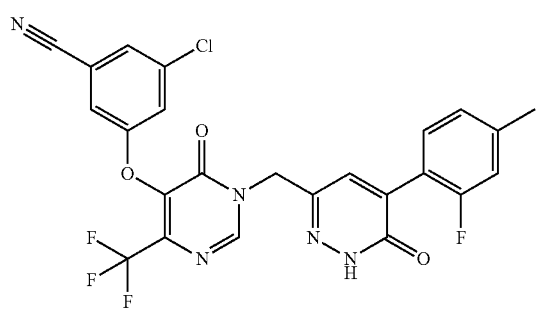 [SMILES: Cc1ccc(-c2cc(Cn3cnc(C(F)(F)F)c(Oc4cc(Cl)cc(C#N)c4)c3=O)n[nH]c2=O)c(F)c1] | 3-chloro-5-((1-((5-(2-fluoro-4-methylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 532, 534 ¹H NMR (DMSO-d6, 400 MHz) δ 13.19 (s, 1H), 8.81 (s, 1H), 7.80 (s, 1H), 7.74 (s, 1H), 7.73 (s, 1H), 7.70 (s, 1H), 7.42-7.46 (m, 1H), 7.11-7.17 (m, 2H), 5.20 (s, 2H), 2.37 (s, 3H). |

-continued

| Example | Structure | IUPAC Name | MS (M + H)+/NMR |
|---|---|---|---|
| 43 | 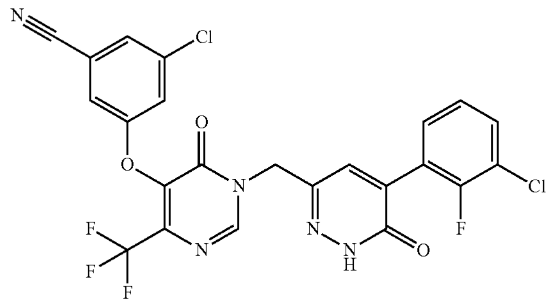 [SMILES: N#Cc1cc(Cl)cc(Oc2c(C(F)(F)F)ncn(Cc3cc(-c4cccc(Cl)c4F)c(=O)[nH]n3)c2=O)c1] | 3-chloro-5-((1-((5-(3-chloro-2-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 552, 554<br>¹H NMR (DMSO-d6, 400 MHz)<br>δ 13.28 (s, 1H), 8.76 (s, 1H), 7.74 (s, 1H), 7.68 (s, 1H), 7.65 (s, 1H), 7.64 (s, 1H), 7.27-7.59 (m, 3H), 5.15 (s, 2H). |
| 44 | 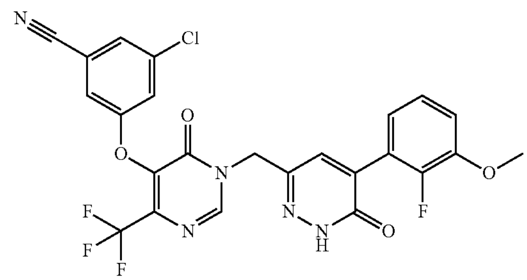 [SMILES: COc1cccc(-c2cc(Cn3cnc(C(F)(F)F)c(Oc4cc(Cl)cc(C#N)c4)c3=O)n[nH]c2=O)c1F] | 3-chloro-5-((1-((5-(2-fluoro-3-methoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 548, 550<br>¹H NMR (DMSO-d6, 400 MHz)<br>δ 13.17 (s, 1H), 8.76 (s, 1H), 7.75 (s, 1H), 7.69 (s, 1H), 7.65 (s, 1H), 7.59 (s, 1H), 7.17-7.22 (m, 2H), 6.96 (d, J = 6.4 Hz, 1H), 5.15 (s, 2H), 3.83 (s, 3H). |
| 45 | 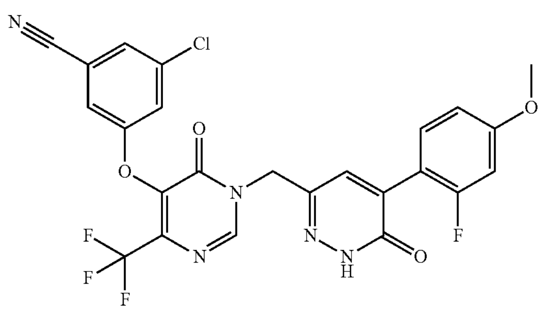 [SMILES: COc1ccc(-c2cc(Cn3cnc(C(F)(F)F)c(Oc4cc(Cl)cc(C#N)c4)c3=O)n[nH]c2=O)c(F)c1] | 3-chloro-5-((1-((5-(2-fluoro-4-methoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 548, 550<br>¹H NMR (DMSO-d6, 400 MHz)<br>δ 13.11 (s, 1H), 8.76 (s, 1H), 7.75 (s, 1H), 7.68 (s, 1H), 7.65-7.66 (m, 1H), 7.55 (s, 1H), 7.49-7.50 (m, 1H), 6.84-6.92 (m, 2H), 5.15 (s, 2H), 3.77 (s, 3H). |
| 46 | 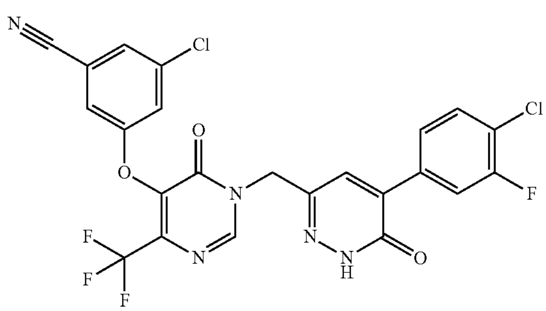 [SMILES: N#Cc1cc(Cl)cc(Oc2c(C(F)(F)F)ncn(Cc3cc(-c4ccc(Cl)c(F)c4)c(=O)[nH]n3)c2=O)c1] | 3-chloro-5-((1-((5-(4-chloro-3-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 552, 554<br>¹H NMR (DMSO-d6, 400 MHz)<br>δ 13.28 (s, 1H), 8.77 (s, 1H), 7.96 (d, J = 9.2 Hz, 1H), 7.83 (s, 1H), 7.65-7.75 (m, 5H), 5.16 (s, 2H). |
| 47 | 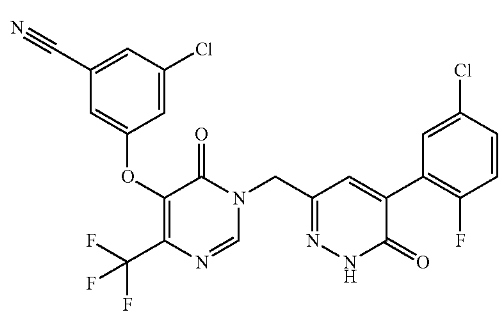 [SMILES: N#Cc1cc(Cl)cc(Oc2c(C(F)(F)F)ncn(Cc3cc(-c4cc(Cl)ccc4F)c(=O)[nH]n3)c2=O)c1] | 3-chloro-5-((1-((5-(5-chloro-2-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 552, 554<br>¹H NMR (DMSO-d6, 400 MHz)<br>δ 13.28 (s, 1H), 8.77 (s, 1H), 7.75-7.53 (m, 6H), 7.35-7.37 (m, 1H), 5.16 (s, 2H). |

| Example | Structure | IUPAC Name | MS (M + H)⁺/NMR |
|---|---|---|---|
| 48 | 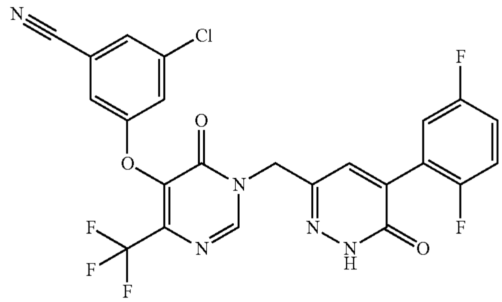 | 3-chloro-5-((1-((5-(2,5-difluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 536, 538 ¹H NMR (DMSO-d6, 400 MHz) δ 13.32 (s, 1H), 8.81 (s, 1H), 7.79 (d, J = 1.6 Hz, 1H), 7.73-7.69 (m, 3H), 7.45-7.37 (m, 3H), 5.20 (s, 2H). |
| 49 | 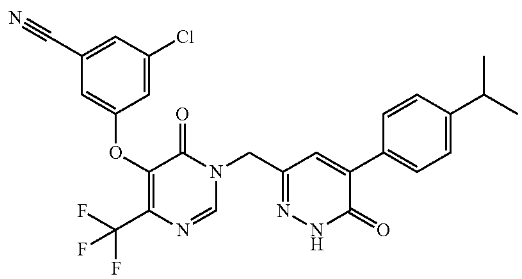 | 3-chloro-5-((1-((5-(4-isopropylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 552, 554 ¹H NMR (DMSO-d6, 400 MHz) δ 13.10 (s, 1H), 8.79 (s, 1H), 7.78-7.68 (m, 6H), 7.33 (d, J = 8.4 Hz, 2H), 5.18 (s, 2H), 2.91 (m, 1H), 1.22 (d, J = 6.8 Hz, 6H). |
| 50 | 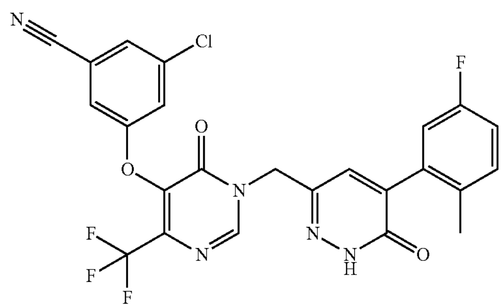 [SMILES: Cc1ccc(F)cc1-c1cc(Cn2cnc(C(F)(F)F)c(Oc3cc(Cl)cc(C#N)c3)c2=O)n[nH]c1=O] | 3-chloro-5-((1-((5-(5-fluoro-2-methylphenyl)-6-oxo-1,6-dihydropyridazin-3-yl)methyl)-6-oxo-4-trifluoromethyl)-1,6-dihydropyrimidin-5-yl)oxy)benzonitrile | MS (ESI) m/z 532, 534 ¹H NMR (DMSO-d6, 400 MHz) δ 13.10 (s, 1H), 879 (s, 1H), 7.78-7.68 (m, 5H), 7.33 (d, J = 8.4 Hz, 2H), 5.18 (s, 2H), 2.07 (s, 3H). |
| 51 | 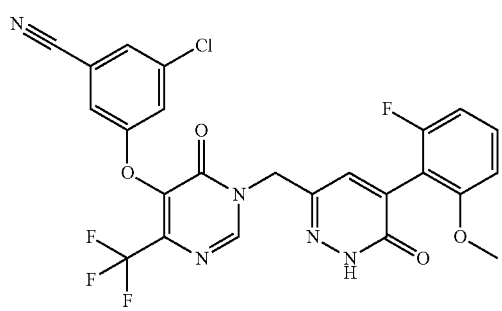 [SMILES: COc1cccc(F)c1-c1cc(Cn2cnc(C(F)(F)F)c(Oc3cc(Cl)cc(C#N)c3)c2=O)n[nH]c1=O] | 3-chloro-5-((1-((5-(2-fluoro-6-methoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 548, 550 ¹H NMR (DMSO-d6, 400 MHz) δ 13.12 (s, 1H), 7.80(s, 1H), 7.70 (s, 1H), 7.69 (s, 1H), 7.58 (s, 1H), 7.43-7.49 (m, 1H), 6.97 (d, J = 8.4 Hz, 1H), 6.91 (t, J = 8.8 Hz, 1H), 5.21 (s, 2H), 3.75 (s, 3H). |
| 52 | 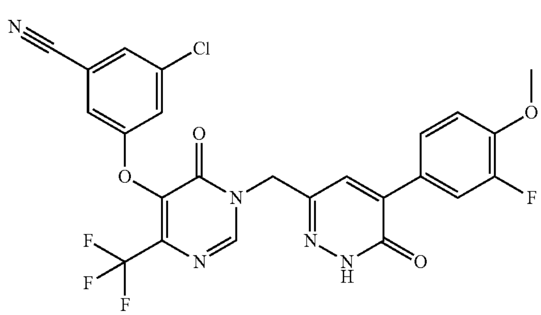 [SMILES: COc1ccc(-c2cc(Cn3cnc(C(F)(F)F)c(Oc4cc(Cl)cc(C#N)c4)c3=O)n[nH]c2=O)cc1F] | 3-chloro-5-((1-((5-(3-fluoro-4-methoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 548, 550 ¹H NMR (DMSO-d6, 400 MHz) δ 13.13 (s, 1H). 8.83 (s, 1H), 7.85 (d, J = 1.6 Hz, 1H), 7.64-7.82 (m, 5H), 7.24 (m, 1H), 5.15 (s, 2H), 3.86 (s, 3H). |

-continued

| Example | Structure | IUPAC Name | MS (M + H)+/NMR |
|---|---|---|---|
| 53 | 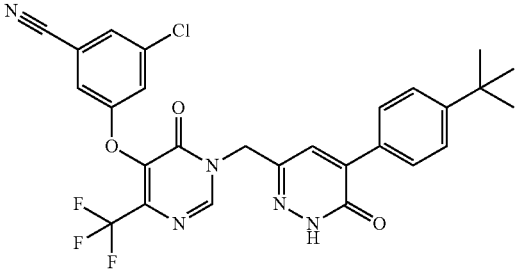 [SMILES: CC(C)(C)c1ccc(-c2cc(Cn3cnc(C(F)(F)F)c(Oc4cc(Cl)cc(C#N)c4)c3=O)n[nH]c2=O)cc1] | 3-((1-((5-(4-(tert-butyl)phenyl)-6-oxo-1,6-dihydropyridazin-3-yl)methyl)-6-oxo-4-(trifluoromethyl)-1,6-dihydropyrimidin-5-yl)oxy)-5-chlorobenzonitrile | MS (ESI) m/z 556, 558 ¹H NMR (DMSO-d6, 400 MHz) δ 13.08 (s, 1H), 8.77 (s, 1H), 7.75-7.65 (m, 6H), 7.45 (d, J = 8.4 Hz, 2H), 5.15 (s, 2H), 1.26 (s, 9H). |
| 54 | 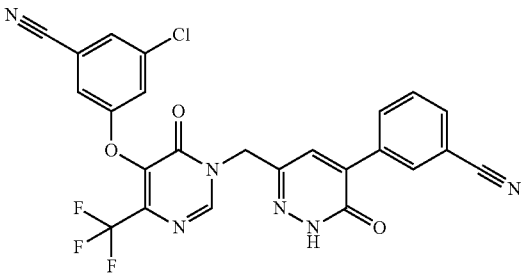 [SMILES: N#Cc1cc(Cl)cc(Oc2c(C(F)(F)F)ncn(Cc3cc(-c4cccc(C#N)c4)c(=O)[nH]n3)c2=O)c1] | 3-chloro-5-((1-((5-(3-cyanophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 525, 527 ¹H NMR (DMSO-d6, 400 MHz) δ 13.29 (s, 1H), 8.78 (s, 1H), 8.26 (s, 1H), 8.14 (d, J = 8.0 H, 1H), 7.91-7.64 (m, 6H), 5.16 (s, 2H). |
| 55 | 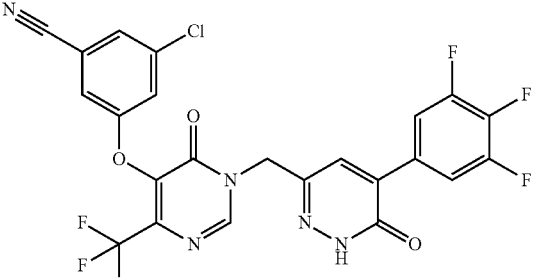 | 3-chloro-5-((6-oxo-1-((6-oxo-5-(3,4,5-trifluorophenyl)-1,6-dihydropyridazin-3-yl)methyl)-4-(trifluoromethyl)-1,6-dihydropyrimidin-5-yl)oxy)benzonitrile | MS (ESI) m/z 554, 556 ¹H NMR (DMSO-d6, 400 MHz) δ 13.33 (s, 1H), 8.78 (s, 1H), 7.90-7.85 (m, 3H), 7.74 (s, 1H), 7.67 (s, 1H), 7.67 (s, 1H), 5.15 (s, 2H). |
| 56 | 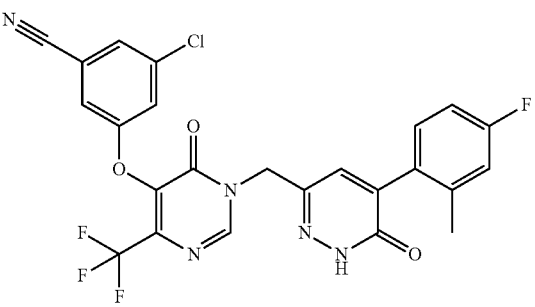 [SMILES: Cc1cc(F)ccc1-c1cc(Cn2cnc(C(F)(F)F)c(Oc3cc(Cl)cc(C#N)c3)c2=O)n[nH]c1=O] | 3-chloro-5-((1-((5-(4-fluoro-2-methylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 532, 534 ¹H NMR (DMSO-d6, 400 MHz) δ 13.16 (s, 1H, 8.79 (s, 1H), 7.78 (s, 1H), 7.72 (s, 1H), 7.68 (s, 1H), 7.48 (s, 1H), 7.06-7.23 (m, 3H), 5.17 (s, 2H), 2.16 (s, 3H). |
| 57 | 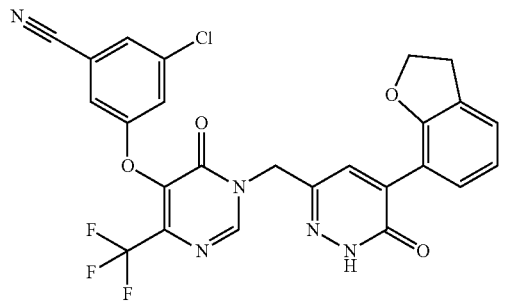 [SMILES: N#Cc1cc(Cl)cc(Oc2c(C(F)(F)F)ncn(Cc3cc(-c4cccc5c4OCC5)c(=O)[nH]n3)c2=O)c1] | 3-chloro-5-((1-((5-(2,3-dihydrobenzofuran-7-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 542, 544 ¹H NMR (DMSO-d6, 400 MHz) δ 13.10 (s, 1H), 8.81 (s, 1H), 7.80 (s, 1H), 7.79 (s, 1H), 7.73 (s, 1H), 7.68 (s, 1H), 7.61 (d, J = 7.6 Hz, 1H), 7.30 (d, J = 6.8 Hz, 1H), 6.90 (t, J = 7.6 Hz, 1H), 5.20 (s, 2H), 4.55 (t, J = 8.8 Hz, 2H), 3.19 (t, J = 8.4 Hz, 2H). |

| Example | Structure | IUPAC Name | MS (M + H)+/NMR |
|---|---|---|---|
| 58 | 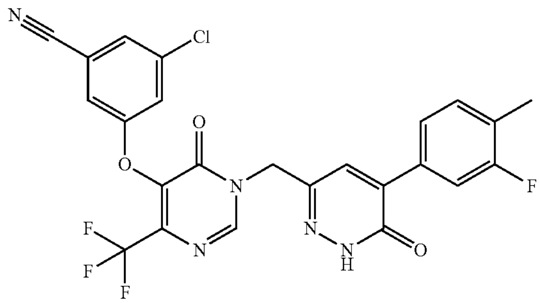 [SMILES: Cc1ccc(-c2cc(Cn3cnc(C(F)(F)F)c(Oc4cc(Cl)cc(C#N)c4)c3=O)n[nH]c2=O)cc1F] | 3-chloro-5-((1-((5-(3-fluoro-4-methylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 532, 534<br>¹H NMR (DMSO-d6, 400 MHz)<br>δ 13.19 (s, 1H), 8.80 (s, 1H), 7.80 (s, 1H), 7.37-7.77 (m, 6H), 5.19 (s, 2H), 2.28 (s, 3H). |
| 59 | 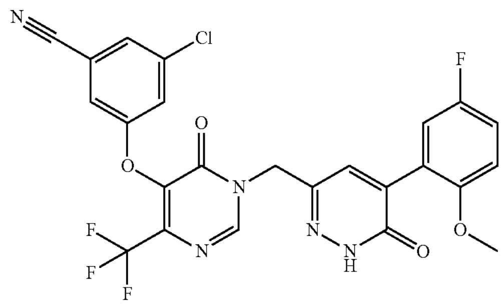 [SMILES: COc1ccc(F)cc1-c1cc(Cn2cnc(C(F)(F)F)c(Oc3cc(Cl)cc(C#N)c3)c2=O)n[nH]c1=O] | 3-chloro-5-((1-((5-(5-fluoro-2-methoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 548, 550<br>¹H NMR (DMSO-d6, 400 MHz)<br>δ 13.07 (s, 1H), 8.77 (s, 1H), 7.75 (s, 1H), 7.69 (s, 1H), 7.65 (s, 1H), 7.54 (s, 1H), 7.06-7.24 (m, 3H), 5.14 (s, 2H), 3.69 (s, 3H). |
| 60 | 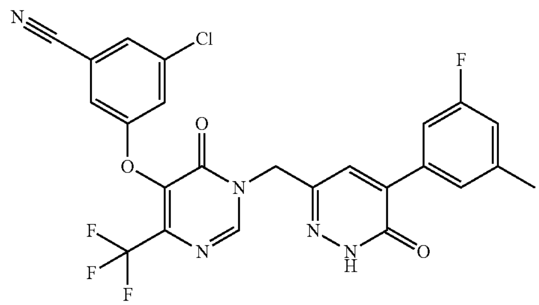 [SMILES: Cc1cc(F)cc(-c2cc(Cn3cnc(C(F)(F)F)c(Oc4cc(Cl)cc(C#N)c4)c3=O)n[nH]c2=O)c1] | 3-chloro-5-((1-((5-(3-fluoro-5-methylphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 532, 534<br>¹H NMR (DMSO-d6, 400 MHz)<br>δ 13.24 (s, 1H), 8.82 (s, 1H), 7.82 (s, 1H), 7.73 (s, 1H), 7.69 (s, 1H), 7.59 (s, 1H), 7.56 (d, J = 10.0 Hz, 1H), 7.53 (s, 1H), 7.16 (d, J = 9.6 Hz, 1H), 5.21 (s, 2H), 2.38 (s, 3H). |
| 61 | 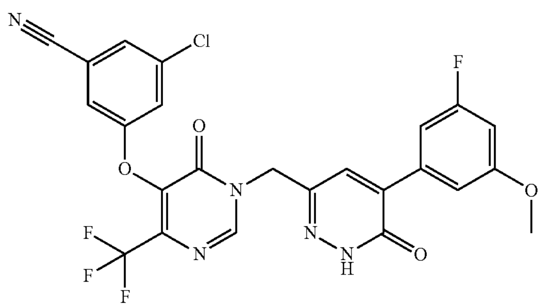 [SMILES: COc1cc(F)cc(-c2cc(Cn3cnc(C(F)(F)F)c(Oc4cc(Cl)cc(C#N)c4)c3=O)n[nH]c2=O)c1] | 3-chloro-5-((1-((5-(3-fluoro-5-methoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 548, 550<br>¹H NMR (DMSO-d6, 400 MHz)<br>δ 13.22 (s, 1H), 8.80 (s, 1H), 7.83 (s, 1H), 7.77 (s, 1H), 7.70 (s, 1H), 7.67 (s, 1H), 7.31 (s, 1H), 7.30 (d, J = 10.4 Hz, 1H), 6.95 (d, J = 11.2 Hz, 1H), 5.19 (s, 2H), 3.81 (s, 3H). |
| 62 | 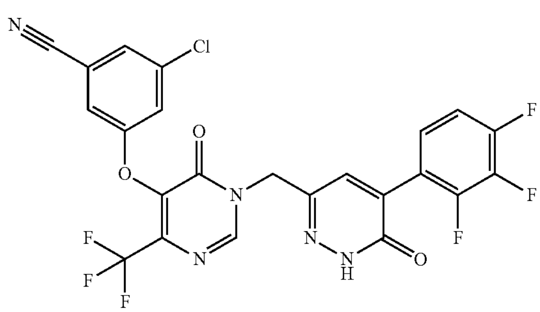 [SMILES: N#Cc1cc(Cl)cc(Oc2c(C(F)(F)F)ncn(Cc3cc(-c4ccc(F)c(F)c4F)c(=O)[nH]n3)c2=O)c1] | 3-chloro-5-((6-oxo-1-((6-oxo-5-(2,3,4-trifluorophenyl)-1,6-dihydropyridazin-3-yl)methyl)-4-(trifluoromethyl)-1,6-dihydropyrimidin-5-yl)oxy)benzonitrile | MS (ESI) m/z 554, 556<br>¹H NMR (DMSO-d6, 400 MHz)<br>δ 13.36 (s, 1H), 8.82 (s, 1H), 7.80 (s, 1H), 7.72 (d, J = 10.0 Hz, 1H), 7.70 (s, 1H), 7.68 (s, 1H), 7.48 (s, 1H), 7.44 (t, J = 9.2 Hz, 1H), 5.21 (s, 2H). |

| Example | Structure | IUPAC Name | MS (M + H)⁺/NMR |
|---|---|---|---|
| 63 | 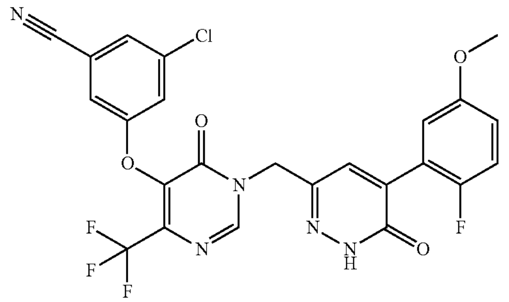 [SMILES: COc1ccc(F)c(-c2cc(Cn3cnc(C(F)(F)F)c(Oc4cc(Cl)cc(C#N)c4)c3=O)n[nH]c2=O)c1] | 3-chloro-5-((1-((5-(2-fluoro-5-methoxyphenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 548, 550<br>¹H NMR (DMSO-d6, 400 MHz) δ 13.19 (s, 1H), 8.79 (s, 1H), 7.77-7.66 (m, 2H), 7.69 (s, 1H), 7.65 (s, 1H), 7.21 (d, J = 9.2 Hz, 1H), 7.08-7.02 (m, 2H), 5.19 (s, 2H), 3.75 (s, 3H). |
| 64 | 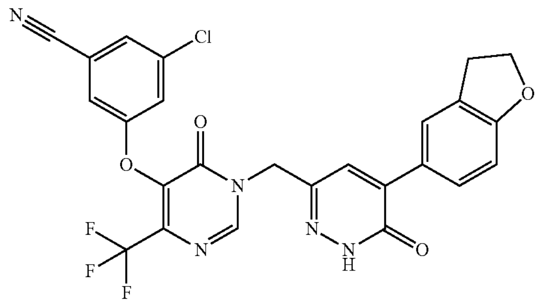 [SMILES: N#Cc1cc(Cl)cc(Oc2c(C(F)(F)F)ncn(Cc3cc(-c4ccc5c(c4)CCO5)c(=O)[nH]n3)c2=O)c1] | 3-chloro-5-((1-((5-(2,3-dihydrobenzofuran-5-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 542, 544<br>¹H NMR (DMSO-d6, 400 MHz) δ 13.02 (s, 1H), 8.76 (s, 1H), 7.77 (s, 1H), 7.75 (s, 1H), 7.69 (s, 1H), 7.66 (s, 1H), 7.65-7.63 (m, 2H), 6.81 (d, J = 8.4 Hz, 1H), 5.21 (s, 2H), 4.55 (t, J = 8.8 Hz, 2H), 3.19 (t, J = 8.4 Hz, 2H). |
| 65 | 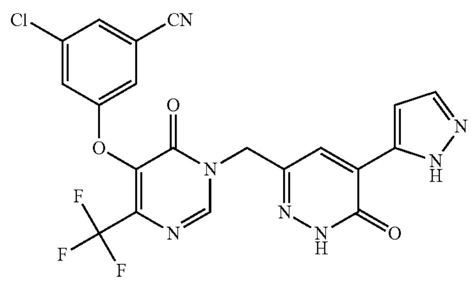 [SMILES: N#Cc1cc(Cl)cc(Oc2c(C(F)(F)F)ncn(Cc3cc(-c4ccn[nH]4)c(=O)[nH]n3)c2=O)c1] | 3-chloro-5-((6-oxo-1-((6-oxo-5-(1H-pyrazol-5-yl)-1,6-dihydropyridazin-3-yl)methyl)-4-(trifluoromethyl)-1,6-dihydropyrimidin-5-yl)oxy)benzonitrile | MS (ESI): m/z 490, 492<br>¹H NMR (CD3OD-d6, 400 MHz): δ 8.57 (s, 1H), 7.98 (s, 1H), 7.68 (s, H), 7.51 (s, 1H), 7.36 (s, 2H), 7.16 (s, 1H), 5.24 (s, 2H). |
| 66 | 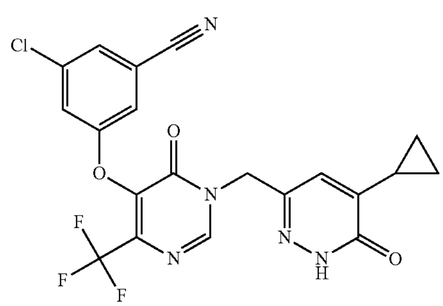 [SMILES: N#Cc1cc(Cl)cc(Oc2c(C(F)(F)F)ncn(Cc3cc(C4CC4)c(=O)[nH]n3)c2=O)c1] | 3-chloro-5-((1-((5-cyclopropyl-6-oxo-1,6-dihydropyridazin-3-yl)methyl)-6-oxo-4-(trifluoromethyl)-1,6-dihydropyrimidin-5-yl)oxy)benzonitrile | MS (ESI): m/z 464, 466<br>¹H NMR (DMSO-d6, 400 MHz): δ 12.81 (s, 1H, NH), 8.72 (s, 1H, ArH), 7.65-7.78 (m, 3H), ArH), 7.08 (s, 1H, ArH), 5.05 (s, 2H, CH₂), 2.03-2.07 (m, 1H, CH), 0.81-1.03 (m, 4H, CH₂CH₂). |
| 67 | 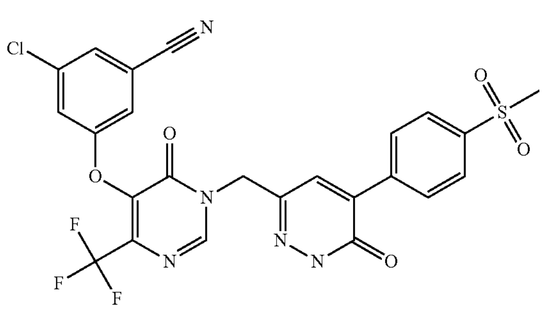 [SMILES: CS(=O)(=O)c1ccc(-c2cc(Cn3cnc(C(F)(F)F)c(Oc4cc(Cl)cc(C#N)c4)c3=O)n[nH]c2=O)cc1] | 3-chloro-5-((1-((5-(4-(methylsulfonyl)phenyl)-6-oxo-1,6-dihydropyridazin-3-yl)methyl)-6-oxo-4-(trifluoromethyl)-1,6-dihydropyrimidin-5-yl)oxy)benzonitrile | MS (ESI): m/z 578, 580<br>¹H NMR (DMSO-d6, 400 MHz) δ 13.29 (s, 1H, 8.77 (s, 1H), 8.03 (d, J = 8.4 Hz, 2H), 7.97 (d, J = 8.4 Hz, 2H), 7.79 (s, 1H), 7.74 (s, 1H), 7.69 (s, 1H), 7.64 (s, 1H), 5.17 (s, 2H), 3.22 (s, 3H). |

| Example | Structure | IUPAC Name | MS (M + H)+/NMR |
|---|---|---|---|
| 68 | 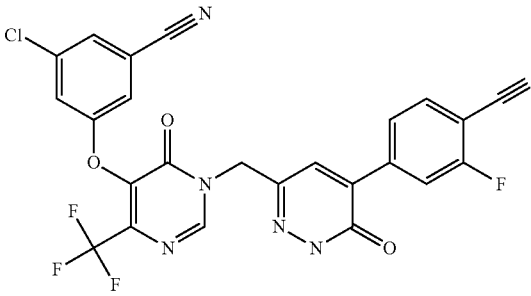 | 4-(6-((5-(3-chloro-5-cyanophenoxy)-6-oxo-4-(trifluoromethyl)pyrimidin-1(6H)-yl)methyl)-3-oxo-2,3-dihydropyridazin-4-yl)-2-fluorobenzonitrile | MS (ESI): m/z 543, 545<br>$^1$H NMR (DMSO-d6, 400 MHz) δ 13.39 (s, 1H, 8.78 (s, 1H), 8.00-8.05 (m, 2H), 7.86-7.89 (m, 2H), 7.75 (s, 1H), 7.78 (s, 1H) 7.65 (s, 1H), 5.17 (s, 2H). |
| 69 | 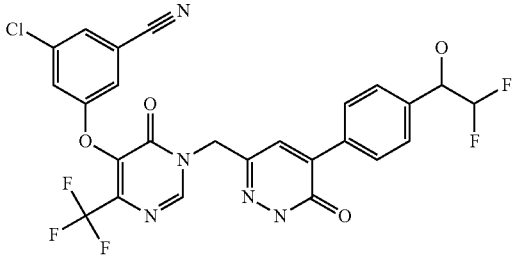 [SMILES: N#Cc1cc(Cl)cc(Oc2c(C(F)(F)F)ncn(Cc3cc(-c4ccc(C(O)C(F)F)cc4)c(=O)[nH]n3)c2=O)c1] | 3-chloro-5-((1-((5-(4-(2,2-difluoro-1-hydroxyethyl)phenyl)-6-oxo-1,6-dihydropyridazin-3-yl)methyl)-6-oxo-4-(trifluoromethyl)-1,6-dihydropyrimidin-5-yl)oxy)benzonitrile | MS (ESI): m/z 580, 582<br>$^1$H NMR (DMSO-d6, 400 MHz) δ 13.14 (s, 1H, 8.78 (s, 1H), 7.81 (d, J = 8.4 Hz, 2H), 7.65-7.76 (m, 4H), 7.48 (d, J = 8.4 Hz, 2H), 6.01 (td, J = 4.0 Hz, 56.0 Hz, 1H), 5.17 (s, 2H), 4.76-4.82 (m, 1H). |
| 70 | 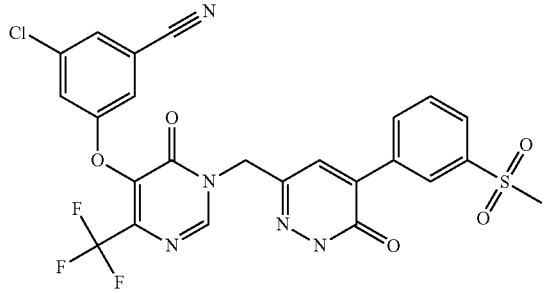 [SMILES: CS(=O)(=O)c1cccc(-c2cc(Cn3cnc(C(F)(F)F)c(Oc4cc(Cl)cc(C#N)c4)c3=O)n[nH]c2=O)c1] | 3-chloro-5-((1-((5-(3-(methylsulfonyl)phenyl)-6-oxo-1,6-dihydropyridazin-3-yl)methyl)-6-oxo-4-(trifluoromethyl)-1,6-dihydropyrimidin-5-yl)oxy)benzonitrile | MS (ESI): m/z 578, 580<br>$^1$H NMR (DMSO-d6, 400 MHz) δ 13.27 (s, 1H, 8.78 (s, 1H), 8.37 (s, 1H), 8.11 (d, J = 8.0 Hz, 1H), 7.98 (d, J = 7.6 Hz, 1H), 7.85 (s, 1H), 7.63-7.75 (m, 4H), 5.18 (s, 2H) 3.21 (s, 3H). |
| 71 | 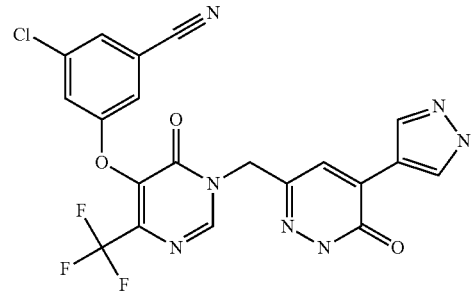 [SMILES: N#Cc1cc(Cl)cc(Oc2c(C(F)(F)F)ncn(Cc3cc(-c4cn[nH]c4)c(=O)[nH]n3)c2=O)c1] | 3-chloro-5-((6-oxo-1-((6-oxo-5-(1H-pyrazol-4-yl)-1,6-dihydropyridazin-3-yl)methyl)-4-(trifluoromethyl)-1,6-dihydropyrimidin-5-yl)oxy)benzonitrile | MS (ESI): m/z 490, 492<br>$^1$H NMR (DMSO-d6, 400 MHz) δ 12.99 (s, 1H, 8.76 (s, 1H), 8.24-8.38 (m, 2H), 7.77 (s, 1H), 7.74 (s, 1H), 7.67 (s, 1H), 7.63 (s, 1H), 5.12 (s, 2H) |
| 72 | 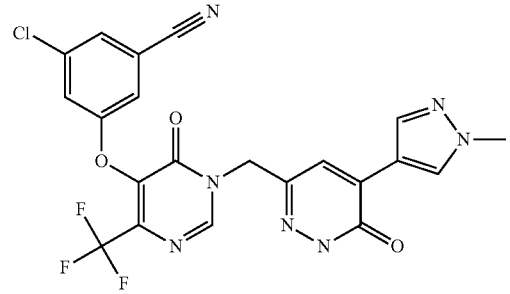 [SMILES: Cn1cc(-c2cc(Cn3cnc(C(F)(F)F)c(Oc4cc(Cl)cc(C#N)c4)c3=O)n[nH]c2=O)cn1] | 3-chloro-5-((1-((5-(1-methyl-1H-pyrazol-4-yl)-6-oxo-1,6-dihydropyridazin-3-yl)methyl)-6-oxo-4-(trifluoromethyl)-1,6-dihydropyrimidin-5-yl)oxy)benzonitrile | MS (ESI): m/z 504, 506<br>$^1$H-NMR(DMSO-d6, 400 MHz) δ 13.01 (s, 1H, 8.77 (s, 1H), 8.50 (s, 1H), 8.10 (s, 1H), 7.73-7.75 (m, 2H), 7.67 (s, 1H), 7.63 (s, 1H), 5.12 (s, 2H), 3.85 (s, 3H). |

| Example | Structure | IUPAC Name | MS (M + H)⁺/NMR |
|---|---|---|---|
| 73 | 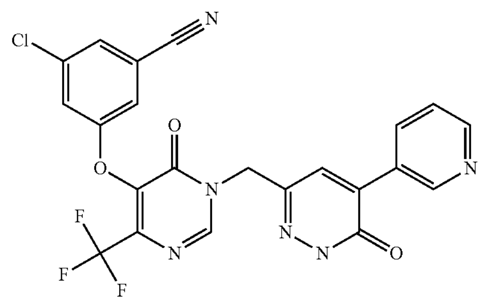 [SMILES: N#Cc1cc(Cl)cc(Oc2c(C(F)(F)F)ncn(Cc3cc(-c4cccnc4)c(=O)[nH]n3)c2=O)c1] | 3-chloro-5-((6-oxo-1-((6-oxo-5-(pyridin-3-yl)-1,6-dihydropyridazin-3-yl)methyl)-4-(trifluoromethyl)-1,6-dihydropyrimidin-5-yl)oxy)benzonitrile | MS (ESI): m/z 501, 503<br>$^1$H NMR (DMSO-d6, 400 MHz) δ 13.37 (s, 1H), 9.14 (s, 1H), 8.80 (s, 1H), 8.74 (d, J = 4.4 Hz 1H), 8.51 (d, J = 8.4 Hz 1H), 7.92 (s, 1H), 7.73-7.77 (m, 2H), 7.67 (s, 1H), 7.63 (s, 1H), 5.18 (s, 2H). |
| 74 | 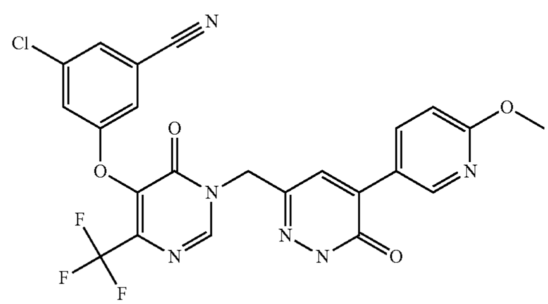 [SMILES: COc1ccc(-c2cc(Cn3cnc(C(F)(F)F)c(Oc4cc(Cl)cc(C#N)c4)c3=O)n[nH]c2=O)cn1] | 3-chloro-5-((1-((5-(6-methoxypyridin-3-yl)-6-oxo-1,6-dihydropyridazin-3-yl)methyl)-6-oxo-4-(trifluoromethyl)-1,6-dihydropyrimidin-5-yl(oxy)benzonitrile | MS (ESI): m/z 531, 533<br>$^1$H NMR (DMSO-d6, 400 MHz) δ 13.14 (s, 1H, 8.77 (s, 1H), 8.68 (d, J = 2.4 Hz, 1H), 8.15 (dd, J = 2 Hz, 8.8 Hz, 1H), 7.73 (d, J = 4.2 Hz, 2H), 7.67 (s, 1H), 7.63 (s, 1H) 6.99 (d, J = 8.8 Hz, 1H), 5.15 (s, 2H), 3.86 (s, 3H). |
| 75 | 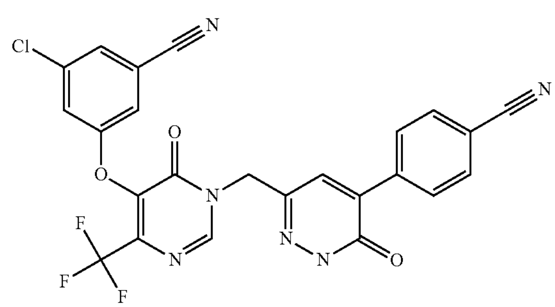 [SMILES: N#Cc1ccc(-c2cc(Cn3cnc(C(F)(F)F)c(Oc4cc(Cl)cc(C#N)c4)c3=O)n[nH]c2=O)cc1] | 3-chloro-5-((1-((5-(4-cyanophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI): m/z 525, 527<br>$^1$H-NMR (DMSO-d6, 400 MHz) δ 13.29 (s, 1H), 8.76 (s, 1H), 7.99 (d, J = 8.4 Hz, 2H), 7.91 (d, J = 8.4 Hz, 2H), 7.80 (s, 1H), 7.74 (s, 1H), 7.68 (s, 1H), 7.64 (s, 1H), 5.16 (s, 2H). |
| 76 | 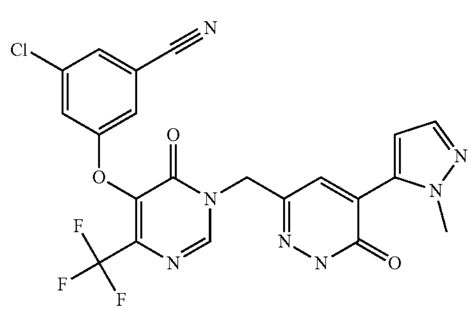 [SMILES: Cn1nccc1-c1cc(Cn2cnc(C(F)(F)F)c(Oc3cc(Cl)cc(C#N)c3)c2=O)n[nH]c1=O] | 3-chloro-5-((1-((5-(1-methyl-1H-pyrazol-5-yl)-6-oxo-1,6-dihydropyridazin-3-yl)methyl)-6-oxo-4-(trifluoromethyl)-1,6-dihydropyrimidin-5-yl)oxy)benzonitrile | MS (ESI): m/z 504, 506<br>$^1$H NMR (DMSO-d6, 400 MHz) δ 13.30 (s, 1H), 8.77 (s, 1H), 7.74 (s, 1H), 7.68 (s, 1H), 7.62-7.65 (s, 2H), 7.45 (d, J = 2.0 Hz, 1H), 6.50 (d, J = 2.0 Hz, 1H), 5.15 (s, 2H), 3.73 (s, 3H). |

EXAMPLE 77

3-chloro-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile

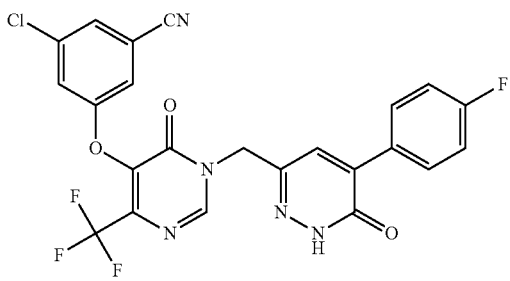 [SMILES: N#Cc1cc(Cl)cc(Oc2c(C(F)(F)F)ncn(Cc3cc(-c4ccc(F)cc4)c(=O)[nH]n3)c2=O)c1]

Step 1 ethyl 2-(4-fluorophenyl)-2-oxoacetate

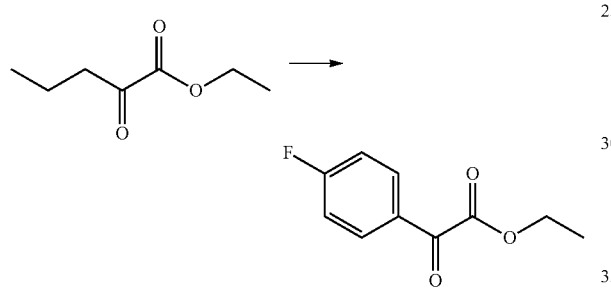

Into a 10-L round-bottom flask purged and maintained with an inert atmosphere of nitrogen, was placed a solution of diethyl oxalate (360 g, 2.46 mol, 1.00 equiv) in tetrahydrofuran (3000 mL). This was followed by the addition of a solution of 4-fluorophenylmagnesium bromide in tetrahydrofuran (1.9 L, 1 N 0.78 equiv) dropwise with stirring at −78° C. in 2.5 hr. The resulting solution was stirred for 30 min at −78° C., then slowly warmed to −20° C. The reaction was then quenched by the addition of 500 mL of 2 M HCl. The resulting solution was extracted with 2×500 mL of ethyl acetate and the organic layers combined. The resulting mixture was washed with 2×200 mL of brine. The mixture was dried over anhydrous magnesium sulfate and concentrated under reduced pressure. The crude product was purified by distillation under reduced pressure (5 mm Hg) and the fraction was collected at 106° C. This resulted in 290 g of ethyl 2-(4-fluorophenyl)-2-oxoacetate as a yellow oil.

Step 2 ethyl 5-((tert-butyldiphenylsilyl)oxy)-2-(4-fluorophenyl)-2-hydroxy-4-oxopentanoate

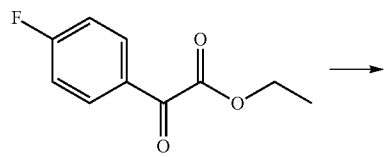

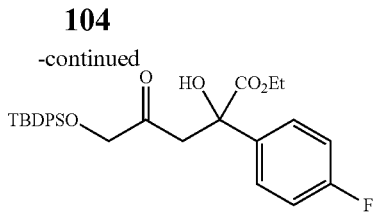

Into a 250-mL sealed tube purged and maintained with an inert atmosphere of nitrogen, was placed ethyl 2-(4-fluorophenyl)-2-oxoacetate (55 g, 280 mmol, 1.00 equiv), 1-[(tert-butyldiphenylsilyl)oxy]propan-2-one (110 g, 352 mmol, 1.26 equiv), acetic acid (33 g, 550 mmol, 1.96 equiv), pyrrolidine (7.8 g, 93 mmol, 0.33 equiv). The resulting solution was stirred overnight at 85° C. and then applied onto a silica gel column with ethyl acetate/petroleum ether (1:60-1:10). This resulted in 45 g of ethyl 5-[(tert-butyldiphenylsilyl)oxy]-2-(4-fluorophenyl)-2-hydroxy-4-oxopentanoate as brown oil.

Step 3 6-[[(tert-butyldiphenylsilyl)oxy]methyl]-4-(4-fluorophenyl)-2,3-dihydropyridazin-3-one

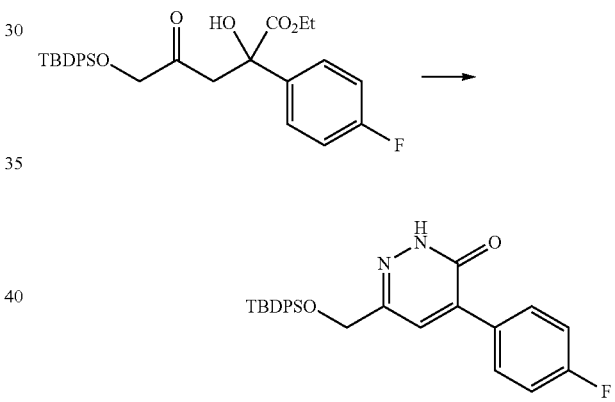

Into a 1000-mL 4-necked round-bottom flask purged and maintained with an inert atmosphere of nitrogen, was placed a solution of ethyl 5-[(tert-butyldiphenylsilyl)oxy]-2-(4-fluorophenyl)-2-hydroxy-4-oxopentanoate (292 g, 574 mmol) in acetic acid (520 mL). This was followed by the addition of hydrazine hydrate (115 g, 2.30 mol) dropwise with stirring below 30° C. in 30 min. The resulting solution was stirred for 3 h at r.t., then, heated to 80° C. for 2 hr. The reaction mixture was then poured into 2000 mL of water/ice. The resulting solution was extracted with 3×1000 of ethyl acetate and the organic layers combined. The resulting mixture was washed with 2000 mL of 5% NaHCO$_3$ and 1000 mL of brine. The mixture was dried over anhydrous sodium sulfate and concentrated under vacuum. The crude product was purified by re-crystallization from n-hexane to afford 6-[[(tert-butyldiphenylsilyl)oxy]methyl]-4-(4-fluorophenyl)-2,3-dihydropyridazin-3-one (150 g) as a white solid.

Step 4 6-[[(tert-butyldiphenylsilyl)oxy]methyl]-4-(4-fluorophenyl)-2-(oxan-2-yl)-2,3-dihydropyridazin-3-one

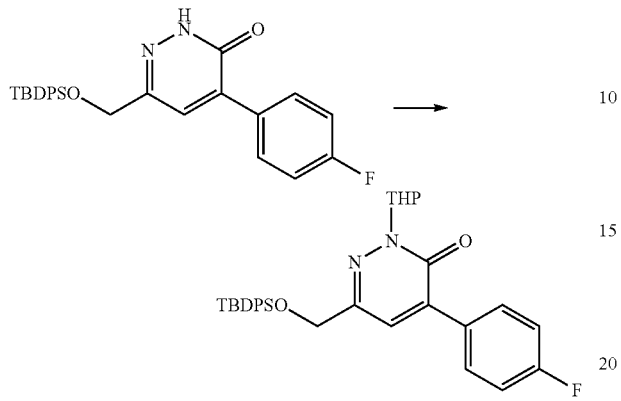

Into a 2000-mL round-bottom flask purged and maintained with an inert atmosphere of nitrogen, was placed a solution of 6-[[(tert-butyldiphenylsilyl)oxy]methyl]-4-(4-fluorophenyl)-2,3-dihydropyridazin-3-one (150 g, 327 mmol, 1.00 equiv) in toluene (1.2 L), 3,4-dihydro-2H-pyran (80 g, 951 mmol, 2.91 equiv), PPTS (15 g, 59.8 mmol, 0.18 equiv). The resulting solution was stirred for 5 h at 90° C. To this added additional DHP (55 g, 654 mmol), and the mixture was stirred overnight at 90° C. The reaction mixture was cooled to room temperature and then poured into 1000 mL of 5% NaHCO$_3$. The resulting solution was extracted with 2×500 mL of ethyl acetate and the organic layers combined. The resulting mixture was washed with 500 mL of brine. The mixture was dried over anhydrous sodium sulfate and concentrated under vacuum. This resulted in 220 g (crude) of 6-[[(tert-butyldiphenylsilyl)oxy]methyl]-4-(4-fluorophenyl)-2-(oxan-2-yl)-2,3-dihydropyridazin-3-one as brown oil.

Step 5 4-(4-fluorophenyl)-6-(hydroxymethyl)-2-(oxan-2-yl)-2,3-dihydropyridazin-3-one

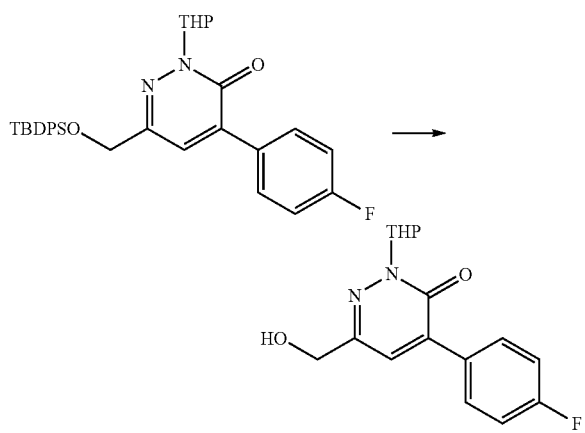

Into a 2000-mL round-bottom flask purged and maintained with an inert atmosphere of nitrogen, was placed a solution of 6-[[(tert-butyldiphenylsilyl)oxy]methyl]-4-(4-fluorophenyl)-2-(oxan-2-yl)-2,3-dihydropyridazin-3-one (220 g, 324 mmol, 1.00 equiv, 80%) in tetrahydrofuran (1.1 L). This was followed by the addition of Bu$_4$NF (87 g, 333 mmol, 1.03 equiv) in several batches at 20° C. in 5 min. The resulting solution was stirred for 30 min at room temperature and then poured into 1000 mL of 5% NaHCO$_3$. The resulting solution was extracted with 2×500 mL of ethyl acetate and the organic layers combined. The resulting mixture was washed with 1000 mL of brine. The mixture was dried over anhydrous sodium sulfate and concentrated under vacuum. The residue was applied onto a silica gel column with ethyl acetate/petroleum ether (1:10-1:1). This resulted in 75 g of 4-(4-fluorophenyl)-6-(hydroxymethyl)-2-(oxan-2-yl)-2,3-dihydropyridazin-3-one as a white solid.

MS (ESI) m/z 305 (M+H)$^+$

Step 6 6-(bromomethyl)-4-(4-fluorophenyl)-2-(tetrahydro-2H-pyran-2-yl)pyridazin-3(2H)-one

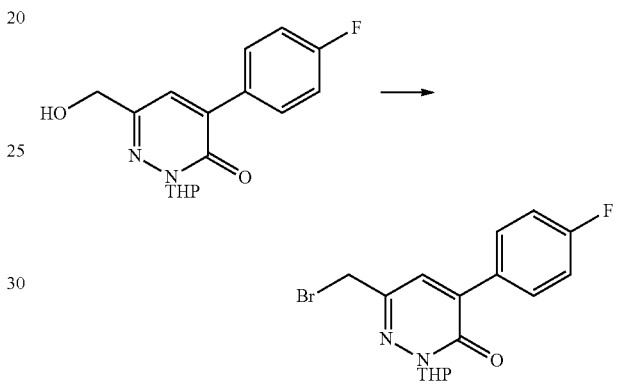

To a stirring solution of 4-(4-fluorophenyl)-6-(hydroxymethyl)-2-(tetrahydro-2H-pyran-2-yl)pyridazin-3(2H)-one (10 g, 32.9 mmol) in DCM (40 mL) at 0° C. was added CBr$_4$ (13.08 g, 39.4 mmol) followed by a slow addition of a solution of triphenylphosphine (10.34 g, 39.4 mmol) in DCM (10 mL). The resulting mixture was allowed to stir at 0° C. for 1 hr and then concentrated under reduced pressure. Diethyl ether (500 mL) was added to the crude mixture and solids were filtered out. The filtrate was concentrated under reduced pressure and the crude product was purified by column chromatography on silica gel (ethyl acetate/hexane (0%-60%) as eluent) to afford 6-(bromomethyl)-4-(4-fluorophenyl)-2-(tetrahydro-2H-pyran-2-yl)pyridazin-3(2H)-one as a white solid (9.86 g).

MS (ESI) m/z 367, 369 (M+H)$^+$

Step 7 3-chloro-5-((1-((5-(4-fluorophenyl)-6-oxo-1-(tetrahydro-2H-pyran-2-yl)-1,6-dihydropyridazin-3-yl)methyl)-6-oxo-4-(trifluoromethyl)-1,6-dihydropyrimidin-5-yl)oxy)benzonitrile

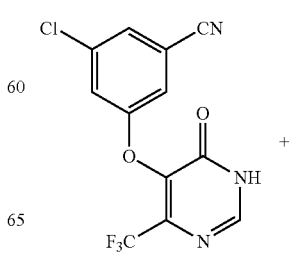

+

-continued

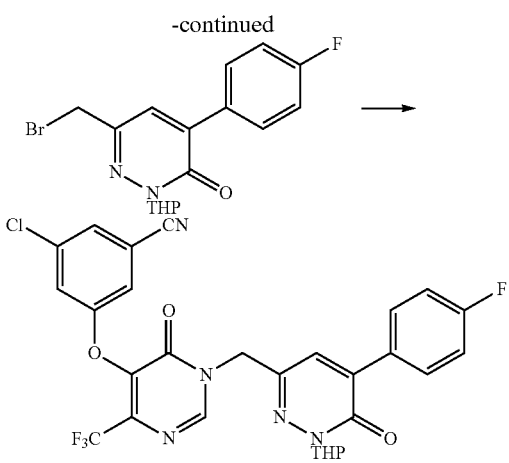

To a mixture of 6-(bromomethyl)-4-(4-fluorophenyl)-2-(tetrahydro-2H-pyran-2-yl) pyridazin-3(2H)-one (10.59 g, 28.8 mmol), and 3-chloro-5-((6-oxo-4-(trifluoromethyl)-1,6-dihydropyrimidin-5-yl)oxy)benzonitrile (9.10 g, 28.8 mmol) in DMF (35 mL) was added DIPEA (6.55 mL, 37.5 mmol) at 0° C. After 30 min the reaction mixture was warmed up to room temperature and stirring was continued for an additional 1 hr. The mixture was concentrated under reduced pressure and water (200 mL) was added. The resulting precipitate was collected by filtration and washed with water (2×50 mL) followed by diethyl ether (3×50 mL) to afford 3-chloro-5-((1-((5-(4-fluorophenyl)-6-oxo-1-(tetrahydro-2H-pyran-2-yl)-1,6-dihydropyridazin-3-yl)methyl)-6-oxo-4-(trifluoromethyl)-1,6-dihydropyrimidin-5-yl)oxy)benzonitrile as a white solid (16.27 g).

MS (ESI) m/z 601, 602 (M+H)$^+$

Step 8 3-chloro-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile

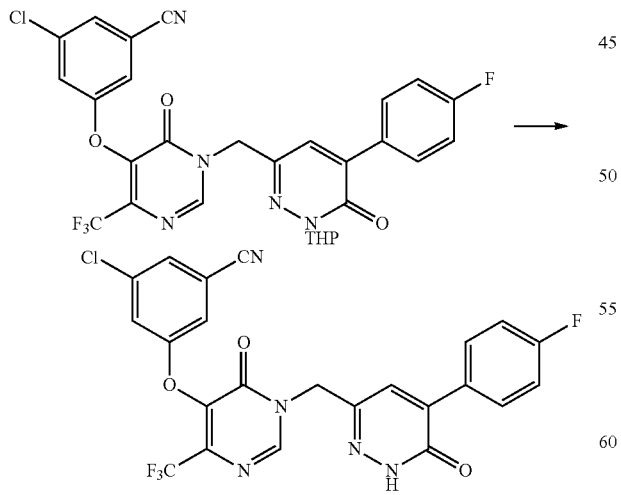

A solution of 3-chloro-5-((1-((5-(4-fluorophenyl)-6-oxo-1-(tetrahydro-2H-pyran-2-yl)-1,6-dihydropyridazin-3-yl)methyl)-6-oxo-4-(trifluoromethyl)-1,6-dihydropyrimidin-5-yl)oxy)benzonitrile (15.78 g, 26.2 mmol) in TFA (40.4 mL, 524 mmol) was stirred at r.t. for 1 hr. TFA was removed under reduced pressure and diethyl ether (250 mL) was added. The resulting solid was collected by filtration and washed with diethyl ether (2×125 mL) to afford 3-chloro-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile as a white solid (11.67 g).

MS (ESI) m/z 518, 520 (M+H)$^+$
$^1$H NMR: (DMSO-d6, 400 MHz)
δ 13.13 (s, 1H), 8.74 (s, 1H), 7.87 (t, J=6.8 Hz, 2H), 7.62-7.72 (m, 4H), 7.26 (t, J=6.8 Hz, 2H), 5.14 (s, 2H).

EXAMPLE 78

3-chloro-5-((1-((5-(6-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile

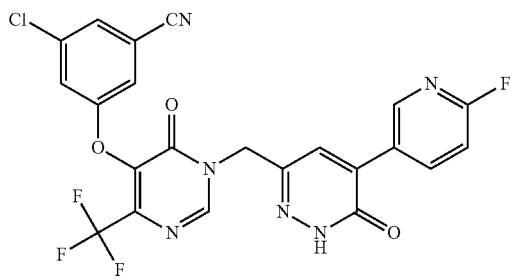 [SMILES: N#Cc1cc(Cl)cc(Oc2c(C(F)(F)F)ncn(Cc3cc(-c4ccc(F)nc4)c(=O)[nH]n3)c2=O)c1]

Step 1: 3-chloro-5-((1-((5-(6-fluoropyridin-3-yl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile

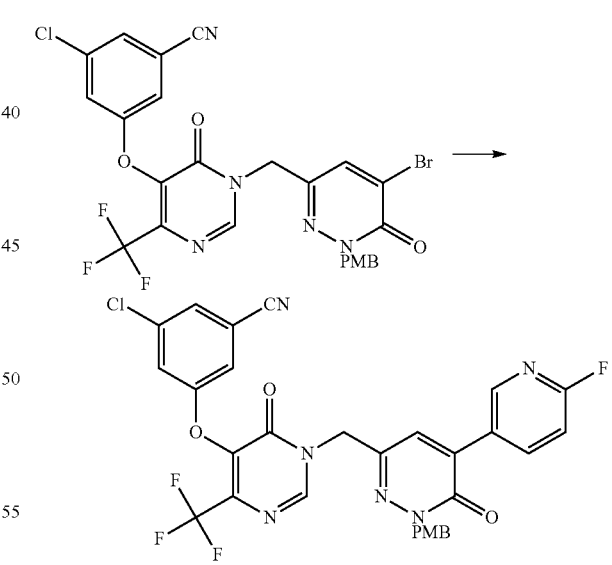

To a solution of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (80.0 mg, 0.13 mmol) in 1,4-dioxane/H$_2$O (5 mL/1 mL) was added (2-fluoro-5-pyridine)boronic acid (41 mg, 0.26 mmol), Pd(dppf)Cl$_2$ (15.0 mg) and potassium carbonate (35 mg, 0.26 mmol) at r.t. The mixture was stirred at 90° C. for 1 hr. After cooling to r.t., the mixture was diluted with water (10 mL) and extracted with ethyl acetate (20 mL×3).

The combined organic extracts were dried over sodium sulfate, filtered and concentrated under reduced pressure to give the desired product 3-chloro-5-((1-((5-(6-fluoropyridin-3-yl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (50 mg).

MS (ESI) m/z 639, 641 (M+H)+

Step 2: 3-chloro-5-((1-((5-(6-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile

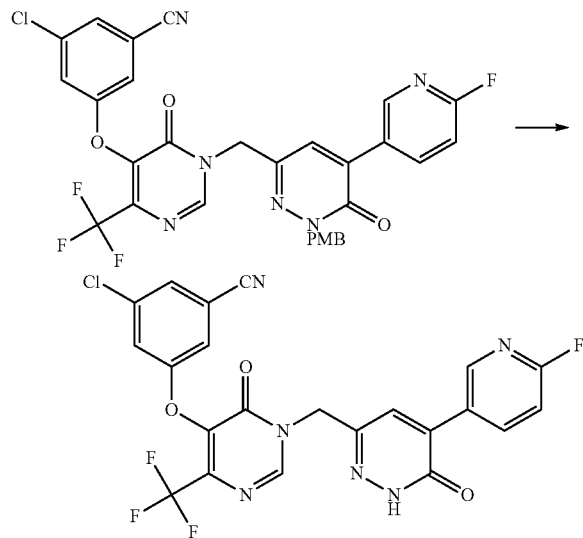

To a solution of 3-chloro-5-((1-((5-(6-fluoropyridin-3-yl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (50 mg, 0.08 mmol) in acetonitrile/$H_2O$ (5 mL/1 mL) was added CAN (0.22 g, 0.4 mmol). The resulting mixture was stirred at r.t. overnight. LCMS indicated the reaction was completed. The reaction mixture was diluted with ethyl acetate and washed with water, dried over sodium sulfate, filtered and concentrated under reduced pressure. The residue was purified by preparative HPLC to afford the title product 3-chloro-5-((1-((5-(6-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile (20 mg).

$^1$H (DMSO-d6, 400 MHz) δ 13.28 (s, 1H), 8.77 (s, 1H), 8.68 (s, 1H), 8.41 (dd, J=2.4, 8.4 Hz 1H), 7.83 (s, 1H), 7.74 (s, 1H), 7.68 (s, 1H), 7.64 (s, 1H), 7.61 (dd, J=2.4, 8.4 Hz, 1H), 5.16 (s, 2H).

MS (ESI) m/z 519, 521 (M+H)+

Using an analogous procedure to that given for Example 78, and the corresponding boronic acid or boronate ester in Step 1 instead of (2-fluoro-5-pyridine)boronic acid, Examples 79-89 were also prepared and characterized as indicated in the table below. Example 90 in the table below was also prepared from 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile according to the procedure given for Step 2 in Example 78.

| Example | Structure | IUPAC Name | MS (M + H)+/NMR |
|---------|-----------|------------|-----------------|
| 79 | 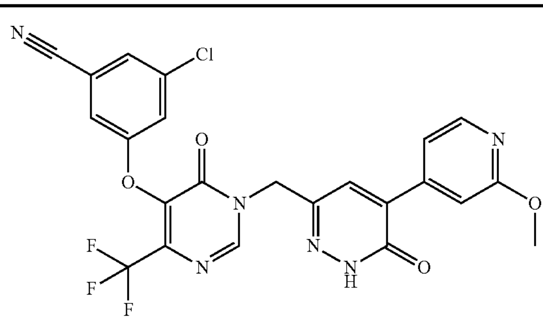 | 3-chloro-5-((1-((5-(2-methoxypyridin-4-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 446, 448 $^1$H NMR: (DMSO-d6, 400 MHz) δ 13.27 (s, 1H), 8.81 (s, 1H), 7.81 (s, 1H), 7.74 (s, 1H), 7.70 (s, 1H), 7.80 (s, 1H), 7.43-7.40 (m, 2H), 7.20 (d, J = 2.4 Hz, 1H), 5.20 (s, 2H), 3.84 (s, 3H). |
| 80 | 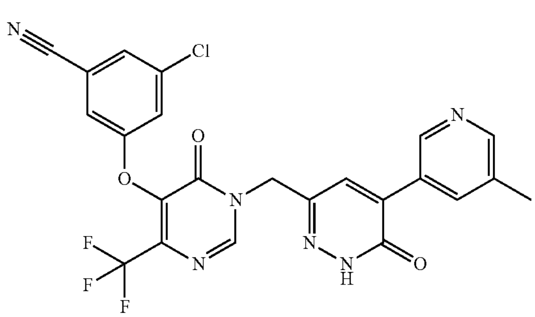 | 3-chloro-5-((1-((5-(5-methylpyridin-3-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 445, 447 $^1$H NMR: (DMSO-d6, 400 MHz) δ 13.27 (s, 1H), 8.81 (s, 1H), 7.81 (s, 1H), 7.74 (s, 1H), 7.70 (s, 1H), 7.80 (s, 1H), 7.43-7.40 (m, 2H), 7.20 (d, J = 2.4 Hz, 1H), 5.20 (s, 2H,), 2.37 (s, 3 H). |

-continued

| Example | Structure | IUPAC Name | MS (M + H)+/NMR |
|---|---|---|---|
| 81 | 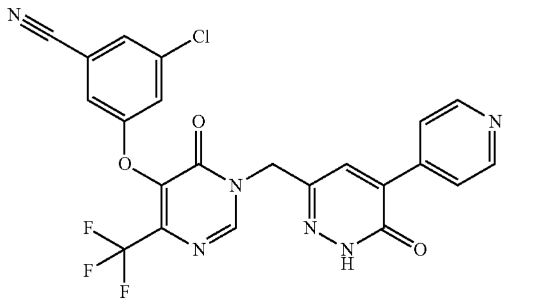 [SMILES: N#Cc1cc(Cl)cc(Oc2c(C(F)(F)F)ncn(Cc3cc(-c4ccncc4)c(=O)[nH]n3)c2=O)c1] | 3-chloro-5-((6-oxo-1-((6-oxo-5-(pyridin-4-yl)-1,6-dihydropyridazin-3-yl)methyl)-4-(trifluoromethyl)-1,6-dihydropyrimidin-5-yl)oxy)benzonitrile | MS (ESI) m/z 501, 503 $^1$H NMR: (DMSO-d6, 400 MHz)δ 13.56 (s, 1H), 8.88 (d, J = 10.4 Hz, 2H), 8.81 (s, 1H), 8.32 (s, 1H), 8.29 (s, 1H), 8.07 (s, 1H), 7.74 (s, 1H), 7.66 (s, 1H), 7.64 (s, 1H), 5.21 (s, 2H). |
| 82 | 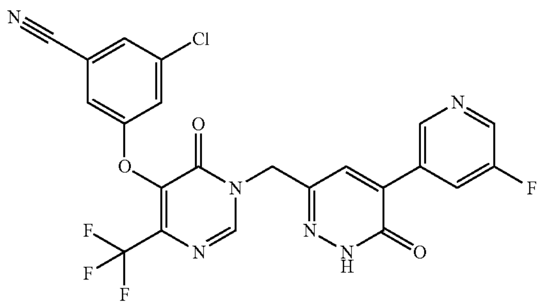 [SMILES: N#Cc1cc(Cl)cc(Oc2c(C(F)(F)F)ncn(Cc3cc(-c4cncc(F)c4)c(=O)[nH]n3)c2=O)c1] | 3-chloro-5-((1-((5-(5-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 519, 521 $^1$H NMR: (DMSO-d6, 400 MHz)δ 13.34 (s, 1H), 8.87 (s, 1H), 8.77 (s, 1H), 8.63 (s, 1H), 8.18 (d, J = 10.4 Hz, 1H), 7.91 (s, 1H), 7.73 (s, 1H), 7.67 (s, 1H), 7.64 (d, J = 13.6 Hz, 1H), 5.16 (s, 2H). |
| 83 | 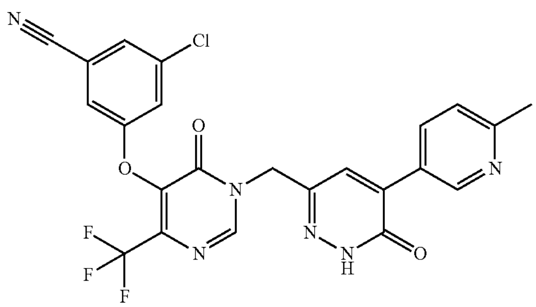 [SMILES: Cc1ccc(-c2cc(Cn3cnc(C(F)(F)F)c(Oc4cc(Cl)cc(C#N)c4)c3=O)n[nH]c2=O)cn1] | 3-chloro-5-((1-((5-(6-methylpyridin-3-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 515, 517 $^1$H NMR: (DMSO-d6, 400 MHz) δ 13.45 (s, 1H), 9.19 (s, 1H), 8.83 (s, 1H), 8.69 (d, J = 7.9 Hz 1H), 8.02 (s, 1H), 7.87 (d, J = 8.2 Hz, 1H), 7.73 (s, 1H), 7.67 (s, 1H), 7.64 (s, 1H), 5.20 (s, 2H), 2.71 (s, 3H). |
| 84 | 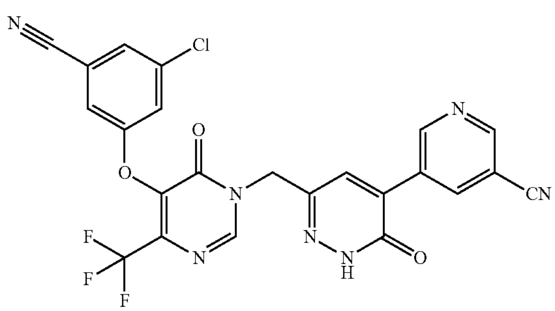 [SMILES: N#Cc1cc(Cl)cc(Oc2c(C(F)(F)F)ncn(Cc3cc(-c4cncc(C#N)c4)c(=O)[nH]n3)c2=O)c1] | 5-(6-((5-(3-chloro-5-cyanophenoxy)-6-oxo-4-(trifluoromethyl)pyrimidin-1(6H)-yl)methyl)-3-oxo-2,3-dihydropyridazin-4-yl)nicotinonitrile | MS (ESI) m/z 526, 528 $^1$H NMR: (DMSO-d6, 400 MHz) δ 13.42 (s, 1H), 9.27 (s, 1H), 9.08 (s, 1H), 8.81 (s, 1H), 8.73 (s, 1H), 7.97(s, 1H), 7.76 (s, 1H), 7.69 (s, 1H), 7.65 (s, 1H), 5.20 (s, 2H). |
| 85 | 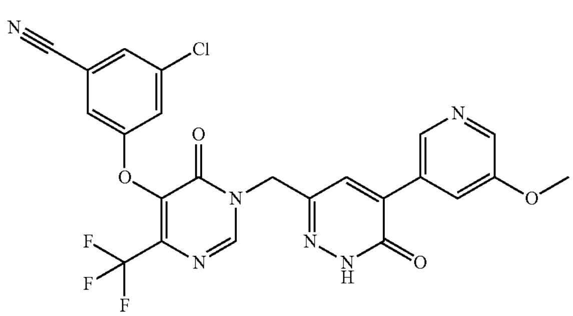 [SMILES: COc1cncc(-c2cc(Cn3cnc(C(F)(F)F)c(Oc4cc(Cl)cc(C#N)c4)c3=O)n[nH]c2=O)c1] | 3-chloro-5-((1-((5-(5-methoxypyridin-3-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 531, 533 $^1$H NMR: (Methanol-d4, 400 MHz) δ 8.98 (s, 1H), 8.61 (s, 1H), 8.59 (s, 1H), 8.50 (s, 1H), 8.00 (s, 1H), 7.53 (s, 1H), 7.37 (s, 1H), 7.33 (s, 1H), 5.27 (s, 2H), 4.06 (s, 3H). |

-continued

| Example | Structure | IUPAC Name | MS (M + H)+/NMR |
|---|---|---|---|
| 86 | 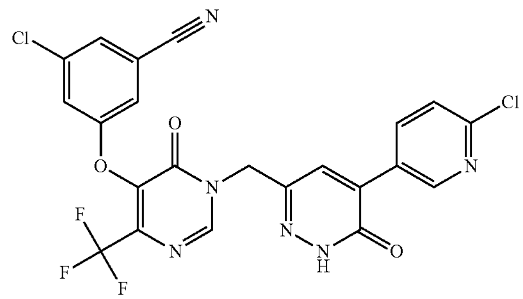 [SMILES: N#Cc1cc(Cl)cc(Oc2c(C(F)(F)F)ncn(Cc3cc(-c4ccc(Cl)nc4)c(=O)[nH]n3)c2=O)c1] | 3-chloro-5-((1-((5-(6-chloropyridin-3-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 535, 537<br>1H NMR: (DMSO-d6, 400 MHz) δ 13.30 (s, 1H), 8.83 (s, 1H), 8.77 (s, 1H), 8.29 (d, J = 8.4 Hz, 1H), 7.85 (s, 1H), 7.74 (s, 1H), 7.68 (s, 1H), 7.63 (s, 1H), 7.61 (d, J = 8.8 Hz, 1H), 5.16 (s, 2H), 4.06 (s, 3H). |
| 87 | 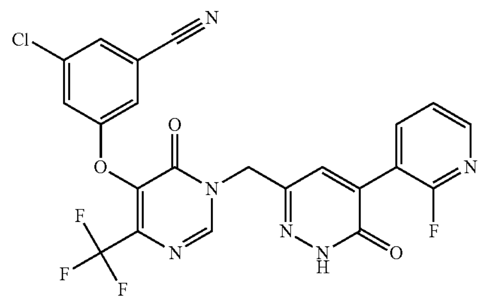 [SMILES: N#Cc1cc(Cl)cc(Oc2c(C(F)(F)F)ncn(Cc3cc(-c4cccnc4F)c(=O)[nH]n3)c2=O)c1] | 3-chloro-5-((1-((5-(2-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 519, 521<br>1H NMR: (DMSO-d6, 400 MHz) δ 13.30 (s, 1H), 8.83 (s, 1H), 8.77 (s, 1H), 8.29 (d, J = 8.4 Hz, 1H), 7.85 (s, 1H), 7.74 (s, 1H), 7.68 (s, 1H), 7.63 (s, 1H), 7.61 (d, J = 8.8 Hz, 1H), 5.16 (s, 2H).. |
| 88 | 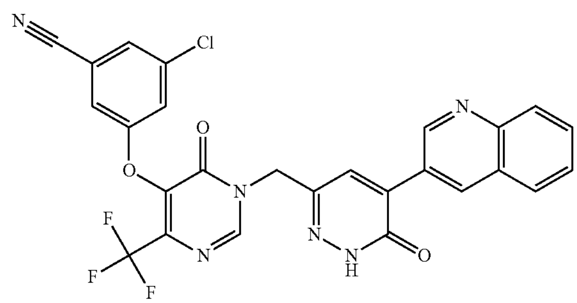 [SMILES: N#Cc1cc(Cl)cc(Oc2c(C(F)(F)F)ncn(Cc3cc(-c4cnc5ccccc5c4)c(=O)[nH]n3)c2=O)c1] | 3-chloro-5-((6-oxo-1-((6-oxo-5-(quinolin-3-yl)-1,6-dihydropyridazin-3-yl)methyl)-4-(trifluoromethyl)-1,6-dihydropyrimidin-5-yl)oxy)benzonitrile | MS (ESI) m/z 551, 553<br>1H NMR: (DMSO-d6, 400 MHz) δ 9.28 (d, J = 2.0 Hz, 1H), 8.95 (s, 1H), 8.82 (s, 1H), 8.06-8.09 (m 2H), 8.03 (s, 1H), 7.84 (t, J = 7.6 Hz, 1H), 7.76 (s, 1H), 7.66-7.72 (m, 3H), 5.23 (s, 2H). |
| 89 | 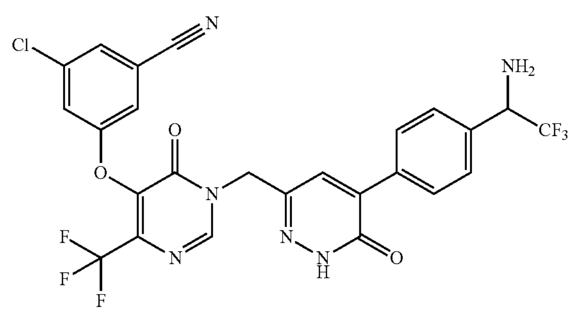 [SMILES: N#Cc1cc(Cl)cc(Oc2c(C(F)(F)F)ncn(Cc3cc(-c4ccc(C(N)C(F)(F)F)cc4)c(=O)[nH]n3)c2=O)c1] | 3-((1-((5-(4-(1-amino-2,2,2-trifluoroethyl)phenyl)-6-oxo-1,6-dihydropyridazin-3-yl)methyl)-6-oxo-4-(trifluoromethyl)-1,6-dihydropyrimidin-5-yl)oxy)-5-chlorobenzonitrile | MS (ESI) m/z 597, 599<br>1H NMR (CDCl3, 400 MHz): δ 13.20 (s, 1H), 8.77 (s, 1H), 7.60-7.90 (m, 8H), 5.30 (t, J = 7.2, Hz, 1H), 5.16 (s, 2H). |
| 90 | 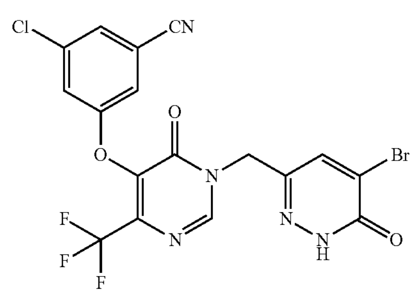 | 3-((1-((5-bromo-6-oxo-1,6-dihydropyridazin-3-yl)methyl)-6-oxo-4-(trifluoromethyl)-1,6-dihydropyrimidin-5-yl)oxy)-5-chlorobenzonitrile | MS (ESI) m/z 502, 504<br>1H NMR: (DMSO-d6, 400 MHz) δ 13.38 (s, 1H), 8.75 (s, 1H), 8.09 (s, 1H), 7.78-7.67 (m, 3H), 5.12 (s, 2H). |

EXAMPLE 91

3-chloro-5-((1-((5-chloro-6-oxo-1,6-dihydro-pyridazin-3-yl)methyl)-6-oxo-4-(trifluoromethyl)-1,6-dihydropyrimidin-5-yl)oxy)benzonitrile

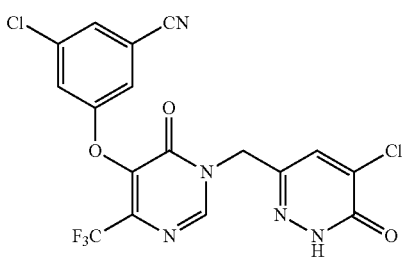 [SMILES: N#Cc1cc(Cl)cc(Oc2c(C(F)(F)F)ncn(Cc3cc(Cl)c(=O)[nH]n3)c2=O)c1]

Step 1: methyl 5,6-dichloropyridazine-3-carboxylate

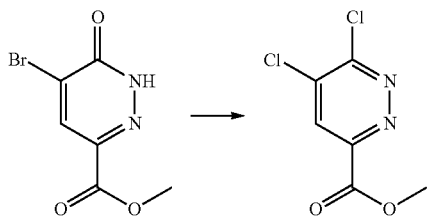

A solution of methyl 5-bromo-6-oxo-1,6-dihydro-pyridazine-3-carboxylate (2 g, 8.62 mmol) in POCl₃ was heated to reflux for 4 hr. After cooling to r.t., the mixture was concentrated under reduced pressure and the residue was poured into ice-water and extracted with ethyl acetate (3×30 mL). The combined organic extracts were dried over sodium sulfate, filtered, concentrated under reduced pressure and the residue was purified with silica gel chromatography (petroleum ether/ethyl acetate (10:1) as eluent) to give methyl 5,6-dichloropyridazine-3-carboxylate (1.3 g).

Step 2: methyl 5-chloro-6-hydroxypyridazine-3-carboxylate

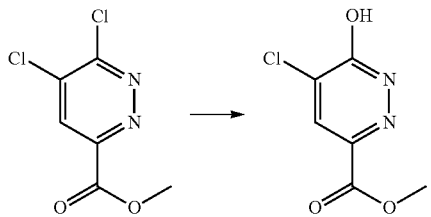

A solution of methyl 5,6-dichloropyridazine-3-carboxylate (1.3 g, 6.31 mmol) in AcOH was heated at reflux for 6 hr. After cooling to r.t., the reaction mixture was concentrated under reduced pressure to give methyl 5-chloro-6-hydroxypyridazine-3-carboxylate (1.3 g) which was used without further purification.

Step 3: methyl 5-chloro-1-(4-methoxybenzyl)-6-oxo-1,6-dihydropyridazine-3-carboxylate

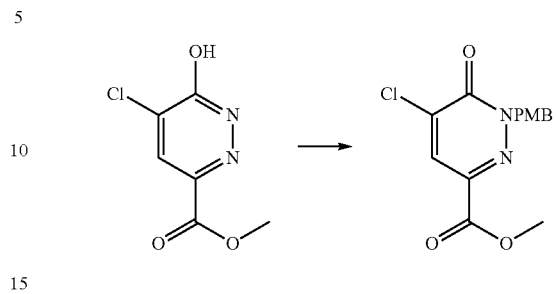

To a suspension of methyl 5-chloro-6-hydroxypyridazine-3-carboxylate (1.3 g) and potassium carbonate (2.61 g, 18.9 mmol) in DMF at r.t. was added PMBCl (1.5 g, 9.61 mmol). The resulting mixture was stirred at r.t. overnight. The reaction mixture was poured into water and extracted with ethyl acetate (3×30 mL). The combined organic layers were dried on sodium sulfate, filtered and concentrated under reduced pressure. The residue was purified by silical gel chromatography (petroleum ether/ethyl acetate (5:1) as eluent) to afford methyl 5-chloro-1-(4-methoxybenzyl)-6-oxo-1,6-dihydropyridazine-3-carboxylate (1.5 g).

$^1$H-NMR (CDCl₃, 400 MHz): δ 7.97 (s, 1H), 7.43 (d, 2H, J=8.0 Hz), 6.83 (d, 2H, J=8.0 Hz), 5.35 (s, 2H), 3.95 (s, 3H), 3.76 (s, 3H).

Using the above intermediate, the title compound was prepared by following similar procedures to Steps 5-7 and Step 9 of Example 22.

$^1$H NMR (DMSO-d6, 400 MHz): δ 13.44 (s, 1H), 8.73 (s, 1H), 7.87 (s, 1H), 7.75 (s, 1H), 7.68 (s, 1H), 7.64 (s, 1H), 5.09 (s, 2H).

MS (ESI) m/z 458, 460, 462 (M+H)⁺.

EXAMPLE 92

3-chloro-5-((1-((5-(dimethylamino)-6-oxo-1,6-dihydropyridazin-3-yl)methyl)-6-oxo-4-(trifluoromethyl)-1,6-dihydropyrimidin-5-yl)oxy)benzonitrile

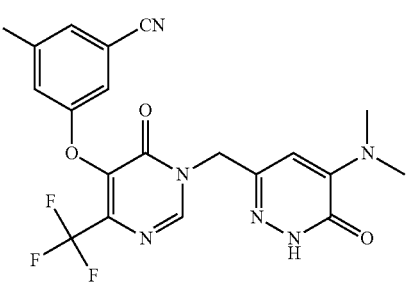

Step 1: 3-chloro-5-((1-((5-(dimethylamino)-6-oxo-1,6-dihydropyridazin-3-yl)methyl)-6-oxo-4-(trifluoromethyl)-1,6-dihydropyrimidin-5-yl)oxy)benzonitrile

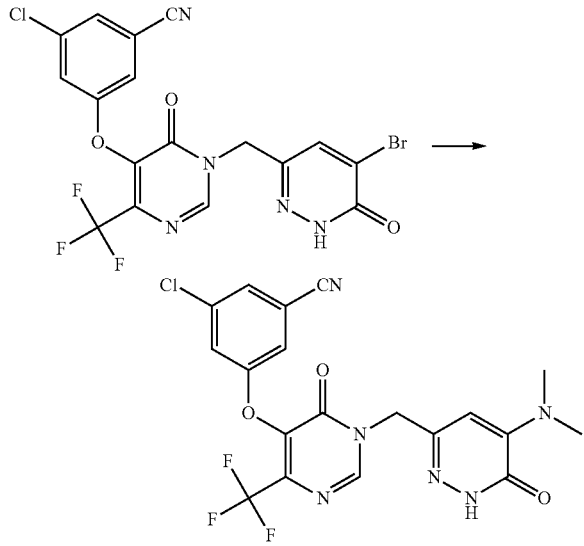

A solution of 3-((1-((5-bromo-6-oxo-1,6-dihydropyridazin-3-yl)methyl)-6-oxo-4-(trifluoromethyl)-1,6-dihydropyrimidin-5-yl)oxy)-5-chlorobenzonitrile (50 mg, 0.10 mmol) and dimethylamine (45 mg, 1 mmol) in NMP (3 mL) was stirred under microwave irradiation at 120° C. for 10 min. After cooling to r.t., the mixture was concentrated under reduced pressure. This crude was purified by preparative HPLC to give 3-chloro-5-((1-((5-(dimethylamino)-6-oxo-1,6-dihydropyridazin-3-yl)methyl)-6-oxo-4-(trifluoromethyl)-1,6-dihydropyrimidin-5-yl)oxy)benzonitrile (30 mg).

$^1$H NMR (DMSO-d6, 400 MHz): δ 13.32 (s, 1H), 8.69 (s, 1H), 7.75 (d, J=1.2 Hz, 1H), 7.63-7.69 (m, 2H), 6.25 (s, 1H), 5.00 (s, 2H), 3.03 (s, 6H),

MS (ESI) m/z 467, 469 (M+H)$^+$

EXAMPLE 93

3-chloro-5-((6-oxo-1-((6-oxo-5-(1H-pyrazol-1-yl)-1,6-dihydropyridazin-3-yl)methyl)-4-(trifluoromethyl)-1,6-dihydropyrimidin-5-yl)oxy)benzonitrile

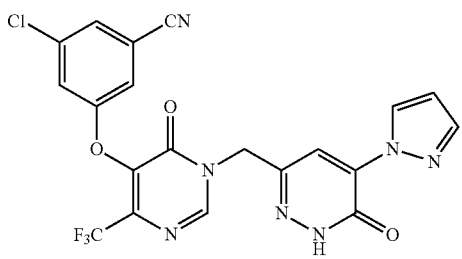 [SMILES: N#Cc1cc(Cl)cc(Oc2c(C(F)(F)F)ncn(Cc3cc(-n4cccn4)c(=O)[nH]n3)c2=O)c1]

Step 1: 3-chloro-5-((1-((1-(4-methoxybenzyl)-6-oxo-5-(1H-pyrazol-1-yl)-1,6-dihydropyridazin-3-yl)methyl)-6-oxo-4-(trifluoromethyl)-1,6-dihydropyrimidin-5-yl)oxy)benzonitrile

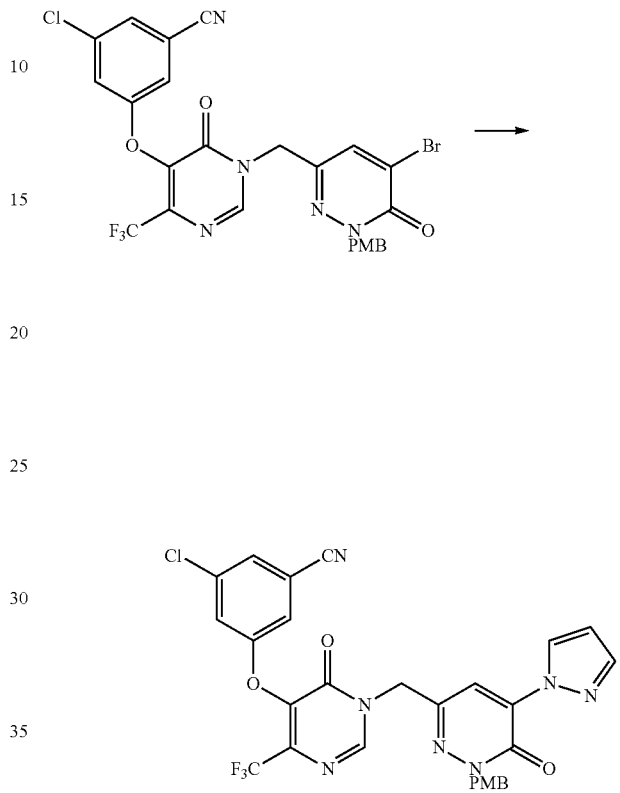

A mixture of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (100 mg, 0.161 mmol), 1H-pyrazole (12 mg, 0.177 mmol) and potassium carbonate (44 mg, 0.322 mmol) in 1,4-1,4-dioxane (10 mL) was stirred overnight at 80° C. After cooling to r.t., the mixture was diluted with water and extracted with ethyl acetate. The organic layer was washed with water and brine, dried over sodium sulfate, filtered and concentrated under reduced pressure. The crude product was purified by preparative TLC (petroleum ether/ethyl acetate (2:1) as eluent) to afford 3-chloro-5-((1-((1-(4-methoxybenzyl)-6-oxo-5-(1H-pyrazol-1-yl)-1,6-dihydropyridazin-3-yl)methyl)-6-oxo-4-(trifluoromethyl)-1,6-dihydropyrimidin-5-yl)oxy)benzonitrile (82 mg).

MS (ESI): m/z 610, 612 (M+H)$^+$

Using the above intermediate, the title compound was prepared by following a similar procedure to Step 2 of Example 78.

$^1$H NMR (Methanol-d4, 400 MHz) δ 9.01-9.02 (m, 1H), 8.56 (s, 1H), 8.02 (s, 1H), 7.80 (s, 1H), 7.52 (s, 1H), 7.37 (s, 2H), 6.52 (s, 1H), 5.26 (s, 2H).

MS (ESI) m/z 490, 492 (M+H)$^+$

EXAMPLE 94

3-chloro-5-((6-oxo-1-((6-oxo-5-(1H-1,2,3-triazol-1-yl)-1,6-dihydropyridazin-3-yl)methyl)-4-(trifluoromethyl)-1,6-dihydropyrimidin-5-yl)oxy)benzonitrile

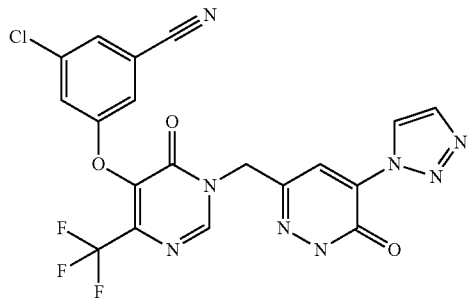 [SMILES: N#Cc1cc(Cl)cc(Oc2c(C(F)(F)F)ncn(Cc3cc(-n4ccnn4)c(=O)[nH]n3)c2=O)c1]

The title compound was prepared in an analogous manner to Example 93.

MS (ESI) m/z 491, 493

$^1$H NMR: (DMSO-d6, 400 MHz): 13.77 (s, 1H), 8.95 (s, 1H), 8.79 (s, 1H), 8.35 (s, 1H), 8.28 (s, 1H), 7.96 (s, 1H), 7.67 (s, 1H), 7.64 (s, 1H), 5.26 (s, 2H).

EXAMPLE 95

6-((5-(3-chloro-5-cyanophenoxy)-6-oxo-4-(trifluoromethyl)pyrimidin-1(6H)-yl)methyl)-3-oxo-2,3-dihydropyridazine-4-carbonitrile

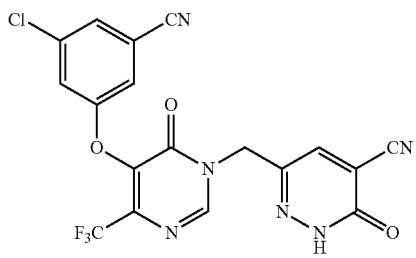 [SMILES: N#Cc1cc(Cl)cc(Oc2c(C(F)(F)F)ncn(Cc3cc(C#N)c(=O)[nH]n3)c2=O)c1]

Step 1: 6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazine-4-carbonitrile

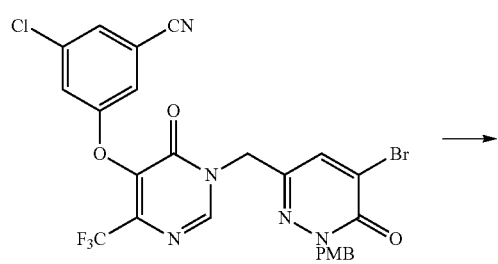

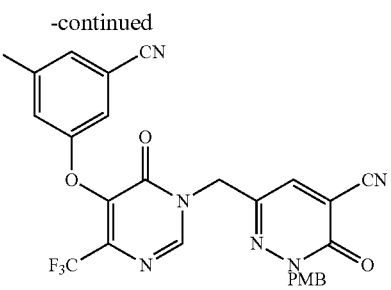

To a solution of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (0.3 g, 0.5 mmol) in DMF (5 mL) were added ZnCN$_2$ (68 mg, 0.58 mmol) and Pd(PPh$_3$)$_4$ (0.2 g, 0.17 mmol). The mixture was stirred at 120° C. overnight. After cooling to r.t., the mixture was poured into water and extracted with ethyl acetate (60 mL×3). The combined organic extracts were washed with water and brine, dried over anhydrous sodium sulfate, filtered and concentrated under reduced pressure. The residue was purified by column chromatography on silica gel (petroleum ether/ethyl acetate (2:1 to 1:1) as eluent) to afford 6-((5-(3-chloro-5-cyanophenoxy)-6-oxo-4-(trifluoromethyl)pyrimidin-1(6H)-yl)methyl-2-(4-methoxybenzyl)-3-oxo-2,3-dihydropyridazine-4-carbonitrile (150 mg).

MS (ESI): m/z 569, 571 (M+H)$^+$

Using the above intermediate, the title compound was prepared by following a similar procedure to Step 2 of Example 78.

$^1$H NMR (DMSO-d6, 400 MHz) δ 13.87 (s, 1H), 8.74 (s, 1H), 8.23 (s, 1H), 7.80-7.66 (m, 3H), 5.13 (s, 2H).

MS (ESI): m/z 449, 451 (M+H)$^+$

EXAMPLE 96

3-chloro-5-((1-((5-(methylsulfonyl)-6-oxo-1,6-dihydropyridazin-3-yl)methyl)-6-oxo-4-(trifluoromethyl)-1,6-dihydropyrimidin-5-yl)oxy)benzonitrile

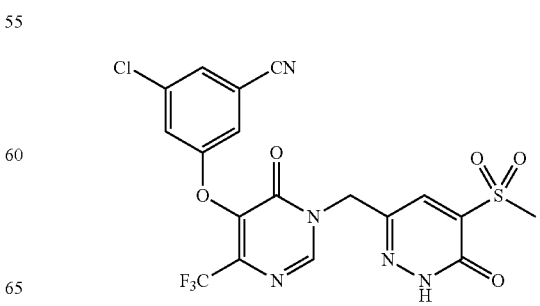

121

Step 1: 3-chloro-5-((1-((1-(4-methoxybenzyl)-5-(methylsulfonyl)-6-oxo-1,6-dihydropyridazin-3-yl)methyl)-6-oxo-4-(trifluoromethyl)-1,6-dihydropyrimidin-5-yl)oxy)benzonitrile

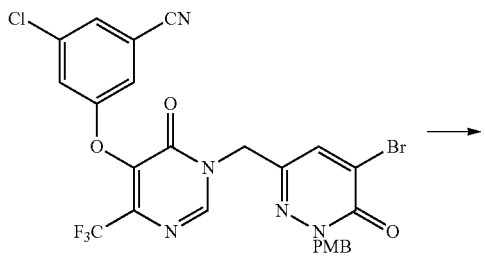

To a solution of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (220 mg, 0.35 mmol) in DMSO (3 mL) was added $CH_3SO_2Na$ (180 mg, 1.8 mmol). The mixture was stirred at room temperature for 3 hr. The reaction mixture was poured into water, extracted with ethyl acetate (60 mL×3). The organic layer was washed with water and brine, dried over anhydrous sodium sulfate, filtered and concentrated under reduced pressure. The residue was purified by preparative TLC to afford 3-chloro-5-((1-((1-(4-methoxybenzyl)-5-(methylsulfonyl)-6-oxo-1,6-dihydropyridazin-3-yl)methyl)-6-oxo-4-(trifluoromethyl)-1,6-dihydropyrimidin-5-yl)oxy)benzonitrile (210 mg).

MS (ESI): m/z 622, 624 (M+H)+

Using the above intermediate, the title compound was prepared by following a similar procedure to Step 2 of Example 78.

MS (ESI): m/z 502, 504 (M+H)+

1HNMR (DMSO-d6, 400 MHz) δ 13.87 (s, 1H), 8.79 (s, 1H), 8.15 (s, 1H), 7.78 (s, 1H), 7.70 (s, 1H), 7.68 (s, 1H), 5.25 (s, 2H), 3.37 (s, 3H)

EXAMPLE 97

3-chloro-5-((1-((5-(ethylsulfonyl)-6-oxo-1,6-dihydropyridazin-3-yl)methyl)-6-oxo-4-(trifluoromethyl)-1,6-dihydropyrimidin-5-yl)oxy)benzonitrile

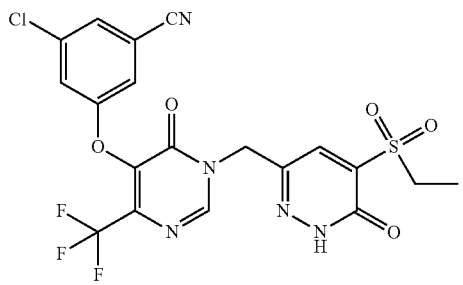 [SMILES: CCS(=O)(=O)c1cc(Cn2cnc(C(F)(F)F)c(Oc3cc(Cl)cc(C#N)c3)c2=O)n[nH]c1=O]

The title compound was prepared in analogous manner to Example 96.

MS (ESI) m/z 516, 518

1H NMR: (DMSO-d6, 400 MHz)

122

δ 13.88 (s, 1H), 8.79 (s, 1H), 8.16 (s, 1H), 7.78-7.68 (m, 3H), 5.25 (s, 2H), 3.50 (q, J=7.2 Hz, 2H), 1.13 (t, J=7.2 Hz, 3H).

EXAMPLE 98

3-chloro-5-((1-((5-(5-fluoropyridin-2-yl)-6-oxo-1,6-dihydropyridazin-3-yl)methyl)-6-oxo-4-(trifluoromethyl)-1,6-dihydropyrimidin-5-yl)oxy)benzonitrile

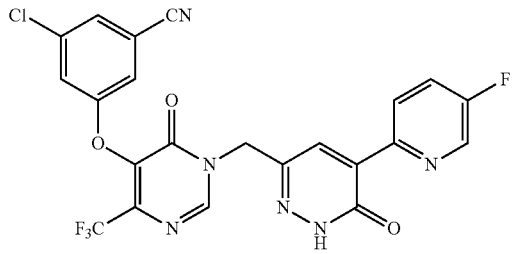 [SMILES: N#Cc1cc(Cl)cc(Oc2c(C(F)(F)F)ncn(Cc3cc(-c4ccc(F)cn4)c(=O)[nH]n3)c2=O)c1]

Step 1: 3-chloro-5-((1-((5-(5-fluoropyridin-2-yl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile

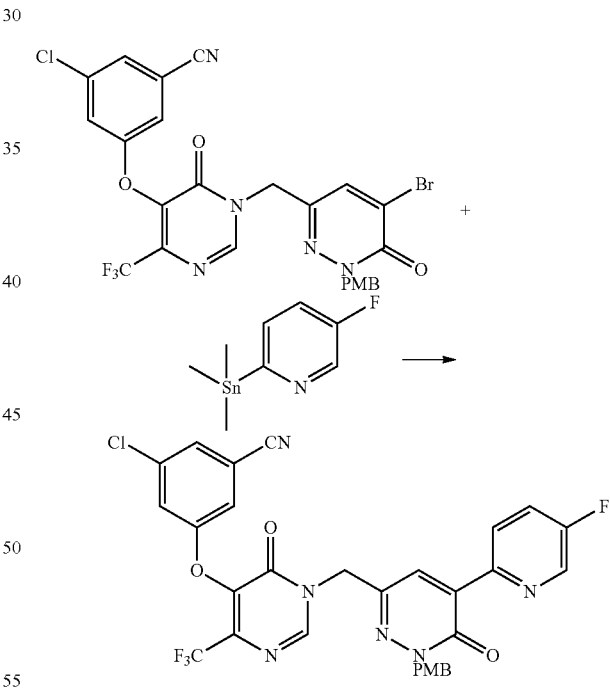

A mixture of 5-fluoro-2-(trimethylstannyl)pyridine (94 mg, 0.362 mmol), 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (150 mg, 0.242 mmol) and Pd(PPh3)4 (14 mg, 0.012 mmol) in DME (10 mL) was stirred overnight at 80° C. After the reaction was finished, the mixture was filtered and the filtrate was concentrated under reduced pressure. The crude product was purified by preparative TLC (petroleum ether/ethyl acetate (2:1) to afford 3-chloro-5-((1-((5-(5-fluoropyridin-2-yl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (110 mg).

MS (ESI): m/z 639, 641 (M+H)$^+$

Using the above intermediate, the title compound was prepared by following a similar procedure to Step 2 of Example 78.

$^1$H NMR (DMSO-d4, 400 MHz): δ 13.37 (s, 1H), 8.81 (s, 1H), 8.72-8.75 (m, 2H), 8.30 (s, 1H), 7.85-7.86 (m, 1H), 7.76 (s, 1H), 7.65-7.69 (m, 2H), 5.26 (s, 2H).

MS (ESI) m/z 519, 521 (M+H)$^+$

EXAMPLE 99

3-chloro-5-((1-((5-(5-chloropyridin-2-yl)-6-oxo-1,6-dihydropyridazin-3-yl)methyl)-6-oxo-4-(trifluoromethyl)-1,6-dihydropyrimidin-5-yl)oxy)benzonitrile

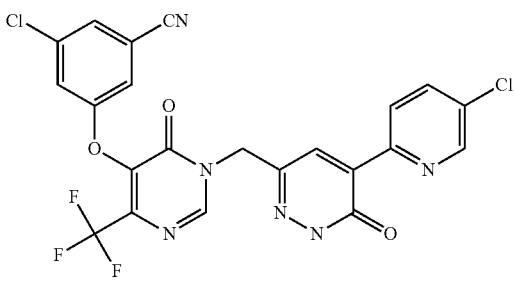 [SMILES: N#Cc1cc(Cl)cc(Oc2c(C(F)(F)F)ncn(Cc3cc(-c4ccc(Cl)cn4)c(=O)[nH]n3)c2=O)c1]

The title compound was prepared in an analogous manner to Example 98.

MS (ESI) m/z 535, 537

$^1$H NMR: (DMSO-d6, 400 MHz) δ 13.39 (s, 1H), 8.78 (s, 1H), 8.73 (d, J=2.4 Hz, 1H), 8.58 (d, J=8.8 Hz, 1H), 8.32 (s, 1H), 8.03-8.05 (m, 1H), 7.74 (s, 1H), 7.63-7.67 (m, 2H), 5.23 (s, 2H).

EXAMPLE 100 methyl 6-((5-(3-chloro-5-cyanophenoxy)-6-oxo-4-(trifluoromethyl)pyrimidin-1(6H)-yl)methyl)-3-oxo-2,3-dihydropyridazine-4-carboxylate

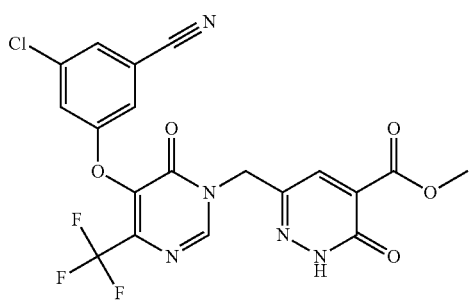 [SMILES: COC(=O)c1cc(Cn2cnc(C(F)(F)F)c(Oc3cc(Cl)cc(C#N)c3)c2=O)n[nH]c1=O]

Step 1: methyl 6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazine-4-carboxylate

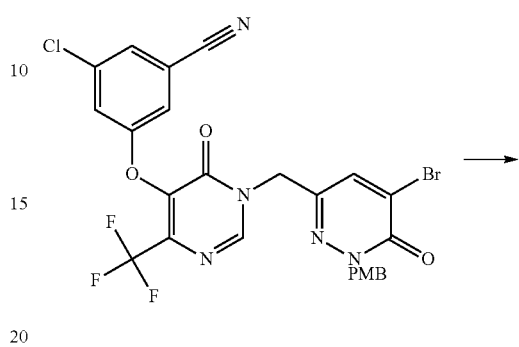

A mixture of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (400 mg, 0.64 mmol), triethyl amine (0.4 mL, 2.8 mmol) and Pd(dppf)Cl$_2$ (50 mg) in a 1:1 mixture of DMF/methanol (10 mL) was heated to 70° C. with stirring under carbon monooxide (50 psi) for 20 hr. After the reaction was finished, the mixture was poured into water and extracted with ethyl acetate. The organic layer was washed with brine, dried over sodium sulfate, filtered and concentrated under reduced pressure. The residue was purified by preparative TLC (petroleum ether/ethyl acetate (1:1) as eluent) to afford methyl 6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazine-4-carboxylate (300 mg).

MS (ESI) m/z 602, 604 (M+H)$^+$

Using the above intermediate, the title compound was prepared by following a similar procedure to Step 2 of Example 78.

$^1$H NMR (DMSO-d6, 400 MHz): δ 13.46 (s, 1H), 8.76 (s, 1H), 7.93 (s, 1H), 7.77 (s, 1H), 7.70 (s, 1H), 6.66 (s, 1H), 5.16 (s, 2H), 3.79 (s, 3H).

MS (ESI) m/z 482, 484 (M+H)$^+$

EXAMPLE 101

6-((5-(3-chloro-5-cyanophenoxy)-6-oxo-4-(trifluoromethyl)pyrimidin-1(6H)-yl)methyl)-3-oxo-2,3-dihydropyridazine-4-carboxamide

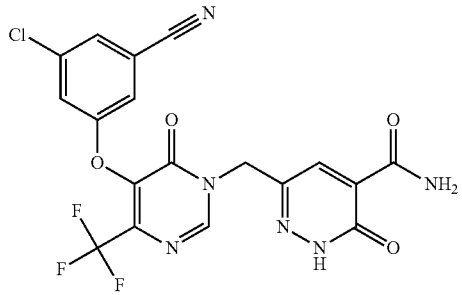 [SMILES: N#Cc1cc(Cl)cc(Oc2c(C(F)(F)F)ncn(Cc3cc(C(N)=O)c(=O)[nH]n3)c2=O)c1]

Step 1: 6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazine-4-carboxamide

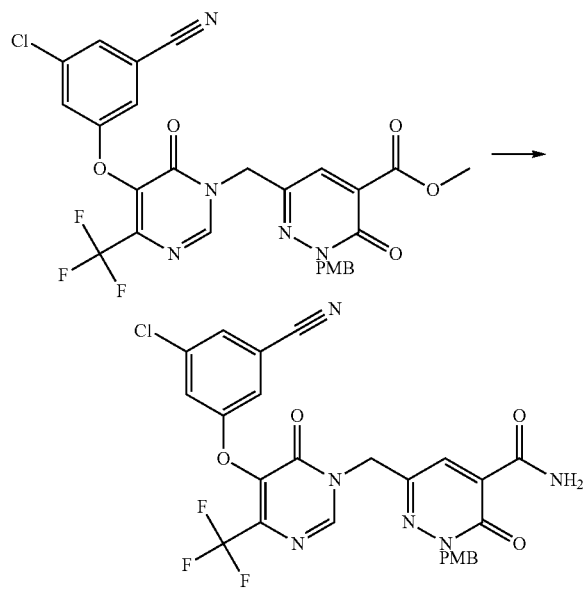

To a mixture of methyl 6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazine-4-carboxylate (150 mg, 0.25 mmol) in 5 mL of THF was added NH$_4$OH (1 mL, 17 mmol) at 10° C. The resulting mixture was stirred for 2.5 hr at r.t. After finished, the mixture was diluted with ethyl acetate and washed with brine, dried over anhydrous sodium sulfate, filtered and concentrated under reduced pressure. The residue was purified by preparative TLC to afford 6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazine-4-carboxamide (120 mg).

MS (ESI): m/z 587, 589 (M+H)$^+$

Using the above intermediate, the title compound was prepared by following a similar procedure to Step 2 of Example 78.

$^1$H NMR (DMSO-d6, 400 MHz): δ 13.72 (s, 1H), 8.79 (s, 1H), 8.77 (s, 1H), 8.21 (s, 1H), 8.05 (s, 1H), 7.77 (s, 1H), 7.69 (s, 1H), 6.66 (s, 1H), 5.24 (s, 2H).

MS (ESI): m/z 467, 469 (M+H)$^+$

EXAMPLE 102

3-chloro-5-((1-((5-(difluoromethyl)-6-oxo-1,6-dihydropyridazin-3-yl)methyl)-6-oxo-4-(trifluoromethyl)-1,6-dihydropyrimidin-5-yl)oxy)benzonitrile

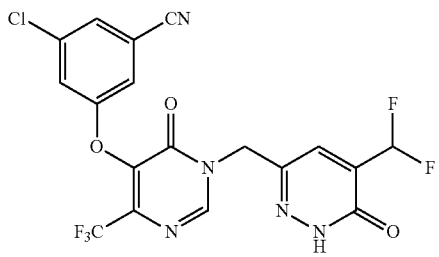 [SMILES: N#Cc1cc(Cl)cc(Oc2c(C(F)(F)F)ncn(Cc3cc(C(F)F)c(=O)[nH]n3)c2=O)c1]

Step 1: (E)-methyl-3-(6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazin-4-yl)acrylate

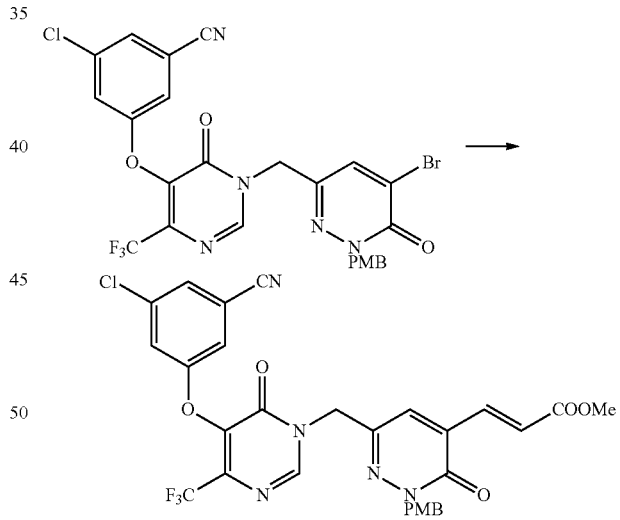

To a solution of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (0.3 g, 0.68 mmol), ethyl acrylate (40.4 mL, 3.4 mmol) and triethylamine (0.3 mL, 2.0 mmol) in DMF (15 mL) was added Pd(OAc)$_2$ (30 mg, 0.14 mmol) and P(o-tolyl)$_3$ (40 mg, 0.14 mmol) successively under a nitrogen atmosphere. The resulting yellow suspension was stirred at 100° C. under a nitrogen atmosphere overnight. After cooling to r.t., the mixture was poured into ice-water, extracted with ethyl acetate, and the combined organic extracts were washed with brine, dried over sodium sulfate, filtered and concentrated under reduced pressure. The residue was purified by column chromatography on silica gel (petroleum ether/ethyl acetate (10:1 to 5:1) as eluent) to afford (E)-methyl-3-(6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazin-4-yl)acrylate (220 mg).
MS (ESI): m/z 642, 644 (M+H)+

Step 2: 3-chloro-5-((1-((5-formyl-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile

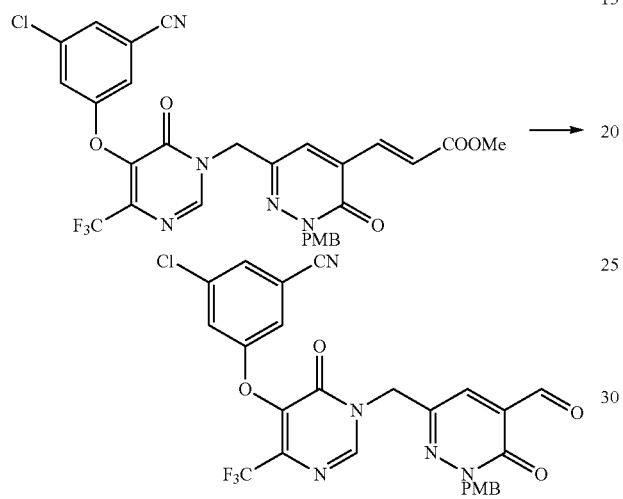

To a solution of (E)-methyl 3-(6-((5-(3-chloro-5-cyanophenoxy)-6-oxo-4-(trifluoromethyl)pyrimidin-1(6H)-yl)methyl)-2-(4-methoxybenzyl)-3-oxo-2,3-dihydropyridazin-4-yl)acrylate (220 mg, 0.34 mmol) in a mixture solvent of dichloromethane (5 mL) and methanol (1 mL) was stirred at −65° C. for 15 min under O₃. (Me)₂S (2 mL) was added, then the mixture was concentrated under reduced pressure and purified by chromatography on silica gel (petroleum ether/ethyl acetate (5:1 to 3:1) as eluent) to give the desired product 3-chloro-5-((1-((5-formyl-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (110 mg).
MS (ESI): m/z 572, 574 (M+H)+

Step 3: 3-chloro-5-((1-((5-(difluoromethyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile

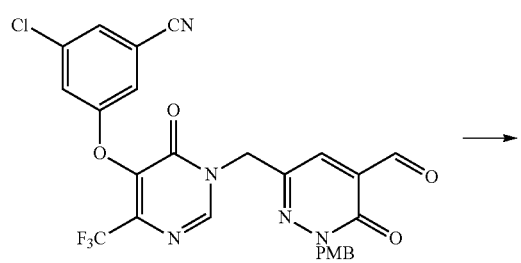

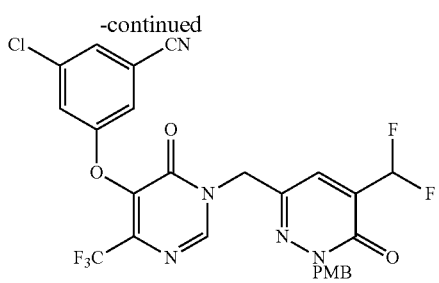

A solution of 3-chloro-5-((1-((5-formyl-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (110 mg, 0.19 mmol) in 5 mL of dry dichloromethane was cooled to −45° C. DAST (62 mg, 0.39 mmol) was added and the resulting mixture was stirred at room temperature for 1 hr. The mixture was partitioned between water and dichloromethane and the organic layer was washed with water and brine, dried over sodium sulfate, filtered and concentrated under reduced pressure. The residue was purified by preparative HPLC to afford 3-chloro-5-((1-((5-(difluoromethyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (35 mg).
MS (ESI): m/z 594, 596 (M+H)+

Step 4: 3-chloro-5-((1-((5-(difluoromethyl)-6-oxo-1,6-dihydropyridazin-3-yl)methyl)-6-oxo-4-(trifluoromethyl)-1,6-dihydropyrimidin-5-yl)oxy)benzonitrile

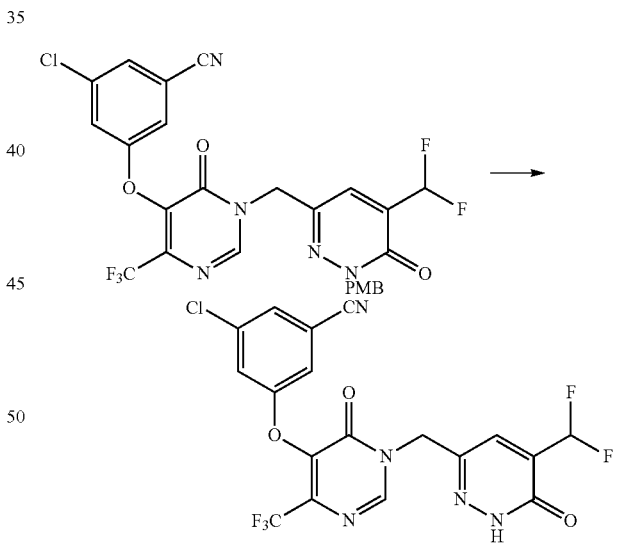

To a solution of 3-chloro-5-((1-((5-(difluoromethyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (100 mg, 0.16 mmol) in acetonitrile (4 mL) and H₂O (1 mL) was added Ce(NH₄)₂(NO₃)₆ (0.48 g, 0.8 mmol) in portions. The mixture was stirred at room temperature overnight, poured into water and extracted with ethyl acetate (60 mL×3). The combined organic layers were washed with water and brine, dried over anhydrous sodium sulfate, filtered and concentrated under reduced pressure. The residue was purified by preparative TLC to give 3-chloro-5-((1-

((5-(difluoromethyl)-6-oxo-1,6-dihydropyridazin-3-yl)methyl)-6-oxo-4-(trifluoromethyl)-1,6-dihydropyrimidin-5-yl)oxy)benzonitrile (30 mg).

¹H-NMR (DMSO-d6, 400 MHz): δ 13.42 (s, 1H), 8.76 (s, 1H), 7.63-7.77 (m, 4H), 6.75 (s, 1H), 5.16 (s, 2H).

MS (ESI): m/z 474, 476 (M+H)⁺

EXAMPLE 103

3-chloro-5-((6-oxo-1-((6-oxo-5-(2,2,2-trifluoro-1-hydroxyethyl)-1,6-dihydropyridazin-3-yl)methyl)-4-(trifluoromethyl)-1,6-dihydropyrimidin-5-yl)oxy)benzonitrile

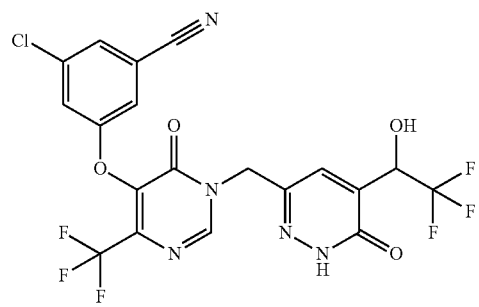 [SMILES: N#Cc1cc(Cl)cc(Oc2c(C(F)(F)F)ncn(Cc3cc(C(O)C(F)(F)F)c(=O)[nH]n3)c2=O)c1]

Step 1: 3-chloro-5-((1-((1-(4-methoxybenzyl)-6-oxo-5-(2,2,2-trifluoro-1-hydroxyethyl)-1,6-dihydropyridazin-3-yl)methyl)-6-oxo-4-(trifluoromethyl)-1,6-dihydropyrimidin-5-yl)oxy)benzonitrile

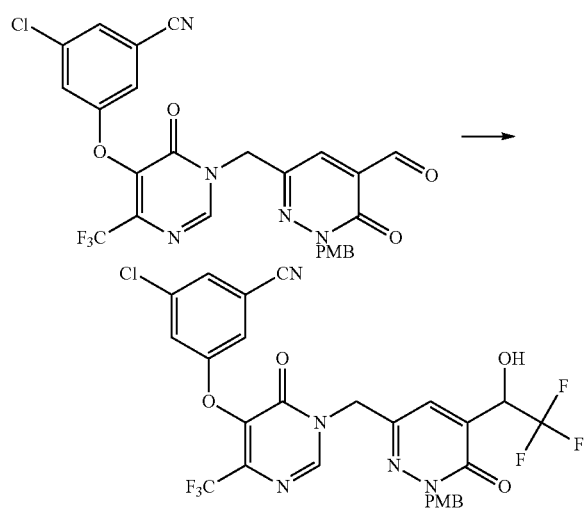

A solution of 3-chloro-5-((1-((5-formyl-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (790 mg, 1.38 mmol) and CsF (168 mg, 1.1 mmol) in 5 mL of anhydrous THF was cooled to −20° C. TMSCF₃ (204 mg, 1.1 mmol) was added at same temperature. After addition, the resulting mixture was stirred at room temperature overnight. The mixture was diluted with water and extracted with ethyl acetate. The combined organic extracts were washed with water and brine, dried over sodium sulfate, filtered and concentrated under reduced pressure. The residue was purified by preparative HPLC to afford 3-chloro-5-((1-((1-(4-methoxybenzyl)-6-oxo-5-(2,2,2-trifluoro-1-hydroxyethyl)-1,6-dihydropyridazin-3-yl)methyl)-6-oxo-4-(trifluoromethyl)-1,6-dihydropyrimidin-5-yl)oxy)benzonitrile (300 mg).

MS (ESI): m/z 642, 644 (M+H)⁺

Using the above intermediate, the title compound was prepared by following a similar procedure to Step 2 of Example 78.

MS (ESI): m/z 522, 524 (M+H)⁺

¹H-NMR (CD3OD-d6, 400 MHz): δ 8.54 (s, 1H), 7.76 (s, 1H), 7.52 (s, 1H), 7.34 (s, 2H), 5.33 (q, J=6.4 Hz, 1H), 5.17-5.23 (m, 2H).

EXAMPLE 104

3-chloro-5-((1-((5-(1,1-difluoroethyl)-6-oxo-1,6-dihydropyridazin-3-yl)methyl)-6-oxo-4-(trifluoromethyl)-1,6-dihydropyrimidin-5-yl)oxy)benzonitrile

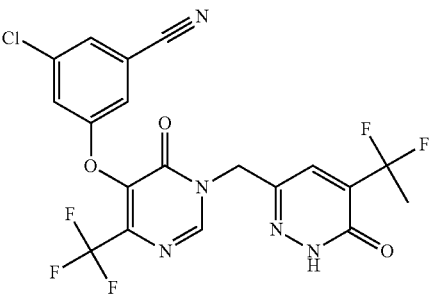 [SMILES: CC(F)(F)c1cc(Cn2cnc(C(F)(F)F)c(Oc3cc(Cl)cc(C#N)c3)c2=O)n[nH]c1=O]

Step 1: 3-chloro-5-((1-((5-(1-ethoxyvinyl)-1-(4-methoxybenzyl)-6-oxo-1,6-dihydro pyridazin-3-yl)methyl)-6-oxo-4-(trifluoromethyl)-1,6-dihydropyrimidin-5-yl)oxy)benzonitrile

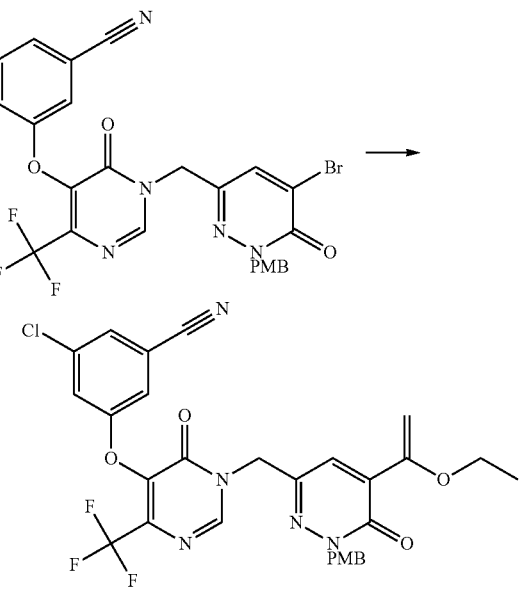

To a mixture of 3-((1-((5-bromo-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (600 mg, 0.97 mmol), tributyl(1-ethoxyvinyl)stannane (418 mg, 1.16 mmol) in toluene (8 mL) was added Pd(PPh$_3$)$_4$ (112 mg, 0.09 mmol) under a nitrogen atmosphere. The resulting yellow suspension was stirred at 120° C. overnight under a nitrogen atmosphere. After cooling to r.t., the mixture was poured into ice-water and extracted with ethyl acetate. The combined organic extracts were washed with brine, dried over sodium sulfate, filtered and concentrated under reduced pressure. The residue was purified by column chromatography on silica gel (petroleum ether/ethyl acetate (5:1 to 2:1) as eluent) to afford 3-chloro-5-((1-((5-(1-ethoxyvinyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (400 mg).

MS (ESI): m/z 614, 616 (M+H)$^+$

Step 2: 3-((1-((5-acetyl-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile

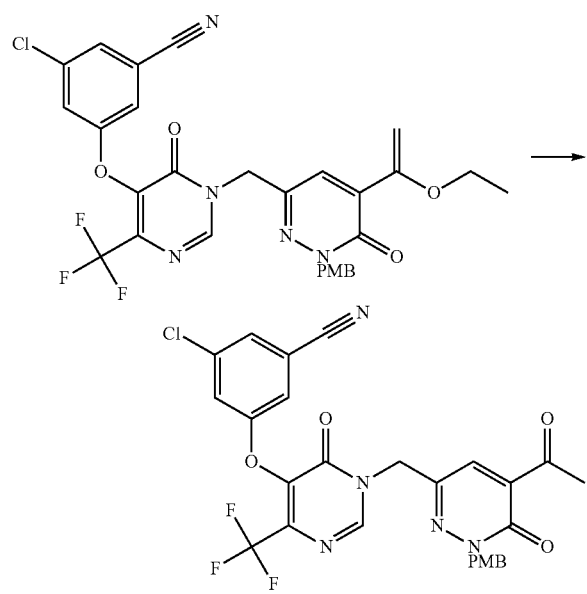

To a solution of 3-chloro-5-((1-((5-(1-ethoxyvinyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (400 mg, 0.65 mmol) in 1,4-dioxane (6 mL) was added HCl/1,4-dioxane (4 N, 6 mL), the solution was stirred at room temperature overnight. LCMS showed that the reaction was completed. The mixture was diluted with water and extracted with ethyl acetate. The combined organic layers were dried over anhydrous sodium sulfate, filtered and concentrated under reduced pressure. The residue was purified by preparative TLC (petroleum ether/ethyl acetate (1:1) to give 3-((1-((5-acetyl-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (360 mg).

MS (ESI) m/z 586, 588 (M+H)$^+$

Step 3: 3-chloro-5-((1-((5-(1,1-difluoroethyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile

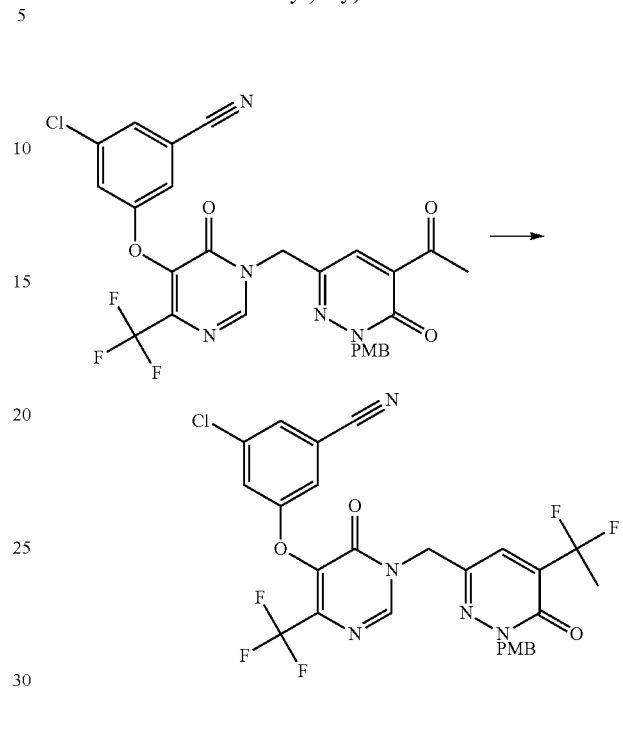

To a solution of 3-((1-((5-acetyl-1-(4-methoxybenzyl)-6-oxo-1,6-dihydropyridazin-3-yl)methyl)-6-oxo-4-(trifluoromethyl)-1,6-dihydropyrimidin-5-yl)oxy)-5-chlorobenzonitrile (360 mg, 0.62 mmol) in dichloromethane (8 mL) was added DAST (595 mg, 3.69 mmol). The mixture was stirred at r.t. for 4 hr. LCMS showed that the reaction was completed. The mixture was quenched with water and extracted with ethyl acetate. The combined organic extracts were dried over anhydrous sodium sulfate, filtered and concentrated under reduced pressure to give 3-chloro-5-((1-((5-(1,1-difluoroethyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (150 mg).

MS (ESI) m/z 608, 610 (M+H)$^+$

Step 4: 3-chloro-5-((1-((5-(1,1-difluoroethyl)-6-oxo-1,6-dihydropyridazin-3-yl)methyl)-6-oxo-4-(trifluoromethyl)-1,6-dihydropyrimidin-5-yl)oxy)benzonitrile

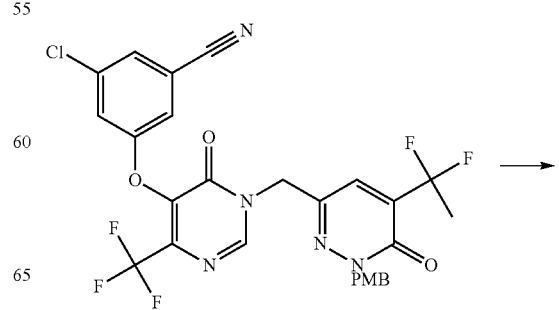

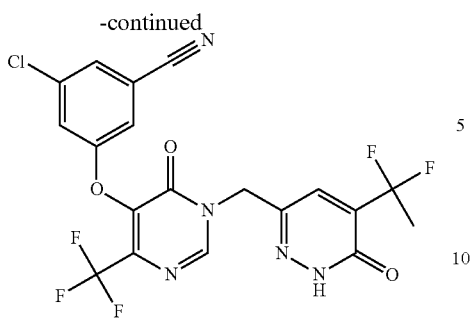

To a mixture of 3-chloro-5-((1-((5-(1,1-difluoroethyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (150 mg, 0.25 mmol) in acetonitrile/H$_2$O (3 mL/1.5 mL) was added CAN (1.1 g, 1.98 mmol). The mixture was stirred at room temperature for 3 hr then filtered. The filtrate was concentrated under reduced pressure and the residue was purified by preparative HPLC to give the title compound (35 mg).

$^1$H NMR (DMSO-d6, 400 MHz): δ 13.38 (s, 1H), 8.76 (s, 1H), 7.77 (s, 1H), 7.73 (s, 1H), 7.69 (s, 1H), 7.66 (d, 1H, J=1.6 Hz), 5.18 (s, 2H), 1.97 (t, J-19.6 Hz, 3H).

MS (ESI) m/z 488, 490 (M+H)$^+$

EXAMPLE 105

3-((1-((5-acetyl-6-oxo-1,6-dihydropyridazin-3-yl)methyl)-6-oxo-4-(trifluoro methyl)-1,6-dihydropyrimidin-5-yl)oxy)-5-chlorobenzonitrile

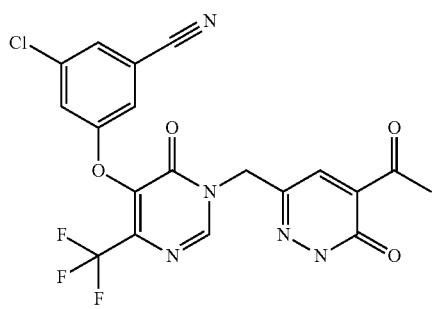 [SMILES: CC(=O)c1cc(Cn2cnc(C(F)(F)F)c(Oc3cc(Cl)cc(C#N)c3)c2=O)n[nH]c1=O]

Using 3-((1-((5-acetyl-6-oxo-1,6-dihydropyridazin-3-yl)methyl)-6-oxo-4-(trifluoromethyl)-1,6-dihydropyrimidin-5-yl)oxy)-5-chlorobenzonitrile, the title compound was prepared using a similar procedure to Step 4 of Example 104.

MS (ESI) m/z 466, 468 (M+H)$^+$ $^1$H NMR (DMSO-d6, 400 MHz): δ 13.49 (s, 1H), 8.74 (s, 1H), 7.79 (s, 1H), 7.74 (s, 1H), 7.61-7.64 (m, 2H), 5.15 (s, 2H), 2.46 (s, 3H).

EXAMPLE 106

3-chloro-5-((1-((5-methoxy-6-oxo-1,6-dihydropyridazin-3-yl)methyl)-6-oxo-4-(trifluoromethyl)-1,6-dihydropyrimidin-5-yl)oxy)benzonitrile

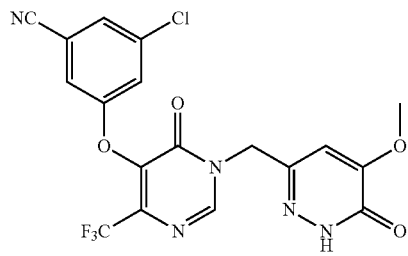 [SMILES: COc1cc(Cn2cnc(C(F)(F)F)c(Oc3cc(Cl)cc(C#N)c3)c2=O)n[nH]c1=O]

Step 1: 6-(hydroxymethyl)-4-methoxy-2-(4-methoxybenzyl)pyridazin-3(2H)-one

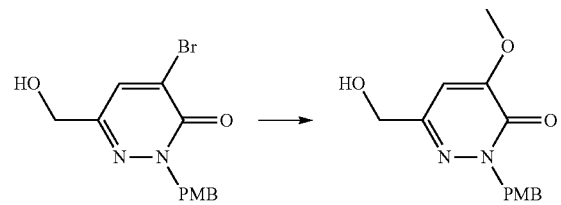

To a solution of 4-bromo-6-(hydroxymethyl)-2-(4-methoxybenzyl)pyridazin-3(2H)-one (500 mg, 1.54 mmol) in methanol (10 mL) was added KOH (431 mg, 7.69 mmol). The mixture was stirred at 50° C. overnight. After cooling to r.t., the mixture was diluted with H$_2$O, extracted with ethyl acetate. The organic layer was dried over anhydrous sodium sulfate, filtered and concentrated under reduced pressure. The residue was purified by preparative TLC (dichloromethane/methanol (20:1) as eluent) to give the desired product 6-(hydroxymethyl)-4-methoxy-2-(4-methoxybenzyl)pyridazin-3(2H)-one (270 mg).

MS (ESI) m/z 277 (M+H)$^+$

Step 2: 6-(chloromethyl)-4-methoxy-2-(4-methoxybenzyl)pyridazin-3(2H)-one

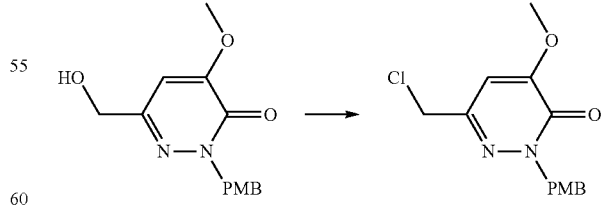

To a solution of 6-(hydroxymethyl)-4-methoxy-2-(4-methoxybenzyl)pyridazin-3(2H)-one (290 mg, 1.05 mmol) in dichloromethane (10 mL) was added DIPEA (407 mg, 3.15 mmol) and methanesulfonyl chloride (361 mg, 3.15 mmol). The mixture was stirred at room temperature overnight, then diluted with DCM and washed with water. The organic layer was dried over anhydrous sodium sulfate, filtered and concentrated under reduced pressure. The residue was purified by preparative TLC (petroleum ether/ethyl acetate (3:1) as eluent) to give 6-(chloromethyl)-4-methoxy-2-(4-methoxybenzyl)pyridazin-3(2H)-one (180 mg).

MS (ESI) m/z 295, 297 (M+H)⁺

Step 3: 3-chloro-5-((1-((5-methoxy-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile

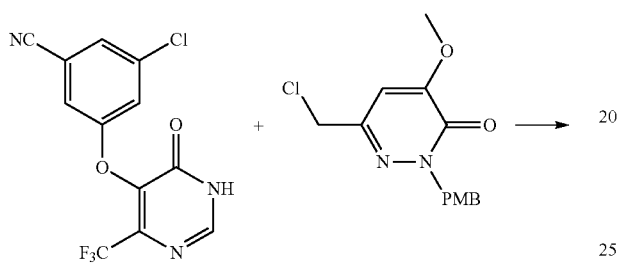

To a solution of 6-(chloromethyl)-4-methoxy-2-(4-methoxybenzyl)pyridazin-3(2H)-one (180 mg, 0.61 mmol) in DMF (5 mL) was added 3-chloro-5-((6-oxo-4-(trifluoromethyl)-1,6-dihydropyrimidin-5-yl)oxy)benzonitrile (231 mg, 0.73 mmol), potassium carbonate (168 mg, 1.22 mmol) and LiBr (106 mg, 1.22 mmol). The mixture was stirred at 80° C. overnight. After cooling to r.t., the mixture was diluted with water and then extracted with ethyl acetate. The combined organic layers were dried over anhydrous sodium sulfate, filtered and concentrated under reduced pressure give 3-chloro-5-((1-((5-methoxy-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (270 mg).

MS (ESI) m/z 574 (M+H)⁺

Using the intermediate above, the title compound was prepared using a similar procedure to Step 9 in Example 22.

¹H NMR: (CD₃OD, 400 MHz) δ 8.51 (s, 1H), 7.53 (s, 1H), 7.35 (s, 2H), 6.87 (s, 1H), 5.16 (s, 2H), 3.89 (s, 3H).

MS (ESI) m/z 454 (M+H)⁺

EXAMPLE 107

3-chloro-5-((1-((5-hydroxy-6-oxo-1,6-dihydropyridazin-3-yl)methyl)-6-oxo-4-(trifluoromethyl)-1,6-dihydropyrimidin-5-yl)oxy)benzonitrile

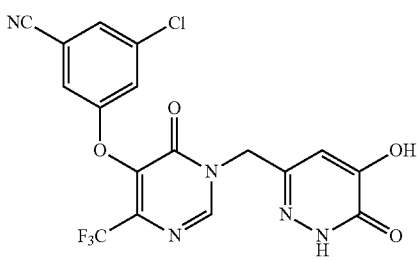 [SMILES: N#Cc1cc(Cl)cc(Oc2c(C(F)(F)F)ncn(Cc3cc(O)c(=O)[nH]n3)c2=O)c1]

Step 1: 6-(hydroxymethyl)-2-(4-methoxybenzyl)-4-((4-methoxybenzyl)oxy)pyridazin-3(2H)-one

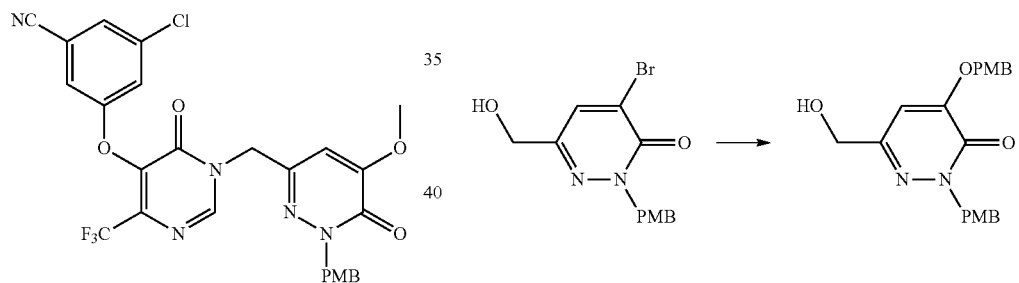

To a solution of 4-bromo-6-(hydroxymethyl)-2-(4-methoxybenzyl)pyridazin-3(2H)-one (300 mg, 0.85 mmol) in THF (7 mL) were added KOH (477 mg, 8.50 mmol) and 4-methoxylbenzyl alcohol (352 mg, 2.55 mmol). The mixture was stirred at 80° C. for 1 hr. After cooling to r.t., the mixture was diluted with H₂O and extracted with ethyl acetate. The organic layer was dried over anhydrous sodium sulfate, filtered and purified by preparative TLC (petroleum ether/ethyl acetate (1:1) as eluent) to give the desired product 6-(hydroxymethyl)-2-(4-methoxybenzyl)-4-((4-methoxybenzyl)oxy)pyridazin-3(2H)-one (188 mg).

MS (ESI) m/z 383 (M+H)⁺

Using an analogous procedure to that given for Example 106, and the above intermediate in place of the 6-(hydroxymethyl)-4-methoxy-2-(4-methoxybenzyl)pyridazin-3(2H)-one in Step 2, the title compound was prepared.

¹H NMR: (CD₃OD, 400 MHz) δ 8.52 (s, 1H), 7.55 (s, 1H), 7.36 (d, J=1.2 Hz, 2H), 6.74 (s, 1H), 5.12 (s, 2H).

MS (ESI) m/z 440 (M+H)⁺

EXAMPLE 108

3-chloro-5-((1-((5-(4-fluorophenoxy)-6-oxo-1,6-dihydropyridazin-3-yl)methyl)-6-oxo-4-(trifluoromethyl)-1,6-dihydropyrimidin-5-yl)oxy)benzonitrile

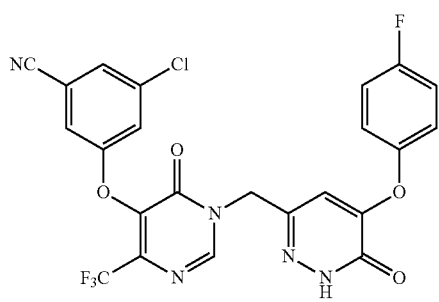 [SMILES: N#Cc1cc(Cl)cc(Oc2c(C(F)(F)F)ncn(Cc3cc(Oc4ccc(F)cc4)c(=O)[nH]n3)c2=O)c1]

Step 1: 4-(4-fluorophenoxy)-6-(hydroxymethyl)-2-(4-methoxybenzyl)pyridazin-3(2H)-one

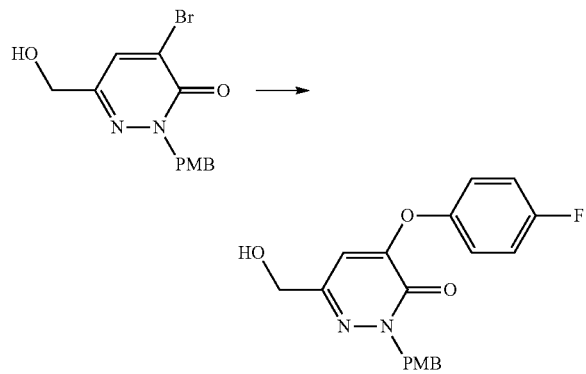

To a solution of 4-bromo-6-(hydroxymethyl)-2-(4-methoxybenzyl)pyridazin-3(2H)-one (200 mg, 0.62 mmol) in DMF (5 mL) was added 4-fluorophenol (103 mg, 0.92 mmol) and potassium carbonate (170 mg, 1.23 mmol). The mixture was stirred at 80° C. overnight. After cooling to r.t., the mixture was diluted with water and extracted with ethyl acetate. The organic layer was dried over anhydrous sodium sulfate, filtered and concentrated. The residue was purified by preparative TLC (petroleum ether/ethyl acetate (1:1) as eluent) to give 4-(4-fluorophenoxy)-6-(hydroxymethyl)-2-(4-methoxybenzyl)pyridazin-3(2H)-one (74 mg).

MS (ESI) m/z 357 (M+H)$^+$

Using an analogous procedure to that given for Example 106, and the above intermediate in Step 2 in place of the 6-(hydroxymethyl)-4-methoxy-2-(4-methoxybenzyl)pyridazin-3(2H)-one, the title compound was prepared.

$^1$H NMR: (DMSO-d$_6$, 400 MHz) δ 13.10 (s, 1H), 8.68 (s, 1H), 7.76 (s, 1H), 7.67 (t, =12.0 Hz, 2H), 7.27 (t, J=8.0 Hz, 2H), 7.18-7.25 (m, 2H), 6.68 (s, 2H), 5.01 (s, 2H).

MS (ESI) m/z 534 (M+H)$^+$

EXAMPLE 109

3-chloro-5-((1-((5-(difluoromethoxy)-6-oxo-1,6-dihydropyridazin-3-yl)methyl)-6-oxo-4-(trifluoromethyl)-1,6-dihydropyrimidin-5-yl)oxy)benzonitrile

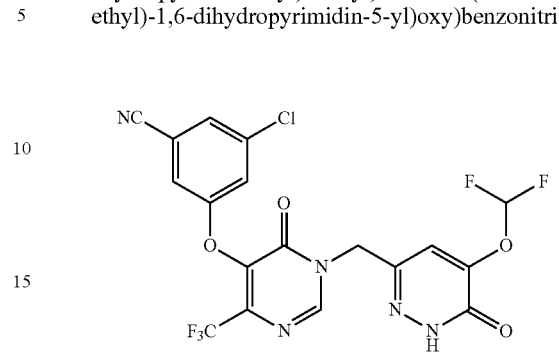

Step 1: 4-(benzyloxy)-6-(hydroxymethyl)-2-(4-methoxybenzyl)pyridazin-3(2H)-one

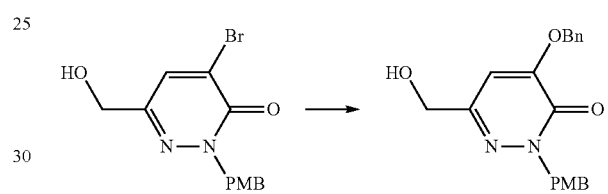

To a solution of 4-bromo-6-(hydroxymethyl)-2-(4-methoxybenzyl)pyridazin-3(2H)-one (1.3 g, 4.0 mmol) in THF (30 mL) were added benzyl alcohol (2.16 g, 20.0 mmol) and KOH (2.24 g, 40.0 mmol). The mixture was stirred at 70° C. for 2 hr. After cooling to r.t., the mixture was diluted with water and extracted with ethyl acetate. The organic layer was dried over anhydrous sodium sulfate, filtered and concentrated. The residue was purified by preparative TLC (petroleum ether/ethyl acetate (1:2) as eluent) to give the desired product 4-(benzyloxy)-6-(hydroxymethyl)-2-(4-methoxybenzyl)pyridazin-3(2H)-one (518 mg).

MS (ESI) m/z 353 (M+H)$^+$

Step 2: 4-(benzyloxy)-6-(((tert-butyldiphenylsilyl)oxy)methyl)-2-(4-methoxybenzyl)pyridazin-3(2H)-one

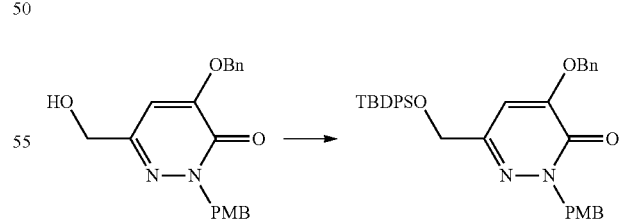

To a solution of 4-(benzyloxy)-6-(hydroxymethyl)-2-(4-methoxybenzyl)pyridazin-3(2H)-one (518 mg, 1.47 mmol) in dichloromethane (15 mL) were added imidazole (200 mg, 2.94 mmol) and TBDPSCl (444 mg, 1.62 mmol). The resulting mixture was stirred at room temperature for 1.5 hr. The mixture was quenched with water, extracted with ethyl acetate. The organic layer was dried over anhydrous sodium sulfate, concentrated under reduced pressure to give 4-(benzyloxy)-6-(((tert-butyldiphenylsilyloxy)methyl)-2-(4-methoxybenzyl)pyridazin-3(2H)-one (680 mg).

MS (ESI) m/z 591 (M+H)⁺

Step 3: 6-((((tert-butyldiphenylsilyl)oxy)methyl)-4-hydroxy-2-(4-methoxybenzyl)pyridazin-3(2H)-one

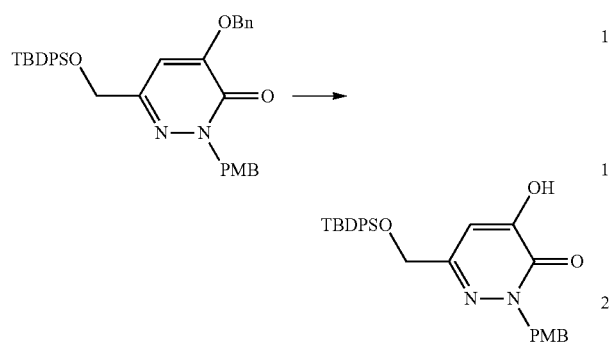

To a solution of 4-(benzyloxy)-6-(((tert-butyldiphenylsilyl)oxy)methyl)-2-(4-methoxybenzyl)pyridazin-3(2H)-one (680 mg, 1.15 mmol) in THF (8 mL) was added Pd/C (0.2 g), purged with hydrogen. The mixture was stirred at room temperature for 2 hr under hydrogen atmosphere (1 atmosphere). The mixture was filtered and concentrated under reduced pressure to give 6-(((tert-butyldiphenylsilyl)oxy)methyl)-4-hydroxy-2-(4-methoxybenzyl)pyridazin-3(2H)-one (546 mg).

MS (ESI) m/z 501 (M+H)⁺

Step 4: 6-(((tert-butyldiphenylsilyl)oxy)methyl)-4-(difluoromethoxy)-2-(4-methoxybenzyl)pyridazin-3(2H)-one

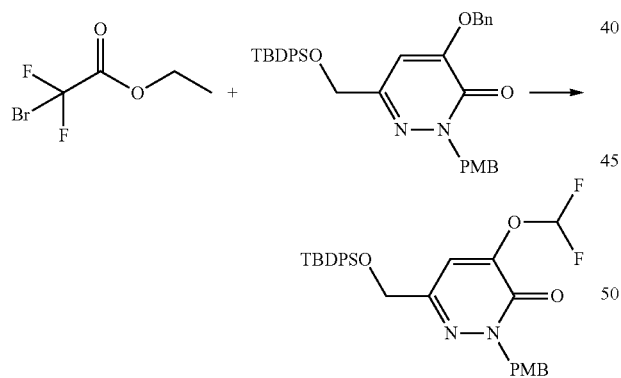

To a solution of 6-(((tert-butyldiphenylsilyl)oxy)methyl)-4-hydroxy-2-(4-methoxybenzyl)pyridazin-3(2H)-one (250 mg, 0.50 mmol) in acetonitrile (20 mL) was added ethyl 2-bromo-2,2-difluoroacetate (507 mg, 2.50 mmol) and potassium carbonate (345 mg, 2.50 mmol). The mixture was stirred at 40° C. for 2 days. After cooling to r.t, the mixture was quenched with water and extracted with ethyl acetate. The organic layer was dried over anhydrous sodium sulfate, filtered and concentrated under reduced pressure to give 6-(((tert-butyldiphenylsilyl)oxy)methyl)-4-(difluoromethoxy)-2-(4-methoxybenzyl)pyridazin-3(2H)-one (275 mg).

MS (ESI) m/z 551 (M+H)⁺

Step 5: 4-(difluoromethoxy)-6-(hydroxymethyl)-2-(4-methoxybenzyl)pyridazin-3(2H)-one

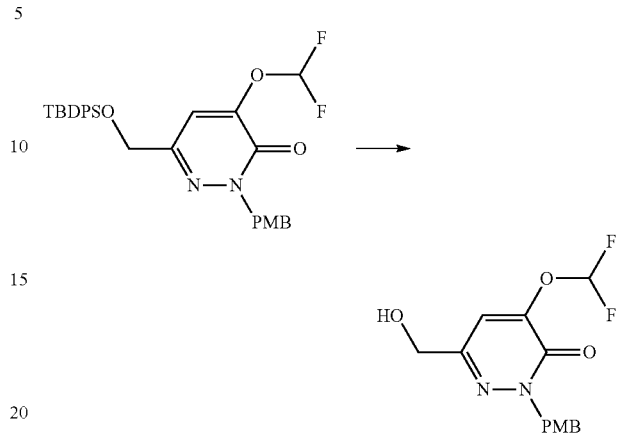

To a solution of 6-(((tert-butyldiphenylsilyl)oxy)methyl)-4-(difluoromethoxy)-2-(4-methoxybenzyl)pyridazin-3(2H)-one (275 mg, 0.50 mmol) in THF (8 mL) was added TBAF (653 mg, 2.50 mmol). The mixture was stirred at room temperature for 1 hr. The mixture was quenched with water and extracted with ethyl acetate. The combined organic extracts were dried over anhydrous sodium sulfate, filtered and concentrated under reduced pressure. The residue was purified by preparative TLC (petroleum ether/ethyl acetate (2:1) as eluent) to give 4-(difluoromethoxy)-6-(hydroxymethyl)-2-(4-methoxybenzyl)pyridazin-3(2H)-one (84 mg).

MS (ESI) m/z 313 (M+H)⁺

Using an analogous procedure to that given for Example 106, and the above intermediate in place of the 6-(hydroxymethyl)-4-methoxy-2-(4-methoxybenzyl)pyridazin-3(2H)-one in Step 2, the title compound was prepared.

¹H NMR: (DMSO-d₆, 400 MHz) δ 13.34 (s, 1H), 8.72 (s, 1H), 7.74 (s, 1H), 7.66 (s, 1H), 7.63 (s, 1H), 7.41 (t, J=72.8 Hz, 1H), 7.29 (s, 1H), 5.10 (s, 2H).

MS (ESI) m/z 490 (M+H)⁺

EXAMPLE 110

3-chloro-5-((6-oxo-1-((3-oxo-6-phenyl-2,3-dihydropyridazin-4-yl)methyl)-4-(trifluoromethyl)-1,6-dihydropyrimidin-5-yl)oxy)benzonitrile

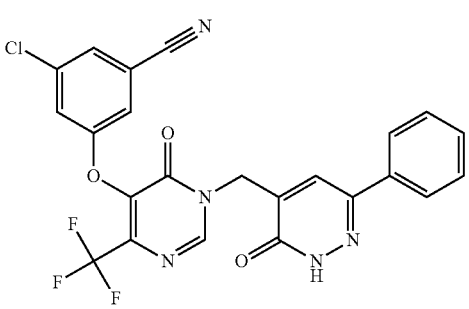 [SMILES: N#Cc1cc(Cl)cc(Oc2c(C(F)(F)F)ncn(Cc3cc(-c4ccccc4)n[nH]c3=O)c2=O)c1]

Step 1: 3-chloro-5-((1-((3-methoxy-6-phenylpyridazin-4-yl)methyl)-6-oxo-4-(trifluoromethyl)-1,6-dihydropyrimidin-5-yl)oxy)benzonitrile

Step 2: 3-chloro-5-((6-oxo-1-((3-oxo-6-phenyl-2,3-dihydropyridazin-4-yl)methyl)-4-(trifluoromethyl)-1,6-dihydropyrimidin-5-yl)oxy)benzonitrile

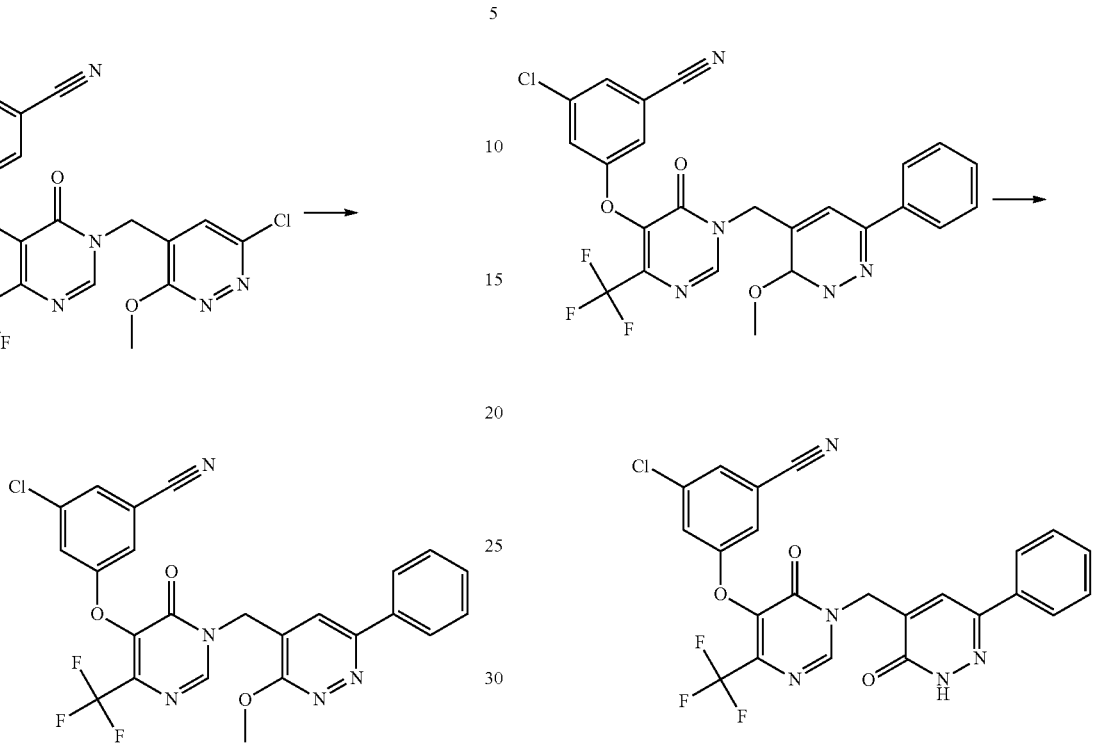

A mixture of 3-chloro-5-((1-((6-chloro-3-methoxypyridazin-4-yl)methyl)-6-oxo-4-(trifluoromethyl)-1,6-dihydropyrimidin-5-yl)oxy)benzonitrile (200 mg, 0.42 mmol), phenyl boronic acid (62 mg, 0.51 mmol), K₃PO₄ (180 mg, 0.85 mmol), Pd(dppf)Cl₂ (20 mg, 0.03 mmol) in 1,4-dioxane/H₂O (3:1) was heated at reflux overnight. After cooling to r.t., the mixture was filtered, and the filtrate was extracted with ethyl acetate. The combined organic layers were dried over sodium sulfate, filtered and concentrated under reduced pressure. The residue was purified by preparative TLC (petroleum ether/ethyl acetate (1:1.5) as eluent) to afford 3-chloro-5-((1-((3-methoxy-6-phenylpyridazin-4-yl)methyl)-6-oxo-4-(trifluoromethyl)-1,6-dihydropyrimidin-5-yl)oxy)benzonitrile (100 mg).

MS (ESI): m/z 514, 516 (M+H)⁺

To a mixture of 3-chloro-5-((1-((3-methoxy-6-phenylpyridazin-4-yl)methyl)-6-oxo-4-(trifluoromethyl)-1,6-dihydropyrimidin-5-yl)oxy)benzonitrile (100 mg, 0.02 mmol) and KI (70 mg, 0.4 mmol) in acetonitrile (3 mL) at r.t. was added TMSCl (45 mg, 0.4 mmol) dropwise. After addition, the mixture was stirred at r.t. for 12 hr. The reaction mixture was quenched with methanol and concentrated under reduced pressure. The residue was purified by preparative HPLC to afford 3-chloro-5-((6-oxo-1-((3-oxo-6-phenyl-2,3-dihydropyridazin-4-yl)methyl)-4-(trifluoromethyl)-1,6-dihydropyrimidin-5-yl)oxy)benzonitrile (25 mg).

$^1$HNMR (DMSO-d6, 400 MHz): δ 13.40 (s, 1H), 8.80 (s, 1H), 7.93 (s, 1H), 7.77-7.83 (m, 2H), 7.72-7.75 (m, 3H), 7.44-7.50 (m, 3H), 5.06 (s, 2H).

MS (ESI): m/z 500, 502 (M+H)⁺

Examples 111-126 in the table below were prepared using the appropriate boronic acid according to the procedure given for Example 110.

| Example | Structure | IUPAC Name | MS (M + H)⁺/NMR |
|---|---|---|---|
| 111 | 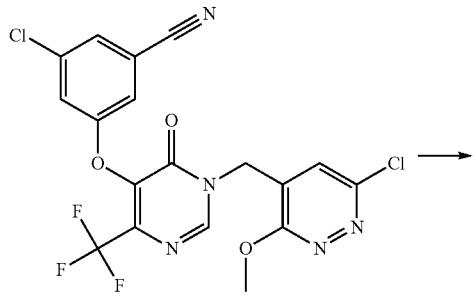 | 3-chloro-5-((1-((6-(1-methyl-1H-pyrazol-4-yl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 504, 506 (M + H)⁺ <br> $^1$H NMR: (DMSO-d6, 400 MHz) <br> δ 13.11 (s, 1H), 8.80 (s, 1H), 8.20 (s, 1H), 7.85 (s, 1H), 7.72-7.75 (m, 3H), 7.59 (s, 1H), 5.00 (s, 2H), 3.85 (s, 3H). |

| Example | Structure | IUPAC Name | MS (M + H)⁺/NMR |
|---|---|---|---|
| 112 | 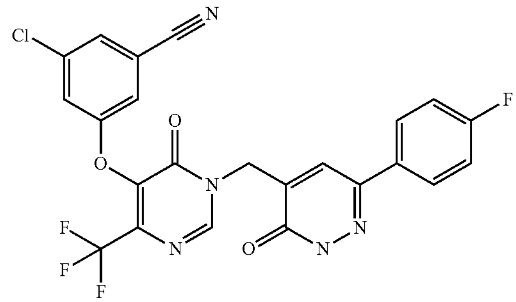 [SMILES: N#Cc1cc(Cl)cc(Oc2c(C(F)(F)F)ncn(Cc3cc(-c4ccc(F)cc4)n[nH]c3=O)c2=O)c1] | 3-chloro-5-((1-((6-(4-fluorophenyl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 518, 520 (M + H)⁺<br>¹H NMR: (DMSO-d6, 400 MHz)<br>δ 13.40 (s, 1H), 8.79 (s, 1H), 7.90-7.91 (m, 3H), 7.86-7.89 (m, 2H), 7.71-7.72 (m, 1H), 7.30-7.34 (m, 2H), 5.05 (s, 2H). |
| 113 | 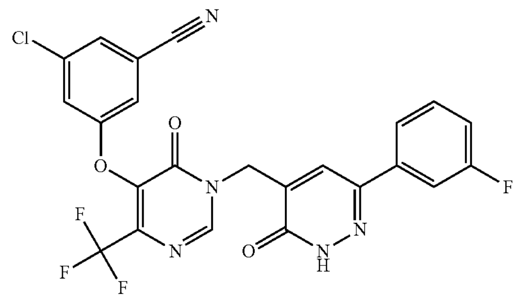 [SMILES: N#Cc1cc(Cl)cc(Oc2c(C(F)(F)F)ncn(Cc3cc(-c4cccc(F)c4)n[nH]c3=O)c2=O)c1] | 3-chloro-5-((1-((6-(3-fluorophenyl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 518, 520 (M + H)⁺<br>¹H NMR: (DMSO-d6, 400 MHz)<br>δ 13.49 (s, 1H), 8.79 (s, 1H), 7.95 (s, 1H), 7.69-7.70 (m, 2H), 7.60-7.66 (m, 3H), 7.46-7.52 (m, 1H), 7.21-7.26 (m, 1H), 5.06 (s, 2H). |
| 114 | 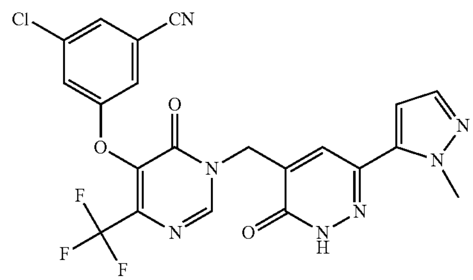 [SMILES: Cn1nccc1-c1cc(Cn2cnc(C(F)(F)F)c(Oc3cc(Cl)cc(C#N)c3)c2=O)c(=O)[nH]n1] | 3-chloro-5-((1-((6-(1-methyl-1H-pyrazol-5-yl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 504, 506 (M + H)⁺<br>¹H NMR: (DMSO-d6, 400 MHz)<br>δ 13.47 (s, 1H), 8.77 (s, 1H), 7.70 (s, 2H), 7.66-7.76 (m, 2H) 7.47 (d, J = 1.6 Hz, 1H), 6.78 (d, J = 2.0 Hz, 1H), 5.03 (s, 2H), 3.98 (s, 3H). |
| 115 | 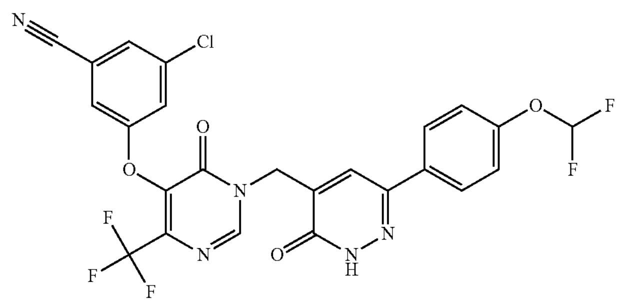 [SMILES: N#Cc1cc(Cl)cc(Oc2c(C(F)(F)F)ncn(Cc3cc(-c4ccc(OC(F)F)cc4)n[nH]c3=O)c2=O)c1] | 3-chloro-5-((1-((6-(4-(difluoromethoxy)phenyl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 566, 568 (M + H)⁺<br>¹H NMR: (DMSO-d6, 400 MHz)<br>δ 13.39 (s, 1H), 8.76 (s, 1H), 7.84-7.88 (m, 3H), 7.68-7.84 (m, 3H), 7.27 (t, J = 73.8 Hz, 1H), 7.24 (m, 2H), 5.02 (s, 2H). |
| 116 | 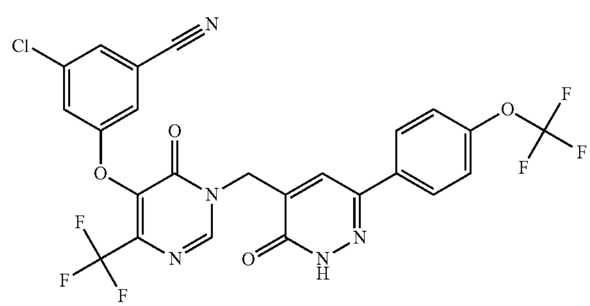 [SMILES: N#Cc1cc(Cl)cc(Oc2c(C(F)(F)F)ncn(Cc3cc(-c4ccc(OC(F)(F)F)cc4)n[nH]c3=O)c2=O)c1] | 3-chloro-5-((6-oxo-1-((3-oxo-6-(4-(trifluoromethoxy)phenyl)-2,3-dihydropyridazin-4-yl)methyl)-4-(trifluoromethyl)-1,6-dihydropyrimidin-5-yl)oxy)benzonitrile | MS (ESI) m/z 584, 586 (M + H)⁺<br>¹H NMR: (DMSO-d6, 400 MHz)<br>δ 13.46 (s, 1H), 8.76 (s, 1H), 7.89-7.92 (m, 3H), 7.74-7.72 (m, 2H), 7.67-7.68 (m, 1H), 7.44 (d, J = 8.0 Hz, 2H), 5.02 (s, 2H). |

-continued

| Example | Structure | IUPAC Name | MS (M + H)+/NMR |
|---|---|---|---|
| 117 | 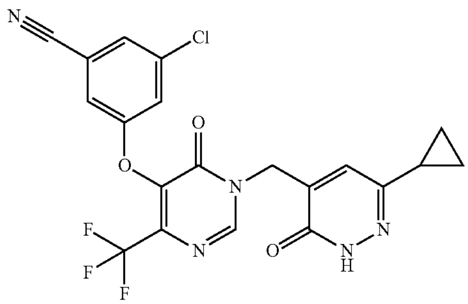 [SMILES: N#Cc1cc(Cl)cc(Oc2c(C(F)(F)F)ncn(Cc3cc(C4CC4)n[nH]c3=O)c2=O)c1] | 3-chloro-5-((1-((6-cyclopropyl-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 464, 466 (M + H)+ <br> 1H NMR: (DMSO-d6, 400 MHz) <br> δ 12.89 (s, 1H), 8.75 (s, 1H), 7.75-7.76 (m, 2H), 7.72 (s, 1H), 7.24 (s, 1H), 4.95 (s, 2H), 1.91 (m, 1H), 0.89 (m, 2H). 0.74 (m, 2H). |
| 118 | 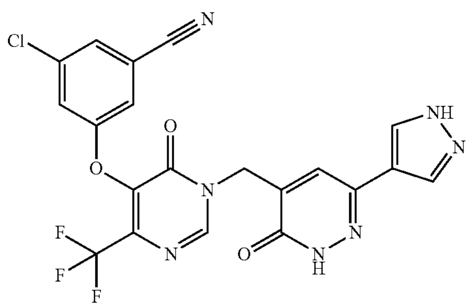 [SMILES: N#Cc1cc(Cl)cc(Oc2c(C(F)(F)F)ncn(Cc3cc(-c4cn[nH]c4)n[nH]c3=O)c2=O)c1] | 3-chloro-5-((6-oxo-1-((3-oxo-6-(1H-pyrazol-4-yl)-2,3-dihydropyridazin-4-yl)methyl)-4-(trifluoromethyl)-1,6-dihydropyrimidin-5-yl)oxy)benzonitrile | MS (ESI) m/z 458, 460 (M + H)+ <br> 1H NMR: (DMSO-d6, 400 MHz) <br> δ 13.09 (s, 1H), 8.80 (s, 1H), 8.09 (m, 2H), 7.72-7.75 (m, 3H), 7.62 (s, 1H), 5.01 (s, 2H). |
| 119 | 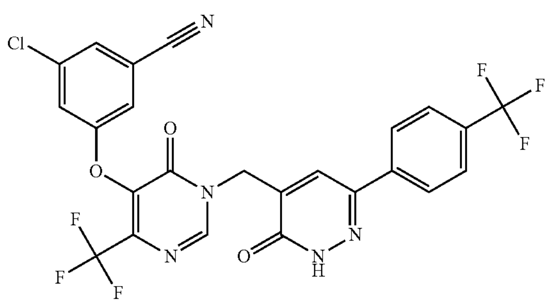 [SMILES: N#Cc1cc(Cl)cc(Oc2c(C(F)(F)F)ncn(Cc3cc(-c4ccc(C(F)(F)F)cc4)n[nH]c3=O)c2=O)c1] | 3-chloro-5-((6-oxo-1-((3-oxo-6-(4-(trifluoromethyl)phenyl)-2,3-dihydropyridazin-4-yl)methyl)-4-(trifluoromethyl)-1,6-dihydropyrimidin-5-yl)oxy)benzonitrile | MS (ESI) m/z 568, 570 (M + H)+ <br> 1H NMR: (DMSO-d6, 400 MHz) <br> δ 13.55 (s, 1H), 8.81 (s, 1H), 8.04-8.06 (m, 2H), 7.98 (s, 1H), 7.83-7.86 (m, 2H), 7.74-7.78 (m, 2H), 7.75 (s, 1H), 5.07 (s, 2H). |
| 120 | 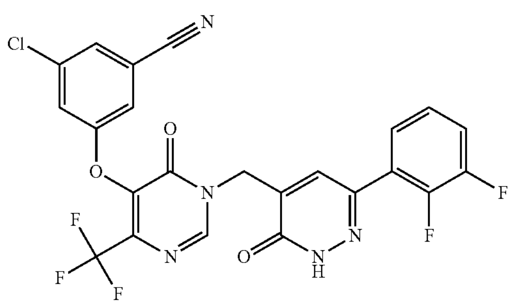 [SMILES: N#Cc1cc(Cl)cc(Oc2c(C(F)(F)F)ncn(Cc3cc(-c4cccc(F)c4F)n[nH]c3=O)c2=O)c1] | 3-chloro-5-((1-((6-(2,3-difluorophenyl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 536, 538 (M + H)+ <br> 1H NMR: (DMSO-d6, 400 MHz) <br> δ 13.62 (s, 1H), 8.78 (s, 1H), 7.74-7.75 (m, 2H), 7.71 (s, 1H), 7.67 (s, 1H), 7.54-7.55 (m, 1H), 7.37-7.39 (m, 1H), 7.32-7.34 (m, 1H), 5.06 (s, 2H). |
| 121 | 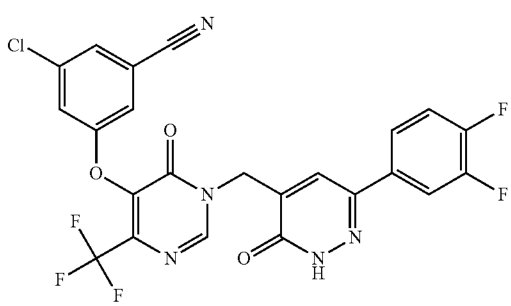 [SMILES: N#Cc1cc(Cl)cc(Oc2c(C(F)(F)F)ncn(Cc3cc(-c4ccc(F)c(F)c4)n[nH]c3=O)c2=O)c1] | 3-chloro-5-((1-((6-(3,4-difluorophenyl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 536, 538 (M + H)+ <br> 1H NMR: (DMSO-d6, 400 MHz) <br> δ 13.50 (s, 1H), 8.80 (s, 1H), 7.92 (s, 1H), 7.88-7.90 (m, 1H), 7.69-7.74 (m, 4H), 7.53-7.55 (m, 1H), 5.05 (s, 2H). |

-continued

| Example | Structure | IUPAC Name | MS (M + H)⁺/NMR |
|---|---|---|---|
| 122 | 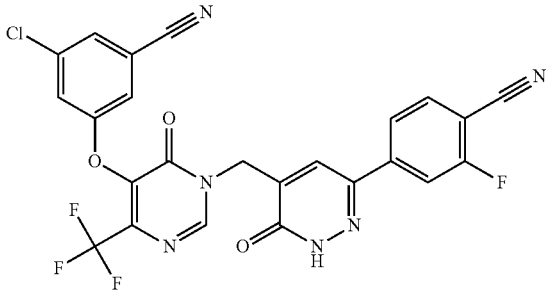 [SMILES: N#Cc1cc(Cl)cc(Oc2c(C(F)(F)F)ncn(Cc3cc(-c4ccc(C#N)c(F)c4)n[nH]c3=O)c2=O)c1] | 4-(5-((5-(3-chloro-5-cyanophenoxy)-6-oxo-4-(trifluoromethyl)pyrimidin-1(6H)-yl)methyl)-6-oxo-1,6-dihydropyridazin-3-yl)-2-fluorobenzonitrile | MS (ESI) m/z 543, 545 (M + H)⁺<br>¹H NMR: (DMSO-d6, 400 MHz)<br>δ 13.72 (s, 1H), 8.80 (s, 1H), 8.03 (t, J = 6.8 Hz, 1H), 7.93-7.95 (m, 2H), 7.90 (d, J = 9.0 Hz, 1H), 7.71-7.73 (m, 2H), 7.68 (s, 1H), 5.06 (s, 2H). |
| 123 | 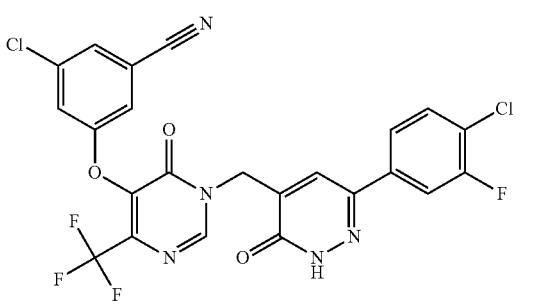 [SMILES: N#Cc1cc(Cl)cc(Oc2c(C(F)(F)F)ncn(Cc3cc(-c4ccc(Cl)c(F)c4)n[nH]c3=O)c2=O)c1] | 3-chloro-5-((1-((6-(4-chloro-3-fluorophenyl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 552, 554 (M + H)⁺<br>¹H NMR: (DMSO-d6, 400 MHz)<br>δ 13.55 (s, 1H), 8.80 (s, 1H), 7.94 (s, 1H), 7.88 (d, J = 10.4 Hz, 1H), 7.71-7.74 (m, 3H), 7.67-7.69 (m, 2H), 5.06 (s, 2H). |
| 124 | 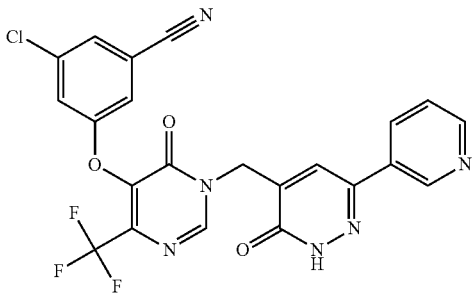 [SMILES: N#Cc1cc(Cl)cc(Oc2c(C(F)(F)F)ncn(Cc3cc(-c4cccnc4)n[nH]c3=O)c2=O)c1] | 3-chloro-5-((6-oxo-1-((3-oxo-6-(pyridin-3-yl)-2,3-dihydropyridazin-4-yl)methyl)-4-(trifluoromethyl)-1,6-dihydropyrimidin-5-yl)oxy)benzonitrile | MS (ESI) m/z 501, 503 (M + H)⁺<br>¹H NMR: (DMSO-d6, 400 MHz)<br>δ 13.74 (s, 1H), 9.22 (s, 1H), 8.82 (m, 2H), 8.64 (d, J = 8.2 Hz, 1H), 8.04 (s, 1H), 7.89 (t, J = 8.0 Hz, 1H), 7.74-7.69 (m, 3H), 5.09 (s, 2H). |
| 125 | 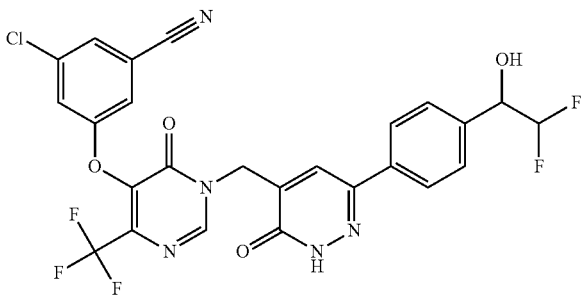 [SMILES: N#Cc1cc(Cl)cc(Oc2c(C(F)(F)F)ncn(Cc3cc(-c4ccc(C(O)C(F)F)cc4)n[nH]c3=O)c2=O)c1] | 3-chloro-5-((1-((6-(4-(2,2-difluoro-1-hydroxyethyl)phenyl)-3-oxo-2,3-dihydropyridazin-4-yl)methyl)-6-oxo-4-(trifluoromethyl)-1,6-dihydropyrimidin-5-yl)oxy)benzonitrile | MS (ESI) m/z 580, 582 (M + H)⁺<br>¹H NMR: (DMSO-d6, 400 MHz)<br>δ 13.42 (s, 1H), 9.22 (s, 1H), 8.80 (s, 1H), 7.82 (d, J = 8.2 Hz, 2H), 7.71-7.74 (m, 3H), 7.53 (d, J = 8.2 Hz, 2H), 6.01 (td, J = 56.0 Hz, J = 4.2 Hz, 1H), 5.06 (s, 2H), 4.79 (td, J = 12.0 Hz, J = 3.8 Hz, 1H). |
| 126 | 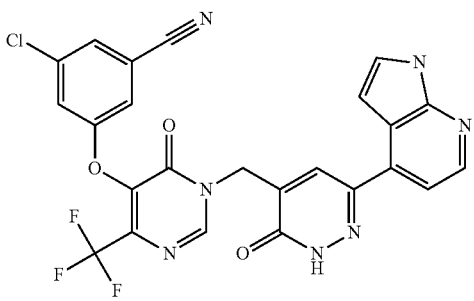 [SMILES: N#Cc1cc(Cl)cc(Oc2c(C(F)(F)F)ncn(Cc3cc(-c4ccnc5[nH]ccc45)n[nH]c3=O)c2=O)c1] | 3-chloro-5-((6-oxo-1-((3-oxo-6-(1H-pyrrolo[2,3-b]pyridin-4-yl)-2,3-dihydropyridazin-4-yl)methyl)-4-(trifluoromethyl)-1,6-dihydropyrimidin-5-yl)oxy)benzonitrile | MS (ESI) m/z 540, 542 (M + H)⁺<br>¹H NMR: (DMSO-d6, 400 MHz)<br>δ 13.69 (s, 1H), 12.13 (s, 1H), 8.76 (s, 1H), 8.38 (d, J = 5.2 Hz, 1H), 8.07 (s, 1H), 7.75-7.73 (m, 2H), 7.70 (s, 1H), 7.61 (s, 1H), 7.52 (d, J = 5.2 Hz, 1H), 6.87 (s, 1H), 5.11 (s, 2H). |

EXAMPLE 127

3-chloro-5-((1-((1-methyl-3,6-dioxo-1,2,3,6-tetrahydropyridazin-4-yl)methyl)-6-oxo-4-(trifluoromethyl)-1,6-dihydro pyrimidin-5-yl)oxy)benzonitrile

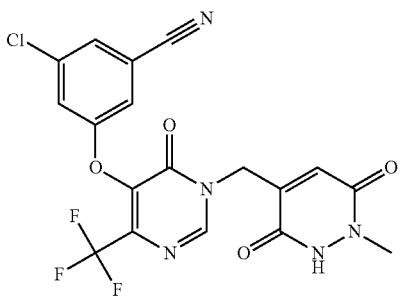 [SMILES: Cn1[nH]c(=O)c(Cn2cnc(C(F)(F)F)c(Oc3cc(Cl)cc(C#N)c3)c2=O)cc1=O]

Step 1: 3-chloro-5-((1-((3-methoxy-1-methyl-6-oxo-1,6-dihydropyridazin-4-yl)methyl)-6-oxo-4-(trifluoromethyl)-1,6-dihydropyrimidin-5-yl)oxy)benzonitrile

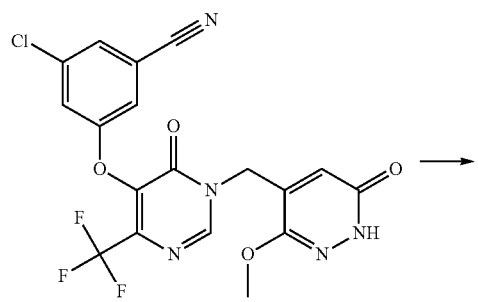

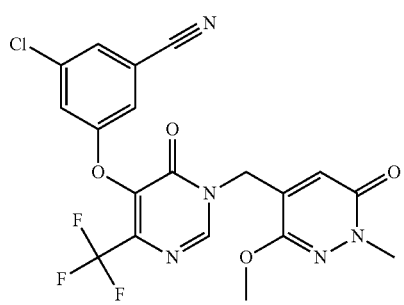

To a solution of 3-chloro-5-((1-((3-methoxy-6-oxo-1,6-dihydropyridazin-4-yl)methyl)-6-oxo-4-(trifluoromethyl)-1,6-dihydropyrimidin-5-yl)oxy)benzonitrile (75 mg, 0.16 mmol) in 1,4-dioxane/DMF (6 mL/0.6 mL) were added potassium carbonate (100 mg, 0.72 mmol) and MeI (0.6 mL, 9.2 mmol) at r.t. The resulting mixture was stirred at 60° C. for 4 hr under a nitrogen atmosphere. After cooling, the mixture was diluted with ethyl acetate and washed with brine, dried over anhydrous sodium sulfate, filtered and concentrated under reduced pressure. The residue was purified by preparative TLC to afford 3-chloro-5-((1-((3-methoxy-1-methyl-6-oxo-1,6-dihydropyridazin-4-yl)methyl)-6-oxo-4-(trifluoromethyl)-1,6-dihydropyrimidin-5-yl)oxy)benzonitrile (50 mg).

$^1$H NMR (CDCl3, 400 MHz): δ 8.29 (s, 1H), 7.41 (s, 1H), 7.19 (s, 1H), 7.04 (s, 1H), 6.87 (s, 1H), 4.92 (s, 2H), 3.90 (s, 3H), 3.64 (s, 3H).

MS (ESI) m/z 468, 470 (M+H)$^+$

The title compound was prepared from above intermediate according to the procedure given for Step 2 of Example 17.

$^1$H NMR (DMSO-d6, 400 MHz): δ 11.73 (s, 1H), 8.69 (s, 1H), 7.75-7.72 (m, 3H), 6.87 (s, 1H), 4.94 (s, 2H), 3.44 (s, 3H).

MS (ESI) m/z 468, 470 (M+H)$^+$

EXAMPLE 128

3-chloro-5-((1-((6-(difluoromethyl)-3-oxo-2,3-dihydropyridazin-4-yl)methyl)-6-oxo-4-(trifluoromethyl)-1,6-dihydropyrimidin-5-yl)oxy)benzonitrile

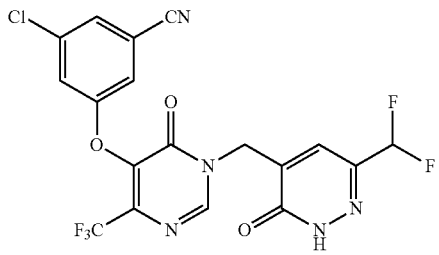 [SMILES: N#Cc1cc(Cl)cc(Oc2c(C(F)(F)F)ncn(Cc3cc(C(F)F)n[nH]c3=O)c2=O)c1]

Step 1: methyl 5-(hydroxymethyl)-6-methoxypyridazine-3-carboxylate

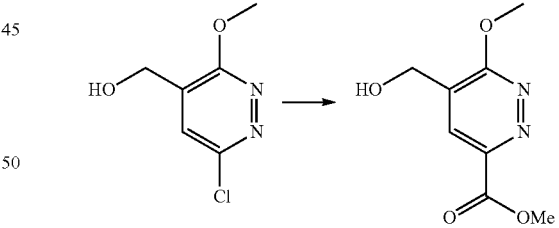

To a solution of (6-chloro-3-methoxypyridazin-4-yl)methanol (4.6 g, 26.4 mmol), triethyl amine (7.4 mL) and Pd(dppf)$_2$Cl$_2$ (0.5 g, 1 mmol) in 30 mL of methanol and ethyl acetate (10 mL) was stirred under carbon monoxide (50 psi) at 70° C. overnight. Then the reaction mixture was poured into water, extracted with ethyl acetate (15 mL×3). The organic extracts were washed with water and brine, dried over anhydrous sodium sulfate, filtered and concentrated under reduced pressure. The residue was purified by column (petroleum ether/ethyl acetate (5:1 to 2:1) as eluent) to give methyl 5-(hydroxymethyl)-6-methoxypyridazine-3-carboxylate (2.1 g).

MS (ESI) m/z 199 (M+H)$^+$

Step 2: methyl 5-(((tert-butyldimethylsilyl)oxy)
methyl)-6-methoxypyridazine-3-carboxylate Step 4: 4-(((tert-butyldimethylsilyl)oxy)methyl)-3-
methoxy-6-((((tetrahydro-2H-pyran-2-yl)oxy)methyl)
pyridazine

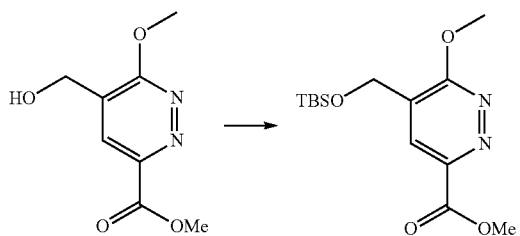 [SMILES: COC(=O)c1cc(CO)c(OC)nn1 ; COC(=O)c1cc(CO[Si](C)(C)C(C)(C)C)c(OC)nn1]

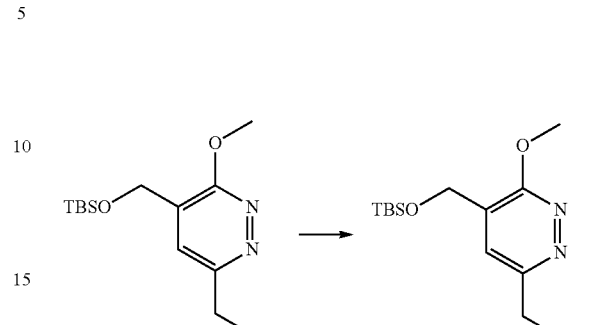

To a solution of methyl 5-(hydroxymethyl)-6-methoxypyridazine-3-carboxylate (2.1 g, 10.6 mmol) in THF (150 mL) was added TBSCl (4.55 g, 30.2 mmol) and imidazole (2.05 g, 30.2 mmol) at r.t. Then the resulting reaction was stirred at room temperature overnight. The reaction mixture was filtered and the filtrate was washed with water. The organic layer was dried over magnesium sulfate, filtered and concentrated under reduced pressure to afford methyl 5-(((tert-butyldimethylsilyl)oxy)methyl)-6-methoxypyridazine-3-carboxylate (2.1 g).

MS (ESI) m/z 313 (M+H)+

Step 3: (5-(((tert-butyldimethylsilyl)oxy)methyl)-6-methoxypyridazin-3-yl)methanol To a solution of (5-(((tert-butyldimethylsilyl)oxy)methyl)-6-methoxypyridazin-3-yl)methanol (1.5 g, 5.3 mmol) in acetonitrile (10 mL) was added DHP (0.53 g, 6.3 mmol) and PPTS (126 mg, 0.5 mmol) at r.t. The mixture was stirred at 80° C. for 16 hr. After cooling to r.t., the mixture was concentrated under reduced pressure. The residue was purified by column chromatography on a silica gel (petroleum ether/ethyl acetate (10:1) as eluent) to give 4-(((tert-butyldimethylsilyl)oxy)methyl)-3-methoxy-6-((((tetrahydro-2H-pyran-2-yl)oxy)methyl)pyridazine (0.9 g).

MS (ESI) m/z 369 (M+H)+

Step 5: (3-methoxy-6-(((tetrahydro-2H-pyran-2-yl)oxy)methyl)pyridazin-4-yl)methanol

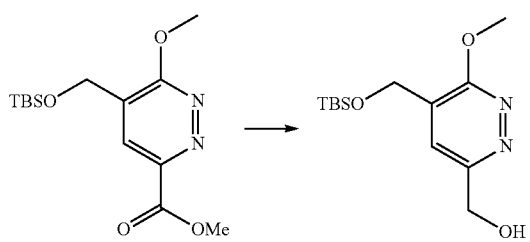 [SMILES: COC(=O)c1cc(CO[Si](C)(C)C(C)(C)C)c(OC)nn1 ; COc1nnc(CO)cc1CO[Si](C)(C)C(C)(C)C]

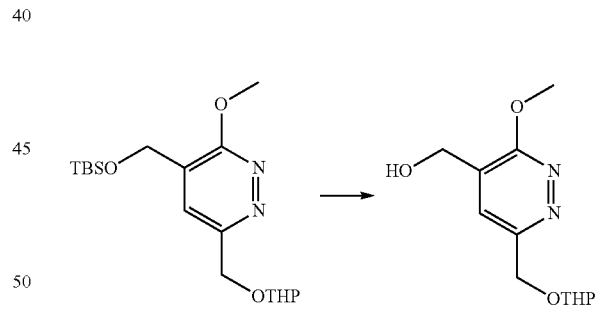

To a solution of methyl 5-(((tert-butyldimethylsilyl)oxy)methyl)-6-methoxypyridazine-3-carboxylate (2.1 g, 6.7 mmol) in ethanol (15 mL) was added NaBH4 (0.38 g, 10.0 mmol) and CaCl2 (0.37 g, 3.4 mmol) at 0° C. The mixture was stirred for 1 hr at room temperature, then quenched by addition of water (20 mL), acidified to pH=8 using HCl solution (2 M) and extracted with ethyl acetate (15 mL ×3). The combined organic extracts were dried over sodium sulfate, filtered and concentrated under reduced pressure to give (5-(((tert-butyldimethylsilyl)oxy)methyl)-6-methoxypyridazin-3-yl)methanol (1.5 g).

MS (ESI) m/z 285 (M+H)+

A solution of 4-(((tert-butyldimethylsilyl)oxy)methyl)-3-methoxy-6-((((tetrahydro-2H-pyran-2-yl)oxy)methyl)pyridazine (0.9 g, 2.4 mmol) and TBAF (3.2 g, 12.2 mmol) in THF (20.0 mL) was stirred for 1.0 h at r.t. Water was added and the resulting mixture was extracted with ethyl acetate. The combined organics were dried over sodium sulfate, filtered and concentrated under reduced pressure. The residue was purified by preparative TLC (petroleum ether/ethyl acetate (1:2) as eluent) to give the (3-methoxy-6-(((tetrahydro-2H-pyran-2-yl)oxy)methyl)pyridazin-4-yl)methanol (0.6 g).

MS (ESI) m/z 255 (M+H)+

Step 6: 3-chloro-5-((1-((3-methoxy-6-(((tetrahydro-2H-pyran-2-yl)oxy)methyl)pyridazin-4-yl)methyl)-6-oxo-4-(trifluoromethyl)-1,6-dihydropyrimidin-5-yl)oxy)benzonitrile

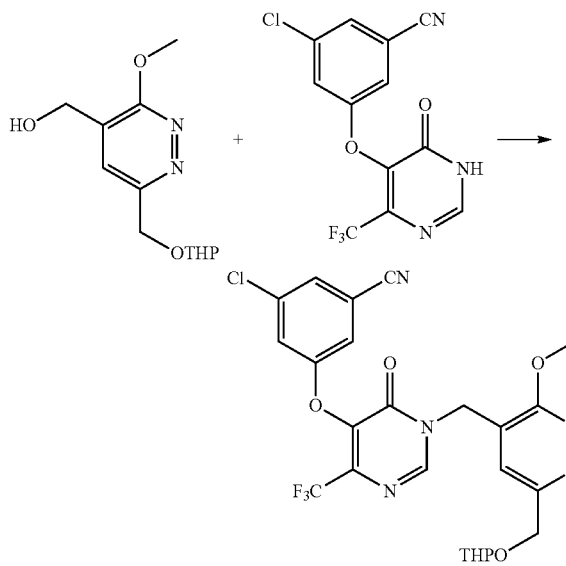

To a solution of (3-methoxy-6-(((tetrahydro-2H-pyran-2-yl)oxy)methyl)pyridazin-4-yl)methanol (0.6 g, 2.4 mmol), 3-chloro-5-((6-oxo-4-(trifluoromethyl)-1,6-dihydropyrimidin-5-yl)oxy)benzonitrile (0.76 g, 2.4 mmol) and PPh$_3$ (1.3 g, 4.8 mmol) in dichloromethane (10.0 mL) was added DEAD (0.84 g, 4.8 mmol) at 0° C. under a nitrogen atmosphere. The mixture was stirred at r.t for 1 h, quenched with water (10 mL) and extracted with dichloromethane (20 mL×3). The combined organic extracts were dried over sodium sulfate, filtered and concentrated under reduced pressure. The crude product was purified by preparative TLC (petroleum ether/ethyl acetate (1:1) as eluent) to give 3-chloro-5-((1-((3-methoxy-6-(((tetrahydro-2H-pyran-2-yl)oxy)methyl)pyridazin-4-yl)methyl)-6-oxo-4-(trifluoromethyl)-1,6-dihydropyrimidin-5-yl)oxy)benzonitrile (1.2 g).

MS (ESI) m/z 552, 554 (M+H)$^+$

Step 7: 3-chloro-5-((1-((6-(hydroxymethyl)-3-methoxypyridazin-4-yl)methyl)-6-oxo-4-(trifluoromethyl)-1,6-dihydropyrimidin-5-yl)oxy)benzonitrile

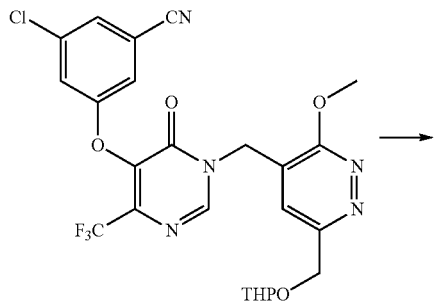

To a solution of 3-chloro-5-((1-((3-methoxy-6-(((tetrahydro-2H-pyran-2-yl)oxy)methyl)pyridazin-4-yl)methyl)-6-oxo-4-(trifluoromethyl)-1,6-dihydropyrimidin-5-yl)oxy)benzonitrile (1.2 g, 2.2 mmol) in methanol (10 mL) was added HCl/methanol (1 N, 10 mL) at r.t. The resulting mixture was stirred at room temperature for 1 hr and concentrated under reduced pressure to give 3-chloro-5-((1-((6-(hydroxymethyl)-3-methoxypyridazin-4-yl)methyl)-6-oxo-4-(trifluoromethyl)-1,6-dihydropyrimidin-5-yl)oxy)benzonitrile (1.0 g).

MS (ESI) m/z 468, 470 (M+H)$^+$

Step 8: 3-chloro-5-((1-((6-formyl-3-methoxypyridazin-4-yl)methyl)-6-oxo-4-(trifluoromethyl)-1,6-dihydropyrimidin-5-yl)oxy)benzonitrile

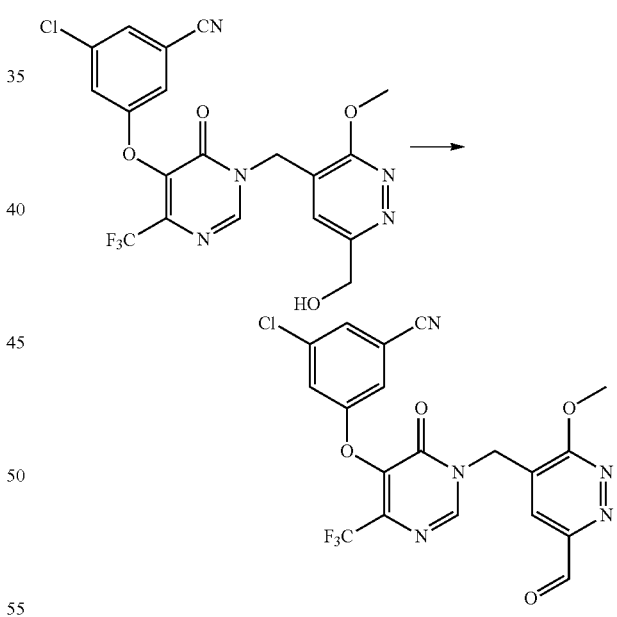

To a solution of 3-chloro-5-((1-((6-(hydroxymethyl)-3-methoxypyridazin-4-yl)methyl)-6-oxo-4-(trifluoromethyl)-1,6-dihydropyrimidin-5-yl)oxy)benzonitrile (1.0 g, 2.1 mmol) in dichloromethane (20 mL) was added Dess-Martin periodinane (1.36 g, 3.2 mmol) at 0° C. under a nitrogen atmosphere. The mixture was stirred at r.t for 1 hr, quenched with water (10 mL) and extracted with dichloromethane (20 mL×3). The combined organic extracts were dried over sodium sulfate, filtered and concentrated under reduced pressure. The crude product was purified by preparative TLC (petroleum ether/ethyl acetate (1:1) as eluent) to give 3-chloro-5-((1-((6-formyl-3-methoxypyridazin-4-yl)methyl)-6-oxo-4-(trifluoromethyl)-1,6-dihydropyrimidin-5-yl)oxy)benzonitrile (0.6 g).

MS (ESI) m/z 466, 468 (M+H)+

Step 9: 3-chloro-5-((1-((6-(difluoromethyl)-3-methoxypyridazin-4-yl)methyl)-6-oxo-4-(trifluoromethyl)-1,6-dihydropyrimidin-5-yl)oxy)benzonitrile

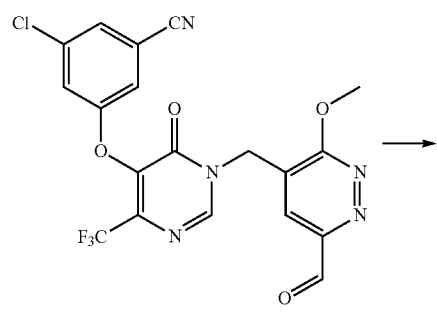

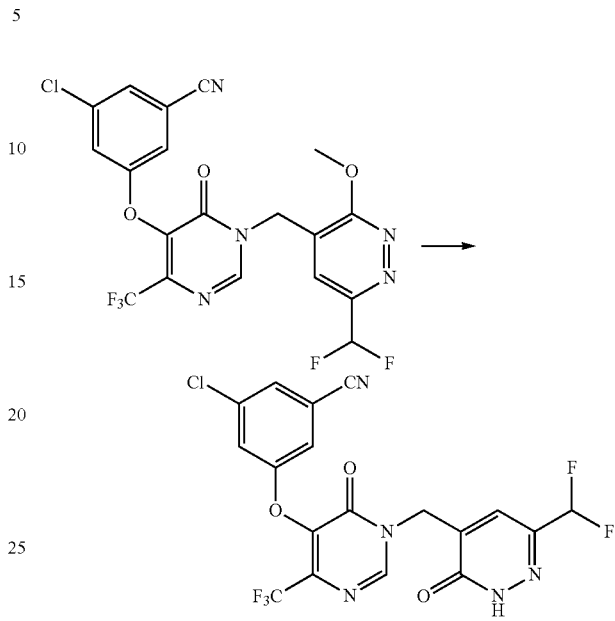

To a stirred mixture of 3-chloro-5-((1-((6-formyl-3-methoxypyridazin-4-yl)methyl)-6-oxo-4-(trifluoromethyl)-1,6-dihydropyrimidin-5-yl)oxy)benzonitrile (0.14 g, 0.3 mmol) in dichloromethane (5 mL) was added DAST (0.43 g, 1.6 mmol) at r.t., and the mixture was stirred under a nitrogen atmosphere for 16 hr. The mixture was quenched with H₂O and extracted with dichloromethane. The organic layer was washed with water, dried over anhydrous sodium sulfate, filtered and concentrated under reduced pressure. The residue was purified by chromatography on silica gel (petroleum ether/ethyl acetate (2:1) as eluent) to give 3-chloro-5-((1-((6-(difluoromethyl)-3-methoxypyridazin-4-yl)methyl)-6-oxo-4-(trifluoromethyl)-1,6-dihydropyrimidin-5-yl)oxy)benzonitrile (90 mg).

MS (ESI) m/z 488, 490 (M+H)+

Step 10: 3-chloro-5-((1-((6-(difluoromethyl)-3-oxo-2,3-dihydropyridazin-4-yl)methyl)-6-oxo-4-(trifluoromethyl)-1,6-dihydropyrimidin-5-yl)oxy)benzonitrile To a mixture of 3-chloro-5-((1-((6-(difluoromethyl)-3-methoxypyridazin-4-yl)methyl)-6-oxo-4-(trifluoromethyl)-1,6-dihydropyrimidin-5-yl)oxy)benzonitrile (90 mg, 0.2 mmol) and KI (100 mg, 0.6 mmol) in acetonitrile (3 mL) was added TMSCl (33 mg, 0.3 mmol). The mixture was stirred at r.t for 1 hr, quenched with water and extracted with ethyl acetate. The combined organic extracts were washed with brine, dried over sodium sulfate, filtered and concentrated under reduced pressure. The residue was purified by preparative HPLC to afford 3-chloro-5-((1-((6-(difluoromethyl)-3-oxo-2,3-dihydropyridazin-4-yl)methyl)-6-oxo-4-(trifluoromethyl)-1,6-dihydropyrimidin-5-yl)oxy)benzonitrile (35 mg).

¹HNMR (Methanol-d4, 400 MHz) δ 13.62 (s, 1H), 8.72 (s, 1H), 7.73 (s, 1H), 7.71 (s, 1H), 7.68 (s, 1H), 7.66 (s, 1H), 6.78 (t, J=56.0 Hz, 1H), 4.99 (s, 2H).

MS (ESI) m/z 474, 476 (M+H)+

EXAMPLE 129

3-chloro-5-((1-((6-(1,1-difluoroethyl)-3-oxo-2,3-dihydropyridazin-4-yl)methyl)-6-oxo-4-(trifluoromethyl)-1,6-dihydropyrimidin-5-yl)oxy)benzonitrile

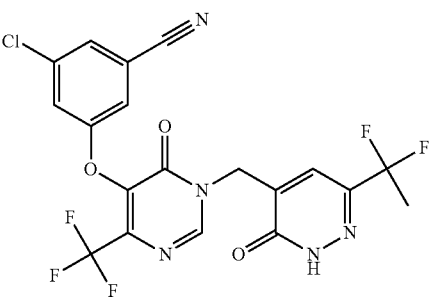 [SMILES: CC(F)(F)c1cc(Cn2cnc(C(F)(F)F)c(Oc3cc(Cl)cc(C#N)c3)c2=O)c(=O)[nH]n1]

Step 1: 4-(tert-butoxymethyl)-6-(1-ethoxyvinyl)-3-methoxypyridazine

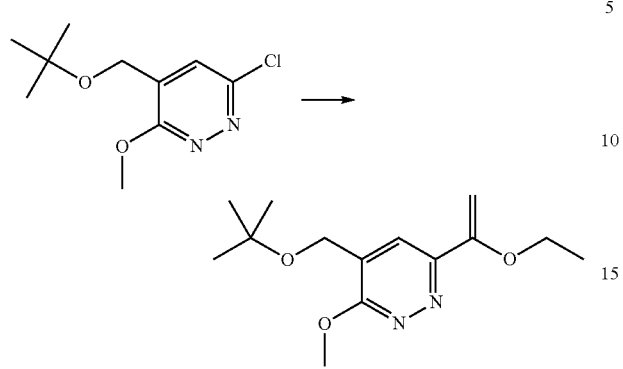

To a mixture of 4-(tert-butoxymethyl)-6-chloro-3-methoxypyridazine (1 g, 5.7 mmol), tributyl(1-ethoxyvinyl)stannane (6.2 g, 17.2 mmol) in toluene (10 mL) was added Pd(PPh$_3$)$_4$ (0.6 g, 0.57 mmol) under N$_2$. The resulting yellow suspension was stirred at 120° C. overnight under a nitrogen atmosphere. After cooling to r.t., the mixture was poured into ice-water, extracted with ethyl acetate, and the combined organic extracts were washed with brine, dried over sodium sulfate, filtered and concentrated under reduced pressure. The residue was purified by column chromatography on silica gel (petroleum ether/ethyl acetate (5:1 to 2:1) as eluent) to afford 4-(tert-butoxymethyl)-6-(1-ethoxyvinyl)-3-methoxypyridazine (400 mg).

MS (ESI): m/z 267 (M+H)$^+$

Step 2: 1-(5-(tert-butoxymethyl)-6-methoxypyridazin-3-yl)ethanone

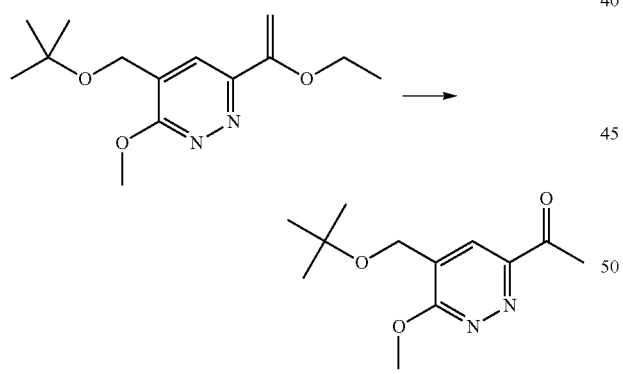

To a solution of 4-(tert-butoxymethyl)-6-(1-ethoxyvinyl)-3-methoxypyridazine (400 mg, 1.5 mmol) in 1,4-dioxane (6 mL) was added HCl/1,4-dioxane (3N, 6 mL), the solution was stirred at room temperature overnight. The mixture was diluted with water and extracted with ethyl acetate. The combined organic extracts were dried over anhydrous sodium sulfate, filtered and concentrated under reduced pressure. The residue was purified by preparative TLC (petroleum ether/ethyl acetate (1:1) as eluent) to give 1-(5-(tert-butoxymethyl)-6-methoxy pyridazin-3-yl)ethanone (240 mg).

MS (ESI) m/z 239 (M+H)$^+$

Step 3: 4-(tert-butoxymethyl)-6-(1,1-difluoroethyl)-3-methoxypyridazine

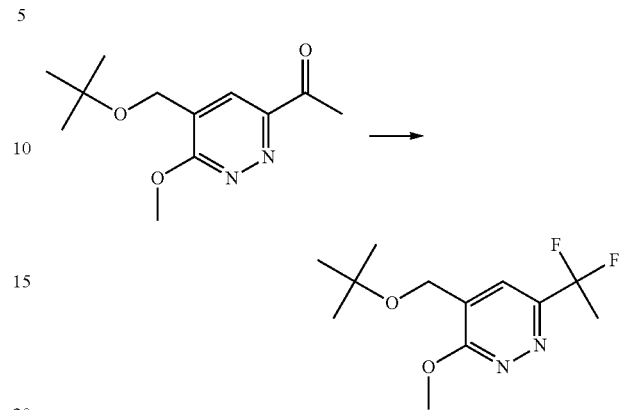

To a solution of 1-(5-(tert-butoxymethyl)-6-methoxy-pyridazin-3-yl)ethanone (240 mg, 1.0 mmol) in dichloromethane (8 mL) was added DAST (0.8 mL, 6.1 mmol). The mixture was stirred at r.t. for 4 hr. LCMS showed that the reaction was completed. The mixture was quenched with water and extracted with ethyl acetate. The combined organic extracts were dried over anhydrous sodium sulfate, filtered and concentrated under reduced pressure to give 4-(tert-butoxymethyl)-6-(1,1-difluoroethyl)-3-methoxypyridazine (150 mg).

MS (ESI) m/z 261 (M+H)$^+$

Step 4: (6-(1,1-difluoroethyl)-3-methoxypyridazin-4-yl)methanol

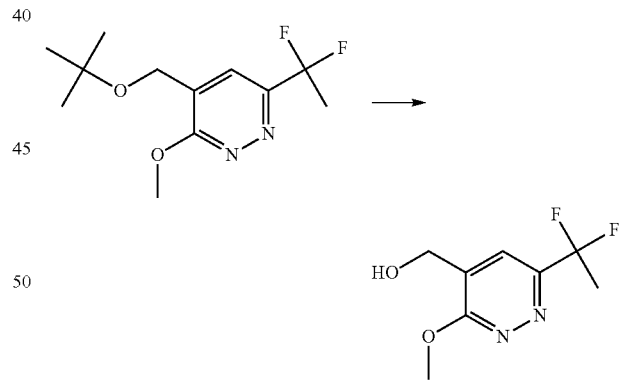

To a solution of 4-(tert-butoxymethyl)-6-(1,1-difluoroethyl)-3-methoxypyridazine (150 mg, 0.58 mmol) in dichloromethane (8 mL) was added 4N HCl/methanol (3 mL). The mixture was stirred at room temperature for 3 hr, then quenched with water and extracted with dichloromethane. The organic layer was dried over anhydrous sodium sulfate, concentrated under reduced pressure and purified by preparative TLC (petroleum ether/ethyl acetate (1:1.5) as eluent) to give (6-(1,1-difluoroethyl)-3-methoxypyridazin-4-yl)methanol (110 mg).

MS (ESI) m/z 205 (M+H)$^+$

Step 5: (6-(1,1-difluoroethyl)-3-methoxypyridazin-4-yl)methyl methanesulfonate

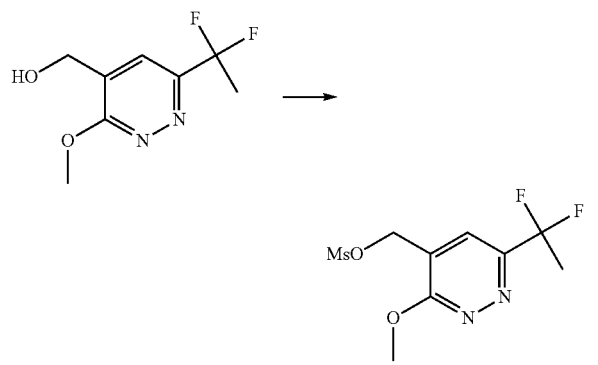

To a solution of (6-(1,1-difluoroethyl)-3-methoxypyridazin-4-yl)methanol (110 mg, 0.54 mmol) in dichloromethane (6 mL) was added DIPEA (209 mg, 1.6 mmol) and methanesulfonyl chloride (75 mg, 0.62 mmol) dropwise. The mixture was stirred at room temperature for 2 hr. The mixture was diluted with water and extracted with dichloromethane. The organic layer was dried over anhydrous sodium sulfate, filtered and concentrated under reduced pressure to give (6-(1,1-difluoroethyl)-3-methoxypyridazin-4-yl)methyl methanesulfonate (120 mg).

MS (ESI) m/z 283 (M+H)$^+$

Step 6: 3-chloro-5-((1-((6-(1,1-difluoroethyl)-3-methoxypyridazin-4-yl)methyl)-6-oxo-4-(trifluoromethyl)-1,6-dihydropyrimidin-5-yl)oxy)benzonitrile

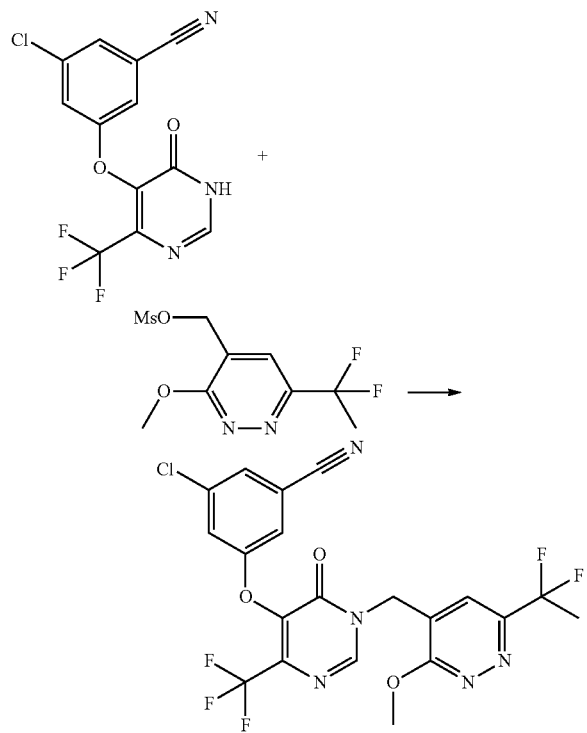

To a solution of (6-(1,1-difluoroethyl)-3-methoxypyridazin-4-yl)methyl methanesulfonate (120 mg, 0.54 mmol) in DMF (5 mL) was added 3-chloro-5-((6-oxo-4-(trifluoromethyl)-1,6-dihydropyrimidin-5-yl)oxy)benzonitrile (187 mg, 0.59 mmol), TEA (0.23 mL, 1.6 mmol). The mixture was stirred at 30° C. for 2 hr. After cooling to r.t., the mixture was diluted with water, extracted with ethyl acetate. The organic layer was dried over anhydrous sodium sulfate, filtered and concentrated under reduced pressure to give 3-chloro-5-((1-((6-(1,1-difluoroethyl)-3-methoxypyridazin-4-yl)methyl)-6-oxo-4-(trifluoromethyl)-1,6-dihydropyrimidin-5-yl)oxy)benzonitrile (120 mg).

MS (ESI) m/z 502, 504 (M+H)$^+$

Step 7: 3-chloro-5-((1-((6-(1,1-difluoroethyl)-3-oxo-2,3-dihydropyridazin-4-yl)methyl)-6-oxo-4-(trifluoromethyl)-1,6-dihydropyrimidin-5-yl)oxy)benzonitrile

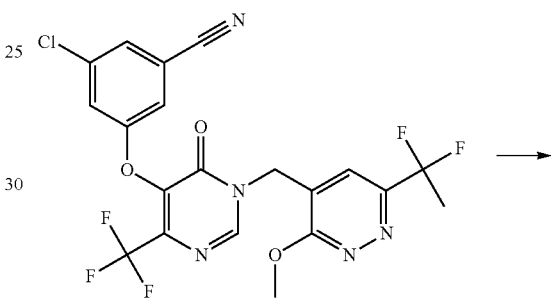

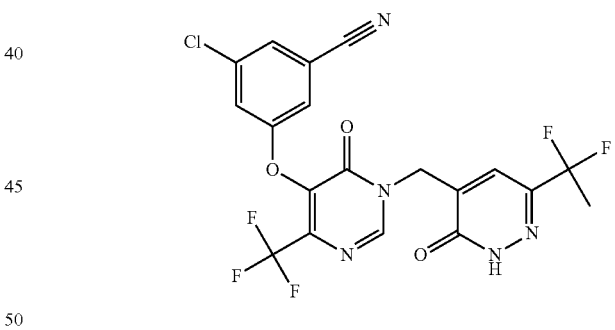

To a mixture of 3-chloro-5-((1-((6-(1,1-difluoroethyl)-3-methoxypyridazin-4-yl)methyl)-6-oxo-4-(trifluoromethyl)-1,6-dihydropyrimidin-5-yl)oxy)benzonitrile (120 mg, 0.24 mmol) and KI (79.5 mg, 0.48 mmol) in acetonitrile (4 mL) was added TMSCl (51.7 mg, 0.48 mmol) dropwise at r.t. After addition, the mixture was stirred at 30° C. for 3 hr. After cooling to r.t., the mixture was quenched with MeOH and concentrated under reduce pressure. The residue was purified by preparative HPLC to afford 3-chloro-5-((1-((6-(1,1-difluoroethyl)-3-oxo-2,3-dihydropyridazin-4-yl)methyl)-6-oxo-4-(trifluoromethyl)-1,6-dihydropyrimidin-5-yl)oxy)benzonitrile (35 mg).

$^1$H NMR (DMSO-d6, 400 MHz): δ 13.53 (s, 1H), 8.72 (s, 1H), 7.67-7.72 (m, 4H), 5.10 (s, 2H), 1.85-1.90 (m, 3H).

MS (ESI): m/z 488, 490 (M+H)$^+$

EXAMPLE 130

3-((1-((2-(tert-butyl)-6-oxo-1,6-dihydropyrimidin-5-yl)methyl)-6-oxo-4-(trifluoromethyl)-1,6-dihydropyrimidin-5-yl)oxy)-5-chlorobenzonitrile

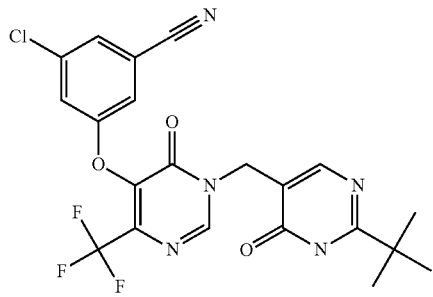 [SMILES: CC(C)(C)c1ncc(Cn2cnc(C(F)(F)F)c(Oc3cc(Cl)cc(C#N)c3)c2=O)c(=O)[nH]1]

Step 1: ethyl 2-(tert-butyl)-4-hydroxypyrimidine-5-carboxylate

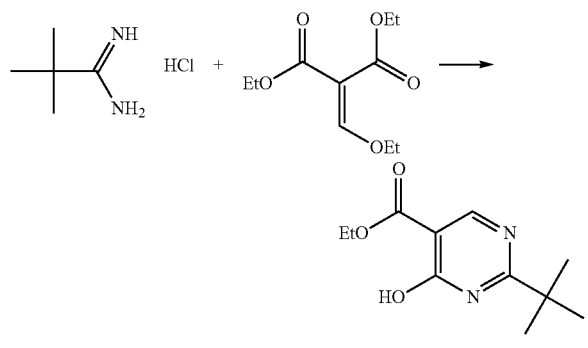

To a solution of pivalimidamide hydrochloride (2.0 g, 14.8 mmol) in ethanol (30 mL) was added freshly prepared EtONa (1.0 g, 14.8 mmol) at r.t. After stirred at r.t. for 20 min, diethyl 2-(ethoxymethylene)malonate (3.2 g, 14.8 mmol) was added. The mixture was stirred at r.t. for another 18 hr. After finished, the mixture was concentrated under reduced pressure and 30 mL of water was added to the residue. The mixture was then acidified to pH=5 with AcOH. The precipitate was collected by filtration and dried to give ethyl 2-(tert-butyl)-4-hydroxypyrimidine-5-carboxylate (1.5 g).

MS (ESI): m/z 225 (M+H)$^+$

Step 2: ethyl 2-(tert-butyl)-4-methoxypyrimidine-5-carboxylate

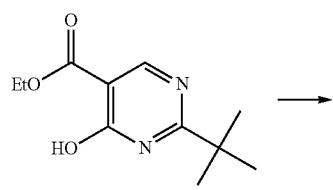

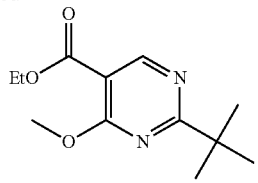

A mixture of ethyl 2-(tert-butyl)-4-hydroxypyrimidine-5-carboxylate (900 mg, 4 mmol), CH$_3$I (852 mg, 6.0 mmol) and potassium carbonate (1.1 g, 8 mmol) in DMF (10 mL) was stirred at r.t. for 1.5 hr. After finished, the mixture was diluted with water (20 mL) and extracted with ethyl acetate (20 mL×3). The combined organic extracts were dried over sodium sulfate, filtered and concentrated under reduced pressure to give the crude product. The residue was purified by preparative TLC (petroleum ether/ethyl acetate (5:1) as eluent) to afford ethyl 2-(tert-butyl)-4-methoxypyrimidine-5-carboxylate (800 mg).

MS (ESI): m/z 239 (M+H)$^+$

Step 3: (2-(tert-butyl)-4-methoxypyrimidin-5-yl)methanol

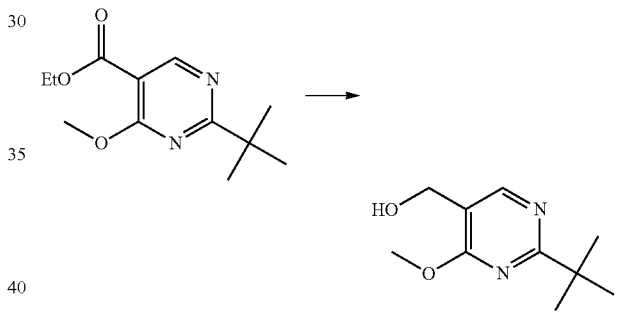

To a solution of ethyl 2-(tert-butyl)-4-methoxypyrimidine-5-carboxylate (800 mg, 3.36 mmol) in THF (10 mL) was added LiAlH$_4$ (383 mg, 10.08 mmol) at −40° C. Then the mixture was stirred at this temperature for 15 min. The reaction was quenched with 0.3 mL water and the mixture was dried over sodium sulfate directly. Then the mixture was filtered and concentrated under reduced pressure. The residue was purified by preparative TLC (petroleum ether/ethyl acetate (2:1) as eluent) (2-(tert-butyl)-4-methoxypyrimidin-5-yl)methanol (300 mg).

MS (ESI) m/z 197 (M+H)$^+$

Step 4: (2-(tert-butyl)-4-methoxypyrimidin-5-yl)methyl methanesulfonate

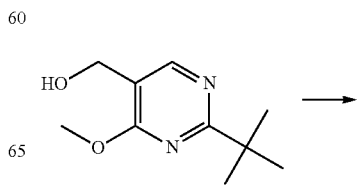

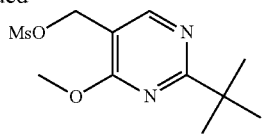

To a solution of (2-(tert-butyl)-4-methoxypyrimidin-5-yl)methanol (130 mg, 0.66 mmol) and DIPEA (128 mg, 0.99 mmol) in dichloromethane (5 mL) was added methanesulfonyl chloride (150 mg, 1.32 mmol) dropwise at 0° C. The mixture was stirred at r.t. for additional 1 hr. The mixture was diluted with dichloromethane (10 mL) and washed with water. The organic layer was dried over sodium sulfate, filtered and concentrated under reduced pressure to give (2-(tert-butyl)-4-methoxypyrimidin-5-yl)methyl methanesulfonate (300 mg) which was used without further purification.

MS (ESI) m/z 275 (M+H)$^+$

Step 5: 3-((1-((2-(tert-butyl)-4-butyl)-5-yl)methyl)-6-oxo-4-(trifluoromethyl)-1,6-dihydropyrimidin-5-yl)oxy)-5-chlorobenzonitrile

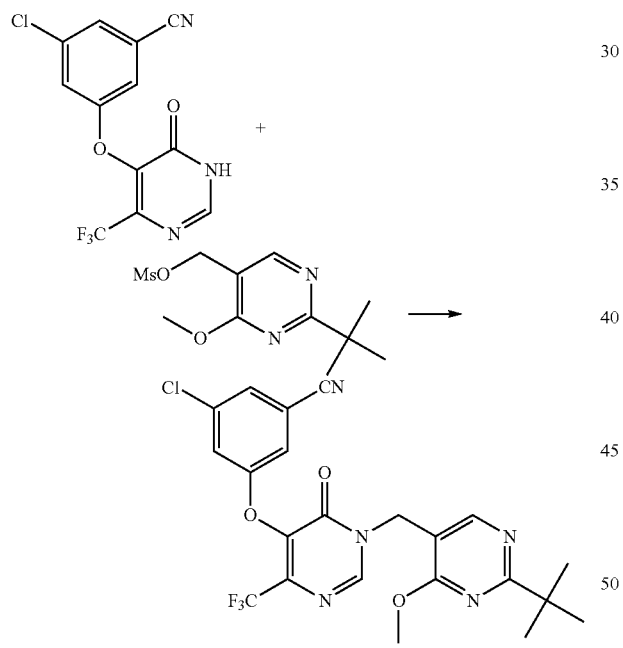

A mixture of (2-(tert-butyl)-4-methoxypyrimidin-5-yl)methyl methanesulfonate (150 mg crude), 3-chloro-5 oxo-4-(trifluoromethyl)-1,6-dihydropyrimidin-5-yl)oxy)benzonitrile (80 mg, 0.25 mmol), LiBr (44 mg, 0.508 mmol) and potassium carbonate (70 mg, 0.508 mmol) in DMF (6 mL) was stirred at 70° C. for 1 hr. After cooling, the mixture was diluted with water (20 mL) and extracted with ethyl acetate (20 mL×3). The combined organic extracts were dried over sodium sulfate, filtered and concentrated under reduced pressure to give 3-((1-((2-(tert-butyl)-4-methoxypyrimidin-5-yl)methyl)-6-oxo-4-(trifluoromethyl)-1,6-dihydropyrimidin-5-yl)oxy)-5-chlorobenzonitrile (100 mg).

MS (ESI) m/z 494, 496 (M+H)$^+$

Step 6: 3-((1-((2-(tert-butyl)-6-oxo-1,6-dihydropyrimidin-5-yl)methyl)-6-oxo-4-(trifluoromethyl)-1,6-dihydropyrimidin-5-yl)oxy)-5-chlorobenzonitrile

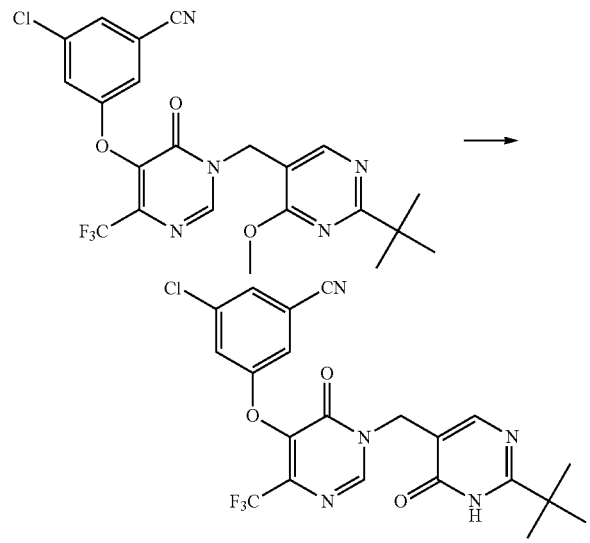

To a mixture of 3-((1-((2-(tert-butyl)-4-methoxypyrimidin-5-yl)methyl)-6-oxo-4-(trifluoromethyl)-1,6-dihydropyrimidin-5-yl)oxy)-5-chlorobenzonitrile (100 mg crude) and KI (120 mg, 0.72 mmol) in acetonitrile (6 mL), TMSCl (78 mg, 0.72 mmol) was added dropwised at r.t. After addition, the mixture was heated to 60° C. for 4 hr. The reaction mixture was quenched with methanol and concentrated under reduced pressure. The residue was purified by preparative HPLC to afford 3-((1-((2-(tert-butyl)-6-oxo-1,6-dihydropyrimidin-5-yl)methyl)-6-oxo-4-(trifluoromethyl)-1,6-dihydropyrimidin-5-yl)oxy)-5-chlorobenzonitrile (65 mg).

$^1$H NMR (CD$_3$OD, 400 MHz): δ 8.75 (s, 1H), 7.92 (s, 1H), 7.72 (s, 1H), 7.65 (s, 1H), 7.63 (s, 1H), 4.84 (s, 2H), 1.23 (s, 9H).

MS (ESI): m/z 480, 482 (M+H)$^+$

EXAMPLE 131

3-Chloro-5-[16-oxo-1-(6-oxo-2-trifluoromethyl-1,6-dihydro-pyrimidin-5-ylmethyl)-4-trifluoromethyl-1,6-dihydro-pyrimidin-5-yloxy]-benzonitrile

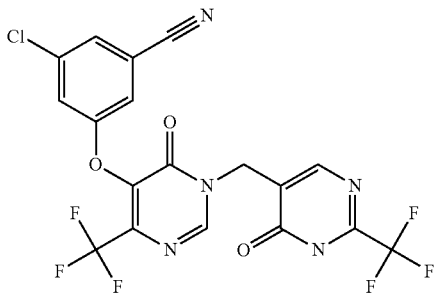 [SMILES: N#Cc1cc(Cl)cc(Oc2c(C(F)(F)F)ncn(Cc3cnc(C(F)(F)F)[nH]c3=O)c2=O)c1]

The title compound was prepared by following Steps 3-6 of Example 130 and using the corresponding ethyl-4- methoxy-2-(trifluoromethyl)pyrimidine-5-carboxylate in Step 3 in place of (2-(tert-butyl)-4-methoxypyrimidin-5-yl)methanol.

MS (ESI) m/z 492, 494

$^1$H NMR: (DMSO-d$_6$, 400 MHz) δ 8.74 (s, 1H), 8.53 (s, 1H), 7.72 (t, J=1.2 Hz, 1H), 7.66 (q, J=1.2 Hz, 1H), 7.63 (t, J=2.0 Hz, 1H), 5.04 (s, 2H).

EXAMPLE 132

3-chloro-5-((1-((2-(methylthio)-6-oxo-1,6-dihydropyrimidin-5-yl)methyl)-6-oxo-4-(trifluoromethyl)-1,6-dihydropyrimidin-5-yl)oxy)benzonitrile

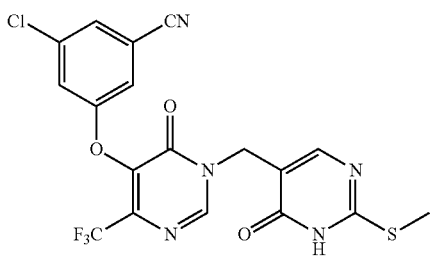 [SMILES: CSc1ncc(Cn2cnc(C(F)(F)F)c(Oc3cc(Cl)cc(C#N)c3)c2=O)c(=O)[nH]1]

Step 1: ethyl 4-methoxy-2-(methylthio)pyrimidine-5-carboxylate

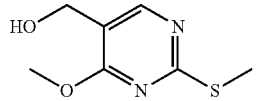

To a solution of ethyl 4-chloro-2-(methylthio)pyrimidine-5-carboxylate (20 g, 86 mmol) in methanol (300 mL) was added MeONa (14 g, 258 mmol) by portions at room temperature for 24 hr. After finished, the mixture was diluted with water (500 mL), extracted with EtOAc (500 mL×2), the organic layer was washed with water and brine, dried over sodium sulfate, filtered and concentrated. The crude product was purified by chromatography on silica gel (petroleum ether/ethyl acetate (10:1 to 6:1) as eluent) to afford ethyl 4-methoxy-2-(methylthio)pyrimidine-5-carboxylate (10 g).

MS (ESI) m/z 229 (M+H)$^+$

Step 2: (4-methoxy-2-(methylthio)pyrimidin-5-yl)methanol

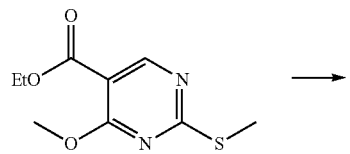

To a solution of ethyl 4-methoxy-2-(methylthio)pyrimidine-5-carboxylate (9 g, 39.4 mmol) in THF (200 mL) was added LiAlH$_4$ (4.5 g, 118 mmol) by portion at −40° C. for 30 min. The reaction was quenched by addition of water (150 mL) and extracted with ethyl acetate (100 mL×2). The combined organic extracts were dried over sodium sulfate, filtered and the solvent was evaporated under reduced pressure to give crude, which was purified by chromatography on silica gel (petroleum ether/ethyl acetate (5:1 to 2:1) as eluent) to afford (4-methoxy-2-(methylthio)pyrimidin-5-yl)methanol (2.5 g).

MS (ESI) m/z 187 (M+H)$^+$

The title compound was subsequently prepared from the above intermediate by following similar procedures to Steps 2 and 3 of Example 4.

MS (ESI) m/z 470, 472 (M+H)$^+$ $^1$H NMR: (DMSO-d6, 400 MHz) δ 12.99 (s, 1H), 8.70 (s, 1H), 7.89 (s, 1H), 7.72 (s, 1H), 7.66 (s, 1H), 7.63 (s, 1H), 4.81 (s, 2H), 2.43 (s, 3H).

EXAMPLE 133

3-chloro-5-((1-((2-methyl-6-oxo-1,6-dihydropyrimidin-5-yl)methyl)-6-oxo-4-(trifluoro methyl)-1,6-dihydropyrimidin-5-yl)oxy)benzonitrile

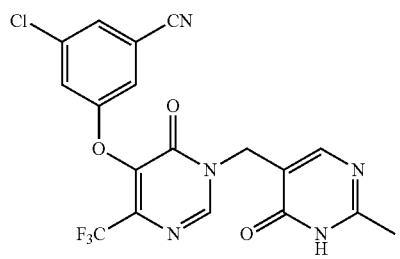 [SMILES: Cc1ncc(Cn2cnc(C(F)(F)F)c(Oc3cc(Cl)cc(C#N)c3)c2=O)c(=O)[nH]1]

Step 1: 3-chloro-5-((1-((4-methoxy-2-(methylsulfonyl)pyrimidin-5-yl)methyl)-6-oxo-4-(trifluoromethyl)-1,6-dihydropyrimidin-5-yl)oxy)benzonitrile

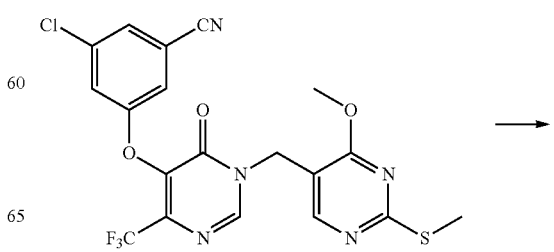

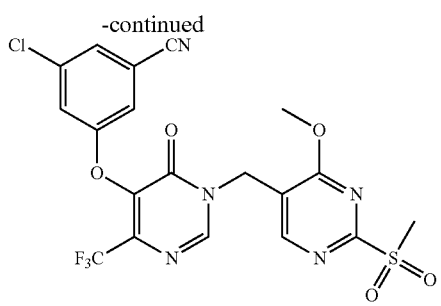

To a solution of 3-chloro-5-((1-((4-methoxy-2-(methylthio)pyrimidin-5-yl)methyl)-6-oxo-4-(trifluoromethyl)-1,6-dihydropyrimidin-5-yl)oxy)benzonitrile (3.0 g, 6.39 mmol) in 50 mL of CH₂Cl₂ was added m-CPBA (3.3 g, 19.1 mmol) and stirred for 20 hr at room temperature. The mixture was diluted with DCM, washed with NaOH (0.5 N, 50 mL), water and brine, dried over sodium sulfate, filtered and concentrated under reduced pressure to give 3-chloro-5-((1-((4-methoxy-2-(methylsulfonyl)pyrimidin-5-yl)methyl)-6-oxo-4-(trifluoromethyl)-1,6-dihydropyrimidin-5-yl)oxy)benzonitrile (1.3 g).

MS (ESI) m/z 516, 518 (M+H)⁺

Step 2: 3-chloro-5-((1-((4-methoxy-2-methylpyrimidin-5-yl)methyl)-6-oxo-4-(trifluoromethyl)-1,6-dihydropyrimidin-5-yl)oxy)benzonitrile

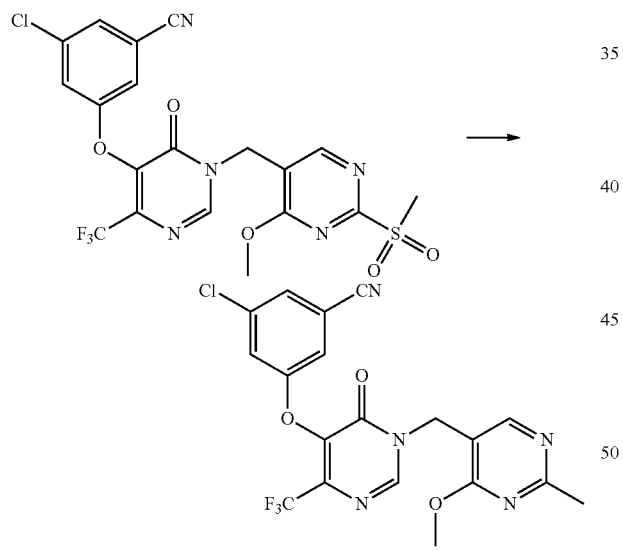

To a solution of 3-chloro-5-((1-((4-methoxy-2-(methylsulfonyl)pyrimidin-5-yl)methyl)-6-oxo-4-(trifluoromethyl)-1,6-dihydropyrimidin-5-yl)oxy)benzonitrile (200 mg, 0.38 mmol) in THF (10 mL) was added 3 M MeMgBr in diethyl ether (0.2 mL, 0.6 mmol) dropwise at room temperature. The mixture was stirred at r.t. for 2 hr. Then the reaction was quenched with water, extracted with ethyl acetate. The combined organic extracts were dried over sodium sulfate, filtered and concentrated under reduced pressure. The residue was purified by preparative TLC (petroleum ether/ethyl acetate (1:1.5) as eluent) to afford 3-chloro-5-((1-((4-methoxy-2-methylpyrimidin-5-yl)methyl)-6-oxo-4-(trifluoromethyl)-1,6-dihydropyrimidin-5-yl)oxy)benzonitrile (64 mg).

MS (ESI) m/z 452, 454 (M+H)⁺

The title compound was subsequently prepared from the above intermediate by following a similar procedure to Step 3 of Example 7.

¹HNMR (DMSO-d6, 400 MHz) δ 8.72 (s, 1H), 8.00 (s, 1H), 7.73 (s, 1H), 7.66 (s, 1H), 7.64 (d, J=2.0 Hz, 1H), 4.87 (s, 2H), 2.36 (s, 3H).

MS (ESI) m/z 438, 440 (M+H)⁺

EXAMPLE 134

3-chloro-5-((4-cyclopropyl-6-oxo-1-((6-oxo-1,6-dihydropyridazin-3-yl)methyl)-1,6-dihydropyrimidin-5-yl)oxy)benzonitrile

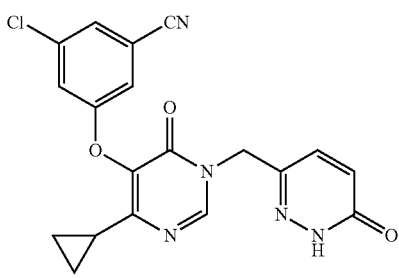 [SMILES: N#Cc1cc(Cl)cc(Oc2c(C3CC3)ncn(Cc3ccc(=O)[nH]n3)c2=O)c1]

By following similar procedures to Steps 3 and 4 of Example 13 and using the appropriate pyrimidinone in place of 3-chloro-5-((4-methyl-6-oxo-1,6-dihydropyrimidin-5-yl)oxy)benzonitrile, the title compound was prepared.

MS (ESI) m/z 395, 396 (M+H)⁺

¹H NMR (DMSO-d6, 500 MHz) δ 12.99 (s, 1H), 8.44 (s, 1H), 7.70 (s, 1H), 7.56-7.43 (m, 3H), 6.88 (d, J=9.6 Hz, 1H), 5.03 (s, 2H), 1.32-1.22 (m, 1H), 1.06-0.83 (m, 4H).

EXAMPLE 135

3-chloro-5-((1-((2-hydroxy-6-oxo-1,6-dihydropyrimidin-5-yl)methyl)-6-oxo-4-(trifluoromethyl)-1,6-dihydropyrimidin-5-yl)oxy)benzonitrile

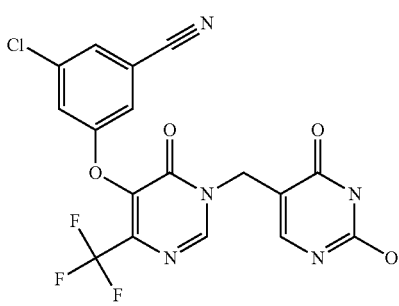 [SMILES: N#Cc1cc(Cl)cc(Oc2c(C(F)(F)F)ncn(Cc3cnc(O)[nH]c3=O)c2=O)c1]

Step 1: 3-Chloro-5-[1-(2,4-dimethoxy-pyrimidin-5-ylmethyl)-6-oxo-4-trifluoromethyl-1,6-dihydro-pyrimidin-5-yloxy]-benzonitrile

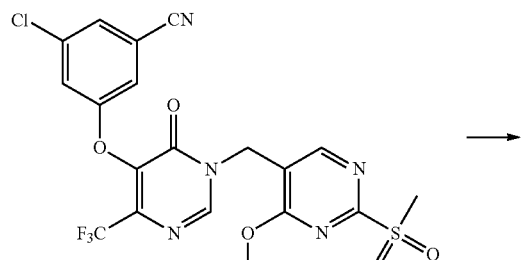

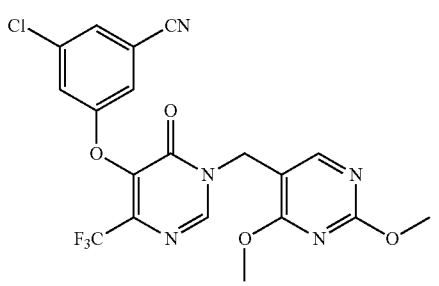

To a solution of 3-chloro-5-((1-((4-methoxy-2-(methylsulfonyl)pyrimidin-5-yl)methyl)-6-oxo-4-(trifluoromethyl)-1,6-dihydropyrimidin-5-yl)oxy)benzonitrile (200 mg, 0.38 mmol) in THF (10 mL) was added NaOMe (150 mg, 2.7 mmol) at room temperature. The mixture was stirred at r.t. for 1.5 hr. Then the reaction was quenched with water, extracted with ethyl acetate. The combined organic extracts were dried over sodium sulfate, filtered and concentrated under reduced pressure. The residue was purified by preparative TLC (petroleum ether/ethyl acetate (1:1.5) as eluent) to afford 3-Chloro-5-[1-(2,4-dimethoxy-pyrimidin-5-ylmethyl)-6-oxo-4-trifluoromethyl-1,6-dihydro-pyrimidin-5-yloxy]-benzonitrile (45 mg).

MS (ESI) m/z 468, 470 (M+H)$^+$

The title compound was subsequently prepared using the above intermediate and following a similar procedure to that given for Step 3 of Example 7.

$^1$H NMR: (DMSO-d6, 400 MHz) δ 11.24 (s, 1H), 10.98 (s, 1H), 8.64 (s, 1H), 7.72 (s, 1H), 7.67 (s, 1H), 7.63 (s, 1H), 7.52 (s, 1H), 4.69 (s, 2H).

MS (ESI) m/z 440, 442 (M+H)$^+$

EXAMPLE 136

3-chloro-5-((6-oxo-1-((6-oxo-1,6-dihydropyrimidin-5-yl)methyl)-4-(trifluoromethyl)-1,6-dihydropyrimidin-5-yl)oxy)benzonitrile

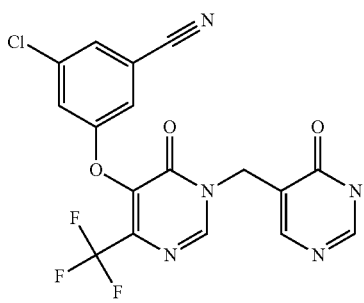 [SMILES: N#Cc1cc(Cl)cc(Oc2c(C(F)(F)F)ncn(Cc3cnc[nH]c3=O)c2=O)c1]

Step 1: (4-methoxy-2-(methylsulfonyl)pyrimidin-5-yl)methanol

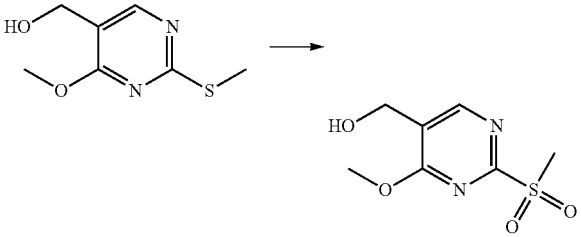

To a stirred solution of (4-methoxy-2-(methylthio)pyrimidin-5-yl)methanol (1.0 g, 5.35 mmol) in 30 mL of dry dichloromethane was added m-CPBA (2.8 g, 16.04 mmol). The mixture was stirred for 20 hr at room temperature, diluted with dichloromethane, washed with NaOH (0.5 N, 50 mL), water and aqueous Na$_2$SO$_3$, dried over sodium sulfate, filtered and concentrated under reduced pressure. The crude product was purified by preparative TLC (ethyl acetate as eluent) to afford (4-methoxy-2-(methylsulfonyl)pyrimidin-5-yl)methanol (240 mg).

MS (ESI) m/z 219 (M+H)$^+$

Step 2: (4-methoxypyrimidin-5-yl)methanol

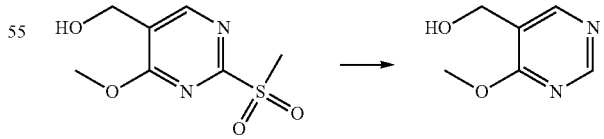

To a solution of (4-methoxy-2-(methylsulfonyl)pyrimidin-5-yl)methanol (174 mg, 0.79 mmol) in 10 mL of dry ethanol was added NaBH$_4$ (61 mg, 1.59 mmol) and the mixture was stirred for 50 mins at room temperature. The mixture was quenched with water, extracted with ethyl acetate. The combined organic layers were dried, filtered and concentrated under reduced pressure. The residue was purified by preparative TLC (ethyl acetate as eluent) to afford (4-methoxypyrimidin-5-yl)methanol (60 mg).

MS (ESI) m/z 141 (M+H)+

The title compound was subsequently prepared from the above intermediate, (4-methoxypyrimidin-5-yl)methanol, by following similar procedures to Steps 2 and 3 of Example 4.

¹HNMR (DMSO-d6, 400 MHz) δ 8.73 (s, 1H), 8.48 (s, 1H), 8.02 (s, 1H), 7.72 (s, 1H), 7.66 (s, 1H), 7.64 (s, 1H), 4.87 (s, 2H).

MS (ESI) m/z 424, 426 (M+H)+

EXAMPLE 137

3-chloro-5-((1-((2-(methylamino)-6-oxo-1,6-dihydropyrimidin-5-yl)methyl)-6-oxo-4-(trifluoromethyl)-1,6-dihydropyrimidin-5-yl)oxy)benzonitrile

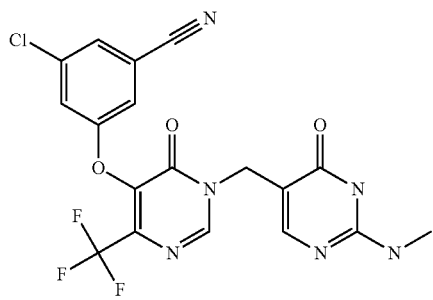 [SMILES: CNc1ncc(Cn2cnc(C(F)(F)F)c(Oc3cc(Cl)cc(C#N)c3)c2=O)c(=O)[nH]1]

Step 1: ethyl 4-((4-methoxybenzyl)oxy)-2-(methylthio)pyrimidine-5-carboxylate

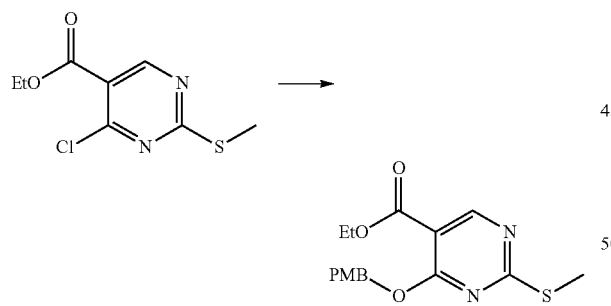

To a solution of ethyl 4-chloro-2-(methylthio)pyrimidine-5-carboxylate (40 g, 172 mmol) in THF (600 mL) was added PMBONa (545 g, 343 mmol) in portions. The mixture was stirred at room temperature for 2 hr. The mixture was quenched with water (500 mL) and extracted with ethyl acetate (500 mL×2). The organic layer was washed with water and brine, dried over sodium sulfate, filtered and the filtrate was concentrated under reduced pressure. The crude product was purified by chromatography on silica gel (petroleum ether:ethyl acetate (10:1 to 5:1) as eluent) to afford ethyl 4-((4-methoxybenzyl)oxy)-2-(methylthio)pyrimidine-5-carboxylate (20 g).

MS (ESI) m/z 335 (M+H)+

Step 2: (4-((4-methoxybenzyl)oxy)-2-(methylthio)pyrimidin-5-yl)methanol

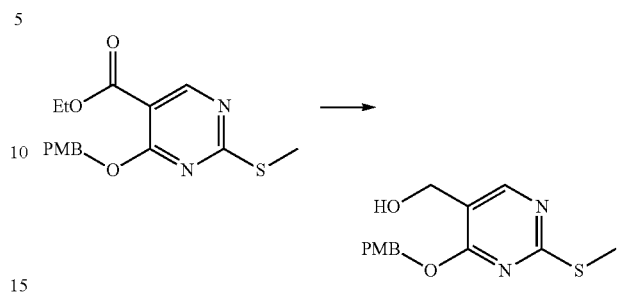

To a solution of ethyl 4-((4-methoxybenzyl)oxy)-2-(methylthio)pyrimidine-5-carboxylate (21 g, 62.7 mmol) in THF (500 mL) was added LiAlH₄ (7.14 g, 188 mmol) in portions at −40° C. The resulting mixture was stirred for 45 min, quenched with water (10 mL) and extracted with ethyl acetate (500 mL). The organic layer was dried over sodium sulfate, filtered and concentrated under reduced pressure. The residue was purified by chromatography on silica gel (petroleum ether/ethyl acetate (5:1 to 2:1) as eluent) to afford (4-((4-methoxybenzyl)oxy-2-(methylthio)pyrimidin-5-yl)methanol (7.5 g).

MS (ESI) m/z 293 (M+H)+

Step 3: 3-chloro-5-((1-((4-((4-methoxybenzyl)oxy)-2-(methylthio)pyrimidin-5-yl)methyl)-6-oxo-4-(trifluoromethyl)-1,6-dihydropyrimidin-5-yl)oxy)benzonitrile

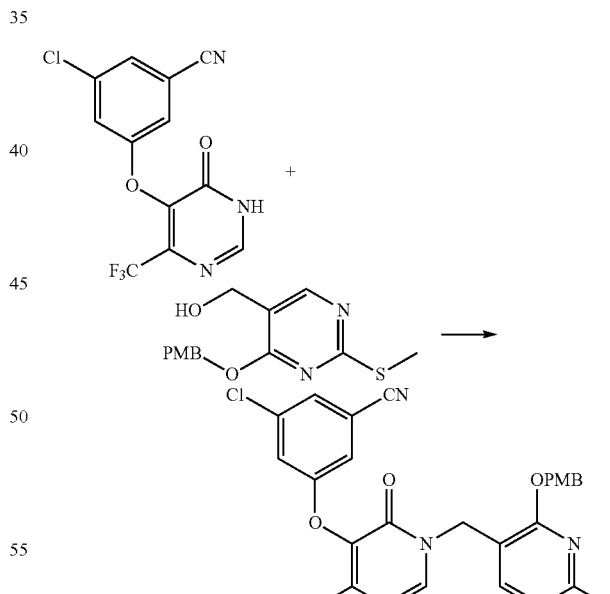

To a solution of (4-((4-methoxybenzyl)oxy)-2-(methylthio)pyrimidin-5-yl)methanol (4.0 g, 14.4 mmol), 3-chloro-5-(6-oxo-4-trifluoromethyl-1,6-dihydro-pyrimidin-5-yloxy)-benzonitrile (5.0 g, 15.9 mmol) and triphenylphosphine (7.5 g, 28.8 mmol) in 150 mL of anhydrous dichloromethane was added DEAD (5.0 g, 28.8 mmol) at −40° C. under a nitrogen atmosphere. The resulting mixture was stirred for 2 hr at room temperature and then concentrated under reduced pressure. The crude product was purified by chromatography on silica gel (petroleum ether: ethyl acetate (10:1 to 5:1) as eluent) to afford 3-chloro-5-((1-((4-((4-methoxybenzyl)oxy)-2-(methylthio)pyrimidin-5-yl)methyl)-6-oxo-4-(trifluoromethyl)-1,6-dihydropyrimidin-5-yl)oxy)benzonitrile (8.8 g) which was used without further purification.

MS (ESI) m/z 590, 592 (M+H)+

Step 4: 3-chloro-5-((1-((4-((4-methoxybenzyl)oxy)-2-(methylsulfonyl)pyrimidin-5-yl)methyl)-6-oxo-4-(trifluoromethyl)-1,6-dihydropyrimidin-5-yl)oxy)benzonitrile

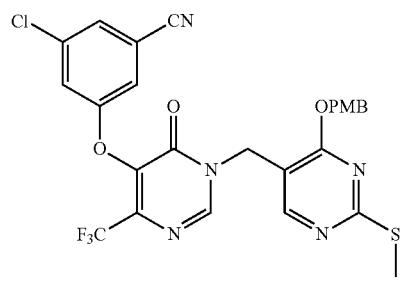

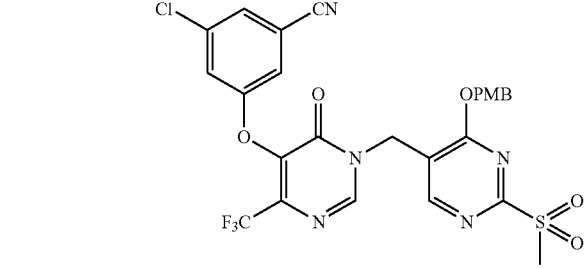

To a solution of 3-chloro-5-((1-((4-((4-methoxybenzyl)oxy)-2-(methylthio)pyrimidin-5-yl)methyl)-6-oxo-4-(trifluoromethyl)-1,6-dihydropyrimidin-5-yl)oxy)benzonitrile (4.0 g, 6.78 mmol) in 100 mL of dichloromethane was added m-CPBA (3.5 g, 20.3 mmol). The mixture was stirred for 5 hr at room temperature. The mixture was diluted with dichloromethane, washed with NaOH (0.5 N, 100 mL), water, aq. Na2SO3 and brine, dried over sodium sulfate, filtered and concentrated under reduced pressure to give 3-chloro-5-((1-((4-((4-methoxybenzyl)oxy)-2-(methylsulfonyl)pyrimidin-5-yl)methyl)-6-oxo-4-(trifluoromethyl)-1,6-dihydropyrimidin-5-yl)oxy)benzonitrile (3.0 g).

MS (ESI) m/z 622, 624 (M+H)+

Step 5: 3-chloro-5-((1-((4-((4-methoxybenzyl)oxy)-2-(methylamino)pyrimidin-5-yl)methyl)-6-oxo-4-(trifluoromethyl)-1,6-dihydropyrimidin-5-yl)oxy)benzonitrile

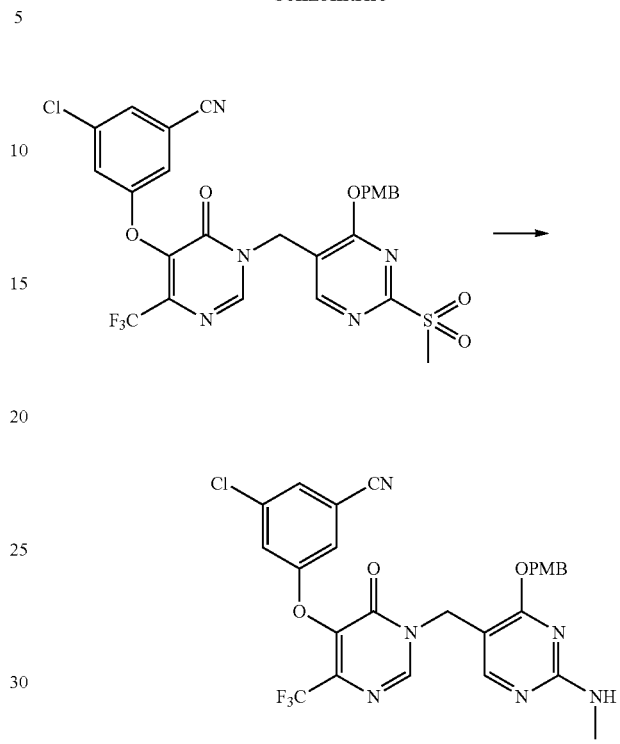

To a solution of 3-chloro-5-((1-((4-((4-methoxybenzyl)oxy)-2-(methylsulfonyl)pyrimidin-5-yl)methyl)-6-oxo-4-(trifluoromethyl)-1,6-dihydropyrimidin-5-yl)oxy)benzonitrile (200 mg, 0.32 mmol) in THF (5 mL) was added 2M MeNH2 in methanol (0.7 mL, 1.28 mmol) at room temperature and the mixture was stirred at r.t. for 36 hr. The mixture was concentrated under reduced pressure and purified by preparative TLC (petroleum ether/ethyl acetate (1:1) as eluent) to afford 3-chloro-5-((1-((4-((4-methoxybenzyl)oxy)-2-(methylamino)pyrimidin-5-yl)methyl)-6-oxo-4-(trifluoromethyl)-1,6-dihydropyrimidin-5-yl)oxy)benzonitrile (70 mg).

MS (ESI) m/z 573, 575 (M+H)+

Step 6: 3-chloro-5-((1-((2-(methylamino)-6-oxo-1,6-dihydropyrimidin-5-yl)methyl)-6-oxo-4-(trifluoromethyl)-1,6-dihydropyrimidin-5-yl)oxy)benzonitrile

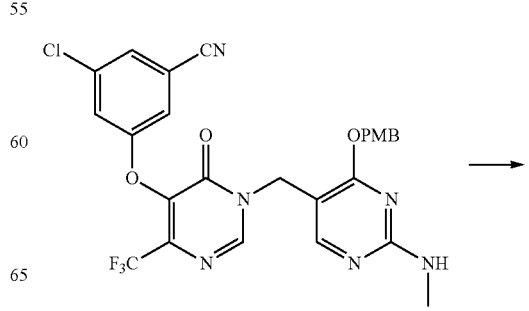

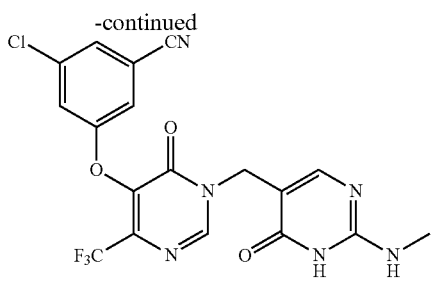

To a solution of 3-chloro-5-((1-((4-((4-methoxybenzyl)oxy)-2-(methylamino)pyrimidin-5-yl)methyl)-6-oxo-4-(trifluoromethyl)-1,6-dihydropyrimidin-5-yl)oxy)benzonitrile (50 mg, 0.08 mmol) in a mixture solvent of acetonitrile (15 mL) and H$_2$O (7 mL) was added CAN (143 mg, 0.26 mmol) at room temperature. The reaction mixture was stirred at r.t. for 48 hr. The mixture was concentrated under reduced pressure and purified by preparative HPLC to afford 3-chloro-5-((1-((2-(methylamino)-6-oxo-1,6-dihydropyrimidin-5-yl)methyl)-6-oxo-4-(trifluoromethyl)-1,6-dihydropyrimidin-5-yl)oxy)benzonitrile (12 mg).

$^1$H NMR (Methanol-d4, 400 MHz): δ 8.62 (s, 1H), 7.80 (s, 1H), 7.53 (s, 1H), 7.39 (s, 1H), 7.30 (s, 1H), 4.89 (s, 2H), 2.98 (s, 3H).

MS (ESI) m/z 453, 455 (M+H)$^+$

By following similar procedures to Steps 1-5 of Example 137 and using sodium methoxide in methanol in Step 1 in place of the PMBONa in THF, the following compound was also synthesized and characterized as indicated in the table below.

| Example | Structure | IUPAC Name | MS (M + H)$^+$/NMR |
|---|---|---|---|
| 138 | 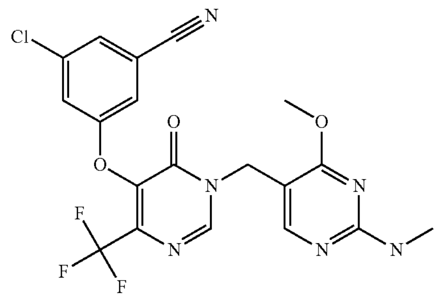 [SMILES: CNc1ncc(Cn2cnc(C(F)(F)F)c(Oc3cc(Cl)cc(C#N)c3)c2=O)c(OC)n1] | 3-chloro-5-((1-((4-methoxy-2-(methylamino)pyrimidin-5-yl)methyl)-6-oxo-4-(trifluoromethyl)-1,6-dihydropyrimidin-5-yl)oxy)benzonitrile | MS (ESI) m/z 467, 469 $^1$H NMR (DMSO-d6, 400 MHz) δ 8.58 (s, 1H), 8.10 (s, 1H), 7.64 (s, 1H), 7.50-7.53 (m, 3H), 4.90 (s, 2H), 3.93 (s, 3H), 2.85 (s, 3H). |

Starting with 3-chloro-5-((1-((4-((4-methoxybenzyl)oxy)-2-(methylsulfonyl)pyrimidin-5-yl)methyl)-6-oxo-4-(trifluoromethyl)-1,6-dihydropyrimidin-5-yl)oxy)benzonitrile, Examples 139-145 in the table below were prepared using similar procedures to Steps 5 and 6 of Example 137.

| Example | Structure | IUPAC Name | MS (M + H)$^+$/NMR |
|---|---|---|---|
| 139 | 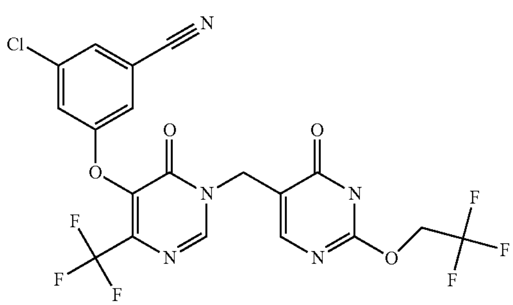 [SMILES: N#Cc1cc(Cl)cc(Oc2c(C(F)(F)F)ncn(Cc3cnc(OCC(F)(F)F)[nH]c3=O)c2=O)c1] | 3-Chloro-5-{6-oxo-1-[6-oxo-2-(2,2,2-trifluoro-ethoxy)-1,6-dihydro-pyrimidin-5-ylmethyl]-4-trifluoromethyl-1,6-dihydro-pyrimidin-5-yloxy}-benzonitrile | MS (ESI) m/z 522, 524 $^1$H NMR: (DMSO-d6, 400 MHz) δ 13.09 (s, 1H), 8.73 (s, 1H), 7.88 (s, 1H), 7.75 (s, 1H), 7.69 (s, 1H), 7.66 (s, 1H), 5.02 (q, J = 8.4 Hz, 2H), 4.84 (s, 2H). |
| 140 | 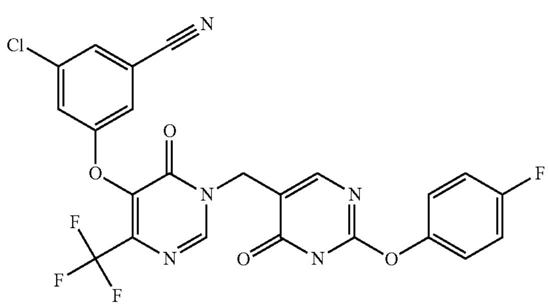 [SMILES: N#Cc1cc(Cl)cc(Oc2c(C(F)(F)F)ncn(Cc3cnc(Oc4ccc(F)cc4)[nH]c3=O)c2=O)c1] | 3-Chloro-5-{1-[2-(4-fluoro-phenoxy)-6-oxo-1,6-dihydro-pyrimidin-5-ylmethyl]-6-oxo-4-trifluoromethyl-1,6-dihydro-pyrimidin-5-yloxy}-benzonitrile | MS (ESI) m/z 536, 538 $^1$H NMR: (DMSO-d6, 400 MHz) δ 13.16 (s, 1H), 8.74 (s, 1H), 7.75 (s, 2H), 7.67 (d, J = 9.6 Hz, 2H), 7.23-7.27 (m, 4H), 4.84 (s, 2H). |

-continued

| Example | Structure | IUPAC Name | MS (M + H)+/NMR |
|---|---|---|---|
| 141 | 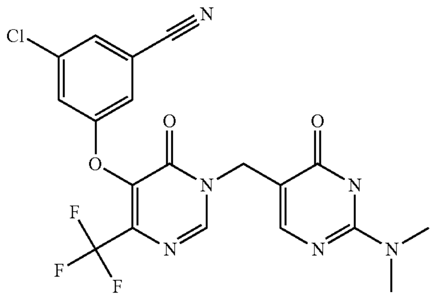 | 3-Chloro-5-[1-(2-dimethylamino-6-oxo-1,6-dihydro-pyrimidin-5-ylmethyl)-6-oxo-4-trifluoromethyl-1,6-dihydro-pyrimidin-5-yloxy]-benzonitrile | MS (ESI) m/z 467, 469<br>$^1$H NMR: (DMSO-d6, 400 MHz)<br>δ 8.70 (s, 1H), 7.72 (s, 2H), 7.64 (s, 1H), 7.61 (s, 1H), 4.72 (s, 2H), 2.97 (s, 6H). |
| 142 | 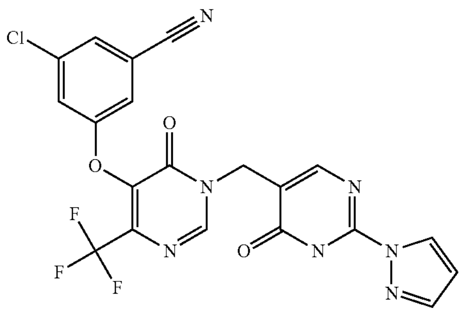 [SMILES: N#Cc1cc(Cl)cc(Oc2c(C(F)(F)F)ncn(Cc3cnc(-n4cccn4)[nH]c3=O)c2=O)c1] | 3-Chloro-5-[6-oxo-1-(6-oxo-2-pyrazol-1-yl-1,6-dihydro-pyrimidin-5-ylmethyl)-4-trifluoromethyl-1,6-dihydro-pyrimidin-5-yloxy]-benzonitrile | MS (ESI) m/z 490, 492<br>$^1$H NMR: (DMSO-d6, 400 MHz)<br>δ 8.75 (s, 1H), 8.51 (s, 1H), 7.91-8.11 (m, 2H), 7.73 (s, 1H), 7.67 (s, 1H), 7.63 (s, 1H), 6.62 (s, 1H), 4.90 (s, 2H). |
| 143 | 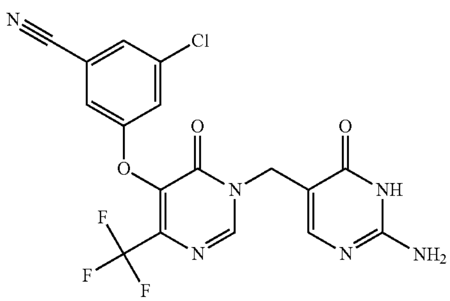 [SMILES: N#Cc1cc(Cl)cc(Oc2c(C(F)(F)F)ncn(Cc3cnc(N)[nH]c3=O)c2=O)c1] | 3-((1-((2-amino-6-oxo-1,6-dihydropyrimidin-5-yl)methyl)-6-oxo-4-(trifluoromethyl)-1,6-dihydropyrimidin-5-yl)oxy)-5-chlorobenzonitrile | MS (ESI) m/z 439, 441<br>$^1$H NMR: (DMSO-d6, 400 MHz)<br>δ 8.65 (s, 1H), 8.25 (s, 2H), 7.74 (s, 1H), 7.73 (s, 1H), 7.66 (s, 1H), 7.63 (s, 1H), 4.76 (s, 2H). |
| 144 | 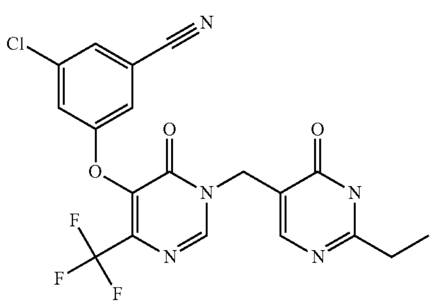 | 3-chloro-5-((1-((2-ethyl-6-oxo-1,6-dihydropyrimidin-5-yl)methyl)-6-oxo-4-(trifluoromethyl)-1,6-dihydropyrimidin-5-yl)oxy)benzonitrile | MS (ESI) m/z 452, 454<br>$^1$H NMR: (Methanol-d4, 400 MHz)<br>δ 8.65 (s, 1H), 8.12 (s, 1H), 7.53 (s, 1H), 7.38 (s, 1H), 7.31 (s, 1H), 4.99 (s, 2H), 2.82 (q, J = 7.6 Hz, 2H), 1.35 (t, J = 7.6 Hz, 3H). |
| 145 | 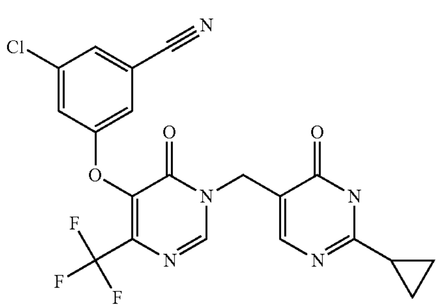 [SMILES: N#Cc1cc(Cl)cc(Oc2c(C(F)(F)F)ncn(Cc3cnc(C4CC4)[nH]c3=O)c2=O)c1] | 3-chloro-5-((1-((2-cyclopropyl-6-oxo-1,6-dihydropyrimidin-5-yl)methyl)-6-oxo-4-(trifluoromethyl)-1,6-dihydropyrimidin-5-yl)oxy)benzonitrile | MS (ESI) m/z 464, 466<br>$^1$H NMR: (DMSO-d6, 400 MHz)<br>δ 8.72 (s, 1H), 7.84 (s, 1H), 7.73 (s, 1H), 7.66 (s, 1H), 7.63 (s, 1H), 4.80 (s, 2H), 1.82-1.87 (m, 1H), 0.94-0.99 (m, 4H). |

EXAMPLE 146

3-chloro-5-((1-((2-(4-fluorophenyl)-6-oxo-1,6-dihydropyrimidin-5-yl)methyl)-6-oxo-4-(trifluoromethyl)-1,6-dihydropyrimidin-5-yl)oxy)benzonitrile

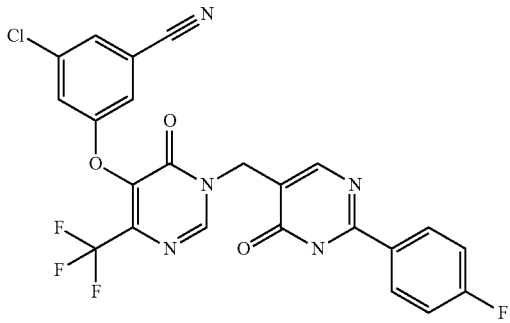 [SMILES: N#Cc1cc(Cl)cc(Oc2c(C(F)(F)F)ncn(Cc3cnc(-c4ccc(F)cc4)[nH]c3=O)c2=O)c1]

Step 1: 3-chloro-5-((1-((2-(4-fluorophenyl)-4-((4-methoxybenzyl)oxy)pyrimidin-5-yl)methyl)-6-oxo-4-(trifluoromethyl)-1,6-dihydropyrimidin-5-yl)oxy)benzonitrile

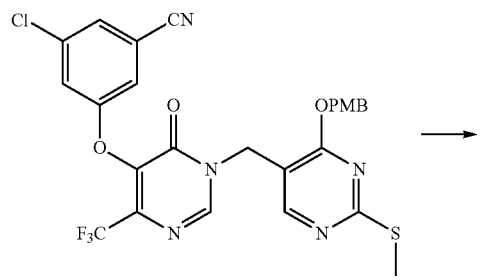

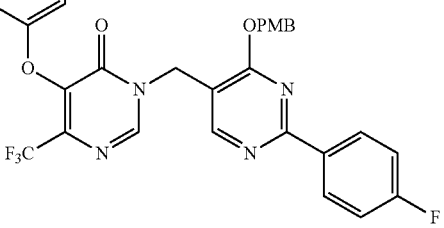

A mixture of 3-chloro-5-((1-((4-((4-methoxybenzyl)oxy)-2-(methylthio)pyrimidin-5-yl)methyl)-6-oxo-4-(trifluoromethyl)-1,6-dihydropyrimidin-5-yl)oxy)benzonitrile (200 mg, 0.33 mmol), (4-fluorophenyl)boronic acid (50 mg, 0.33 mmol), CuTC (129 mg, 0.67 mmol) and Pd(PPh$_3$)$_4$ (40 mg, 0.03 mmol) in THF (20 mL) was stirred for 2 hr at 90° C. under a nitrogen atmosphere. After cooling to r.t., the mixture was concentrated under reduced pressure and purified by preparative TLC (petroleum ether/ethyl acetate (2:1) as eluent) to afford 3-chloro-5-((1-((2-(4-fluorophenyl)-4-((4-methoxybenzyl)oxy)pyrimidin-5-yl)methyl)-6-oxo-4-(trifluoromethyl)-1,6-dihydropyrimidin-5-yl)oxy)benzonitrile (120 mg).

MS (ESI) m/z 638, 640 (M+H)$^+$

The title compound was subsequently prepared from the above intermediate by following a similar procedure to Step 6 of Example 137.

$^1$HNMR (DMSO-d6, 400 MHz) δ 8.78 (s, 1H), 8.08-8.11 (m, 3H), 7.72 (s, 1H), 7.67 (s, 1H), 7.64 (s, 1H), 7.33 (t, J=8.8 Hz, 2H), 4.91 (s, 2H).

MS (ESI) m/z 518, 520 (M+H)$^+$

By substituting the appropriate boronic acid in Step 1, Examples 147-153 in the table below were prepared in an analogous manner to Example 146

| Example | Structure | IUPAC Name | MS (M + H)$^+$/NMR |
|---|---|---|---|
| 147 | 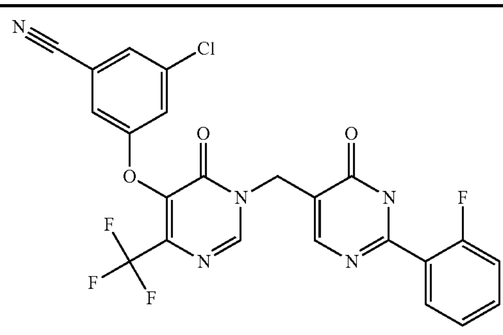 | 3-chloro-5-((1-((2-(2-fluorophenyl)-6-oxo-1,6-dihydropyrimidin-5-yl)methyl)-6-oxo-4-(trifluoromethyl)-1,6-dihydropyrimidin-5-yl)oxy)benzonitrile | MS (ESI) m/z 518, 520 $^1$H NMR: (DMSO-d6, 400 MHz) δ 8.78 (s, 1H), 8.10 (s, 1H), 7.73 (s, 1H), 7.68 (s, 1H), 7.55-7.65 (m, 3H), 7.29-7.36 (m, 2H), 4.91 (s, 2H). |
| 148 | 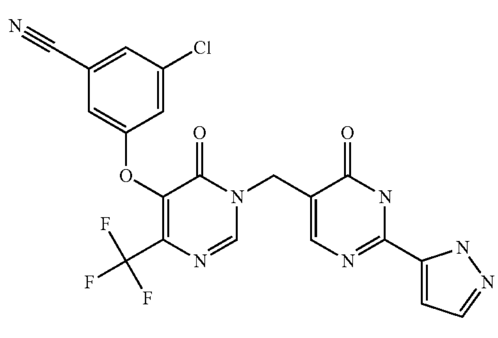 [SMILES: N#Cc1cc(Cl)cc(Oc2c(C(F)(F)F)ncn(Cc3cnc(-c4ccn[nH]4)[nH]c3=O)c2=O)c1] | 3-chloro-5-((6-oxo-1-((6-oxo-2-(1H-pyrazol-5-yl)-1,6-dihydropyrimidin-5-yl)methyl)-4-(trifluoromethyl)-1,6-dihydropyrimidin-5-yl)oxy)benzonitrile | MS (ESI) m/z 490, 492 $^1$H NMR: (DMSO-d6, 400 MHz) δ 8.77 (s, 1H), 7.99 (s, 1H), 7.85 (s, 1H), 7.72 (s, 1H), 7.67 (s, 1H), 7.63 (s, 1H), 6.89 (s, 1H), 4.87 (s, 2H). |

| Example | Structure | IUPAC Name | MS (M + H)+/NMR |
|---|---|---|---|
| 149 | 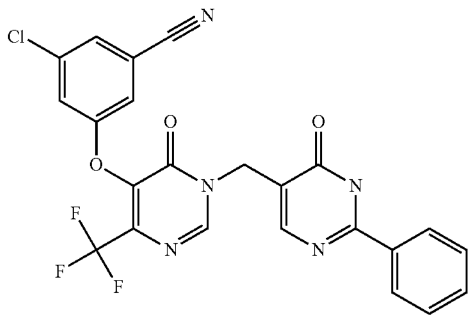 [SMILES: N#Cc1cc(Cl)cc(Oc2c(C(F)(F)F)ncn(Cc3cnc(-c4ccccc4)[nH]c3=O)c2=O)c1] | 3-chloro-5-((6-oxo-1-((6-oxo-2-phenyl-1,6-dihydropyrimidin-5-yl)methyl)-4-(trifluoromethyl)-1,6-dihydropyrimidin-5-yl)oxy)benzonitrile | MS (ESI) m/z 500, 502<br>$^1$H NMR: (DMSO-d6, 400 MHz) δ 8.79 (s, 1H), 8.11 (s, 1H), 8.03 (d, J = 7.2 Hz, 2H), 7.73 (s, 1H), 7.68 (s, 1H), 7.65 (s, 1H), 7.40-7.42 (m, 3H), 4.92 (s, 2H). |
| 150 | 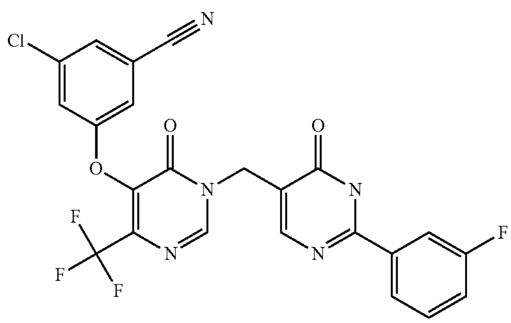 [SMILES: N#Cc1cc(Cl)cc(Oc2c(C(F)(F)F)ncn(Cc3cnc(-c4cccc(F)c4)[nH]c3=O)c2=O)c1] | 3-chloro-5-((1-((2-(3-fluorophenyl)-6-oxo-1,6-dihydropyrimidin-5-yl)methyl)-6-oxo-4-(trifluoromethyl)-1,6-dihydropyrimidin-5-yl)oxy)benzonitrile | MS (ESI) m/z 518, 520<br>$^1$H NMR: (DMSO-d6, 400 MHz) δ13.05 (s, 1H), 8.78 (s, 1H), 8.12 (s, 1H), 7.84-7.91 (m, 2H), 7.73 (s, 1H), 7.68 (s, 1H), 7.65 (s, 1H), 7.55 (dd, J = 8.0 Hz, 14.4 Hz, 1H), 7.41 (t, J = 7.6 Hz, 1H), 4.93 (s, 2H). |
| 151 | 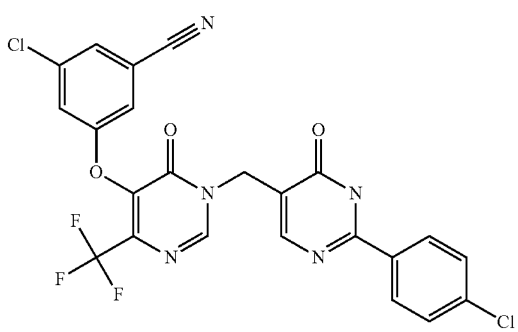 [SMILES: N#Cc1cc(Cl)cc(Oc2c(C(F)(F)F)ncn(Cc3cnc(-c4ccc(Cl)cc4)[nH]c3=O)c2=O)c1] | 3-chloro-5-((1-((2-(4-chlorophenyl)-6-oxo-1,6-dihydropyrimidin-5-yl)methyl)-6-oxo-4-(trifluoromethyl)-1,6-dihydropyrimidin-5-yl)oxy)benzonitrile | MS (ESI) m/z 534, 536<br>$^1$H NMR: (DMSO-d6, 400 MHz) δ8.78 (s, 1H), 8.11 (s, 1H), 8.04 (d, J = 8.4 Hz, 2H), 7.72 (s, 1H), 7.67 (s, 1H), 7.64 (s, 1H), 7.57 (d, J = 8.4 Hz, 2H), 4.91 (s, 2H). |
| 152 | 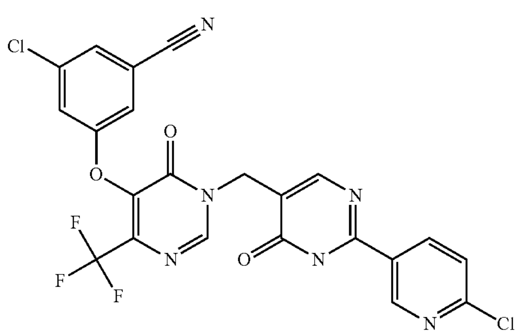 [SMILES: N#Cc1cc(Cl)cc(Oc2c(C(F)(F)F)ncn(Cc3cnc(-c4ccc(Cl)nc4)[nH]c3=O)c2=O)c1] | 3-chloro-5-((1-((2-(6-chloropyridin-3-yl)-6-oxo-1,6-dihydropyrimidin-5-yl)methyl)-6-oxo-4-(trifluoromethyl)-1,6-dihydropyrimidin-5-yl)oxy)benzonitrile | MS (ESI) m/z 535, 537<br>$^1$H NMR: (DMSO-d6, 400 MHz) δ8.99 (s, 1H), 8.78 (s, 1H), 8.40 (d, J = 6.4 Hz, 1H), 8.16 (s, 1H), 7.73 (s, 1H), 7.65-7.69 (m, 3H), 4.94 (s, 2H). |

| Example | Structure | IUPAC Name | MS (M + H)+/NMR |
|---|---|---|---|
| 153 | 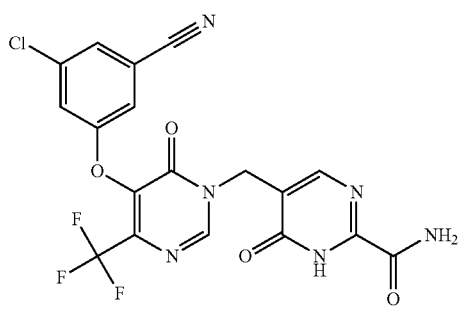 [SMILES: N#Cc1cc(Cl)cc(Oc2c(C(F)(F)F)ncn(Cc3cnc(C(N)=O)[nH]c3=O)c2=O)c1] | 3-chloro-5-((6-oxo-1-((6-oxo-2-(4-(trifluoromethoxy)phenyl)-1,6-dihydropyrimidin-5-yl)methyl)-4-(trifluoromethyl)-1,6-dihydropyrimidin-5-yl)oxy)benzonitrile | MS (ESI) m/z 584, 586<br>1H NMR: (DMSO-d6, 400 MHz) δ8.81 (s, 1H), 8.18-8.20 (m, 3H), 7.76 (s, 1H), 7.71 (s, 1H), 7.67 (s, 1H), 7.53 (d, J = 8.8 Hz, 2H), 4.96 (s, 2H). |

EXAMPLE 154

5-((5-(3-chloro-5-cyanophenoxy)-6-oxo-4-(trifluoromethyl)pyrimidin-1(6H)-yl)methyl)-6-oxo-1,6-dihydropyrimidine-2-carboxamide

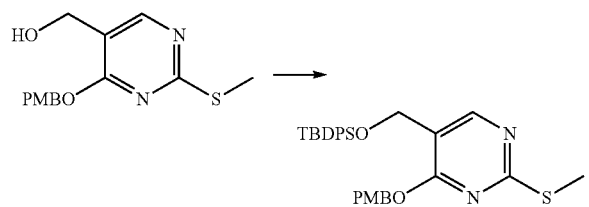

Step 1: 5-(((tert-butyldiphenylsilyl)oxy)methyl)-4-((4-methoxybenzyl)oxy)-2-(methylthio)pyrimidine

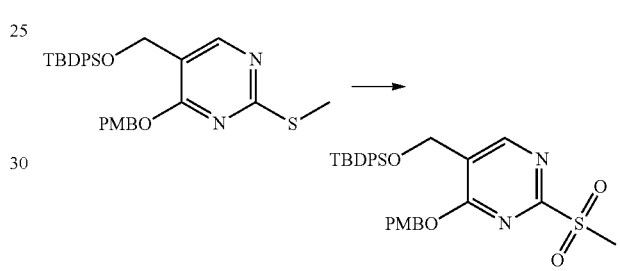

A mixture of (4-((4-methoxybenzyl)oxy)-2-(methylthio)pyrimidin-5-yl)methanol (4.33 g, 14.8 mol), TBDPSCl (4.47 g, 16.3 mol) and imidazole (2.02 g, 29.7 mol) in THF (450 mL) was stirred at 20° C. for 2 hr. The reaction mixture was quenched with 100 mL of H₂O and extracted with ethyl acetate (200 mL×3). The combined organic extracts were dried over sodium sulfate, filtered and concentrated under reduced pressure to give 5-(((tert-butyldiphenylsilyl)oxy)methyl)-4-((4-methoxybenzyl)oxy)-2-(methylthio)pyrimidine (8 g) was used without further purification.

MS (ESI) m/z 531 (M+H)+.

Step 2: 5-(((tert-butyldiphenylsilyl)oxy)methyl)-4-((4-methoxybenzyl)oxy)-2-(methylsulfonyl)pyrimidine

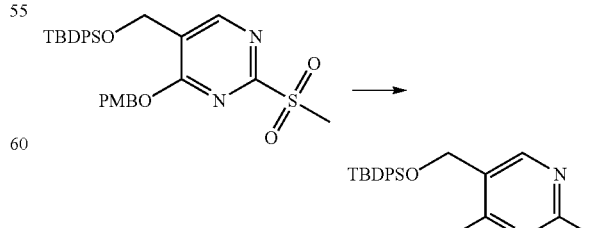

A mixture of 5-(((tert-butyldiphenylsilyl)oxy)methyl)-4-((4-methoxybenzyl)oxy)-2-(methylthio)pyrimidine (3 g, 5.65 mmol) and m-CPBA (3.90 g, 22.6 mmol) in dichloromethane (10 mL) was stirred at r.t. for 2 hr. After the reaction was complete, the mixture was quenched by 100 mL of Na₂SO₃ and extracted with dichloromethane (20 mL×3). The combined organic extracts were washed with NaHCO₃ solution, dried over sodium sulfate, filtered and concentrated under reduced pressure to give the desired product 5-(((tert-butyldiphenylsilyl)oxy)methyl)-4-((4-methoxybenzyl)oxy)-2-(methylsulfonyl)pyrimidine (2.95 g).

MS (ESI) m/z 563 (M+H)+

Step 3: 5-(((tert-butyldiphenylsilyl)oxy)methyl)-4-((4-methoxybenzyl)oxy)pyrimidine-2-carbonitrile To a solution of 5-(((tert-butyldiphenylsilyl)oxy)methyl)-4-((4-methoxybenzyl)oxy)-2-(methylsulfonyl)

(2.95 g, 5.24 mmol) in DMSO (50 mL) was added KCN (0.37 g, 5.76 mmol). Then the mixture was stirred at 60° C. for 16 hr. After cooling, the mixture was diluted with water and extracted with ethyl acetate. The combined organic extracts were washed with NaHCO₃ solution, dried over sodium sulfate, filtered and concentrated under reduced pressure. The residue was purified by chromatography on silica gel (petroleum ether/ethyl acetate (5:1 to 3:1) as eluent) to give 5-(((tert-butyl diphenylsilyl)oxy)methyl)-4-((4-methoxybenzyl)oxy)pyrimidine-2-carbonitrile (1.95 g).

¹H NMR (CDCl₃, 400 MHz) δ 8.74 (s, 1H), 7.59-7.61 (m, 4H), 7.34-7.42 (m, 8H), 6.83 (d, J=8.8 Hz, 2H), 5.30 (s, 2H), 4.69 (s, 2H), 3.77 (s, 3H), 1.05 (s, 9H).

MS (ESI) m/z 510 (M+H)⁺

Step 4: 5-(((tert-butyldiphenylsilyl)oxy)methyl)-4-((4-methoxybenzyl)oxy)pyrimidine-2-carboxamide

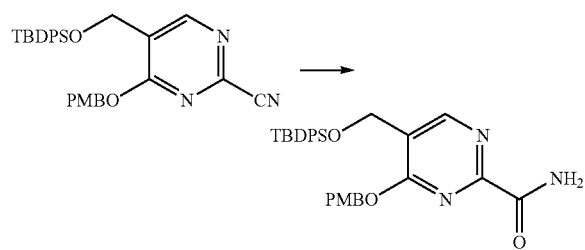

To a solution of 5-(((tert-butyldiphenylsilyl)oxy)methyl)-4-((4-methoxybenzyl)oxy)pyrimidine-2-carbonitrile (0.3 g, 0.59 mmol) in THF/H₂O (3 mL/3 mL) were added H₂O₂ (30 wt. % in H₂O) (106 mg, 2.94 mmol) and NaOH (71 mg, 1.76 mmol). Then the mixture was stirred at r.t. for 3 hr. The mixture was diluted with water and extracted with ethyl acetate (100 mL×3). The combined organic extracts were washed with Na₂SO₃ solution, dried over magnesium sulfate, filtered and concentrated under reduced pressure to give the desired product 5-(((tert-butyldiphenylsilyloxy)methyl)-4-((4-methoxybenzyl)oxy)pyrimidine-2-carboxamide (280 mg).

MS (ESI) m/z 528 (M+H)⁺.

Step 5: 5-(hydroxymethyl)-4-((4-methoxybenzyl)oxy)pyrimidine-2-carboxamide

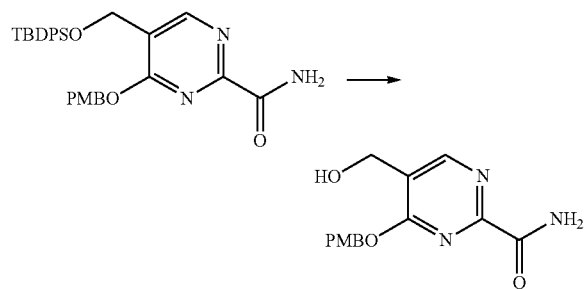

To a solution of 5-(((tert-butyldiphenylsilyl)oxy)methyl)-4-((4-methoxybenzyl)oxy)pyrimidine-2-carboxamide (0.28 g, 0.53 mmol) in THF (5 mL) was added TBAF (0.69 g, 2.65 mmol). The reaction mixture was stirred at r.t. for 2 hr. After the reaction was completed, the solution was diluted with ethyl acetate (50 mL). The organic layer was wash with dilute HCl, dried over sodium sulfate, filtered and concentrated under reduced pressure to give 5-(hydroxymethyl)-4-((4-methoxybenzyl)oxy)pyrimidine-2-carboxamide (96 mg).

MS (ESI) m/z 290 (M+H)⁺.

Step 6: 5-((5-(3-chloro-5-cyanophenoxy)-6-oxo-4-(trifluoromethyl)pyrimidin-1(6H)-yl)methyl)-4-((4-methoxybenzyl)oxy)pyrimidine-2-carboxamide

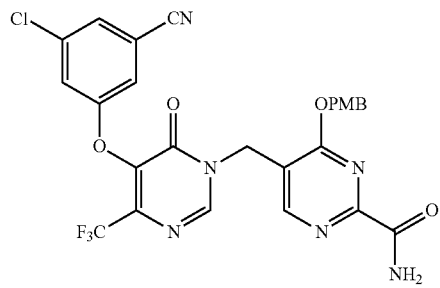

The above intermediate was prepared from 5-(((tert-butyldiphenylsilyl)oxy)methyl)-2-(1-ethoxyvinyl)-4-((4-methoxybenzyl)oxy)pyrimidine following a similar procedure to Step 2 of Example 4.

MS (ESI) m/z 587, 589 (M+H)⁺

Step 7: 5-((5-(3-chloro-5-cyanophenoxy)-6-oxo-4-(trifluoromethyl)pyrimidin-1(6H)-yl)methyl)-6-oxo-1,6-dihydropyrimidine-2-carboxamide

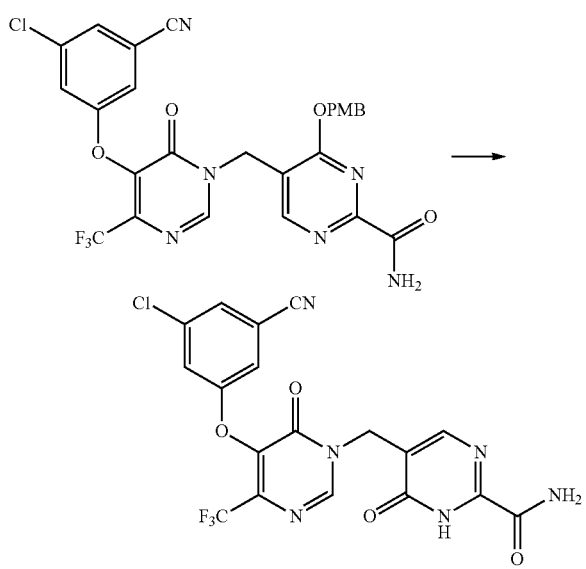

To a solution of 5-((5-(3-chloro-5-cyanophenoxy)-6-oxo-4-(trifluoromethyl)pyrimidin-1(6H)-yl)methyl)-4-((4-methoxybenzyl)oxy)pyrimidine-2-carboxamide (120 mg, 0.20 mmol) in 1,4-dioxane (2 mL) was added HCl/methanol solution (2 mL, 4 M). The mixture was stirred at room temperature for 2 hr. The solvent was removed under reduced pressure. The residue was purified by preparative HPLC to give the desired product 5-((5-(3-chloro-5-cyanophenoxy)-6-oxo-4-(trifluoromethyl)pyrimidin-1 (6H)-yl) methyl)-6-oxo-1,6-dihydropyrimidine-2-carboxamide (37 mg).

¹HNMR (DMSO-d6, 400 MHz) δ 8.74 (s, 1H), 8.31 (s, 1H), 8.06 (s, 1H), 7.97 (s, 1H), 7.72 (s, 1H), 7.66 (s, 1H), 7.62 (t, J=2.0 Hz, 1H), 4.87 (s, 2H).

MS (ESI) m/z 467, 469 (M+H)⁺

EXAMPLE 155

5-((5-(3-chloro-5-cyanophenoxy)-6-oxo-4-(trifluoromethyl)pyrimidin-1(6H)-yl)methyl)-6-oxo-1,6-dihydropyrimidine-2-carbonitrile

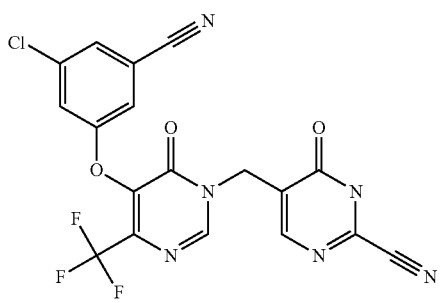 [SMILES: N#Cc1cc(Cl)cc(Oc2c(C(F)(F)F)ncn(Cc3cnc(C#N)[nH]c3=O)c2=O)c1]

The title compound was prepared from 5-(((tert-butyldiphenylsilyl)oxy)methyl)-4-((4-methoxybenzyl)oxy)pyrimidine-2-carbonitrile (Step 3 of Example 154) using procedures similar to Steps 5-7 of Example 154.

MS (ESI) m/z 449, 451 (M+H)⁺
¹H NMR: (DMSO-d6, 400 MHz)
δ 8.73 (s, 1H), 8.38 (s, 1H), 7.73 (s, 1H), 7.67 (s, 1H), 7.65 (d, J=2.0 Hz, 1H), 5.00 (s, 2H).

EXAMPLE 156

3-((1-((2-acetyl-6-oxo-1,6-dihydropyrimidin-5-yl)methyl)-6-oxo-4-(trifluoromethyl)-1,6-dihydropyrimidin-5-yl)oxy)-5-chlorobenzonitrile

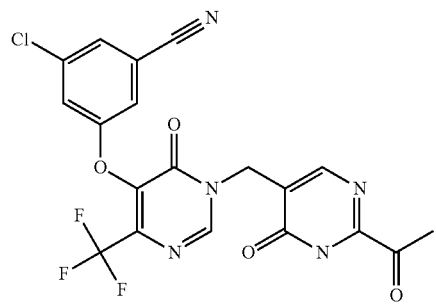 [SMILES: CC(=O)c1ncc(Cn2cnc(C(F)(F)F)c(Oc3cc(Cl)cc(C#N)c3)c2=O)c(=O)[nH]1]

Step 1: 5-(((tert-butyldiphenylsilyl)oxy)methyl)-2-(1-ethoxyvinyl)-4-((4-methoxybenzyl)oxy)pyrimidine

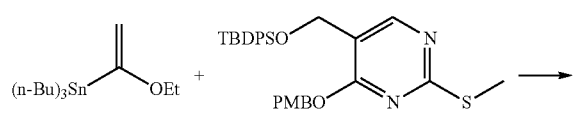

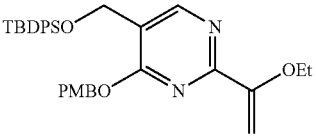

To a solution of 5-(((tert-butyldiphenylsilyl)oxy)methyl)-4-((4-methoxybenzyl)oxy)-2-(methylthio)pyrimidine (1 g, 1.89 mmol), tributyl(1-ethoxyvinyl)stannane (1.5 g, 4.15 mmol) and CuBr.Me₂S (0.87 g, 4.15 mmol) in THF (15 mL) was added Pd(PPh₃)₄ (0.22 g, 0.19 mmol). The mixture was stirred at reflux for 16 hr under a nitrogen atmosphere. After cooling, the mixture was added water (10 mL), and extracted with ethyl acetate (10 mL×3). The combined organic extracts were washed with brine, dried over anhydrous sodium sulfate, filtered and concentrated under reduced pressure. The residue was purified by silica gel column (petroleum ether/ethyl acetate (10:1) as eluent) to afford 5-(((tert-butyldiphenylsilyl)oxy)methyl)-2-(1-ethoxyvinyl)-4-((4-methoxybenzyl)oxy)pyrimidine (0.63 g) as a light yellow solid.

MS (ESI) m/z 528 (M+H)⁺.

Step 2: (2-(1-ethoxyvinyl)-4-((4-methoxybenzyl)oxy)pyrimidin-5-yl)methanol

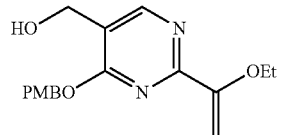

The above intermediate was prepared from 5-(((tert-butyldiphenylsilyl)oxy)methyl)-2-(1-ethoxyvinyl)-4-((4-methoxybenzyl)oxy)pyrimidine by following a similar procedure to Step 5 of Example 154.

Step 3: (2-(1-ethoxyvinyl)-4-((4-methoxybenzyl)oxy)pyrimidin-5-yl)methyl methanesulfonate

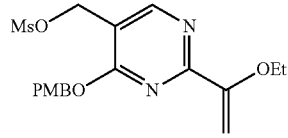

The above intermediate was prepared from (2-(1-ethoxyvinyl)-4-((4-methoxybenzyl)oxy)pyrimidin-5-yl)methanol by following a similar procedure to Step 1 of Example 2.

MS (ESI) m/z 275 (M+H)⁺

Step 4: 3-chloro-5-((1-((2-(1-ethoxyvinyl)-4-((4-methoxybenzyl)oxy)pyrimidin-5-yl)methyl)-6-oxo-4-(trifluoromethyl)-1,6-dihydropyrimidin-5-yl)oxy)benzonitrile

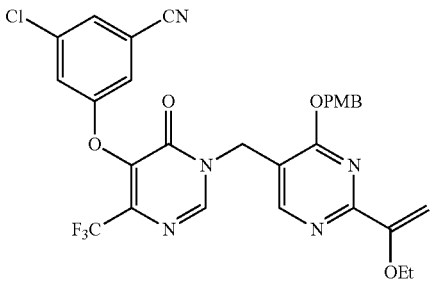

The above intermediate was prepared from (2-(1-ethoxyvinyl)-4-((4-methoxybenzyl)oxy)pyrimidin-5-yl)methyl methanesulfonate by following a similar procedure to Step 2 of Example 2.

MS (ESI) m/z 614, 616 (M+H)$^+$

The title compound was prepared from 3-chloro-5-((1-((2-(1-ethoxyvinyl)-4-((4-methoxybenzyl)oxy)pyrimidin-5-yl)methyl)-6-oxo-4-(trifluoromethyl)-1,6-dihydropyrimidin-5-yl)oxy)benzonitrile by following a similar procedure to Step 7 of Example 154.

$^1$HNMR (DMSO-d6, 400 MHz) δ 8.75 (s, 1H), 8.08 (s, 1H), 7.73 (s, 1H), 7.67 (s, 1H), 7.65 (d, J=2.0 Hz, 1H), 4.91 (s, 2H), 2.47 (s, 3H).

MS (ESI): m/z 466, 468 (M+H)$^+$

EXAMPLE 157

3-chloro-5-((1-((2-(difluoromethyl)-6-oxo-1,6-dihydropyrimidin-5-yl)methyl)-6-oxo-4-(trifluoromethyl)-1,6-dihydropyrimidin-5-yl)oxy)benzonitrile

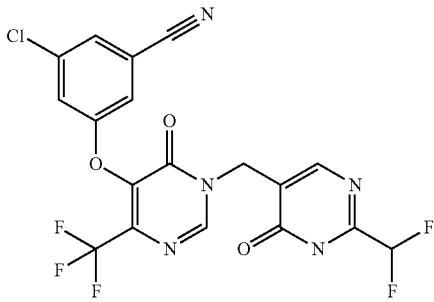 [SMILES: N#Cc1cc(Cl)cc(Oc2c(C(F)(F)F)ncn(Cc3cnc(C(F)F)[nH]c3=O)c2=O)c1]

Step 1: ethyl 2-chloro-4-methoxypyrimidine-5-carboxylate

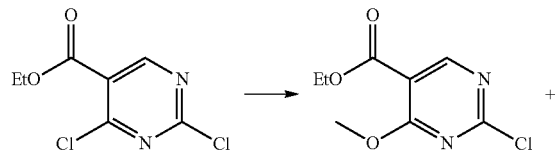

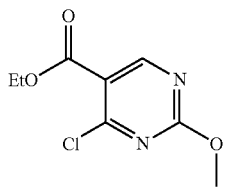

A mixture of ethyl 2,4-dichloropyrimidine-5-carboxylate (20 g, 91 mmol) and MeONa (9.8 g, 182 mmol) in methanol (200 mL) was stirred at r.t. for 2 hr. After finished, the mixture was concentrated under reduced pressure and then 200 mL of water was added. The product was extracted with ethyl acetate (100 mL×3). The combined organic extracts were dried over sodium sulfate, filtered and concentrated under reduced pressure. The crude product was purified by column chromatography on silica gel (petroleum ether/ethyl acetate (100:1 to 20:1) as eluent) to give a 1:1 mixture of ethyl 2-chloro-4-methoxypyrimidine-5-carboxylate and ethyl 4-chloro-2-methoxypyrimidine-5-carboxylate (12 g).

MS (ESI) m/z 217, 219 (M+H)$^+$

Step 2: (2-chloro-4-methoxypyrimidin-5-yl)methanol

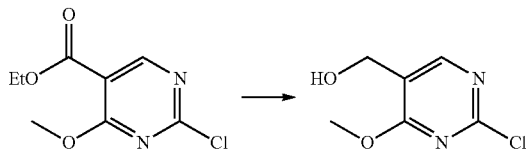

To a solution of ethyl 2-chloro-4-methoxypyrimidine-5-carboxylate and ethyl 4-chloro-2-methoxypyrimidine-5-carboxylate (6 g, 27.8 mmol) in THF (60 mL) was added DIBAL-H (55 mmol, 55 mL, 1.0 M) dropwise at −78° C. under a nitrogen atmosphere, the mixture was stirred at −78° C. for 30 min. The temperature was allowed to rise to room temperature and stirring continued for a further 4 hr. The solution was quenched with aqueous potassium carbonate (150 mL) and extracted with ethyl acetate (300 mL×3). The combined organic extracts were washed with brine, dried over sodium sulfate and concentrated under reduced pressure. The crude product was purified by column chromatography (petroleum ether/ethyl acetate (10:1 to 2:1) as eluent) to give (2-chloro-4-methoxypyrimidin-5-yl)methanol (1.8 g).

MS (ESI) m/z 175, 177 (M+H)$^+$

Step 3: 5-(((tert-butyldiphenylsilyl)oxy)methyl)-2-chloro-4-methoxypyrimidine

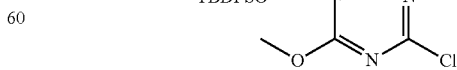

The above intermediate was prepared from (2-chloro-4-methoxypyrimidin-5-yl)methanol by following a similar procedure to Step 1 of Example 154.

MS (ESI) m/z 413, 415 (M+H)$^+$

Step 4: 5-(((tert-butyldiphenylsilyl)oxy)methyl)-4-methoxy-2-vinylpyrimidine

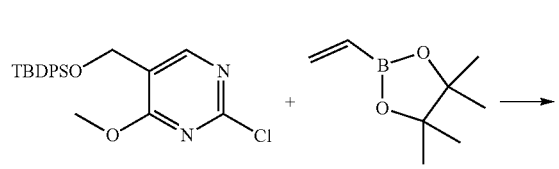

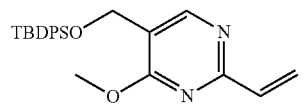

To a solution of 5-(((tert-butyldiphenylsilyl)oxy)methyl)-2-chloro-4-methoxypyrimidine (1.5 g, 3.64 mmol) in 1,4-dioxane/H$_2$O (5 mL/1 mL) was added 4,4,5,5-tetramethyl-2-vinyl-1,3,2-dioxaborolane (0.66 g, 4.37 mmol), Pd(dppf)Cl$_2$ (270 mg, 0.36 mmol) and potassium carbonate (1.12 g, 7.28 mmol). The mixture was stirred at 100° C. for 4 hr. After cooling, the mixture was quenched with water (20 mL) and extracted with ethyl acetate (20 mL×3). The combined organic extracts were dried over sodium sulfate, filtered and concentrated under reduced pressure to give 5-(((tert-butyldiphenylsilyl)oxy)methyl)-4-methoxy-2-vinylpyrimidine (1.12 g).

MS (ESI) m/z 405 (M+H)$^+$

Step 5: 5-(((tert-butyldiphenylsilyl)oxy)methyl)-4-methoxypyrimidine-2-carbaldehyde

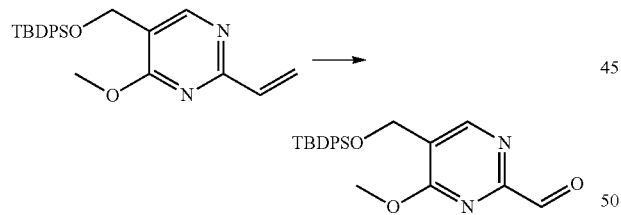

To a solution of 5-(((tert-butyldiphenylsilyl)oxy)methyl)-4-methoxy-2-vinylpyrimidine (2.63 g, 6.51 mmol) in dichloromethane/methanol (120 mL/40 mL) was bubbled O$_3$ (gas) at −78° C. After the solution turned blue, the mixture was stirred at this temperature for 10 min. N$_2$ was bubbled to degas the O$_3$. The mixture was quenched by addition of Me$_2$S and the mixture was concentrated under reduced pressure. The residue was purified by silica gel column (petroleum ether/ethyl acetate (100:1 to 10:1) as eluent) to give 5-(((tert-butyldiphenylsilyl)oxy)methyl)-4-methoxypyrimidine-2-carbaldehyde (1.8 g).

MS (ESI) m/z 407 (M+H)$^+$

Step 6: 5-(((tert-butyldiphenylsilyl)oxy)methyl)-2-(difluoromethyl)-4-methoxypyrimidine

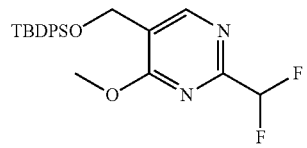

The above intermediate was prepared from 5-(((tert-butyldiphenylsilyl)oxy)methyl)-4-methoxypyrimidine-2-carbaldehyde by following a procedure similar to Step 9 of Example 144.

MS (ESI) m/z 429 (M+H)$^+$.

The title compound was subsequently prepared from the above intermediate using similar procedures to Step 5 of Example 154 followed by Steps 1-2 of Example 2 and Step 10 of Example 128.

$^1$H NMR: (400 MHz, DMSO-I) δ 8.73 (s, 1H), 8.14 (s, 1H), 7.72 (s, 1H), 7.67 (s, 1H), 7.64 (s, 1H), 6.71 (t, J=13.2 Hz, 1H), 4.92 (s, 2H).

MS (ESI) m/z 474, 476 (M+H)$^+$

EXAMPLE 158

3-chloro-5-((6-oxo-1-((6-oxo-2-(1H-pyrrolo[2,3-b]pyridin-4-yl)-1,6-dihydropyrimidin-5-yl)methyl)-4-(trifluoromethyl)-1,6-dihydropyrimidin-5-yl)oxy)benzonitrile

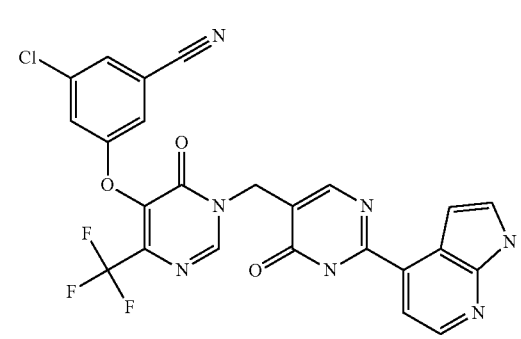 [SMILES: N#Cc1cc(Cl)cc(Oc2c(C(F)(F)F)ncn(Cc3cnc(-c4ccnc5[nH]ccc45)[nH]c3=O)c2=O)c1]

Step 1: 3-chloro-5-((1-((2-chloro-4-methoxypyrimidin-5-yl)methyl)-6-oxo-4-(trifluoromethyl)-1,6-dihydropyrimidin-5-yl)oxy)benzonitrile

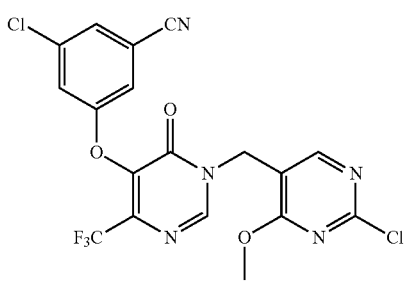 [SMILES: COc1nc(Cl)ncc1Cn1cnc(C(F)(F)F)c(Oc2cc(Cl)cc(C#N)c2)c1=O]

The above intermediate was prepared from (2-chloro-4-methoxypyrimidin-5-yl)methanol and 3-chloro-5-((6-oxo-4-(trifluoromethyl)-1,6-dihydropyrimidin-5-yl)oxy)benzonitrile according to the procedure given for Step 2 of Example 5.

MS (ESI) m/z 472, 473, 474 (M+H)+

Step 2: 3-chloro-5-((1-((4-methoxy-2-(1H-pyrrolo[2,3-b]pyridin-4-yl)pyrimidin-5-yl)methyl)-6-oxo-4-(trifluoromethyl)-1,6-dihydropyrimidin-5-yl)oxy)benzonitrile

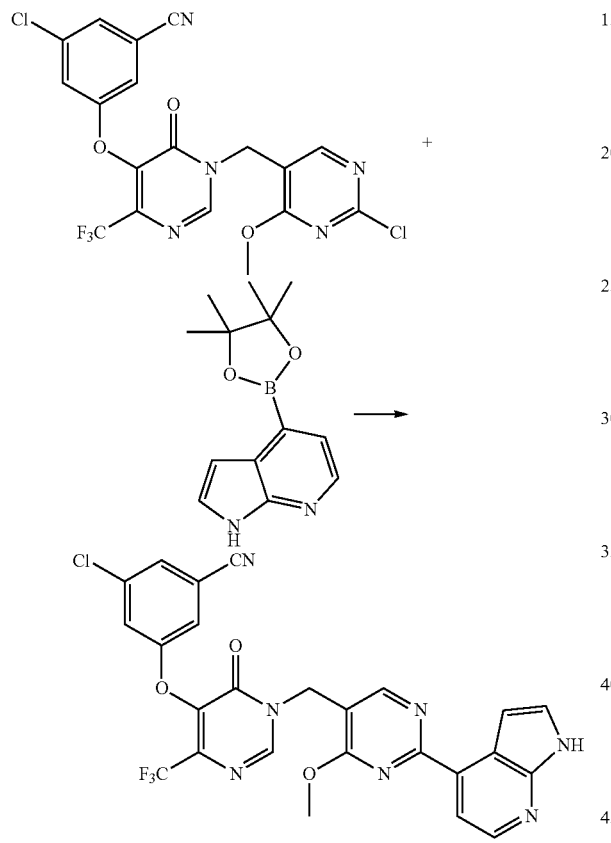

To a solution of 3-chloro-5-((1-((2-chloro-4-methoxypyrimidin-5-yl)methyl)-6-oxo-4-(trifluoromethyl)-1,6-dihydropyrimidin-5-yl)oxy)benzonitrile (155 mg, 0.328 mmol), 4-(4,4,5,5-tetramethyl-1,3,2-dioxaborolan-2-yl)-1H-pyrrolo[2,3-b]pyridine (88 mg, 0.361 mmol) and potassium carbonate (91 mg, 0.657 mmol) in 1,4-dioxane/H$_2$O (6.3 mL, V/V=20:1) was added Pd(dppf)Cl$_2$ (24 mg, 0.033 mmol). The mixture was stirred at 100° C. for 1 h under a nitrogen atmosphere. After cooling, the mixture was added water (10 mL), and extracted with ethyl acetate (10 mL×3). The combined organic extracts were washed with brine, dried over anhydrous sodium sulfate, filtered and concentrated under reduced pressure to give 3-chloro-5-((1-((4-methoxy-2-(1H-pyrrolo[2,3-b]pyridine-4-yl)pyrimidin-5-yl)methyl)-6-oxo-4-(trifluoromethyl)-1,6-dihydropyrimidin-5-yl)oxy)benzonitrile (181 mg).

MS (ESI) m/z 554, 556 (M+H)+

The above intermediate was used to prepare the title compound by following a similar procedure to Step 3 of Example 7.

$^1$H NMR (DMSO-d6, 400 MHz): δ 11.97 (s, 1H), 8.84 (s, 1H), 8.35 (d, J=5.2 Hz, 1H), 8.22 (d, J=12.8 Hz, 1H), 7.69-7.76 (m, 3H), 7.63 (t, J=2.8 Hz, 2H), 6.95 (s, 1H), 5.00 (s, 2H).

MS (ESI): m/z 540, 542 (M+H)+

EXAMPLE 159

3-chloro-5-((1-((2-(4-(difluoromethoxy)phenyl)-6-oxo-1,6-dihydropyrimidin-5-yl)methyl)-6-oxo-4-(trifluoromethyl)-1,6-dihydropyrimidin-5-yl)oxy)benzonitrile

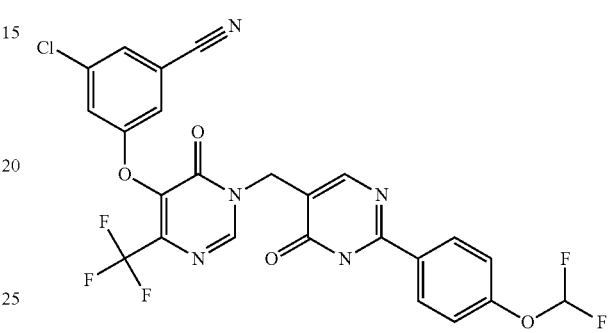

The title compound was prepared in an analogous manner to Example 158

MS (ESI) m/z 566, 568

$^1$H NMR: (DMSO-d6, 400 MHz) δ 8.79 (s, 1H), 8.11-8.13 (m, 3H), 7.74 (s, 1H), 7.69 (s, 1H), 7.66 (s, 1H), 7.37 (t, J=73.6 Hz, 1H), 7.29 (d, J=8.8 Hz, 2H), 4.93 (s, 2H).

EXAMPLE 160

3-chloro-5-((4-(difluoromethyl)-6-oxo-1-((6-oxo-1,6-dihydropyridazin-3-yl)methyl)-1,6-dihydropyrimidin-5-yl)oxy)benzonitrile

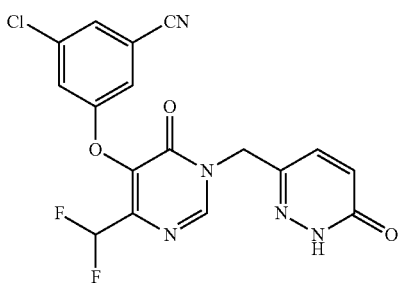 [SMILES: N#Cc1cc(Cl)cc(Oc2c(C(F)F)ncn(Cc3ccc(=O)[nH]n3)c2=O)c1]

Step 1: 6-(difluoromethyl)pyrimidin-4(3H)-one

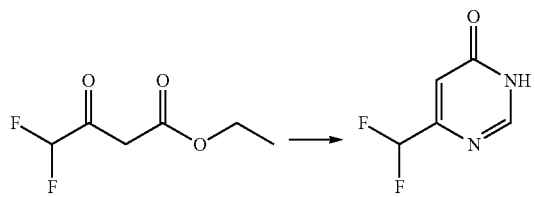

A mixture of sodium (2.91 g, 126.5 mmol) in methanol (70 mL) was stirred at r.t. for 30 min then formamidine acetate (6.3 g, 60 mmol) and ethyl 4,4-difluoro-3-oxobutanoate (5.0 g, 30.1 mmol) were added. The mixture was stirred at 80° C. for 4 hr. After cooling to r.t., the mixture was acidified with HCl to pH=6 and extracted with ethyl acetate (200 mL×5). The combined organic layers were dried over sodium sulfate, filtered and concentrated under reduced pressure to give 6-(difluoromethyl)pyrimidin-4(3H)-one (4.0 g).

MS (ESI): m/z 147 (M+H)$^+$

Step 2: 6-(difluoromethyl)pyrimidin-4(3H)-one

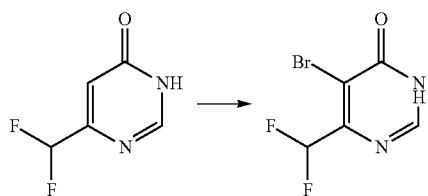 [SMILES: O=c1cc(C(F)F)nc[nH]1 ; O=c1[nH]cnc(C(F)F)c1Br]

To a mixture of compound 6-(difluoromethyl)pyrimidin-4(3H)-one (2.0 g, 13.7 mmol) and AcOK (4.0 g, 41.4 mmol) in acetic acid (20 mL), Br$_2$ (3.3 g, 20.5 mmol) was added under nitrogen atmosphere. The resulting mixture was stirred at 80° C. for 4 hr. Then the mixture was poured into ice water and the precipitate was collected by filtration to give 5-bromo-6-(difluoromethyl)pyrimidin-4(3H)-one (1.1 g).

MS (ESI): m/z 225, 227 (M+H)$^+$

Step 3: 5-bromo-6-(difluoromethyl)-3-(4-methoxybenzyl)pyrimidin-4(3H)-one

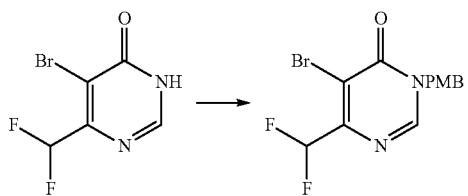

A mixture of 5-bromo-6-(difluoromethyl)pyrimidin-4(3H)-one (1.01 g, 4.49 mmol), PMBCl (735 mg, 4.71 mmol), potassium carbonate (1.24 g, 8.98 mmol) in DMF (10 mL) was stirred at r.t for 4 hr under nitrogen atmosphere. 15 mL of water was added and the precipitate was collected by filtration to give 5-bromo-6-(difluoromethyl)-3-(4-methoxybenzyl)pyrimidin-4(3H)-one (700 mg).

MS (ESI): m/z 345, 347 (M+H)$^+$

Step 4: 3-chloro-5-((4-(difluoromethyl)-1-(4-methoxybenzyl)-6-oxo-1,6-dihydropyrimidin-5-yl)oxy)benzonitrile

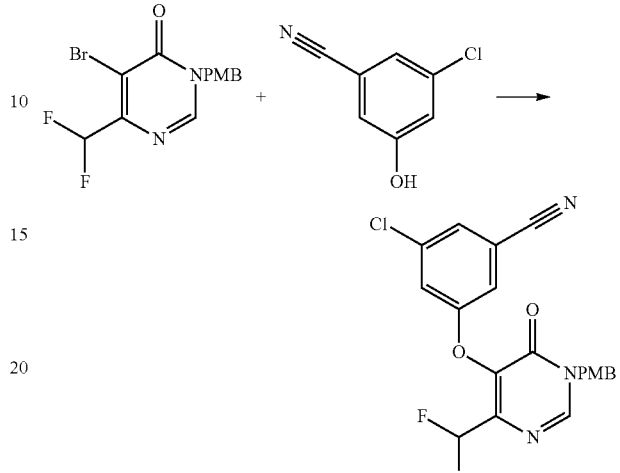

A mixture of 3-chloro-5-hydroxybenzonitrile (1.57 g, 11.6 mmol), 5-bromo-6-(difluoromethyl)-3-(4-methoxybenzyl)pyrimidin-4(3H)-one (2.0 g, 5.81 mmol) and t-BuOK (1.43 g, 12.8 mmol) in NMP (10 mL) was stirred at 120° C. overnight. After cooling to r.t., the mixture was diluted with 20 mL of water and extracted with ethyl acetate (100 mL×3). The combined organic layers were dried over sodium sulfate, filtered and concentrated under reduced pressure. Then methanol (10 mL) was added and the precipitate was collected by filtration to afford 3-chloro-5-((4-(difluoromethyl)-1-(4-methoxybenzyl)-6-oxo-1,6-dihydropyrimidin-5-yl)oxy)benzonitrile (1.0 g).

MS (ESI): m/z 418, 420 (M+H)$^+$

Step 5: 3-chloro-5-((4-(difluoromethyl)-6-oxo-1,6-dihydropyrimidin-5-yl)oxy)benzonitrile

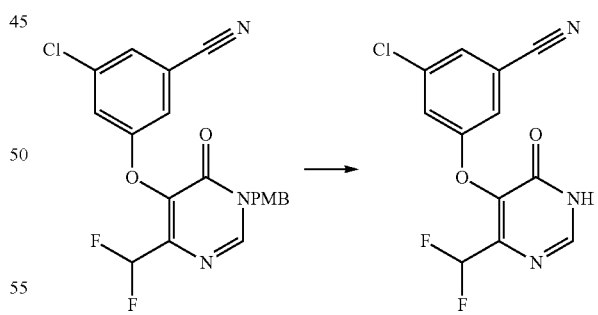

A solution of compound 3-chloro-5-((4-(difluoromethyl)-1-(4-methoxybenzyl)-6-oxo-1,6-dihydropyrimidin-5-yl)oxy)benzonitrile (400 mg, 0.96 mmol) in TFA (5 mL) was stirred under microwave irradiation at 100° C. for 10 min. After cooling to r.t, the mixture was concentrated under reduced pressure. Then methanol (10 mL) was added and the precipitate was collected by filtration to provide 3-chloro-5-((4-(difluoromethyl)-6-oxo-1,6-dihydropyrimidin-5-yl)oxy)benzonitrile (270 mg).

MS (ESI): m/z 298, 300 (M+H)$^+$

The title compound was prepared from the above intermediate by following similar procedures to Steps 2 and 3 of Example 7.

$^1$H NMR (DMSO-d6, 400 MHz): δ 12.92 (s, 1H), 8.66 (s, 1H), 7.72 (s, 1H), 7.58 (s, 1H), 7.52 (s, 1H), 7.46 (d, J=8.0 Hz, 1H), 6.98 (t, J=52 Hz, 1H), 6.83 (s, 1H), 5.07 (s, 2H).

MS (ESI) m/z 406, 408 (M+H)$^+$

EXAMPLE 161

2-fluoro-3-(6-oxo-1-((6-oxo-1,6-dihydropyridazin-3-yl)methyl)-4-(trifluoro methyl)-1,6-dihydropyrimidin-5-yloxy)benzonitrile

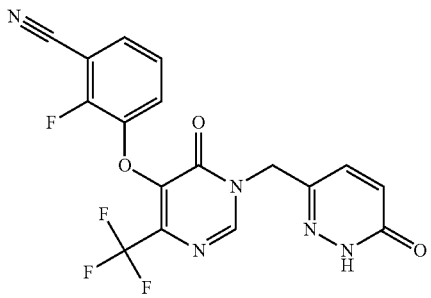 [SMILES: N#Cc1cccc(Oc2c(C(F)(F)F)ncn(Cc3ccc(=O)[nH]n3)c2=O)c1F]

The title compound was prepared in an analogous manner to Example 161 by replacing 3-chloro-5-hydroxybenzonitrile with 2-fluoro-3-hydroxybenzonitrile in Step 4.

$^1$H NMR: (DMSO-d6, 400 MHz) δ 12.95 (s, 1H), 8.73 (s, 1H), 7.63 (t, J=6.8 Hz, 1H), 7.27-7.47 (m, 3H), 6.85-6.87 (m, 1H), 5.09 (s, 2H).

MS (ESI) m/z 408 (M+H)$^+$

EXAMPLE 162

3-chloro-5-(4-(difluoromethoxy)-6-oxo-1-((6-oxo-1,6-dihydropyridazin-3-yl)methyl)-1,6-dihydro pyrimidin-5-yloxy)benzonitrile

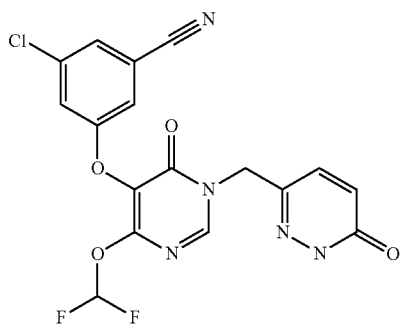 [SMILES: N#Cc1cc(Cl)cc(Oc2c(OC(F)F)ncn(Cc3ccc(=O)[nH]n3)c2=O)c1]

Step 1: diethyl 2-(3-chloro-5-cyanophenoxy)malonate

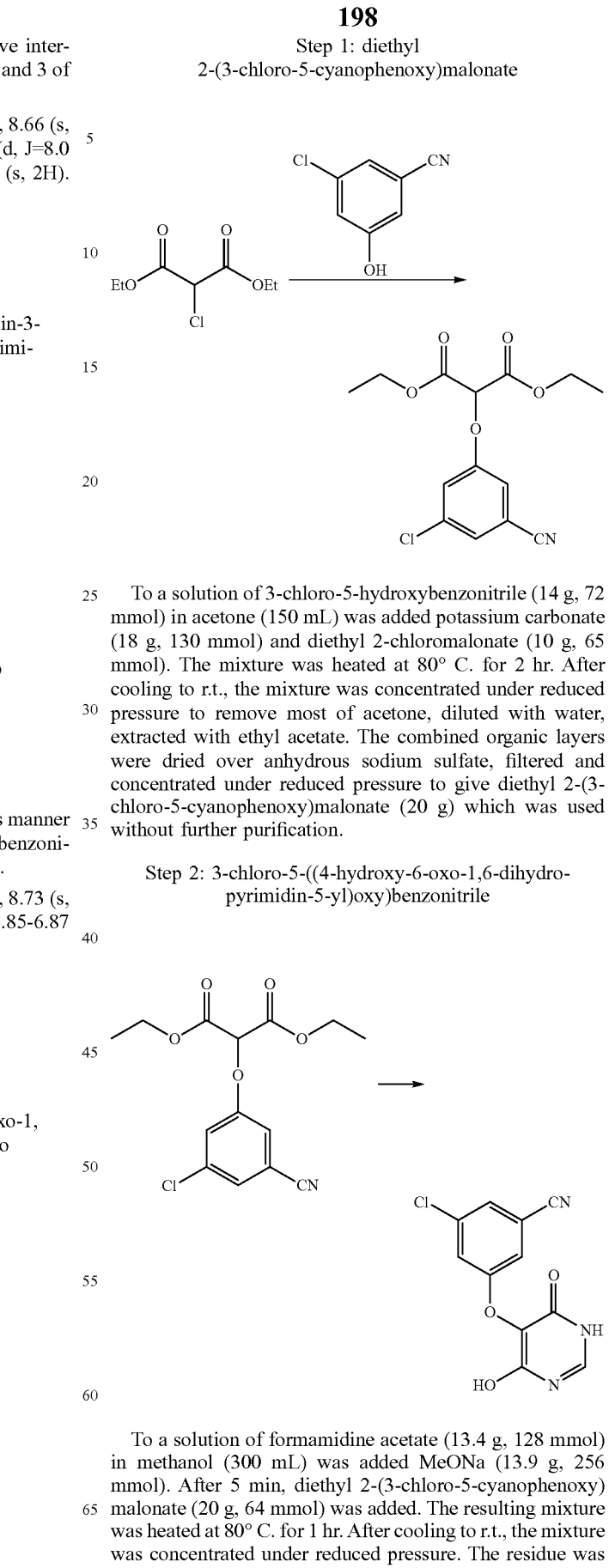

To a solution of 3-chloro-5-hydroxybenzonitrile (14 g, 72 mmol) in acetone (150 mL) was added potassium carbonate (18 g, 130 mmol) and diethyl 2-chloromalonate (10 g, 65 mmol). The mixture was heated at 80° C. for 2 hr. After cooling to r.t., the mixture was concentrated under reduced pressure to remove most of acetone, diluted with water, extracted with ethyl acetate. The combined organic layers were dried over anhydrous sodium sulfate, filtered and concentrated under reduced pressure to give diethyl 2-(3-chloro-5-cyanophenoxy)malonate (20 g) which was used without further purification.

Step 2: 3-chloro-5-((4-hydroxy-6-oxo-1,6-dihydropyrimidin-5-yl)oxy)benzonitrile

To a solution of formamidine acetate (13.4 g, 128 mmol) in methanol (300 mL) was added MeONa (13.9 g, 256 mmol). After 5 min, diethyl 2-(3-chloro-5-cyanophenoxy) malonate (20 g, 64 mmol) was added. The resulting mixture was heated at 80° C. for 1 hr. After cooling to r.t., the mixture was concentrated under reduced pressure. The residue was dissolved in water acidified to pH=5 and extracted with ethyl acetate. The combined organic layers were dried over anhydrous sodium sulfate, filtered and concentrated under reduced pressure. The residue was purified by preparative HPLC to give 3-chloro-5-((4-hydroxy-6-oxo-1,6-dihydropyrimidin-5-yl)oxy)benzonitrile (2.4 g).

MS (ESI) m/z 264, 266 (M+H)+

Step 3: 3-chloro-5-((4-(difluoromethoxy)-6-oxo-1,6-dihydropyrimidin-5-yl)oxy)benzonitrile

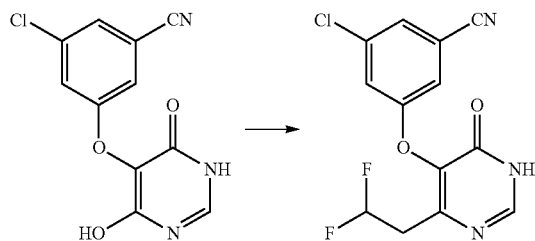 [SMILES: N#Cc1cc(Cl)cc(Oc2c(O)nc[nH]c2=O)c1 ; N#Cc1cc(Cl)cc(Oc2c(CC(F)F)nc[nH]c2=O)c1]

To a solution of 3-chloro-5-((4-hydroxy-6-oxo-1,6-dihydropyrimidin-5-yl)oxy)benzonitrile (1.4 g, 5.31 mmol) in DMF (20 mL) was added potassium carbonate (18.4 g, 132 mmol), then sodium 2-chloro-2,2-difluoroacetate (1.62 g, 10.6 mmol) was added. The mixture was stirred at 80° C. for 2 hr. After cooling to r.t., the mixture was diluted with water, then extracted with ethyl acetate. The combined organic layers were dried over anhydrous sodium sulfate, filtered and concentrated under reduced pressure. The residue was purified by preparative TLC (petroleum ether/ethyl acetate (1:2) as eluent) to give 3-chloro-5-((4-(difluoromethoxy)-6-oxo-1,6-dihydropyrimidin-5-yl)oxy)benzonitrile (500 mg).

MS (ESI) m/z 314, 316 (M+H)+

By following the similar procedures to Steps 2 and 3 of Example 7 and submitting 3-chloro-5-((4-(difluoromethyl)-6-oxo-1,6-dihydropyrimidin-5-yl)oxy)benzonitrile in place of 2,5-dichloro-3-((6-oxo-4-(trifluoromethyl)-1,6-dihydropyrimidin-5-yl)oxy)benzonitrile, the title compound was obtained.

$^1$H NMR: (DMSO-d6, 400 MHz) δ 12.96 (s, 1H), 8.65 (s, 1H), 7.70 (s, 1H), 7.67 (t, =72.0 Hz, 1H), 7.52-7.47 (m, 3H), 6.88-6.85 (m, 1H), 5.08 (s, 2H).

MS (ESI) m/z 422 (M+H)+

EXAMPLE 163

3-(difluoromethoxy)-5-(6-oxo-1-((6-oxo-1,6-dihydropyridazin-3-yl)methyl)-4-(trifluoromethyl)-1,6-dihydropyrimidin-5-yloxy)benzonitrile

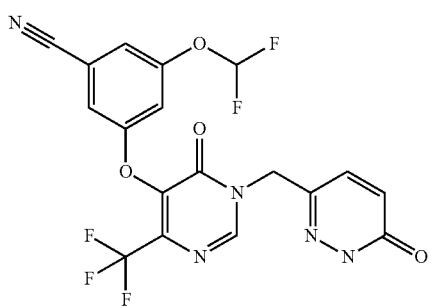 [SMILES: N#Cc1cc(Oc2c(C(F)(F)F)ncn(Cc3ccc(=O)[nH]n3)c2=O)cc(OC(F)F)c1]

Step 1: 3,5-dimethoxybenzonitrile

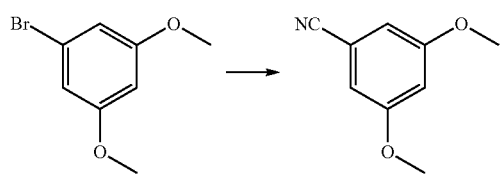

A mixture of 1-bromo-3,5-dimethoxybenzene (5 g, 23 mmol) and CuCN (6 g, 67 mmol) in DMF (60 mL) was heated to reflux (160-170° C.) for 10 h under $N_2$. After cooling to r.t., the mixture was diluted with ethyl acetate, poured into 10% aqueous $NH_4OH$, extracted with ethyl acetate. The combined organic layers were washed with brine, dried over sodium sulfate, filtered and concentrated under reduced pressure. The residue was purified by column (petroleum ether/ethyl acetate (15:1) as eluent) to afford 3,5-dimethoxybenzonitrile (2.3 g).

$^1$H NMR (CDCl3, 400 MHz): δ 6.76 (d, J=2.0 Hz, 2H), 6.65 (t, J=2.0 Hz, 1H), 3.81 (s, 6H).

Step 2: 3,5-dihydroxybenzonitrile

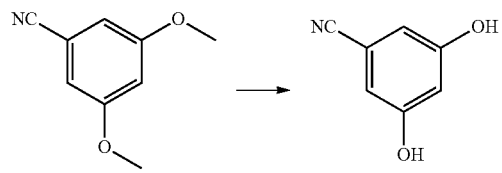

To a solution of 3,5-dimethoxybenzonitrile (2 g, 12.2 mmol) in dichloromethane (20 mL) was added slowly $BBr_3$ (15 mL, 1 M, 15 mmol) at −50° C. under $N_2$. After addition, the mixture was stirred at −50° C. for 2 h and stirred at r.t for 20 hr. The mixture was slowly poured into ice-water with stirring and extracted with dichloromethane. The organic layer was washed with brine, dried over sodium sulfate, filtered and concentrated under reduced pressure. The residue was purified by column (petroleum ether/ethyl acetate (2:1) as eluent) to afford 3,5-dihydroxybenzonitrile (1.43 g).

$^1$H NMR (DMSO-d6, 400 MHz): δ 10.02 (s, 2H), 6.56 (d, J=2.0 Hz, 2H), 6.51 (t, J=2.0 Hz, 1H).

Step 3: 3-hydroxy-5-((1-(4-methoxybenzyl)-6-oxo-4-(trifluoromethyl)-1,6-dihydropyrimidin-5-yl)oxy)benzonitrile

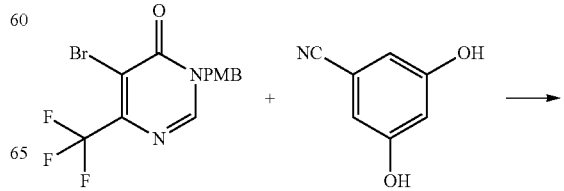

-continued

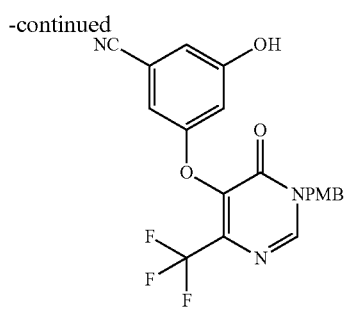

A suspension of 3,5-dihydroxybenzonitrile (1.2 g, 8.9 mmol), 5-bromo-3-(4-methoxybenzyl)-6-(trifluoromethyl) pyrimidin-4(3H)-one (3 g, 8.2 mmol) and potassium carbonate (6 g, 67 mmol) in NMP (40 mL) was stirred at 125° C. for 20 h under N$_2$. After cooling to r.t., the mixture was diluted with water and extracted with ethyl acetate. The organic layer was washed with brine, dried over sodium sulfate, filtered and concentrated under reduced pressure. The residue was purified by column chromatography (petroleum ether/ethyl acetate (3:1) as eluent) to afford 3-hydroxy-5-((1-(4-methoxybenzyl)-6-oxo-4-(trifluoro methyl)-1,6-dihydropyrimidin-5-yl)oxy)benzonitrile (1.9 g).

MS (ESI): m/z 418 (M+H)$^+$

Step 4: 3-(difluoromethoxy)-5-((1-(4-methoxybenzyl)-6-oxo-4-(trifluoromethyl)-1,6-dihydropyrimidin-5-yl)oxy)benzonitrile

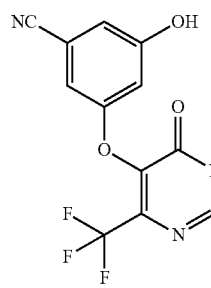 

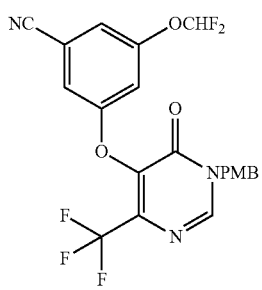

A suspension of 3-hydroxy-5-((1-(4-methoxybenzyl)-6-oxo-4-(trifluoromethyl)-1,6-dihydropyrimidin-5-yl)oxy) benzonitrile (1.8 g, 4.3 mmol), sodium chlorodifluoroacetate (13 g, 85.5 mmol) and potassium carbonate (12.5 g, 90.5 mmol) in DMF (90 mL) was stirred at 85° C. for 16 h under N$_2$. After cooling to r.t., the mixture was poured into ice-water and extracted with ethyl acetate. The organic layer was washed with brine, dried over sodium sulfate, filtered and concentrated under reduced pressure. The residue was purified by column chromatography (petroleum ether/ethyl acetate (3:1) as eluent) to afford 3-(difluoromethoxy)-5-((1-(4-methoxy benzyl)-6-oxo-4-(trifluoromethyl)-1,6-dihydropyrimidin-5-yl)oxy)benzonitrile (1.4 g).

MS (ESI): m/z 468 (M+H)$^+$

Step 5: 3-(difluoromethoxy)-5-((6-oxo-4-(trifluoromethyl)-1,6-dihydropyrimidin-5-yl)oxy)benzonitrile

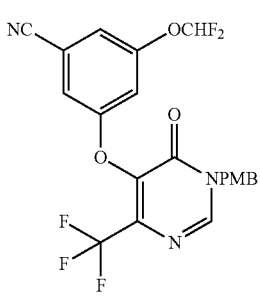

A mixture of 3-(difluoromethoxy)-5-((1-(4-methoxybenzyl)-6-oxo-4-(trifluoromethyl)-1,6-dihydropyrimidin-5-yl) oxy)benzonitrile (1.4 g, 3 mmol) and CAN (8.2 g, 15 mmol) in acetonitrile (15 mL)/water (5 mL) was stirred at r.t. for 5 hr. The mixture was diluted with ethyl acetate and washed with brine, dried over anhydrous sodium sulfate, filtered and concentrated under reduced pressure. The residue was purified by column chromatography on silica gel (petroleum ether/ethyl acetate (2:1) to afford 3-(difluoromethoxy)-5-((6-oxo-4-(trifluoromethyl)-1,6-dihydropyrimidin-5-yl) oxy)benzonitrile (0.67 g).

MS (ESI): m/z 348 (M+H)$^+$

By following similar procedures to Steps 2 and 3 of Example 7 and using 3-chloro-5-((4-(difluoromethyl)-6-oxo-1,6-dihydropyrimidin-5-yl)oxy)benzonitrile in place of 2,5-dichloro-3-((6-oxo-4-(trifluoromethyl)-1,6-dihydropyrimidin-5-yl)oxy)benzonitrile, the title compound was obtained.

$^1$H NMR (DMSO-d6, 400 MHz) δ 12.98 (s, 1H), 8.77 (s, 1H), 7.56 (s, 1H), 7.53-7.48 (m, 2H), 7.37 (s, 1H), 7.36 (t, J=73.2 Hz, 1H), 6.88 (dd, J=9.8 Hz, J=1.4 Hz, 1H), 5.12 (s, 2H).

MS (ESI) m/z 456 (M+H)$^+$

EXAMPLE 164

5-fluoro-2-methyl-3-(6-oxo-1-((6-oxo-1,6-dihydro-pyridazin-3-yl)methyl)-4-(trifluoro methyl)-1,6-di-hydropyrimidin-5-yloxy)benzonitrile

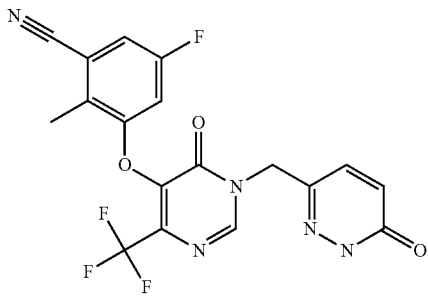 [SMILES: Cc1c(C#N)cc(F)cc1Oc1c(C(F)(F)F)ncn(Cc2ccc(=O)[nH]n2)c1=O]

Step 1: 2-bromo-4-fluoro-6-methoxyaniline

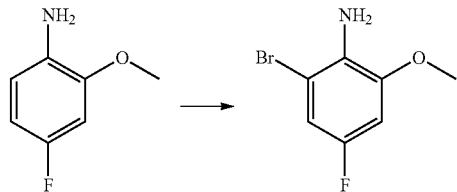

To a solution of 4-fluoro-2-methoxyaniline (14.4 g, 0.1 mol) in 300 mL of dry DMF was added NBS (17.8 g, 0.1 mol) in small portions at 0-5° C. under nitrogen, then the resulting mixture was stirred at room temperature overnight. The mixture was diluted with water, extracted with ethyl acetate. The combined organic layers were washed with water, brine, dried over sodium sulfate, filtered and concentrated under reduced pressure to give 2-bromo-4-fluoro-6-methoxyaniline (28 g crude).

Step 2: 2-amino-5-fluoro-3-methoxybenzonitrile

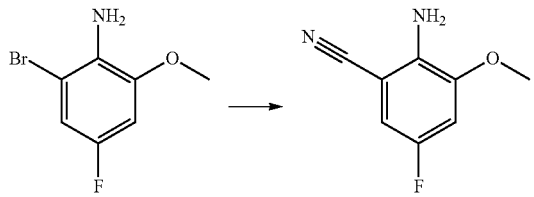

A mixture of 2-bromo-4-fluoro-6-methoxyaniline (28 g crude, 0.1 mol) and CuCN (17.8 g, 0.2 mol) in 200 mL of DMF was stirred at 110° C. for 2 days. After cooling to room temperature, the reaction was poured into water and filtered by cellite. The filtrate was extracted with ethyl acetate. The combined organic layers were washed by water, brine, dried over anhydrous sodium sulfate, filtered and concentrated under reduced pressure to give 2-amino-5-fluoro-3-methoxybenzonitrile (6.9 g) as a yellow solid.

Step 3: 2-bromo-5-fluoro-3-methoxybenzonitrile

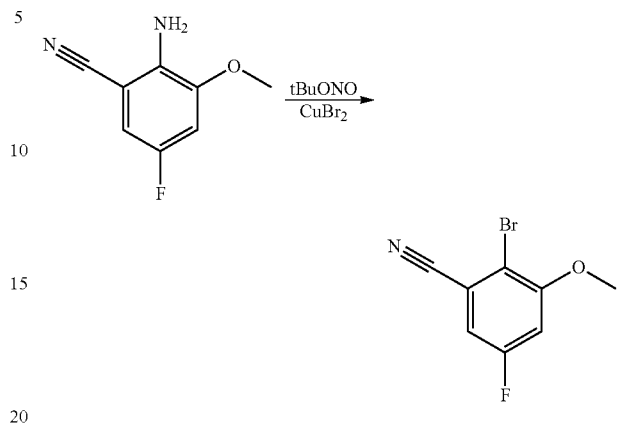

To a suspension of 2-amino-5-fluoro-3-methoxybenzonitrile (6.3 g, 0.038 mol) and CuBr$_2$ (16.9 g, 0.076 mol) in 150 mL of acetonitrile was added tBuONO (7.82 g, 0.076 mol) at room temperature under nitrogen. After the addition, the resulting mixture was stirred at r.t overnight. The mixture was quenched with 200 mL of water and extracted with ethyl acetate. The combined organic layers were washed by brine, dried over sodium sulfate, filtered and concentrated under reduced pressure. The residue was purified by column chromatography on silica gel (petroleum ether:ethyl acetate (20:1) as eluent) to give 2-bromo-5-fluoro-3-methoxybenzonitrile (5.8 g).

$^1$H NMR: (DMSO, 400 MHz) δ 7.00 (dd, J$_1$=7.2 Hz, J$_2$=2.8 Hz, 1H), 6.90 (dd, J$_1$=7.2 Hz, J$_2$=2.8 Hz, 1H), 3.93 (s, 3H).

Step 4: 5-fluoro-3-methoxy-2-methylbenzonitrile

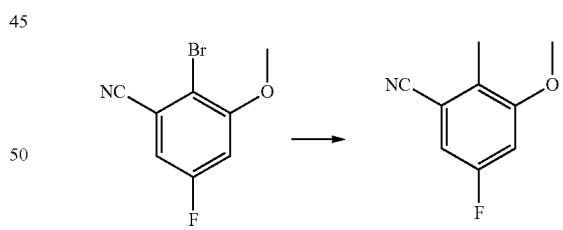

A mixture of 2-bromo-5-fluoro-3-methoxybenzonitrile (2.3 g, 0.01 mmol), MeB(OH)$_2$ (10.9 g, 0.015 mmol), K$_3$PO$_4$ (4.2 g, 0.02 mol), Pd(dppf)Cl$_2$ (230 mg) in 1,4-dioxane/water (3:1) was heated at reflux overnight. After cooling to r.t., the reaction mixture was filtered, and the filtrate was extracted with ethyl acetate. The combined organic layers were dried over sodium sulfate, filtered and concentrated under reduced pressure. The residue was purified by column chromatography on silica gel (petroleum ether:ethyl acetate (20:1) as eluent) to afford 5-fluoro-3-methoxy-2-methylbenzonitrile as a solid (1.23 g).

MS (ESI): m/z 166 (M+H)$^+$

Step 5: 5-fluoro-3-hydroxy-2-methylbenzonitrile

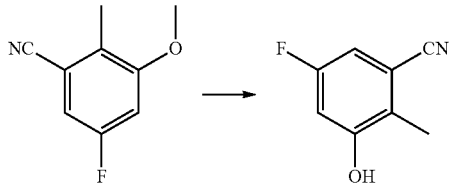

To a solution of 5-fluoro-3-methoxy-2-methylbenzonitrile (330 mg, 2 mmol) in 15 mL of dry dichloromethane was added BBr$_3$ (2 mL, 21 mmol) dropwise at −50° C., then the black solution was warmed to room temperature slowly and stirred for 12 hr. The mixture was cooled to 0° C. and quenched with sat. Na$_2$CO$_3$, extracted with dichloromethane. The combined organic layers were washed with water, brine, dried over sodium sulfate, filtered and concentrated under reduced pressure. The residue was purified by flash chromatography to afford 5-fluoro-3-hydroxy-2-methylbenzonitrile (250 mg) as a white solid.

$^1$H NMR (DMSO-d6, 400 MHz): δ 10.67 (s, 1H), 7.12-6.86 (m, 2H), 2.21 (s, 3H).

By following similar procedures to Steps 2 and 3 of Example 7 and submitting 5-fluoro-3-hydroxy-2-methylbenzonitrile for 2,5-dichloro-3-hydroxybenzonitrile, the title compound was obtained.

$^1$H NMR: (DMSO-d6, 400 MHz) δ 12.99 (s, 1H), 8.76 (s, 1H), 7.56-7.49 (m, 2H), 7.31 (d, J=10.0 Hz, 1H), 6.90 (d, J=10.0 Hz, 1H), 5.12 (s, 2H), 2.39 (s, 3H).

MS (ESI) m/z 422 (M+H)$^+$

EXAMPLE 165

2-fluoro-3-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile

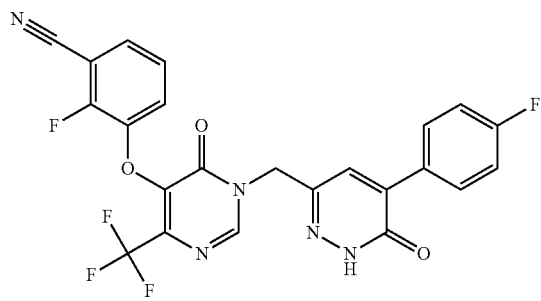 [SMILES: N#Cc1cccc(Oc2c(C(F)(F)F)ncn(Cc3cc(-c4ccc(F)cc4)c(=O)[nH]n3)c2=O)c1F]

Step 1: 4-(4-fluorophenyl)-6-(hydroxymethyl)-2-(4-methoxybenzyl)pyridazin-3(2H)-one

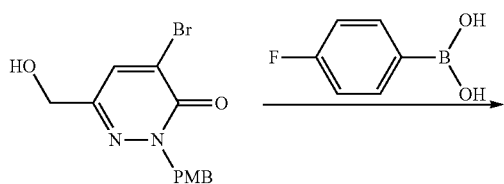

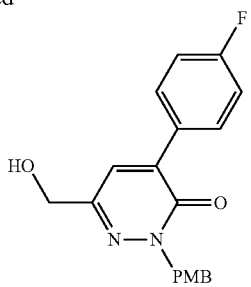

To a solution of compound 4-bromo-6-(hydroxymethyl)-2-(4-methoxybenzyl)pyridazin-3(2H)-one (4 g, 12.3 mmol) in 1, 4-dioxane (100 mL) and water (10 mL) were added (4-fluorophenyl)boronic acid (3.44 g, 24.6 mmol), potassium carbonate (3.4 g, 24.6 mmol) and Pd(dppf)Cl$_2$ (1.8 g, 2.46 mmol). The resulting mixture was stirred at 100° C. for 3 hr. After cooling to r.t., the mixture was diluted with water, extracted with ethyl acetate. The combined organic layers were dried over anhydrous sodium sulfate, filtered and concentrated under reduced pressure. The residue was purified by column chromatography (petroleum ether/ethyl acetate (2:1) as eluent) to give the product 4-(4-fluorophenyl)-6-(hydroxymethyl)-2-(4-methoxybenzyl)pyridazin-3 (2H)-one (3 g).

MS (ESI) m/z 341 (M+H)$^+$

Step 2: 6-(chloromethyl)-4-(4-fluorophenyl)-2-(4-methoxybenzyl)pyridazin-3(2H)-one

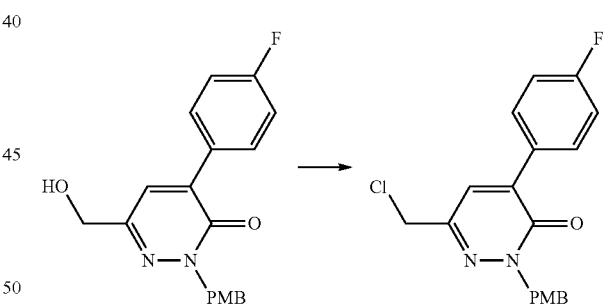

To a solution of compound 4-(4-fluorophenyl)-6-(hydroxymethyl)-2-(4-methoxybenzyl)pyridazin-3(2H)-one (2.5 g, 7.35 mmol) in dichloromethane (40 mL) was added DIPEA (5.70 g, 44.1 mmol) and methansulfonyl chloride (3.37 g, 29.4 mmol). The mixture was stirred at room temperature overnight. The mixture was washed with water, dried over anhydrous sodium sulfate, filtered and concentrated under reduced pressure. The residue was purified by flash chromatography (petroleum ether/ethyl acetate (10:1) as eluent) to give 6-(chloromethyl)-4-(4-fluorophenyl)-2-(4-methoxybenzyl)pyridazin-3(2H)-one (2.5 g).

MS (ESI) m/z 359, 361 (M+H)$^+$

Step 3: 2-fluoro-3-((6-oxo-4-(trifluoromethyl)-1,6-dihydropyrimidin-5-yl)oxy)benzonitrile

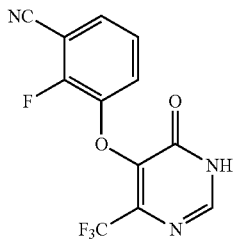 [SMILES: N#Cc1cccc(Oc2c(C(F)(F)F)nc[nH]c2=O)c1F]

The above intermediate was prepared from 2-fluoro-3-cyanophenol and 5-bromo-6-(trifluoromethyl)-4(3H)-pyrimidione in an analogous manner to 3-chloro-5-(6-oxo-4-(trifluoromethyl)-1,6-dihydropyrimidin-5-yloxy)benzonitrile as described in Steps 5-8 of Example 1.

MS (ESI) m/z 420 (M+H)+

Step 4: 2-fluoro-3-((1-((5-(4-fluorophenyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile

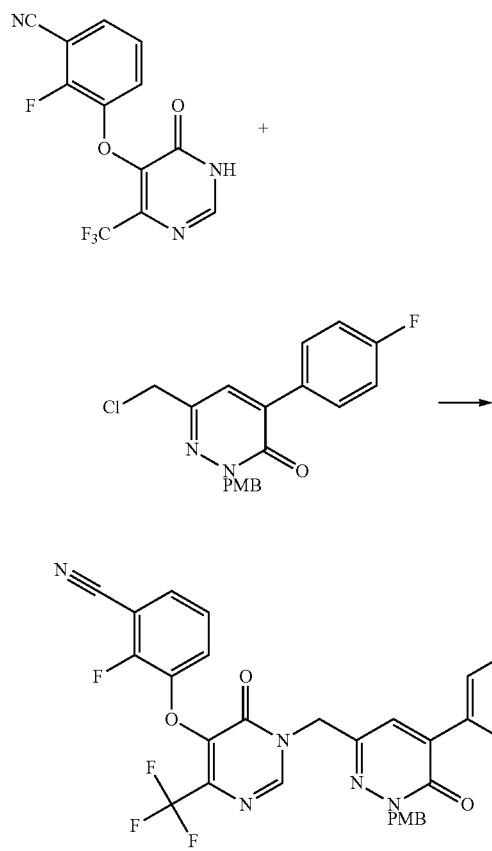

A mixture of 2-fluoro-3-((6-oxo-4-(trifluoromethyl)-1,6-dihydropyrimidin-5-yl)oxy)benzonitrile (100 mg, 0.33 mmol), 6-(chloromethyl)-4-(4-fluorophenyl)-2-(4-methoxybenzyl)pyridazin-3(2H)-one (131 mg, 0.37), LiBr (58 mg, 0.66 mmol) and potassium carbonate (91 mg, 0.66 mmol) in DMF (8 mL) was stirred at 70° C. for 1 hr. After cooling, the mixture was diluted with water (15 mL) and extracted with ethyl acetate (20 mL×2). The combined organic layers were dried over sodium sulfate, filtered and concentrated under reduced pressure to give 2-fluoro-3-((1-((5-(4-fluorophenyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (105 mg).

MS (ESI) m/z 622 (M+H)+

Step 5: 2-fluoro-3-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile

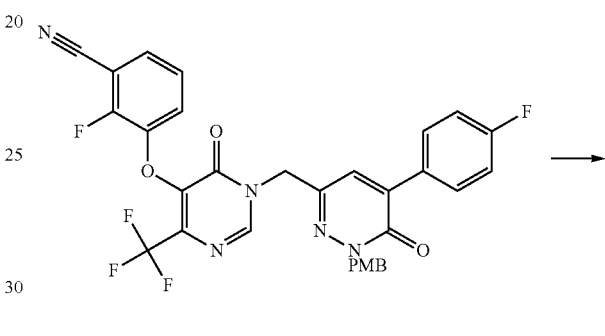

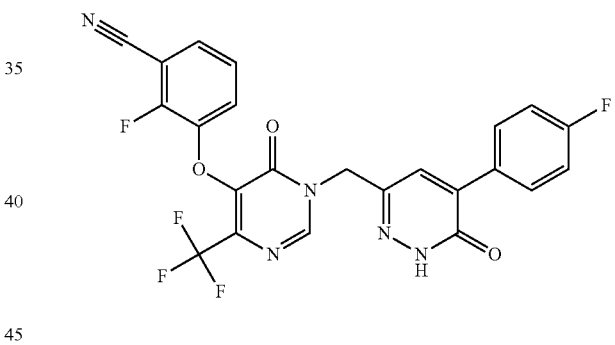

A solution of 2-fluoro-3-((1-((5-(4-fluorophenyl)-1-(4-methoxybenzyl)-6-oxo-1,6-dihydropyridazin-3-yl)methyl)-6-oxo-4-(trifluoromethyl)-1,6-dihydropyrimidin-5-yl)oxy)benzonitrile (105 mg, 0.17 mmol) in 2 mL of TFA and 1 mL of TFAA was stirred at 120° C. for 10 min under microwave irradiation. After cooling, the mixture was concentrated under reduced pressure. The residue was purified by preparative HPLC to afford 2-fluoro-3-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile (49 mg).

$^1$H NMR: (DMSO-d6, 400 MHz) δ 8.75 (s, 1H), 7.87-7.90 (m, 2H), 7.47-7.61 (m, 3H), 7.24-7.31 (m, 3H), 5.15 (s, 2H).

MS (ESI) m/z 502 (M+H)+

By following similar procedures to Steps 4 and 5 of Example 165, and using the appropriate pyrimidinone from Examples 162, 163 and 164) in place of 2-fluoro-3-((6-oxo-4-(trifluoromethyl)-1,6-dihydropyrimidin-5-yl)oxy)benzonitrile, Examples 166-168 in the table below were prepared.

| Example | Structure | IUPAC name | MS (M + H)+/NMR |
|---|---|---|---|
| 166 | 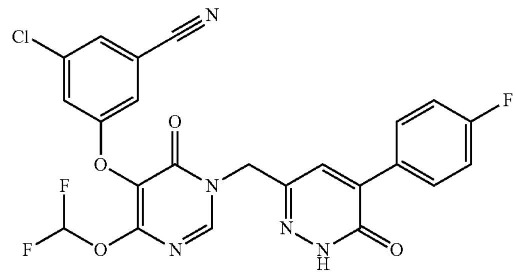 [SMILES: N#Cc1cc(Cl)cc(Oc2c(OC(F)F)ncn(Cc3cc(-c4ccc(F)cc4)c(=O)[nH]n3)c2=O)c1] | 3-chloro-5-((1-((5-(4-fluorophenyl)-6-oxo-1,6-dihydropyridazin-3-yl)methyl)-4-methyl-6-oxo-1,6-dihydropyrimidin-5-yl)oxy)benzonitrile | MS (ESI) m/z 516, 518<br>¹H NMR (DMSO-d6, 400 MHz): δ 13.15 (s, 1H), 8.67 (s, 1H), 7.91-7.84 (m, 3H), 7.71-7.66 (m, 3H), 7.58-7.48 (m, 1H), 7.29-7.25 (m, 2H), 5.13 (s, 2H). |
| 167 | 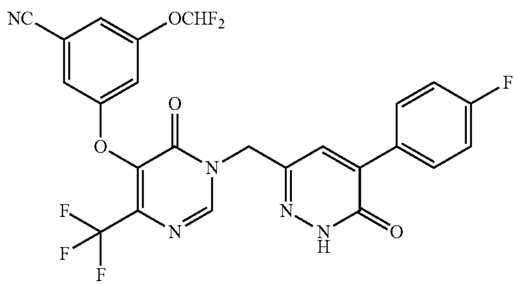 [SMILES: N#Cc1cc(Oc2c(C(F)(F)F)ncn(Cc3cc(-c4ccc(F)cc4)c(=O)[nH]n3)c2=O)cc(OC(F)F)c1] | 3-(difluoromethoxy)-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile | MS (ESI) m/z 550<br>1H NMR (DMSO-d6, 400 MHz): δ 13.18 (s, 1H), 8.79 (s, 1H), 7.95-7.90 (m, 2H), 7.73 (s, 1H), 7.58 (s, 1H), 7.49 (s, 1H), 7.38 (s, 1H), 7.35 (t, J = 73.2 Hz, 1H), 7.33-7.28 (m, 2H), 5.18 (s, 2H). |
| 168 | 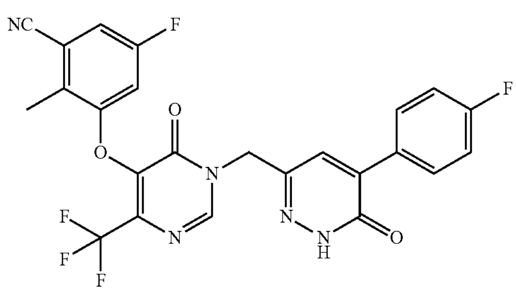 [SMILES: Cc1c(C#N)cc(F)cc1Oc1c(C(F)(F)F)ncn(Cc2cc(-c3ccc(F)cc3)c(=O)[nH]n2)c1=O] | 5-fluoro-3-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)-2-methylbenzonitrile | MS (ESI) m/z 516<br>1H NMR: (DMSO-d6, 400 MHz)<br>δ 13.19 (s, 1H), 8.79 (s, 1H), 7.94~7.90 (m, 2H), 7.73 (s, 1H), 7.56 (dd, J1 = 8.2 Hz, J2 = 2.4 Hz, 1H), 7.36~7.28 (m, 3H), 5.18 (s, 2H), 2.39 (s, 3H). |

EXAMPLE 169

3-chloro-5-((1-((5-(4-fluorophenyl)-6-oxo-1,6-dihydropyridazin-3-yl)methyl)-4-methyl-6-oxo-1,6-dihydropyrimidin-5-yl)oxy)benzonitrile

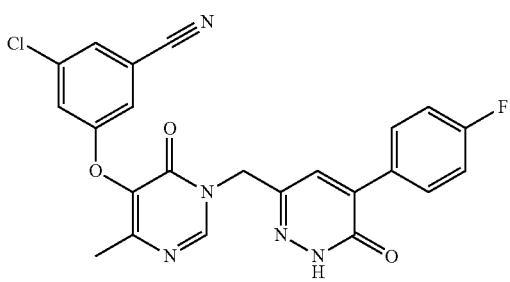 [SMILES: Cc1ncn(Cc2cc(-c3ccc(F)cc3)c(=O)[nH]n2)c(=O)c1Oc1cc(Cl)cc(C#N)c1]

Step 1: ethyl 2-(3-chloro-5-cyanophenoxy)-3-oxobutanoate

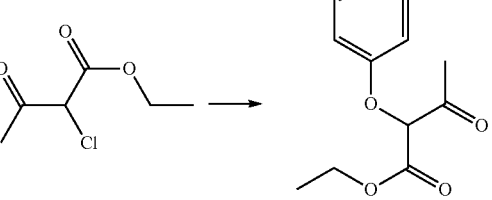

To a solution of 3-chloro-5-hydroxybenzonitrile (15 g, 98 mmol) in DMF (300 mL) was added potassium carbonate (27 g, 195 mmol) and ethyl 2-chloro-3-oxobutanoate (17.7 g, 108 mmol). The mixture was heated at 80° C. overnight. After cooling to r.t, the mixture was diluted with water, extracted with ethyl acetate. The organic layer was dried over anhydrous sodium sulfate, filtered and concentrated under reduced pressure to give ethyl 2-(3-chloro-5-cyanophenoxy)-3-oxobutanoate (20 g) which was used without further purification.

Step 2: 3-chloro-5-((4-methyl-6-oxo-1,6-dihydropyrimidin-5-yl)oxy)benzonitrile

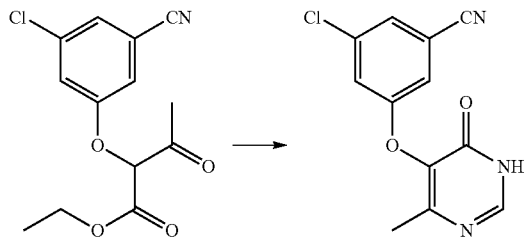 [SMILES: CCOC(=O)C(Oc1cc(Cl)cc(C#N)c1)C(C)=O ; Cc1nc[nH]c(=O)c1Oc1cc(Cl)cc(C#N)c1]

To a solution of formamidine acetate (16.3 g, 156 mmol) in methanol (300 mL) was added MeONa (17 g, 312 mmol). After 5 min, ethyl 2-(3-chloro-5-cyanophenoxy)-3-oxobutanoate (22 g, 78 mmol) was added. The mixture was heated at 90° C. overnight. After cooling to r.t., the mixture was concentrated under reduced pressure. The residue was dissolved in water, acidified to pH=5, extracted with ethyl acetate. The combined organic layers were dried over anhydrous sodium sulfate, filtered and concentrated under reduced pressure. The residue was purified by column chromatography (petroleum ether/ethyl acetate (1:3) as eluent) to give 3-chloro-5-((4-methyl-6-oxo-1,6-dihydropyrimidin-5-yl)oxy)benzonitrile (5.8 g).

MS (ESI) m/z 262, 264 (M+H)+

By following the similar procedure in step 3-4 for Example 165 and using 3-chloro-5-((4-methyl-6-oxo-1,6-dihydropyrimidin-5-yl)oxy)benzonitrile in place of 2-fluoro-3-((6-oxo-4-(trifluoromethyl)-1,6-dihydropyrimidin-5-yl)oxy)benzonitrile, the title compound was obtained.

$^1$H NMR (DMSO-d6, 400 MHz): δ 13.11 (s, 1H), 8.48 (s, 1H), 7.92-7.88 (m, 2H), 7.66-7.69 (m, 2H), 7.48 (s, 1H), 7.41 (s, 1H), 7.27 (t, J=8.8 Hz, 2H), 5.09 (s, 2H), 2.17 (s, 3H)

MS (ESI) m/z 464, 466 (M+H)+

EXAMPLE 170

3-chloro-5-((4-(1,1-difluoroethyl)-1-((5-(4-fluorophenyl)-6-oxo-1,6-dihydropyridazin-3-yl)methyl)-6-oxo-1,6-dihydropyrimidin-5-yl)oxy)benzonitrile

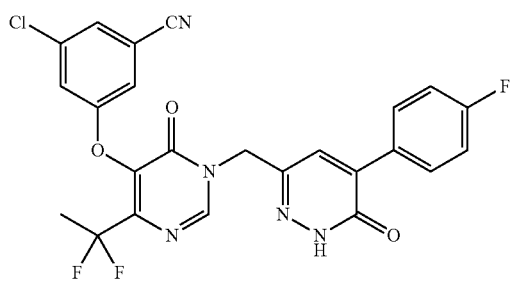 [SMILES: CC(F)(F)c1ncn(Cc2cc(-c3ccc(F)cc3)c(=O)[nH]n2)c(=O)c1Oc1cc(Cl)cc(C#N)c1]

Step 1: 3-chloro-5-((4-(1,1-difluoroethyl)-1-(4-methoxybenzyl)-6-oxo-1,6-dihydropyrimidin-5-yl)oxy)benzonitrile

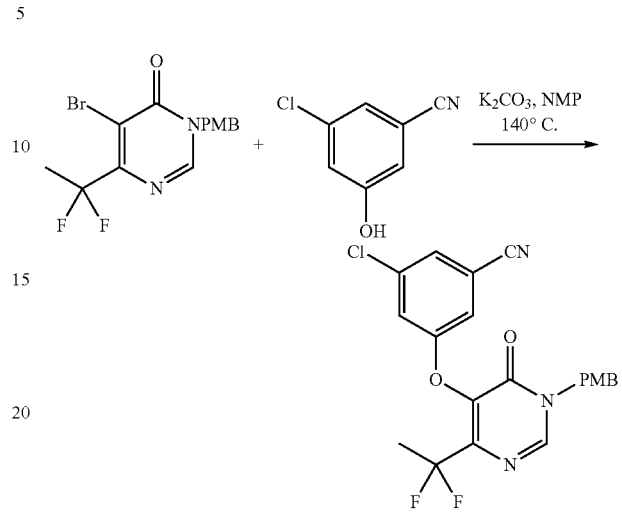

To a solution of compound 5-bromo-6-(1,1-difluoroethyl)-3-(4-methoxybenzyl)pyrimidin-4(3H)-one (3.0 g, 8.56 mmol) in NMP (50 mL) was added potassium carbonate (2.31 g, 16.70 mmol) and 3-chloro-5-hydroxybenzonitrile (3.86 g, 25.07 mmol). The mixture was heated to 140° C. for 6 hr, and then cooled down to 130° C., the mixture was stirred at 130° C. overnight. After cooling, the mixture was diluted with water (200 mL) and extracted with ethyl acetate (100 mL×3). The combined organic layers were washed with brine, dried over sodium sulfate, filtered and concentrated under reduced pressure. The residue was purified by column chromatography on silica gel (petroleum ether:ethyl acetate (20:1 to 8:1) as eluent) to give 3-chloro-5-((4-(1,1-difluoroethyl)-1-(4-methoxybenzyl)-6-oxo-1,6-dihydro pyrimidin-5-yl)oxy)benzonitrile (1.3 g).

MS (ESI) m/z 432, 434 (M+H)+

Using the above intermediate, the title compound was prepared by following similar procedures to Step 5 of Example 163 and Steps 3-4 of Example 165.

$^1$H NMR (CD$_3$OD, 400 MHz): δ 8.54 (s, 1H), 7.86-7.90 (m, 2H), 7.70 (s, 1H), 7.50 (s, 1H), 7.28-7.29 (m, 2H), 7.19 (t, J=8.8 Hz, 2H), 5.24 (s, 2H), 1.96 (t, J=19.2 Hz, 3H).

MS (ESI) m/z 514, 516 (M+H)+

EXAMPLE 171

3-((4-(1,1-difluoroethyl)-1-((5-(4-fluorophenyl)-6-oxo-1,6-dihydropyridazin-3-yl)methyl)-6-oxo-1,6-dihydropyrimidin-5-yl)oxy)-2-fluorobenzonitrile

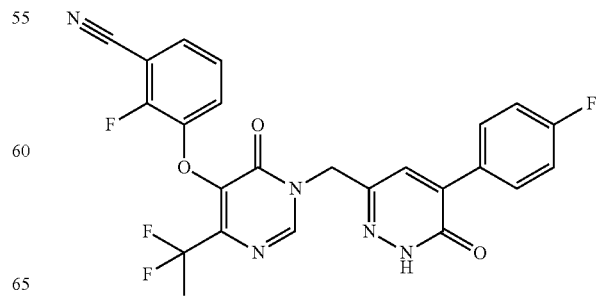

The title compound was prepared in an analogous manner to Example 170, replacing 3-chloro-5-hydroxybenzonitrile with 2-fluoro-3-hydroxybenzonitrile in Step 1.

MS (ESI) m/z 498 (M+H)+

$^1$H NMR (DMSO-d6, 400 MHz) δ 8.68 (s, 1H), 7.90 (m, 2H), 7.71 (s, 1H), 7.57 (s, 1H), 7.29 (m, 4H), 5.14 (s, 2H), 1.93 (t, J=19.6 Hz, 3H).

EXAMPLE 172

3-chloro-5-((1-((6-(difluoromethyl)-3-oxo-2,3-dihydropyridazin-4-yl)methyl)-2-oxo-4-(trifluoromethyl)-1,2-dihydropyridin-3-yl)oxy)benzonitrile

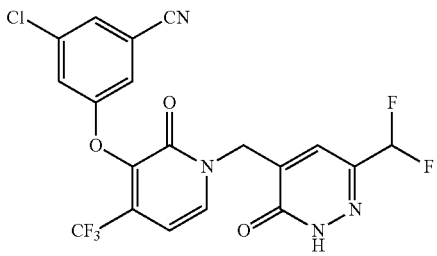 [SMILES: N#Cc1cc(Cl)cc(Oc2c(C(F)(F)F)ccn(Cc3cc(C(F)F)n[nH]c3=O)c2=O)c1]

Step 1: 6-methoxypyridazine-3-carbaldehyde

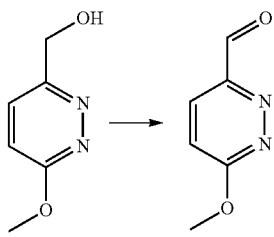

To a stirred solution of (6-methoxypyridazin-3-yl)methanol (13 g, 93 mmol) in 500 mL of anhydrous dichloromethane was added DMP (59 g, 139 mmol). The mixture was stirred for 1 hr at room temperature. The mixture was diluted with dichloromethane, washed with brine, dried over sodium sulfate, filtered and concentrated under reduced pressure. The residue was purified by chromatography on silica gel (petroleum ether:ethyl acetate (15:1 to 10:1) as eluent) to afford 6-methoxypyridazine-3-carbaldehyde (6.0 g).

MS (ESI) m/z 139 (M+H)+

Step 2: 3-(difluoromethyl)-6-methoxypyridazine

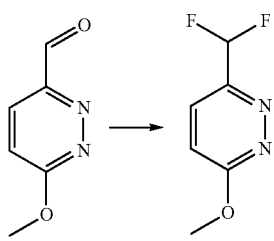

To a stirred solution of 6-methoxypyridazine-3-carbaldehyde (6.0 g, 43.4 mmol) in 100 mL of anhydrous dichloromethane was added DAST (22.7 g, 141.3 mmol). The mixture was stirred for 1 hr at room temperature. The mixture was diluted with dichloromethane, washed with NaHCO$_3$ (0.5 N, 100 mL), water and brine, dried over sodium sulfate, filtered and concentrated under reduced pressure. The crude product was purified by chromatography on silica gel (petroleum ether/ethyl acetate (15:1 to 10:1) as eluent) to afford 3-(difluoromethyl)-6-methoxypyridazine (3.0 g).

MS (ESI) m/z 161 (M+H)+

Step 3: 4-(tert-butoxymethyl)-6-(difluoromethyl)-3-methoxypyridazine

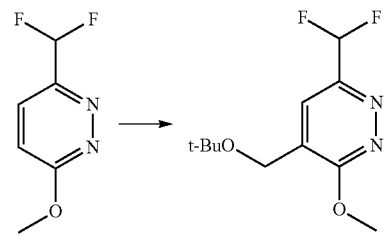 [SMILES: COc1ccc(C(F)F)nn1 ; COc1nnc(C(F)F)cc1COC(C)(C)C]

To a solution of tert-butoxy-acetic acid (0.92 g, 6.88 mmol) in THF/water (20 mol %, 7.76 mL) were added 3-(difluoromethyl)-6-methoxypyridazine (0.7 g, 4.3 mmol) and AgNO$_3$ (74 mg, 0.43 mmol). The mixture was degassed by N$_2$ with stirring at r.t. Then the mixture was heated to 70° C., and then (NH$_4$)$_2$S$_2$O$_8$ (1.7 g, 7.31 mmol) in water (10 mL) was added dropwise. After addition, the mixture was stirred at 70-80° C. for 40 mins. After cooling to r.t., the mixture was extracted with ethyl acetate (10 mL×3). The combined organic layers were washed with brine, dried over sodium sulfate, filtered and concentrated under reduced pressure. The residue was purified by chromatography on silica gel (petroleum ether/ethyl acetate (15:1 to 10:1) as eluent) to afford 4-(tert-butoxymethyl)-6-(difluoromethyl)-3-methoxypyridazine (340 mg)

MS (ESI) m/z 247 (M+H)+

Step 4: (6-(difluoromethyl)-3-methoxypyridazin-4-yl)methanol

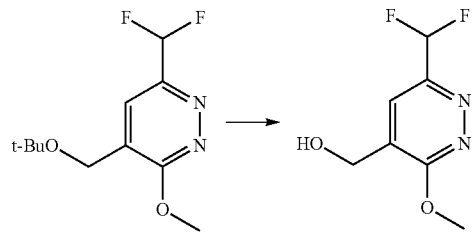 [SMILES: COc1nnc(C(F)F)cc1COC(C)(C)C ; COc1nnc(C(F)F)cc1CO]

To a solution of 4-(tert-butoxymethyl)-6-(difluoromethyl)-3-methoxypyridazine (480 mg, 1.95 mmol) in THF/DCE (1.3 mL/4.5 mL) was stirred at 60° C. for 1 hr. After cooling to r.t, the mixture was concentrated under reduced pressure. The residue was purified by preparative TLC (petroleum ether/ethyl acetate (2:1) as eluent) to give (6-(difluoromethyl)-3-methoxy pyridazin-4-yl)methanol (240 mg)

MS (ESI) m/z 191 (M+H)+

Step 5: 4-(chloromethyl)-6-(difluoromethyl)-3-methoxypyridazine

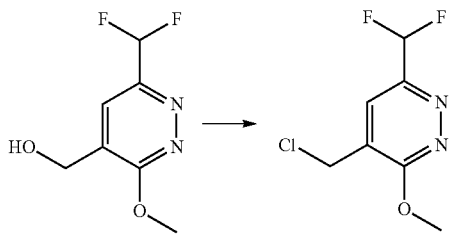

To a solution of compound (6-(difluoromethyl)-3-methoxypyridazin-4-yl)methanol (600 mg, 3.1 mmol) in anhydrous dichloromethane (20 mL) was added dropwise methansulfonyl chloride (1.08 g, 9.4 mmol) and DIPEA (1.22 g, 9.4 mmol) respectively at 0° C. The mixture was stirred at room temperature for 4 hr. Then the mixture was quenched with water and extracted with dichloromethane. The combined organic layers were dried over sodium sulfate, filtered and concentrated under reduced pressure to afford 4-(chloromethyl)-6-(difluoromethyl)-3-methoxypyridazine (710 mg).

MS (ESI) m/z 209, 211 (M+H)$^+$

Step 6: 3-chloro-5-((1-((6-(difluoromethyl)-3-methoxypyridazin-4-yl)methyl)-2-oxo-4-(trifluoromethyl)-1,2-dihydropyridin-3-yl)oxy)benzonitrile

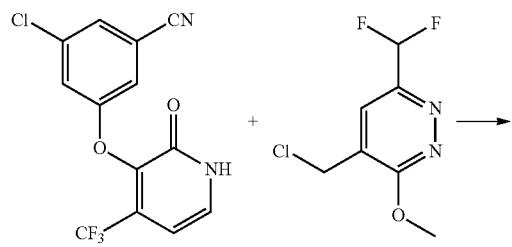

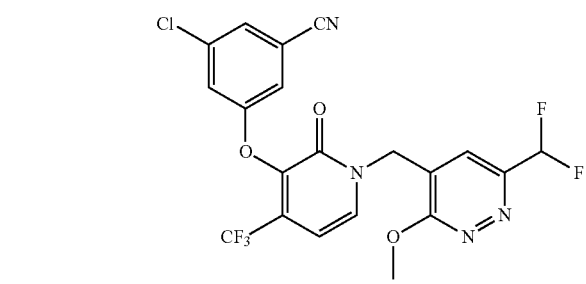

To a solution of 4-(chloromethyl)-6-(difluoromethyl)-3-methoxypyridazine (100 mg, 0.47 mmol) in DMF (15 mL) was added potassium carbonate (132 mg, 0.95 mmol), LiBr (83 mg, 0.95 mmol) and 3-chloro-5-((2-oxo-4-(trifluoromethyl)-1,2-dihydropyridin-3-yl)oxy)benzonitrile (150 mg, 0.47 mmol). The mixture was stirred at room temperature for 20 hr. The mixture was quenched with water and extracted with ethyl acetate. The combined organic layers were dried over sodium sulfate, filtered and concentrated under reduced pressure to afford 3-chloro-5-((1-((6-(difluoromethyl)-3-methoxypyridazin-4-yl)methyl)-2-oxo-4-(trifluoromethyl)-1,2-dihydropyridin-3-yl)oxy)benzonitrile (150 mg).

MS (ESI) m/z 487, 489 (M+H)$^+$

Step 7: 3-chloro-5-((1-((6-(difluoromethyl)-3-oxo-2,3-dihydropyridazin-4-yl)methyl)-2-oxo-4-(trifluoromethyl)-1,2-dihydropyridin-3-yl)oxy)benzonitrile

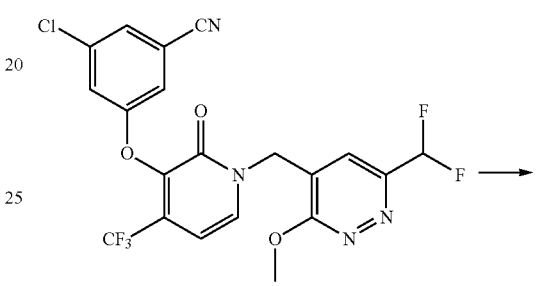

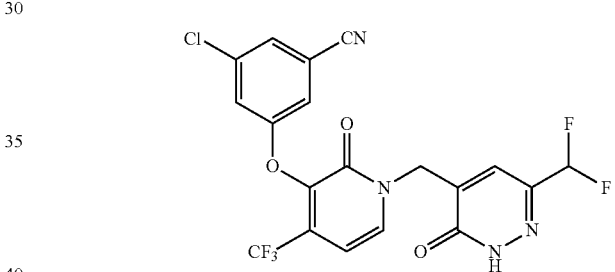

To a mixture of 3-chloro-5-((1-((6-(difluoromethyl)-3-methoxypyridazin-4-yl)methyl)-2-oxo-4-(trifluoromethyl)-1,2-dihydropyridin-3-yl)oxy)benzonitrile (150 mg, 0.31 mmol) and KI (102 mg, 0.62 mmol) in acetonitrile (25 mL) at r.t. was added TMSCl (67 mg, 0.62 mmol) dropwise. After addition, the mixture was stirred at 70° C. for 1.5 hr. After cooling to r.t., the reaction mixture was quenched with methanol and concentrated under reduced pressure. The residue was purified by preparative HPLC to afford the desired product 3-chloro-5-((1-((6-(difluoromethyl)-3-oxo-2,3-dihydropyridazin-4-yl)methyl)-2-oxo-4-(trifluoromethyl)-1,2-dihydropyridin-3-yl)oxy)benzonitrile (101 mg).

$^1$H NMR (DMSO-d6, 400 MHz): δ 13.60 (s, 1H), 7.96 (d, J=7.2 Hz, 1H), 7.69 (s, 1H), 7.60 (s, 1H), 7.55 (s, 1H), 7.39 (s, 1H), 6.77 (t, J=54.0 Hz, 1H), 6.66 (d, J=7.2 Hz, 1H), 4.99 (s, 2H). MS (ESI) m/z 473, 475 (M+H)$^+$

By following similar procedures to Step 6 and 7 of Example 172 and using the appropriate pyrimidinone in place of 3-chloro-5-(2-oxo-4-(trifluoromethyl)-1,2-dihydropyridin-3-yloxy)benzonitrile, Examples 173-177 in the table below were prepared.

| Example | Structure | IUPAC Name | LCMS (M + H)+/1HNMR |
|---|---|---|---|
| 173 | 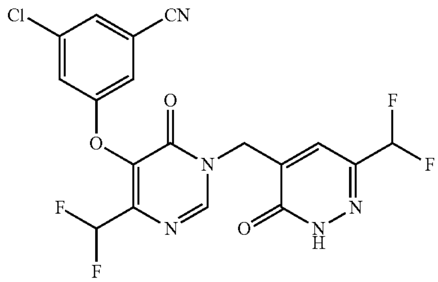 [SMILES: N#Cc1cc(Cl)cc(Oc2c(C(F)F)ncn(Cc3cc(C(F)F)n[nH]c3=O)c2=O)c1] | 3-chloro-5-((4-(difluoromethyl)-1-((6-(difluoromethyl)-3-oxo-2,3-dihydropyridazin-4-yl)methyl)-6-oxo-1,6-dihydropyrimidin-5-yl)oxy)benzonitrile | MS (ESI) m/z 456, 458<br>1HNMR (DMSO-d6, 400 MHz):<br>δ 13.60 (s, 1H), 8.66 (s, 1H), 7.71 (s, 1H), 7.62 (s, 2H), 7.59 (s, 1H), 6.98 (t, J = 52.0 Hz, 1H), 6.77 (t, J = 54.0 Hz, 1H), 4.97 (s, 2H). |
| 174 | 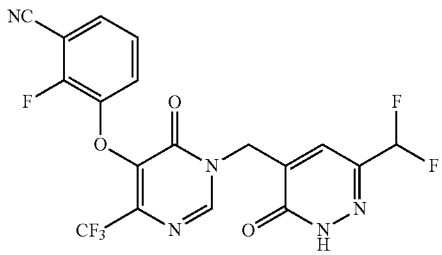 [SMILES: N#Cc1cccc(Oc2c(C(F)(F)F)ncn(Cc3cc(C(F)F)n[nH]c3=O)c2=O)c1F] | 3-((1-((6-(difluoromethyl)-3-oxo-2,3-dihydropyridazin-4-yl)methyl)-6-oxo-4-(trifluoromethyl)-1,6-dihydropyrimidin-5-yl)oxy)-2-fluorobenzonitrile | MS (ESI) m/z 458<br>1HNMR (DMSO-d6, 400 MHz):<br>δ 13.62 (s, 1H), 8.71 (s, 1H), 7.57-7.59 (m, 3H), 7.21 (t, J = 6.8 Hz, 1H), 6.78 (t, J = 52.0 Hz, 1H), 4.98 (s, 2H). |
| 175 | 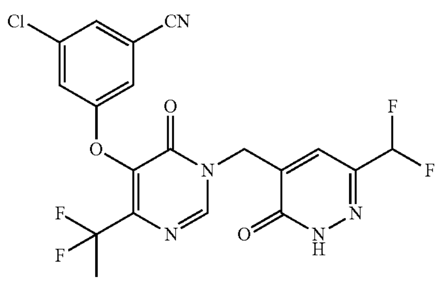 [SMILES: CC(F)(F)c1ncn(Cc2cc(C(F)F)n[nH]c2=O)c(=O)c1Oc1cc(Cl)cc(C#N)c1] | 3-chloro-5-((4-(1,1-difluoroethyl)-1-((6-(difluoromethyl)-3-oxo-2,3-dihydropyridazin-4-yl)methyl)-6-oxo-1,6-dihydropyrimidin-5-yl)oxy)benzonitrile | MS (ESI) m/z 470, 472<br>1HNMR (DMSO-d6, 400 MHz):<br>δ 13.61 (s, 1H), 8.63 (s, 1H), 7.67 (s, 1H), 7.62 (s, 1H), 7.59 (s, 1H), 7.55 (s, 1H), 6.78 (t, J = 54.0 Hz, 1H), 4.97 (s, 2H), 1.90 (t, J = 15.2 Hz, 3H). |
| 176 | 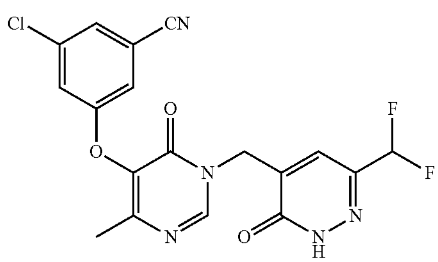 [SMILES: Cc1ncn(Cc2cc(C(F)F)n[nH]c2=O)c(=O)c1Oc1cc(Cl)cc(C#N)c1] | 3-chloro-5-((1-((6-(difluoromethyl)-3-oxo-2,3-dihydropyridazin-4-yl)methyl)-4-methyl-6-oxo-1,6-dihydropyrimidin-5-yl)oxy)benzonitrile | MS (ESI) m/z 420, 422<br>1HNMR (DMSO-d6, 400 MHz):<br>δ 13.60 (s, 1H), 8.46 (s, 1H), 7.65 (s, 1H), 7.50 (s, 1H), 7.47 (s, 1H), 7.45 (s, 1H), 6.78 (t, J = 54.0 Hz, 1H), 4.94 (s, 2H), 2.16 (m, 3H). |
| 177 | 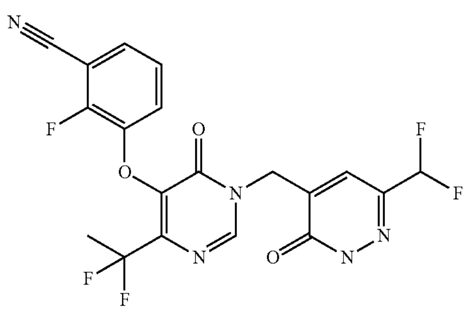 [SMILES: CC(F)(F)c1ncn(Cc2cc(C(F)F)n[nH]c2=O)c(=O)c1Oc1cccc(C#N)c1F] | 3-((4-(1,1-difluoroethyl)-1-((6-(difluoromethyl)-3-oxo-2,3-dihydropyridazin-4-yl)methyl)-6-oxo-1,6-dihydropyrimidin-5-yl)oxy)-2-fluorobenzonitrile | MS (ESI) m/z 454<br>1H NMR (DMSO-d6, 400 MHz):<br>δ 8.68 (s, 1H), 7.58 (m, 2H), 7.46 (d, J = 9.6 Hz, 1H), 7.22 (t, J = 7.6 Hz, 1H), 6.83 (t, J = 13.6 Hz, 1H), 5.01 (s, 2H), 1.95 (t, J = 19.6 Hz, 3H). |

EXAMPLE 178

3-((1-(((6-(1,1-difluoroethyl)-3-oxo-2,3-dihydropyridazin-4-yl)methyl)-6-oxo-4-(trifluoromethyl)-1,6-dihydropyrimidin-5-yl)oxy)-2-fluorobenzonitrile

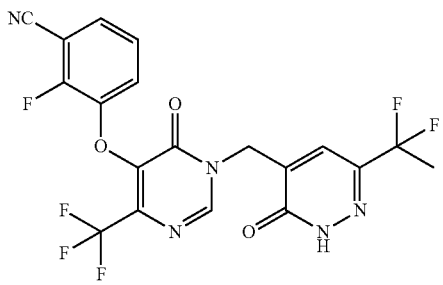 [SMILES: CC(F)(F)c1cc(Cn2cnc(C(F)(F)F)c(Oc3cccc(C#N)c3F)c2=O)c(=O)[nH]n1]

Step 1: 3-(1-ethoxyvinyl)-6-methoxypyridazine

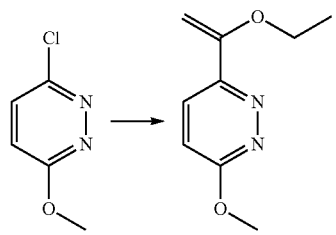

To a mixture of 3-chloro-6-methoxypyridazine (15 g, 103.8 mmol), tributyl(1-ethoxyvinyl)stannane (82.44 g, 228.3 mmol) in toluene (200 mL) was added Pd(PPh$_3$)$_4$ (6 g, 5.19 mmol) under nitrogen atmosphere. The resulting suspension was flushed three times with nitrogen and then stirred at 110° C. for 36 hr. After cooling to room temperature, the mixture was poured into ice-water, filtered through a pad of Celite. The filtrate was extracted with ethyl acetate, and the combined organic layers were washed with brine, dried over sodium sulfate, filtered and concentrated under reduced pressure. The residue was purified by column chromatography on silica gel (petroleum ether/ethyl acetate (15:1 to 10:1) as eluent) to afford the desired product 3-(1-ethoxyvinyl)-6-methoxypyridazine (14 g).
MS (ESI) m/z 181 (M+H)$^+$ Step 2: 1-(6-methoxypyridazin-3-yl)ethanone

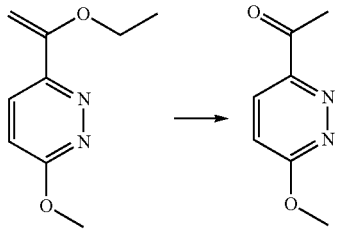

To a solution of 3-(1-ethoxyvinyl)-6-methoxypyridazine (12 g, 66.59 mmol) in 1,4-dioxane (120 mL) was added HCl/1,4-dioxane (24 mL, 4 M) dropwise at 0° C. The mixture was stirred at room temperature for 1 hr. The mixture was quenched with water and extracted with ethyl acetate. The combined organic layers were dried over anhydrous sodium sulfate, filtered and concentrated under reduced pressure. The residue was purified by column chromatography on silica gel (petroleum ether/ethyl acetate (10:1 to 8:1) as eluent) to afford 1-(6-methoxypyridazin-3-yl)ethanone (4.2 g).
MS (ESI) m/z 153 (M+H)$^+$ Step 3: 3-(1,1-difluoroethyl)-6-methoxypyridazine

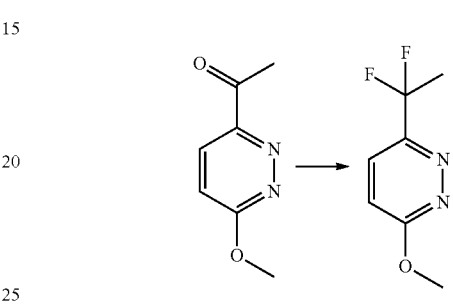

To a solution of 1-(6-methoxypyridazin-3-yl)ethanone (4.2 g, 27.6 mmol) in dichloromethane (45 mL) was added DAST (13.35 mg, 82.81 mmol) dropwise at 0° C. The mixture was stirred at 40° C. for 24 hr. After cooling to r.t., the mixture was quenched with water and extracted with ethyl acetate. The combined organic layers were dried over anhydrous sodium sulfate, filtered and concentrated under reduced pressure. The residue was purified by column chromatography on silica gel (petroleum ether/ethyl acetate (15:1 to 10:1) as eluent) to afford 3-(1,1-difluoroethyl)-6-methoxypyridazine (3.3 g).
MS (ESI) m/z 175 (M+H)$^+$ Step 4: (6-(1,1-difluoroethyl)-3-methoxypyridazin-4-yl)methanol

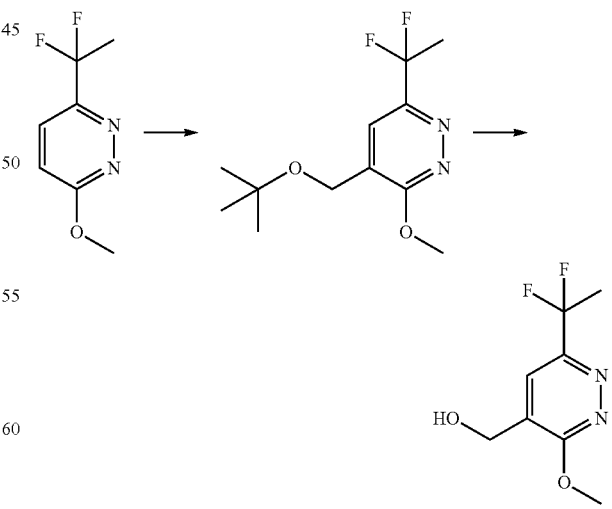

To a mixture of tert-butoxy-acetic acid (4.23 g, 32.04 mmol) in TFA/water (20 mol %, 30 mL) were added 3-(1,1-difluoroethyl)-6-methoxypyridazine (3.1 g, 17.8 mmol) and AgNO₃ (303 mg, 1.78 mmol). The mixture was flushed with nitrogen with stirring at room temperature, then the mixture was heated to 70° C., and (NH₄)₂S₂O₈ (8.12 g, 35.6 mmol) in water (40 mL) was added dropwise. After addition the mixture was stirred at 75° C. for 40 min. After cooling to room temperature, the mixture was extracted with ethyl acetate (20 mL×3), the combined organic layers were washed with brine, dried over sodium sulfate, filtered and concentrated under reduced pressure to afford crude product (4.63 g, crude). A solution of 4-(tert-butoxymethyl)-6-(1,1-difluoroethyl)-3-methoxypyridazine (4.63 g, crude) in TFA/DCE (10 mL/40 mL) was stirred at 60° C. for 1 hr. After cooling to r.t., the mixture was concentrated under reduced pressure. The residue was dissolved in ethyl acetate (20 mL), washed with aqueous potassium carbonate, brine, dried over sodium sulfate, filtered and concentrated under reduced pressure. The residue was purified by column chromatography on silica gel (petroleum ether/ethyl acetate (8:1 to 5:1) as eluent) to afford (6-(1,1-difluoroethyl)-3-methoxy pyridazin-4-yl)methanol (2.1 g).

MS (ESI) m/z 205 (M+H)⁺

Step 5: 4-(chloromethyl)-6-(1,1-difluoroethyl)-3-methoxypyridazine

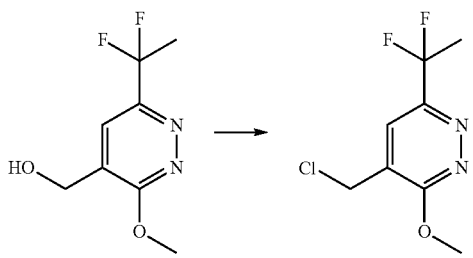

To a solution (6-(1,1-difluoroethyl)-3-methoxypyridazin-4-yl)methanol (180 mg, 0.88 mmol) in dichloromethane (3 mL) was added Et₃N (268 mg, 2.64 mmol) and methanesulfonyl chloride (303 mg, 2.64 mmol) at 0° C. The mixture was stirred at room temperature for 24 hr, quenched with water and extracted with dichloromethane. The combined organic layers were dried over sodium sulfate, filtered and concentrated under reduced pressure. The residue was purified by preparative TLC (petroleum ether/ethyl acetate (2:1) as eluent) to afford 4-(chloromethyl)-6-(1,1-difluoroethyl)-3-methoxypyridazine (120 mg).

MS (ESI) m/z 223 (M+H)⁺

Step 6: 3-((1-(((6-(1,1-difluoroethyl)-3-methoxy-2,3-dihydropyridazin-4-yl)methyl)-6-oxo-4-(trifluoromethyl)-1,6-dihydropyrimidin-5-yl)oxy)-2-fluorobenzonitrile

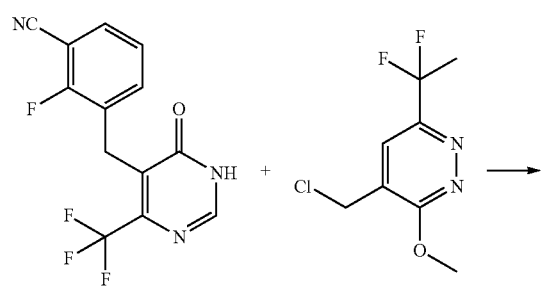

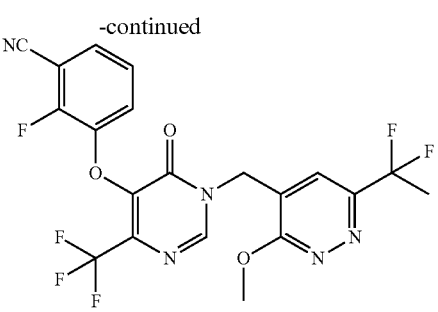

-continued

To a solution of 4-(chloromethyl)-6-(1,1-difluoroethyl)-3-methoxypyridazine (55 mg, 0.25 mmol) in DMF (2 mL) were added potassium carbonate (69 mg, 0.5 mmol), LiBr (43 mg, 0.5 mmol) and 2-fluoro-3-((6-oxo-4-(trifluoromethyl)-1,6-dihydropyrimidin-5-yl)oxy)benzonitrile (82 mg, 0.27 mmol). Then the mixture was stirred at room temperature for 1 hr. The mixture was quenched with water and extracted with ethyl acetate. The combined organic layers were dried over sodium sulfate, filtered, concentrated under reduced pressure. The residue was purified by preparative TLC (petroleum ether/ethyl acetate (2:1) as eluent to afford 3-((1-(((6-(1,1-difluoroethyl)-3-methoxy-2,3-dihydropyridazin-4-yl)methyl)-6-oxo-4-(trifluoromethyl)-1,6-dihydropyrimidin-5-yl)oxy)-2-fluorobenzonitrile (70 mg).

MS (ESI) m/z 486 (M+H)⁺

Step 7: 3-((1-(((6-(1,1-difluoroethyl)-3-oxo-2,3-dihydropyridazin-4-yl)methyl)-6-oxo-4-(trifluoromethyl)-1,6-dihydropyrimidin-5-yl)oxy)-2-fluorobenzonitrile

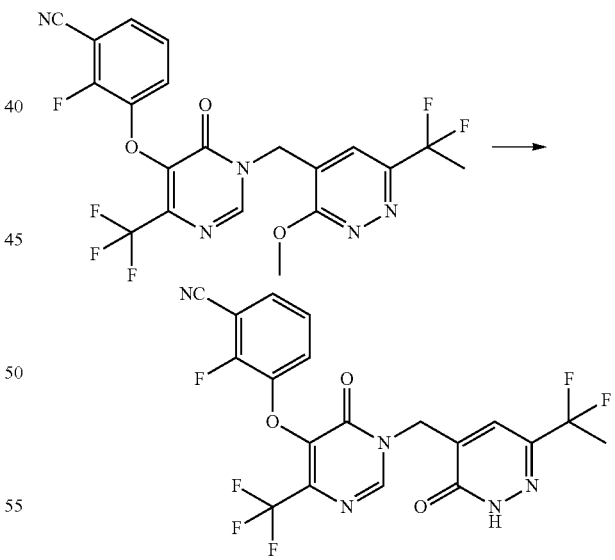

To a mixture of compound 3-((1-(((6-(1,1-difluoroethyl)-3-methoxy-2,3-dihydro pyridazin-4-yl)methyl)-6-oxo-4-(trifluoromethyl)-1,6-dihydropyrimidin-5-yl)oxy)-2-fluorobenzonitrile (70 mg, 0.144 mmol) and KI (48 mg, 0.288 mmol) in 2 mL of acetonitrile was added TMSCl (32 mg, 0.288 mmol) at room temperature. The resulting mixture was stirred for 1 hr at 70° C. After cooling to r.t., the mixture was diluted with ethyl acetate and washed with aq. Na₂S₂O₃ and brine, dried over anhydrous sodium sulfate and concentrated under reduced pressure. The residue was purified by preparative HPLC to afford 3-((1-((6-(1,1-difluoroethyl)-3-oxo-2,3-dihydropyridazin-4-yl)methyl)-6-oxo-4-(trifluoromethyl)-1,6-dihydropyrimidin-5-yl)oxy)-2-fluorobenzonitrile (40 mg).

$^1$H NMR (DMSO-d6, 400 MHz) δ 13.53 (s, 1H), 8.72 (s, 1H), 7.57-7.62 (m, 3H), 7.20 (t, J=8.0 Hz, 1H), 4.98 (s, 2H), 1.89 (t, J=19.2 Hz, 3H).

MS (ESI) m/z 472 (M+H)$^+$

By following similar procedures to Step 6 and 7 of Example 178 and using the appropriate pyrimidinone in place of 2-fluoro-3-((6-oxo-4-(trifluoromethyl)-1,6-dihydropyrimidin-5-yl)oxy)benzonitrile, Examples 179-182 in the table below were prepared.

EXAMPLE 183

Determination of PK Parameters

Male beagle dogs (weight 9-13 kg) were fasted overnight and housed individually. Water was provided ad lib throughout the study. Food was allowed approximately 4 hr post dose. Test compounds were dissolved in 50% DMSO in PEG400 with a final dosing volume of 0.1 mL/kg. The formulations were given intravenous as a bolus injection into the cephalic vein. The vein used for the dosing will not be used for the blood sample collection for the first 4 hr post-dose). Blood samples were drawn from the peripheral vessel from restrained, non-sedated animals at 0.03, 0.13, 0.25, 0.5, 1, 2, 4, 6, 8, 24, 48 and 72 hr. EDTA was used as

| Example | Structure | IUPAC Name | LCMS (M + H)$^+$/$^1$HNMR |
|---|---|---|---|
| 179 | (structure) | 3-chloro-5-((1-((6-(1,1-difluoroethyl)-3-oxo-2,3-dihydropyridazin-4-yl)methyl)-4-(difluoromethyl)-6-oxo-1,6-dihydropyrimidin-5-yl)oxy)benzonitrile | MS (ESI) m/z 470, 472 $^1$HNMR (DMSO-d6, 400 MHz): δ 13.51 (s, 1H), 8.66 (s, 1H), 7.71 (s, 1H), 7.63 (s, 1H), 7.62 (s, 1H), 7.59 (s, 1H), 6.98 (t, J = 52 Hz, 1H), 4.97 (s, 2H), 1.89 (t, J = 19.2 Hz, 3H). |
| 180 | (structure) | 3-chloro-5-((4-(1,1-difluoroethyl)-1-((6-(1,1-difluoroethyl)-3-oxo-2,3-dihydropyridazin-4-yl)methyl)-6-oxo-1,6-dihydropyrimidin-5-yl)oxy)benzonitrile | MS (ESI) m/z 484, 486 $^1$HNMR (DMSO-d6, 400 MHz): δ 13.52 (s, 1H), 8.64 (s, 1H), 7.67 (s, 1H), 7.63 (s, 1H), 7.58 (s, 1H), 7.55 (s, 1H), 4.97 (s, 2H), 1.84-1.84 (m, 6H). |
| 181 | (structure) | 3-chloro-5-((1-((6-(1,1-difluoroethyl)-3-oxo-2,3-dihydropyridazin-4-yl)methyl)-4-methyl-6-oxo-1,6-dihydropyrimidin-5-yl)oxy)benzonitrile | MS (ESI) m/z 434, 436 $^1$HNMR (DMSO-d6, 400 MHz): δ 13.52 (s, 1H), 8.48 (s, 1H), 7.66 (s, 1H), 7.46-7.50 (m, 3H), 4.95 (s, 2H), 2.17 (s, 3H), 1.91 (t, J = 19.2 Hz, 3H) |
| 182 | (structure) | 3-((4-(1,1-difluoroethyl)-1-((6-(1,1-difluoroethyl)-3-oxo-2,3-dihydropyridazin-4-yl)methyl)-6-oxo-1,6-dihydropyrimidin-5-yl)oxy)-2-fluorobenzonitrile | MS (ESI) m/z 468 $^1$H NMR (DMSO-d6, 400 MHz): δ 8.68 (s, 1H), 7.58 (m, 2H), 7.46 (t, J = 8.4 Hz, 1H), 7.21 (t, J = 8.4 Hz, 1H), 5.01 (s, 2H), 1.93-1.97 (m, 6H). | anticoagulant and approximately 0.5 mL aliquots of blood samples were collected at each time point. Plasma samples were obtained by centrifugation at 4° C. and 3000 g for 10 min.

Test compound concentration in dog plasma was determined using a LC/MS/MS method. Typically the LC/MS/MS system consisted of an ACQUITY UPLC system with autosampler system refrigerated at 4° C. during analysis, and an API 4000 mass spectrometer. Chromatographic separation of the analytes was typically achieved on a Phenomenex Kinetex C18, 2.6 µm, 50×2.1 mm column at room temperature with an injection volume of 10 µL. The mobile phase consisting of a solvent A (0.1% formic acid in water/acetonitrile (95/5)) and solvent B (0.1% formic acid in acetonitrile/water (95/5)) was delivered at a flow rate of 600 µL/min. The initial solvent composition (15% solvent B) was increased to 85% over 1.2 min and then raised further to 95% at 1.4 min. Afterwards, the fraction of solvent B was decreased to 15% at 1.41 min and then the column was re-equilibrated, using the initial conditions for 0.09 min prior to the next injection (total run time: 1.50 min). Mass spectrometric detection of the analytes is accomplished using either an ESI or APCI interface operated in the positive or negative ionization mode. Analyte response is measured by multiple reaction monitoring (MRM) of transitions unique to each compound Pharmacokinetic parameters of the test compound were obtained by a noncompartmental analysis using Watson© (Version 7.3, Thermo Electron Corporation). The area under the plasma concentration-time curve (AUC) was calculated by the linear trapezoidal method; clearance (CL) was calculated as $CL=Dose/AUC_{0-inf}$; volume of distribution at steady state (Vss) was calculated as $Vss=CL \times MRT_{0-inf}$; the terminal half-life ($t_{1/2}$) was calculated as 0.693/k, and k was the slope of the terminal regression line, where $AUC_{0-inf}$ is the area under the curve from time zero to infinity and $AUC_{0-t}$ is the area under the curve from time zero to last sampling point.

The terminal half lives of certain compounds of the invention are given in the table below.

| Example # | Dog $t_{1/2}$ (hr) |
|---|---|
| Example 6 | 72 |
| Example 7 | 28 |
| Example 68 | 25 |
| Example 77 | 79 |
| Example 104 | 24 |
| Example 110 | 20 |
| Example 117 | 30 |
| Example 128 | 81 |
| Example 129 | 126 |
| Example 130 | 24 |

The favorable pharmacokinetic profile of certain compounds of the invention is a surprising result and render these compounds suitable for less frequent dosing. Thus, these compounds of the invention can be administered as a single dose, once-daily or less frequently.

EXAMPLE 184

Determination of HIV-1 Reverse Transcriptase Inhibitory Activity

The heterodimeric nucleic acid substrate used in the HIV-1 RT polymerase reactions was generated by annealing the DNA primer, biotinylated pD500 (Sigma Aldrich, USA, 5'-biotin-ttg aaa tga ctg cgg tac ggc-3'), SEQ ID NO. 1 to the nucleotide RNA template t500 (derived from hepatitis C virus [HCV] sequence, IBA, Germany, 5'-GAG GUU CAG GUG GUU UCC ACC GCA ACA CAA UCC UUC CUG GCG ACC UGC GUC AAC GGC GUG UGU UGG ACC GUU UAC CAU GGU GCU GGC UCA AAG ACC UUA GCC GGC CCA AAG GGG CCA AUC ACC CAG AUG UAC ACU AAU GUG GAC CAG GAC CUC GUC GGC UGG CAG GCG CCC CCC GGG GCG CGU UCC UUG ACA CCA UGC ACC UGU GGC AGC UCA GAC CUU UAC UUG GUC ACG AGA CAU GCU GAC GUC AUU CCG GUG CGC CGG CGG GGC GAC AGU AGG GGG AGC CUG CUC UCC CCC AGG CCU GUC UCC UAC UUG AAG GGC UCU UCG GGU GGU CCA CUG CUC UGC CCU UCG GGG CAC GCU GUG GGC AUC UUC CGG GCU GCC GUA UGC ACC CGG GGG GUU GCG AAG GCG GUG GAC UUU GUG CCC GUA GAG UCC AUG GAA ACU ACU AUG CGG UCU CCG GUC UUC ACG GAC AAC UCA UCC CCC GCC GUA CCG CAG UCA UUU CAA-3'), SEQ ID NO 2). The HIV-1 RT wild-type enzyme (final concentration of 83 pM) was combined with an inhibitor or dimethyl sulfoxide (DMSO, 10% in the final reaction mixture) in assay buffer (62.5 mM Tris-HCl [pH 7.8], 1.25 mM dithiothreitol, 7.5 mM $MgCl_2$, 100 mM KCl, 0.03% CHAPS, and 125 µM EGTA). The mixture was then preincubated on an orbital shaker for 30 min at room temperature in microtiter plates (Costar 3365, Corning, USA). A polymerization reaction was initiated by the addition of RNA template/pD500 DNA primer hybrid (16.6 nM final of RNA/DNA hybrid) and dNTPs (2 µM dATP, dGTP, dCTP and 66.6 nM Ru-dUTP (Meso Scale Discovery, USA)). Plate was sealed and incubated for 5-10 min at room temperature on an orbital shaker. Plate was then incubated for 90 min at 37° C. and reactions quenched with 60 µl quenching buffer (50 mM EDTA, 0.7% BSA, 0.7% Tween-20, 0.017% sodium azide in PBS). The resulting solution was incubated at room temperature for an additional 5 min and then 50 µL was transferred to pre-blocked Avidin plates (L15AA, Meso Scale Discovery). Each well of Avidin plate was blocked for 1 h at room temperature with 100 µL 5% BSA in PBS. Blocking solution was removed by tapping vigorously on filter paper to remove all excess liquid. Reaction on pre-blocked avidin plate proceeded for 60 min at room temperature and then contents removed by tapping vigorously on filter paper to remove all excess liquid. After washing plate 3 times with 150 µL 1×PBS and blotting dry between cycles, 150 µL 1× Read Buffer T (4× Read Buffer T, Meso Scale Discovery) was added and incubated for 5 min at room temperature before counting on a Sector Imager 56000 (Meso Scale Discovery). Titration curves and $IC_{50}$ values were calculated using a four parameter logisitc fit according to standard procedures. Briefly, % Inhibition=100×((sample raw value)−(mean value of the low control or 0% inhibition))/((mean value of wells representing 100% inhbition)−(mean value of 0% inhbition)). In this assay, low control wells contain DMSO (0% inhbition) and 100% inhibition wells contain 1 µM efavirenz.

The results of compounds of the invention tested in the above assay are shown in the following table.

| Example # | $IC_{50}$ (nM) |
|---|---|
| Example 1 | 191 |
| Example 2 | 118 |
| Example 3 | 33 |
| Example 4 | 124 |

| Example # | IC$_{50}$ (nM) |
|---|---|
| Example 5 | 6 |
| Example 6 | 8 |
| Example 7 | 8 |
| Example 8 | 9 |
| Example 9 | 109 |
| Example 10 | 7 |
| Example 11 | 124 |
| Example 12 | 32 |
| Example 13 | 29 |
| Example 14 | 109 |
| Example 15 | 13 |
| Example 16 | 12 |
| Example 17 | 179 |
| Example 18 | 5 |
| Example 19 | 31 |
| Example 20 | 24 |
| Example 21 | 29 |
| Example 22 | 3 |
| Example 23 | 38 |
| Example 24 | 24 |
| Example 25 | 9 |
| Example 26 | 5 |
| Example 27 | 14 |
| Example 28 | 5 |
| Example 29 | 3 |
| Example 30 | 4 |
| Example 31 | 5 |
| Example 32 | 13 |
| Example 33 | 7 |
| Example 34 | 7 |
| Example 35 | 8 |
| Example 36 | 4 |
| Example 37 | 5 |
| Example 38 | 110 |
| Example 39 | 10 |
| Example 40 | 70 |
| Example 41 | 59 |
| Example 42 | 7 |
| Example 43 | 9 |
| Example 44 | 4 |
| Example 45 | 6 |
| Example 46 | 5 |
| Example 47 | 11 |
| Example 48 | 9 |
| Example 49 | 15 |
| Example 50 | 165 |
| Example 51 | 358 |
| Example 52 | 4 |
| Example 53 | 70 |
| Example 54 | 8 |
| Example 55 | 11 |
| Example 56 | 76 |
| Example 57 | 11 |
| Example 58 | 4 |
| Example 59 | 125 |
| Example 60 | 7 |
| Example 61 | 11 |
| Example 62 | 10 |
| Example 63 | 10 |
| Example 64 | 3 |
| Example 65 | 5 |
| Example 66 | 7 |
| Example 67 | 12 |
| Example 68 | 7 |
| Example 69 | 10 |
| Example 70 | 15 |
| Example 71 | 5 |
| Example 72 | 7 |
| Example 73 | 11 |
| Example 74 | 17 |
| Example 75 | 20 |
| Example 76 | 99 |
| Example 77 | 4 |
| Example 78 | 6 |
| Example 79 | 6 |
| Example 80 | 14 |
| Example 81 | 9 |
| Example 82 | 7 |
| Example 83 | 14 |
| Example 84 | 27 |
| Example 85 | 14 |
| Example 86 | 6 |
| Example 87 | 18 |
| Example 88 | 17 |
| Example 89 | 18 |
| Example 90 | 6 |
| Example 91 | 6 |
| Example 92 | 6 |
| Example 93 | 11 |
| Example 94 | 48 |
| Example 95 | 8 |
| Example 96 | 336 |
| Example 97 | 247 |
| Example 98 | 9 |
| Example 99 | 7 |
| Example 100 | 23 |
| Example 101 | 153 |
| Example 102 | 20 |
| Example 103 | 74 |
| Example 104 | 15 |
| Example 105 | 19 |
| Example 106 | 12 |
| Example 107 | 223 |
| Example 108 | 316 |
| Example 109 | 7 |
| Example 110 | 3 |
| Example 111 | 10 |
| Example 112 | 5 |
| Example 113 | 6 |
| Example 114 | 7 |
| Example 115 | 7 |
| Example 116 | 21 |
| Example 117 | 6 |
| Example 118 | 7 |
| Example 119 | 12 |
| Example 120 | 3 |
| Example 121 | 5 |
| Example 122 | 6 |
| Example 123 | 6 |
| Example 124 | 6 |
| Example 125 | 8 |
| Example 126 | 4 |
| Example 127 | 434 |
| Example 128 | 4 |

| Example # | IC$_{50}$ (nM) |
|---|---|
| Example 129 | 6 |
| Example 130 | 12 |
| Example 131 | 435 |
| Example 132 | 12 |
| Example 133 | 8 |
| Example 134 | 17 |
| Example 135 | 8 |
| Example 136 | 6 |
| Example 137 | 9 |
| Example 138 | 11 |
| Example 139 | 45 |
| Example 140 | 36 |
| Example 141 | 13 |
| Example 142 | 35 |
| Example 143 | 7 |
| Example 144 | 9 |
| Example 145 | 9 |
| Example 146 | 19 |
| Example 147 | 17 |
| Example 148 | 9 |
| Example 149 | 14 |
| Example 150 | 9 |
| Example 151 | 28 |
| Example 152 | 32 |
| Example 153 | 33 |
| Example 154 | 42 |
| Example 155 | 94 |
| Example 156 | 24 |
| Example 157 | 32 |
| Example 158 | 11 |
| Example 159 | 17 |
| Example 160 | 26 |
| Example 161 | 24 |
| Example 162 | 79 |
| Example 163 | 22 |
| Example 164 | 7 |
| Example 165 | 3 |
| Example 166 | 3 |
| Example 167 | 6 |
| Example 168 | 5 |
| Example 169 | 4 |
| Example 170 | 5 |
| Example 171 | 3 |
| Example 172 | 5 |
| Example 173 | 6 |
| Example 174 | 5 |
| Example 175 | 3 |
| Example 176 | 6 |
| Example 177 | 17 |
| Example 178 | 9 |
| Example 179 | 8 |
| Example 180 | 5 |
| Example 181 | 12 |
| Example 182 | 9 |

The examples described herein serve only to illustrate the invention and its practice. The examples are not to be construed as limitations on the scope or spirit of the invention. While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entireties into the disclosure.

What is claimed is:

1. A compound of Formula Ib:

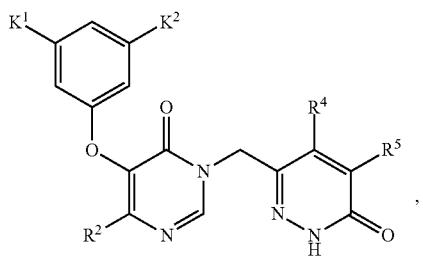

or a pharmaceutically acceptable salt thereof, wherein:

$K^1$ and $K^2$ are each independently F, Br, Cl, OCHF$_2$, CF$_3$ or CN;

$R^2$ is selected from the group consisting of:
(1) H,
(2) $C_{1-6}$ alkyl,
(3) $C_{1-6}$ haloalkyl,
(4) $C_{1-6}$ alkyl substituted with from 1 to 3 substituents each of which is independently OH, O—$C_{1-6}$ alkyl, O—$C_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, S(O)$_2$R$^A$, S(O)$_2$N(R$^A$)R$^B$, N(R$^A$)C(O)R$^B$, N(R$^A$)CO$_2$R$^B$, N(R$^A$)S(O)$_2$R$^B$, N(R$^A$)S(O)$_2$N(R$^A$)R$^B$, OC(O)N(R$^A$)R$^B$, N(R$^A$)C(O)N(R$^A$)R$^B$, or N(R$^A$)C(O)C(O)N(R$^A$)R$^B$,
(5) O—$C_{1-6}$ alkyl in which the alkyl is optionally substituted with 1 to 3 substituents independently selected from OH, O—$C_{1-6}$ alkyl, O—$C_{1-6}$ haloalkyl, CN, N(R$^A$)R$^B$, C(O)N(R$^A$)R$^B$, C(O)R$^A$, CO$_2$R$^A$, SR$^A$, S(O)R$^A$, S(O)$_2$R$^A$, or S(O)$_2$N(R$^A$)R$^B$,
(6) O—$C_{1-6}$ haloalkyl,
(7) halogen,
(8) CN,
(9) NO$_2$,
(10) N(R$^A$)R$^B$,
(11) C(O)N(R$^A$)R$^B$,
(12) C(O)R$^A$,
(13) C(O)—$C_{1-6}$ haloalkyl,
(14) C(O)OR$^A$,
(15) OC(O)R$^A$,
(16) OC(O)N(R$^A$)R$^B$,
(17) SR$^A$,
(18) S(O)R$^A$,
(19) S(O)$_2$R$^A$,
(20) S(O)$_2$N(R$^A$)R$^B$,
(21) N(R$^A$)S(O)$_2$R$^B$,
(22) N(R$^A$)S(O)$_2$N(R$^A$)R$^B$,
(23) N(R$^A$)C(O)R$^B$,
(24) N(R$^A$)C(O)N(R$^A$)R$^B$,
(25) N(R$^A$)C(O)—C(O)N(R$^A$)R$^B$,
(26) N(R$^A$)CO$_2$R$^B$,
(27) N(R$^C$)R$^D$,
(28) C(O)N(R$^C$)R$^D$,
(29) OC(O)N(R$^C$)R$^D$,
(30) S(O)$_2$N(R$^C$)R$^D$,
(31) N(R$^A$)S(O)$_2$N(R$^C$)R$^D$,
(32) N(R$^A$)C(O)N(R$^C$)R$^D$,
(33) N(R$^A$)C(O)—C(O)N(R$^C$)R$^D$,
(34) CycA,
(35) —O-CycA,
(36) ArylA, or
(37) HetA;

$R^4$ and $R^5$ are each independently selected from:
(1) H,
(2) $C_{1-6}$ alkyl, $C_{2-6}$ alkenyl or $C_{2-6}$ alkynyl, each optionally substituted with one or more substituents up to the maximum number allowed by valence selected from OH, O—$C_{1-6}$ alkyl, O—$C_{1-6}$ haloalkyl, CN, NO$_2$, N(R$^A$)R$^B$, C(O)N(R$^A$)R$^B$, C(O)R$^A$, CO$_2$R$^A$, SR$^A$, S(O)R$^A$, S(O)$_2$R$^A$, S(O)$_2$N(R$^A$)R$^B$, N(R$^A$)C(O)R$^B$, N(R$^A$)CO$_2$R$^B$, N(R$^A$)S(O)$_2$R$^B$, N(R$^A$)S(O)$_2$N ($R^A$)$R^B$, OC(O)N($R^A$)$R^B$, N($R^A$)C(O)N($R^A$)$R^B$, N($R^A$)C(O)C(O)N($R^A$)$R^B$, CycB, ArylB and HetB, (3) $C_{1-6}$ haloalkyl optionally additionally substituted with one or more substituents up to the maximum number allowed by valence selected from OH, O—$C_{1-6}$ alkyl, O—$C_{1-6}$ haloalkyl, CN, $NO_2$, N($R^A$)$R^B$, C(O)N($R^A$)$R^B$, C(O)$R^A$, $CO_2R^A$, $SR^A$, S(O)$R^A$, S(O)$_2R^A$, S(O)$_2$N($R^A$)$R^B$, N($R^A$)C(O)$R^B$, N($R^A$)$CO_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, N($R^A$)C(O)C(O)N($R^A$)$R^B$, CycB, ArylB and HetB (4) O—$C_{1-6}$ alkyl in which the alkyl portion is optionally substituted with one or more substituents up to the maximum number allowed by valence selected from OH, O—$C_{1-6}$ alkyl, O—$C_{1-6}$ haloalkyl, CN, $NO_2$, N($R^A$)$R^B$, C(O)N($R^A$)$R^B$, C(O)$R^A$, $CO_2R^A$, $SR^A$, S(O)$R^A$, S(O)$_2R^A$, S(O)$_2$N($R^A$)$R^B$, N($R^A$)C(O)$R^B$, N($R^A$)$CO_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, N($R^A$)C(O)C(O)N($R^A$)$R^B$, CycB, ArylB and HetB, (5) O—$C_{1-6}$ haloalkyl, optionally additionally substituted with one or more substituents up to the maximum number allowed by valence selected from OH, O—$C_{1-6}$ alkyl, O—$C_{1-6}$ haloalkyl, CN, $NO_2$, N($R^A$)$R^B$, C(O)N($R^A$)$R^B$, C(O)$R^A$, $CO_2R^A$, $SR^A$, S(O)$R^A$, S(O)$_2R^A$, S(O)$_2$N($R^A$)$R^B$, N($R^A$)C(O)$R^B$, N($R^A$)$CO_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, N($R^A$)C(O)C(O)N($R^A$)$R^B$, CycB, ArylB and HetB,
(6) halogen,
(7) CN,
(8) $NO_2$,
(9) N($R^A$)$R^B$,
(10) C(O)N($R^A$)$R^B$,
(11) C(O)$R^A$,
(12) C(O)—$C_{1-6}$ haloalkyl,
(13) C(O)O$R^A$,
(14) OC(O)$R^A$,
(15) OC(O)N($R^A$)$R^B$,
(16) $SR^A$,
(17) S(O)$R^A$,
(18) S(O)$_2R^A$,
(19) S(O)$_2$N($R^A$)$R^B$,
(20) N($R^A$)S(O)$_2R^B$,
(21) N($R^A$)S(O)$_2$N($R^A$)$R^B$,
(22) N($R^A$)C(O)$R^B$,
(23) N($R^A$)C(O)N($R^A$)$R^B$,
(24) N($R^A$)C(O)—C(O)N($R^A$)$R^B$,
(25) N($R^A$)$CO_2R^B$,
(26) N($R^C$)$R^D$,
(27) C(O)N($R^C$)$R^D$,
(28) OC(O)N($R^C$)$R^D$,
(29) S(O)$_2$N($R^C$)$R^D$,
(30) N($R^A$)S(O)$_2$N($R^C$)$R^D$,
(31) N($R^A$)C(O)N($R^C$)$R^D$,
(32) N($R^A$)C(O)—C(O)N($R^C$)$R^D$,
(33) OH,
(34) CycB,
(35) ArylB,
(36) HetB,
(37) -J-CycB,
(38) -J-ArylB, and
(39) -J-HetB, or $R^4$ and $R^5$ on adjacent atoms may be joined together with the atoms to which they are attached to form a fused CycC, ArylC or HetC;

CycA, CycB and CycC are independently a carbocyclyl which is a $C_{3-8}$ cycloalkyl, a $C_{5-8}$ cycloalkenyl, or a $C_{7-12}$ bicyclic, saturated or unsaturated, non-aromatic ring system wherein one ring is fused to or bridged with the other ring; wherein the carbocyclyl is optionally substituted with a total of from 1 to 6 substituents, wherein:

(i) from zero to 6 substituents are each independently:
(1) halogen,
(2) CN,
(3) $C_{1-6}$ alkyl,
(4) OH,
(5) O—$C_{1-6}$ alkyl,
(6) $C_{1-6}$ haloalkyl,
(7) O—$C_{1-6}$ haloalkyl,
(8) $C_{1-6}$ alkenyl, or
(9) $C_{1-6}$ alkenyl substituted with CN, and (ii) from zero to 2 substituents are each independently:
(1) CycQ,
(2) AryQ,
(3) HetQ,
(4) HetR,
(5) J-CycQ,
(6) J-AryQ,
(7) J-HetQ,
(8) J-HetR,
(9) $C_{1-6}$ alkyl substituted with CycQ, AryQ, HetQ, HetR, J-CycQ, J-AryQ, J-HetQ, or J-HetR,
(10) $C_{2-6}$ alkenyl substituted with CycQ, AryQ, HetQ, HetR, J-CycQ, J-AryQ, J-HetQ, or J-HetR, or
(11) $C_{2-6}$ alkynyl substituted with CycQ, AryQ, HetQ, HetR, J-CycQ, J-AryQ, J-HetQ, or J-HetR;

ArylA, ArylB and ArylC are independently aryl which is optionally substituted with a total of from 1 to 8 substituents, wherein:

(i) from zero to 8 substituents are each independently:
(1) $C_{1-6}$ alkyl,
(2) $C_{1-6}$ haloalkyl, which is optionally substituted with 1 to 3 additional substituents each of which is independently selected from OH, O—$C_{1-6}$ alkyl, O—$C_{1-6}$ haloalkyl, CN, $NO_2$, N($R^A$)$R^B$, C(O)N($R^A$)$R^B$, C(O)$R^A$, $CO_2R^A$, $SR^A$, S(O)$R^A$, S(O)$_2R^A$, S(O)$_2$N($R^A$)$R^B$, N($R^A$)C(O)$R^B$, N($R^A$)$CO_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
(3) $C_{1-6}$ alkyl substituted with from 1 to 3 substituents each of which is independently selected from OH, O—$C_{1-6}$ alkyl, O—$C_{1-6}$ haloalkyl, CN, $NO_2$, N($R^A$)$R^B$, C(O)N($R^A$)$R^B$, C(O)$R^A$, $CO_2R^A$, $SR^A$, S(O)$R^A$, S(O)$_2R^A$, S(O)$_2$N($R^A$)$R^B$, N($R^A$)C(O)$R^B$, N($R^A$)$CO_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
(4) $C_{2-6}$ alkenyl,
(5) $C_{2-6}$ alkenyl substituted with from 1 to 3 substituents each of which is independently OH, O—$C_{1-6}$ alkyl, O—$C_{1-6}$ haloalkyl, CN, $NO_2$, N($R^A$)$R^B$, C(O)N($R^A$)$R^B$, C(O)$R^A$, $CO_2R^A$, $SR^A$, S(O)$R^A$, S(O)$_2R^A$, S(O)$_2$N($R^A$)$R^B$, N($R^A$)C(O)$R^B$, N($R^A$)$CO_2R^B$, N($R^A$)S(O)$_2R^B$, N($R^A$)S(O)$_2$N($R^A$)$R^B$, OC(O)N($R^A$)$R^B$, N($R^A$)C(O)N($R^A$)$R^B$, or N($R^A$)C(O)C(O)N($R^A$)$R^B$,
(6) $C_{2-6}$ alkynyl,
(7) $C_{2-6}$ alkynyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$, (8) O—$C_{1-6}$ alkyl,
(9) O—$C_{1-6}$ haloalkyl,
(10) OH,
(11) halogen,
(12) CN,
(13) $NO_2$,
(14) $N(R^A)R^B$,
(15) $C(O)N(R^A)R^B$,
(16) $C(O)R^A$,
(17) $C(O)$—$C_{1-6}$ haloalkyl,
(18) $C(O)OR^A$,
(19) $OC(O)N(R^A)R^B$,
(20) $SR^A$,
(21) $S(O)R^A$,
(22) $S(O)_2R^A$,
(23) $S(O)_2N(R^A)R^B$,
(24) $N(R^A)S(O)_2R^B$,
(25) $N(R^A)S(O)_2N(R^A)R^B$,
(26) $N(R^A)C(O)R^B$,
(27) $N(R^A)C(O)N(R^A)R^B$,
(28) $N(R^A)C(O)$—$C(O)N(R^A)R^B$, or
(29) $N(R^A)CO_2R^B$, and (ii) from zero to 2 substituents are each independently:
(1) CycQ,
(2) AryQ,
(3) HetQ,
(4) HetR,
(5) J-CycQ,
(6) AryQ,
(7) HetQ,
(8) HetR,
(9) $C_{1-6}$ alkyl substituted with CycQ, AryQ, HetQ, HetR, CycQ, J-AryQ, J-HetQ, or J-HetR,
(10) $C_{2-6}$ alkenyl substituted with CycQ, AryQ, HetQ, HetR, J-CycQ, J-AryQ, J-HetQ, or J-HetR, or
(11) $C_{2-6}$ alkynyl substituted with CycQ, AryQ, HetQ, HetR, J-CycQ, J-AryQ, J-HetQ, or J-HetR;

HetA, HetB and HetC are independently a heterocyclyl or heteroaryl which is optionally substituted with a total of from 1 to 8 substituents, wherein:

(i) from zero to 8 substituents are each independently:
(1) $C_{1-6}$ alkyl,
(2) $C_{1-6}$ haloalkyl, which is optionally substituted with 1 to 3 additional substituents each of which is independently selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(3) $C_{1-6}$ alkyl substituted with from 1 to 3 substituents each of which is independently selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(4) $C_{2-6}$ alkenyl, (5) $C_{2-6}$ alkenyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(6) $C_{2-6}$ alkynyl,
(7) $C_{2-6}$ alkynyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(8) O—$C_{1-6}$ alkyl,
(9) O—$C_{1-6}$ haloalkyl,
(10) OH,
(11) oxo,
(12) halogen,
(13) CN,
(14) $NO_2$,
(15) $N(R^A)R^B$,
(16) $C(O)N(R^A)R^B$,
(17) $C(O)R^A$,
(18) $C(O)$—$C_{1-6}$ haloalkyl,
(19) $C(O)OR^A$,
(20) $OC(O)N(R^A)R^B$,
(21) $SR^A$,
(22) $S(O)R^A$,
(23) $S(O)_2R^A$,
(24) $S(O)_2N(R^A)R^B$,
(25) $N(R^A)S(O)_2R^B$,
(26) $N(R^A)S(O)_2N(R^A)R^B$,
(27) $N(R^A)C(O)R^B$,
(28) $N(R^A)C(O)N(R^A)R^B$,
(29) $N(R^A)C(O)$—$C(O)N(R^A)R^B$, or
(30) $N(R^A)CO_2R^B$, and (ii) from zero to 2 substituents are each independently:
(1) CycQ,
(2) AryQ,
(3) HetQ,
(4) HetR,
(5) J-CycQ,
(6) J-AryQ,
(7) J-HetQ,
(8) J-HetR,
(9) $C_{1-6}$ alkyl substituted with CycQ, AryQ, HetQ, HetR, J-CycQ, J-AryQ, J-HetQ, or J-HetR,
(10) $C_{2-6}$ alkenyl substituted with CycQ, AryQ, HetQ, HetR, J-CycQ, J-AryQ, J-HetQ, or J-HetR, or
(11) $C_{2-6}$ alkynyl substituted with CycQ, AryQ, HetQ, HetR, J-CycQ, J-AryQ, J-HetQ, or J-HetR;

each CycQ is independently $C_{3-8}$ cycloalkyl or $C_{5-8}$ cycloalkenyl, wherein the cycloalkyl or cycloalkenyl is optionally substituted with from 1 to 4 substituents, each of which is independently halogen, $C_{1-6}$ alkyl, OH, O—$C_{1-6}$ alkyl, $C_{1-6}$ haloalkyl, or O—$C_{1-6}$ haloalkyl;

each AryQ is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $N(R^A)R^B$, C(O)N $(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;

each HetQ is independently a heteroaryl which is optionally substituted with from 1 to 4 substituents each of which is independently halogen, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SO_2R^A$, $N(R^A)C(O)N(R^A)R^B$, or $N(R^A)CO_2R^B$;

each HetR is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)N(R^A)R^B$, $C(O)R^A$, $CO_2R^A$, or $SO_2R^A$;

each J is independently:
(i) O,
(ii) S,
(iii) S(O),
(iv) $S(O)_2$,
(v) O—$C_{1-6}$ alkylene,
(vi) S—$C_{1-6}$ alkylene,
(vii) S(O)—$C_{1-6}$ alkylene,
(viii) $S(O)_2$—$C_{1-6}$ alkylene,
(ix) $N(R^A)$, or
(x) $N(R^A)$—$C_{1-6}$ alkylene;

each $R^A$, $R^B$, $R^C$ and $R^D$ are independently selected from H, $C_{1-6}$ alkyl and $C_{3-6}$cycloalkyl, wherein said $C_{1-6}$ alkyl and $C_{3-6}$cycloalkyl are optionally substituted with one or more substituents up to the maximum number allowed by valence selected from the group consisting of: halogen, OH, CN, $C_{1-4}$alkoxy, $C_{3-6}$cycloalkyl and phenyl;

or alternatively each pair of $R^C$ and $R^D$ together with the nitrogen to which they are both attached form a 4- to 7-membered saturated or mono-unsaturated ring which optionally contains a heteroatom in addition to the N to which $R^C$ and $R^D$ are attached, wherein the additional heteroatom is selected from N, O, and S; wherein the ring is optionally substituted with 1 or 2 substituents each of which is independently $C_{1-6}$ alkyl, $C(O)R^A$, $C(O)OR^A$, $C(O)N(R^A)R^B$, or $S(O)_2R^A$; and wherein the optional S in the ring is optionally in the form of S(O) or $S(O)_2$ each aryl is independently (i) phenyl, (ii) a 9- or 10-membered bicyclic, fused carbocyclic ring system in which at least one ring is aromatic, or (iii) an 11-to 14-membered tricyclic, fused carbocyclic ring system in which at least one ring is aromatic;

each heterocyclyl is independently (i) a 4- to 8-membered, saturated or unsaturated monocyclic ring, (ii) a 7- to 12-membered bicyclic ring system, or (iii) a 10-to 18-membered tricyclic ring system, wherein each ring in (ii) or (iii) is independent of, fused to, or bridged with the other ring or rings and each ring is saturated or unsaturated; wherein the monocyclic ring contains from 1 to 4 heteroatoms and a balance of carbon atoms; the bicyclic ring system or tricyclic ring system contains from 1 to 8 heteroatoms and a balance of carbon atoms, wherein one or more of the rings contain one or more of the heteroatoms; wherein the heteroatoms are selected from N, O and S; and wherein any one or more of the nitrogen and sulfur heteroatoms is optionally oxidized, and any one or more of the nitrogen heteroatoms is optionally quaternized;

each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered heterobicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally S(O) or $S(O)_2$.

2. The compound of Formula Ib according to claim 1, or a pharmaceutically acceptable salt thereof, wherein:
$K^2$ is chloro and $K^1$ is cyano, or
$K^2$ is bromo and $K^1$ is chloro, or
$K^2$ is cyano and $K^1$ is cyano, or
$K^2$ is cyano and $K^1$ is difluoromethoxy, or
$K^2$ is chloro and $K^1$ is chloro, or
$K^2$ is cyano and $K^1$ is fluoro.

3. The compound of Formula Ib according to claim 1, or a pharmaceutically acceptable salt thereof, wherein:
$R^2$ is independently:
(1) H,
(2) $C_{1-3}$ alkyl,
(3) $CF_2H$,
(4) $CF_3$,
(5) $CH_2CF_3$,
(6) $CF_2CH_3$,
(7) $CH_2OH$,
(8) $CH_2OCH_3$,
(9) $CH_2CN$,
(10) $CH_2NH_2$,
(11) $CH_2N(H)CH_3$,
(12) $CH_2N(CH_3)_2$,
(13) $CH_2C(O)NH_2$,
(14) $CH_2C(O)N(H)CH_3$,
(15) $CH_2C(O)N(CH_3)_2$,
(16) $CH_2C(O)CH_3$,
(17) $CH_2CO_2CH_3$,
(18) $CH_2S(O)_2CH_3$,
(19) O—$C_{1-3}$ alkyl,
(20) $OCF_2H$,
(21) $OCF_3$,
(22) Cl,
(23) Br,
(24) F,
(25) CN,
(26) $NO_2$,
(27) $NH_2$,
(28) $N(H)CH_3$,
(29) $N(CH_3)_2$,
(30) $C(O)NH_2$,
(31) $C(O)N(H)CH_3$,
(32) $C(O)N(CH_3)_2$,
(33) $C(O)CH_3$,
(34) $C(O)CF_3$,
(35) $CO_2CH_3$,
(36) $S(O)_2CH_3$, or
(37) cyclopropyl.

4. The compound of Formula Ib according to claim 3, or a pharmaceutically acceptable salt thereof, wherein $R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN.

5. The compound of Formula Ib according to claim 4, or a pharmaceutically acceptable salt thereof, wherein $R^2$ is $CF_3$.

6. The compound of Formula Ib according to claim 1, or a pharmaceutically acceptable salt thereof, wherein:
$R^4$ and $R^5$ are each independently selected from:
(1) H,
(2) $C_{1-6}$ alkyl, $C_{2-6}$ alkenyl or $C_{2-6}$ alkynyl, each optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(3) $C_{1-6}$ haloalkyl optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(4) O—$C_{1-6}$ alkyl in which the alkyl portion is optionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(5) O—$C_{1-6}$ haloalkyl, optionally additionally substituted with one or more substituents up to the maximum number allowed by valence selected from OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, $N(R^A)C(O)C(O)N(R^A)R^B$, $C_{3-8}$ cycloalkyl, phenyl and HetB,
(6) halogen,
(7) OH,
(8) CN
(9) $C(O)R^A$,
(10) $N(R^A)R^B$,
(11) $C(O)N(R^A)R^B$,
(12) $C(O)OR^A$,
(13) $SR^A$,
(14) $S(O)_2R^A$,
(15) $S(O)_2N(R^A)R^B$,
(16) $C_{3-8}$ cycloalkyl,
(17) ArylB,
(18) HetB,
(19) -J-$C_{3-8}$ cycloalkyl,
(20) -J-ArylB, and
(21) -J-HetB.

7. The compound of Formula Ib according to claim 6 or a pharmaceutically acceptable salt thereof, wherein
$R^2$ is selected from H, $CH_3$, $CH_2CH_3$, $CF_2CH_3$, $CF_2H$, $CF_3$, $OCH_3$, $OCF_2H$, $OCF_3$, cyclopropyl, Cl, Br, F, or CN.

8. The compound of Formula Ib according to claim 7, or a pharmaceutically acceptable salt thereof, wherein $R^2$ is $CF_3$ and $R^4$ is H.

9. The compound of Formula Ib according to claim 8 or a pharmaceutically acceptable salt thereof,
wherein
$K^2$ is chloro and $K^1$ is cyano, or
$K^2$ is bromo and $K^1$ is chloro, or
$K^2$ cyano and $K^1$ is cyano, or
$K^2$ cyano and $K^1$ is difluoromethoxy, or
$K^2$ chloro and $K^1$ is chloro, or
$K^2$ cyano and $K^1$ is fluoro.

10. The compound of Formula Ib according to claim 1, or a pharmaceutically acceptable salt thereof, wherein the compound is:
3-chloro-5-((6-oxo-1((5-oxo-5,6-dihydropyrido[2,3-d]pyridazin-8-yl)methyl)-4-(trifluoromethyl)-1,6-dihydropyrimidin-5-yl)oxy)benzonitrile,
3-chloro-5-((6-oxo-1-((6-oxo-1,6-dihydropyridazin-3-yl)methyl)-4-(trifluoromethyl)-1,6-dihydropyrimidin-5-y0oxy)benzonitrile,
3-chloro-5-({6-oxo-1-[(6-oxo-1,6-dihydropyridazin-3-yl)($^2H_2$)methyl]-4-(trifluoromethyl)-1,6-dihydropyrimidin-5-yl}oxy)benzonitrile,
3-chloro-5-((1(5-(3,3-difluorocyclobutyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1((5-isopropyl-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-isopropyl-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1((5-(hydroxymethyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((4-methyl-6-oxo-1-((6-oxo-1,6-dihydropyridazin-3-yl)methyl)-1,6-dihydropyrimidin-5-yl)oxy)benzonitrile,
3-chloro-5-((1-((5-(1-hydroxyethyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(1-fluoroethyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-5-(fluoromethyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(cyclopropyl(hydroxy)methyl)-6-oxo-1,6-dihydropyridazin-3-yl)methyl)-6-oxo-4-(trifluoromethyl)-1,6-dihydropyrimidin-5-yl)oxy)benzonitrile,
3-fluoro-5-((6-oxo-1-((6-oxo-1,6-dihydropyridazin-3-yl)methyl)-4-(trifluoromethyl)-1,6-dihydropyrimidin-5-yl)oxy)benzonitrile,
3-((6-oxo-1-((6-oxo-1,6-dihydropyridazin-3-yl)methyl)-4-(trifluoromethyl)-1,6-dihydropyrimidin-5-yl)oxy)-5-(trifluoromethyl)benzonitrile,
6-((5-(3-chloro-5-(trifluoromethyl)phenoxy)-6-oxo-4-(trifluoromethyl)pyrimidin-1(6H)-yl)methyl)pyridazin-3(2H)-one,
3-chloro-5-((6-oxo-1-((6-oxo-5-phenyl-1,6-dihydropyridazin-3-yl)methyl)-4-(trifluoromethyl) -1,6-dihydropyrimidin-5-yl)oxy)benzonitrile, 3-chloro-5-((6-oxo-1-((6-oxo-5-(4-(trifluoromethoxy)phenyl)-1,6-dihydropyridazin-3-yl)methyl)-4-(trifluoromethyl)-1,6-dihydropyrimidin-5-yl)oxy)benzonitrile, 3-chloro-5-((1-((5-(2-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1((5-(3-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3-chloro-5-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(4-chlorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3,4-difluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(4-(difluoromethoxy)phenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((6-oxo-1-((6-oxo-5-(p-tolyl)-1,6-dihydropyridazin-3-yl)methyl)-4-(trifluoromethyl)-1,6-dihydropyrimidin-5-yl)oxy)benzonitrile, 3-chloro-5-((1-((5-(3-fluoro-4-isopropoxyphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3,5-difluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3-chloro-4-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2,4-difluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3-chlorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(4-fluoro-3-methylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-fluoro-3-methylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-fluoro-5-methylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-chloro-4-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-chloro-3-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-fluoro-4-methylphenyl)-6-oxo-1,6-dihydropyridazin-3-yl)methyl)-6-oxo-4-(trifluoromethyl)-1,6 dihydropyrimidin-5-yl)oxy)benzonitrile, 3-chloro-5-((1-((5-(3-chloro-2-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-fluoro-3-methoxyphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-fluoro-4-methoxyphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(4-chloro-3-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(5-chloro-2-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2,5-difluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(4-isopropylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(5-fluoro-2-methylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2-fluoro-6-methoxyphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3-fluoro-4-methoxyphenyl)-6-oxo-1,6-dihydropyridazin-3-yl)methyl)-6-oxo-4-(trifluoromethyl)-1,6-dihydropyrimidin-5-yl)oxy)benzonitrile, 3-((1-((5-(4-(tert-butyl)phenyl)-6-oxo-1,6-dihydropyridazin-3-yl)methyl)-6-oxo-4-(trifluoromethyl)-1,6-dihydropyrimidin-5-yl)oxy)-5-chlorobenzonitrile, 3-chloro-5-((1-((5-(3-cyanophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((6-oxo-1-((6-oxo-5-(3,4,5-trifluorophenyl)-1,6-dihydropyridazin-3-yl)methyl)-4-(trifluoromethyl)-1,6-dihydropyrimidin-5-yl)oxy)benzonitrile, 3-chloro-5-((1-((5-(4-fluoro-2-methylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(2,3-dihydrobenzofuran-7-yl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3-fluoro-4-methylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(5-fluoro-2-methoxyphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3-fluoro-5-methylphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(3-fluoro-5-methoxyphenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((6-oxo-1-((6-oxo-5-(2,3,4-trifluorophenyl)-1,6-dihydropyridazin-3-yl)methyl)-4-(trifluoromethyl)-1,6-dihydropyrimidin-5-yl)oxy)benzonitrile, 3-chloro-5-((1-((5-(2-fluoro-5-methoxyphenyl)-6-oxo-1,6-dihydroppidazin-3-yl)methyl)-6-oxo-4-(trifluoromethyl)-1,6-dihydropyrimidin-5-yl)oxy)benzonitrile, 3-chloro-5-((1-((5-(2,3-dihydrobenzofuran-5-yl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((6-oxo-1-((6-oxo-5-(1H-pyrazol-5-yl)-1,6-dihydropyridazin-3-yl)methyl)-4-(trifluoromethyl)-1,6-dihydropyrimidin-5-yl)oxy)benzonitrile, 3-chloro-5-((1-((5-cyclopropyl-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(4-(methylsulfonyl)phenyl)-6-oxo-1,6-dihydropyridazin-3-yl)methyl)-6-oxo-4-(trifluoromethyl)-1,6-dihydropyrimidin-5-yl)oxy)benzonitrile,
4-(6-((5-(3-chloro-5-eyanophenoxy)-6-oxo-4-(trifluoromethyl)primidin-1(6H)-yl)methyl)-3-oxo-2,3-dihydropyridazin-4-yl)-2-fluorobenzonitrile,
3-chloro-5-((1-((5-(4-(2,2-difluoro-1-hydroxyethyl)phenyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(3-(methylsulfonyl)phenyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((6-oxo-1-((6-oxo-5-(1H-pyrazol-4-yl)-1,6-dihydropyridazin-3-yl)methyl)-4-(trifluoromethyl)-1,6-dihydropyrimidin-5-yl)oxy)benzonitrile,
3-chloro-5-((1-((5-(1-methyl-1H-pyrazol-4-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((6-oxo-1-((6-oxo-5-(pyridin-3-yl)-1,6-dihydropyridazin-3-yl)methyl)-4-(trifluoromethyl)-1,6-dihydropyrimidin-5-ypoxy)benzonitrile,
3-chloro-5-((1-((5-(6-methoxypyridin-3-yl)-6-oxo-1,6-dihydropyridazin-3-yl)methyl)-6-oxo-4-(-(trifluoromethyl)-1,6-dihydropyrimidin-5-yl)oxy)benzonitrile,
3-chloro-5-((1-((5-(4-cyanophenyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(1-methyl-1H-pyrazol-5-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(4-fluorophenyl)-6-oxo-1,6-dihydropyridazin-3-yl)methyl)-6-oxo-4-trifluoromethyl)-1,6-dihydropyrimidin-5-yl)oxy)benzonitrile,
3-chloro-5-((1-((5-(6-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(2-methoxypyridin-4-yl)-6-oxo-1,6-dihydropyridazin-3-yl)methyl)-6-oxo-4-(trifluoromethyl)-1,6-dihydropyrimi din-5-yl)oxy)benzonitrile,
3-chloro-5-((1-((5-(5-methylpyridin-3-yl)-6-oxo-1,6-dihydropyridazin-3-yl)methyl)-6-oxo-4-(trifluoromethyl)-1,6-dihydropyrimidin-5-yl)oxy)benzonitrile
3-chloro-5-((6-oxo-1-((6-oxo-5-(pyridin-4-yl)-1,6-dihydropyridazin-3-yOmethyl)-4-(trifluoromethyl)-1,6-dihydropyrimidin-5-yl)oxy)benzonitrile
3-chloro-5-((1-((5-(5-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(6-methylpyridin-3-yl)-6-oxo-1,6-dihydropyridazin-3-yl)methyl)-6-oxo-4-(trifluoromethyl)-1,6-dihydropyrimidin-5-yl)oxy)benzonitrile,
5-(6-((5-(3-chloro-5-cyanophenoxy)-6-oxo-4-(trifluoromethyl)pyrimidin-1(6H)-yl)methyl)-3-oxo-2,3-dihydropyridazin-4-yl)nicotinonitrile,
3-chloro-5-((1-((5-(5-methoxypyridin-3-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(6-chloropyridin-3-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(2-fluoropyridin-3-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((6-oxo-1-((6-oxo-5-(quinolin-3-yl)-1,6-dihydropyridazin-3-yl)methyl)-4-(trifluoromethyl)-1,6-dihydropyrimidin-5-yl)oxy)benzonitrile,
3-((1-((5-(4-(1-amino-2,2,2-trifluoroethyl)phenyl)-6-oxo-1,6-dihydropyridazin-3-yl)methyl)-6-oxo-4(-(trifluoromethyl)-1,6-dihydropyrimidin-5-yl)oxy)-5-chlorobenzonitrile,
3-((1-((5-bromo-6-oxo-1,6-dihydropyridazin-3-yl)methyl)-6-oxo-4-(trifluoromethyl)-1,6-dihydropyrimidin-5-yl)oxy)-5-chlorobenzonitrile,
3-chloro-5-((1-((5-chloro-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(dimethylamino)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((6-oxo-1-((6-oxo-5-(1H-1,2,3-triazol-1-yl)-1,6-dihydropyridazin-3-yl)methyl)-4-(trifluoromethyl)-1,6-dihydropyrimi din-5-yl)oxy)benzonitrile,
6-((5-(3-chloro-5-cyanophenoxy)-6-oxo-4-(trifluoromethyl)pyrimidin-1(6H)-yl)methyl)-3-oxo-2,3-dihydropyridazine-4-carbonitrile,
3-chloro-5-((1-((5-(methylsulfonyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(ethylsulfonyl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(5-fluoropyridin-2-yl)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(5-chloropyridin-2-yl)-6-oxo-1,6-dihydropyridazin-3-yl)methyl)-6-oxo-4-(trifluoromethyl)-1,6-dihydropyrimidin-5-yl)oxy)benzonitrile,
methyl 6-((5-(3-chloro-5-cyanophenoxy)-6-oxo-4-(trifluoromethyl)pyrimidin-1(6H)-yl) methyl)-3-oxo-2,3-dihydropyridazine-4-carboxylate,
6-((5-(3-chloro-5-cyanophenoxy)-6-oxo-4-(trifluoromethyl)pyrimidin-1(6H)-yl)methyl)-3-oxo-2,3-dihydropyridazine-4-carboxamide,
3-chloro-5-((1-((5-(difluorometlayl)-6-oxo-1,6-dihydropyridazin-3-yl)methyl)-6-oxo-4-(trifluoromethyl)-1,6-dihydropyrimidin-5-ypoxy)benzonitrile,
3-chloro-5-((6-oxo-1-((6-oxo-5-(2,2,2-trifluoro-1-hydroxyethyl)-1,6-dihydro pyridazin-3-yl)methyl)-4-(trifluoromethyl)-1,6-dihydropyrimidin-5-yl)oxy)benzonitrile,
3-chloro-5-((1-((5-(1,1-difluoroethyl)-6-oxo-1,6-dihydropyridazin-3-yl)methyl)-6-oxo-4-(trifluoromethyl)-1,6-dihydropyrimidin-5-yl)oxy)benzonitrile,
3-((1-((5-acetyl-6-oxo-1,6-dihydropyridazin-3-yl)methyl)-6-oxo-4-(trifluoro methyl)-1,6-dihydropyrimidin-5-yl)oxy)-5-chlorobenzonitrile,
3-chloro-5-((1-((5-methoxy-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-hydroxy-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(4-fluorophenoxy)-6-oxo-1,6-dihydropyridazin-3-yl)methyl)-6-oxo-4-(trifluoromethyl)-1,6-dihydropyrimidin-5-yl)oxy)benzonitrile,
3-chloro-5-((1-((5-(difluoromethoxy)-6-oxo-1,6-dihydropyridazin-3-yl)methyl)-6-oxo-4-(trifluoromethyl)-1,6-dihydropyrimidin-5-ypoxy)benzonitrile, 3-chloro-5-((4-cyclopropyl-6-oxo-1-((6-oxo-1,6-dihydropyridazin-3-yl)methyl)-1,6-dihydropyrimidin-5-ypoxy)benzonitrile, 3-chloro-54(4-(difluoromethyl)-6-oxo-1-((6-oxo-1,6-dihydropyridazin-3-yl)methyl)- 1,6-dihydropyrimidin-5-yl)oxy)benzonitrile, 3-chloro-5-(4-(difluoromethoxy)-6-oxo-1-((6-oxo-1,6-dihydropyridazin-3-yl)methyl) -1,6-dihydropyrimidin-5-yloxy)benzonitrile, 3-(difluoromethoxy)-5-(6-oxo-1-((6-oxo-1,6-dihydropyridazin-3-yl)methyl)-4-(trifluoromethyl)-1,6-dihydropyrimidin-5-yloxy)benzonitrile, 3-chloro-5-((1-((5-(4-fluorophenyl)-6-oxo-1,6-dihydropyridazin-3-yl)methyl)-4-methyl-6-oxo-1,6-dihydropyrimidin-5-yl)oxy)benzonitrile, 3-(difluoromethoxy)-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile, 3-chloro-5-((1-((5-(4-fluorophenyl)-6-oxo-1,6-dihydropyridazin-3-yl)methyl)-4-methyl-6-oxo-1,6-dihydropyrimidin-5-ypoxy)benzonitrile, or 3-chloro-5-((4-(1,1-difluoroethyl)-1-((5-(4-fluorophenyl)-6-oxo-1,6-dihydropyri dazin-3-yl) methyl)-6-oxo-1,6-dihydropyrimidin-5-yl)oxy)benzonitrile, or a pharmaceutically acceptable salt of any of the foregoing compounds.

11. A pharmaceutical composition comprising an effective amount of the compound according to claim 1, or a pharmaceutically acceptable salt thereof, and a pharmaceutically acceptable carrier.

12. A method for the treatment of infection by HIV or for the treatment of AIDS in a subject in need thereof which comprises administering to the subject an effective amount of the compound according to claim 1 or a pharmaceutically acceptable salt thereof.

13. The method of claim 12, further comprising administering to the subject a second HIV antiviral agent selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

14. The pharmaceutical composition of claim 11 further comprising a second HIV antiviral agent selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

15. A compound

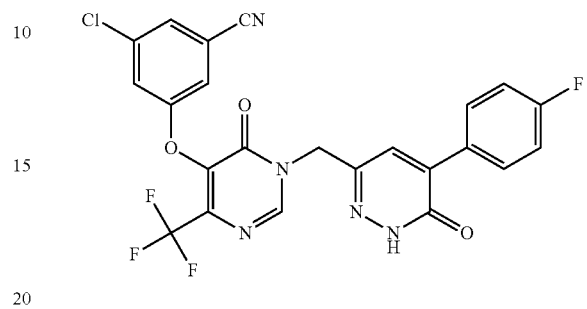

or a pharmaceutically acceptable salt thereof.

16. A pharmaceutical composition comprising an effective amount of the compound according to claim 15, or a pharmaceutically acceptable salt thereof, and a pharmaceutically acceptable carrier.

17. The pharmaceutical composition of claim 16 further comprising a second HIV antiviral agent selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

18. A method for the treatment of infection by HIV or delay in the onset of AIDS in a subject in need thereof which comprises administering to the subject an effective amount of the compound according to claim 15, or a pharmaceutically acceptable salt thereof.

19. The method of claim 18 further comprising administering to the subject a second HIV antiviral agent selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Chemically synthesized

<400> SEQUENCE: 1

```
ttgaaatgac tgcggtacgg c                                        21

<210> SEQ ID NO 2
<211> LENGTH: 501
<212> TYPE: RNA
<213> ORGANISM: Artificial Sequence
<220> FEATURE:
<223> OTHER INFORMATION: Chemically synthesized

<400> SEQUENCE: 2
gagguucagg ugguuuccac cgcaacacaa uccuuccugg cgaccugcgu caacggcgug    60
uguuggaccg uuuaccaugg ugcuggcuca aagaccuuag ccggcccaaa ggggccaauc   120
acccagaugu acacuaaugu ggaccaggac cucgucggcu ggcaggcgcc ccccggggcg   180
cguuccuuga caccaugcac cuguggcagc ucagaccuuu acuuggucac gagacaugcu   240
gacgucauuc cggugcgccg gcggggcgac aguagggga gccugcucuc ccccaggccu    300
gucuccuacu ugaagggcuc uucggguggu ccacugcucu gcccuucggg gcacgcugug   360
ggcaucuucc gggcugccgu augcacccgg gggguugcga aggcggugga cuuugugccc   420
guagagucca uggaaacuac uaugcggucu ccggucuuca cggacaacuc auccccccg    480 gccguaccgc agucauuuca a                                            501
```